US011154598B2

(12) United States Patent
Jauliac et al.

(10) Patent No.: US 11,154,598 B2
(45) Date of Patent: Oct. 26, 2021

(54) COMPOSITIONS COMPRISING SECRETED EXTRACELLULAR VESICLES OF CELLS EXPRESSING NFATC4 USEFUL FOR THE TREATMENT OF CANCER

(71) Applicants: UNIVERSITÉ DE PARIS, Paris (FR); Institut National de la Sante et de la Recherche Medicale (INSERM), Paris (FR); Assistance Publique—Hopitaux de Paris, Paris (FR)

(72) Inventors: Sébastien Jauliac, Clichy (FR); Livia Camargo, Paris (FR)

(73) Assignees: Université de Paris, Paris (FR); Institut National de la Sante et de la Recherce Medicale, Paris (FR); Assistance Publique—Hopitaux de Paris, Paris (FR)

(*) Notice: Subject to any disclaimer, the term of this patent is extended or adjusted under 35 U.S.C. 154(b) by 263 days.

(21) Appl. No.: 16/089,754

(22) PCT Filed: Mar. 29, 2017

(86) PCT No.: PCT/EP2017/057374
§ 371 (c)(1),
(2) Date: Sep. 28, 2018

(87) PCT Pub. No.: WO2017/167788
PCT Pub. Date: Oct. 5, 2017

(65) Prior Publication Data
US 2019/0117688 A1 Apr. 25, 2019

(30) Foreign Application Priority Data
Mar. 29, 2016 (EP) .................................... 16305362

(51) Int. Cl.

| | |
|---|---|
| ***A61K 35/12*** | (2015.01) |
| ***A61K 9/00*** | (2006.01) |
| ***A61K 39/00*** | (2006.01) |
| ***A61K 39/39*** | (2006.01) |
| ***A61P 35/04*** | (2006.01) |
| ***A61K 35/13*** | (2015.01) |
| ***C07K 14/47*** | (2006.01) |
| ***C12Q 1/6886*** | (2018.01) |

(52) U.S. Cl.
CPC ........ *A61K 39/0011* (2013.01); *A61K 9/0019* (2013.01); *A61K 35/12* (2013.01); *A61K 35/13* (2013.01); *A61K 39/39* (2013.01); *A61P 35/04* (2018.01); *C07K 14/47* (2013.01); *C12Q 1/6886* (2013.01); *A61K 2039/55555* (2013.01); *A61K 2039/60* (2013.01)

(58) Field of Classification Search
None
See application file for complete search history.

(56) References Cited

PUBLICATIONS

Mizrak et al., Mol. Ther., 2013, 21: 101-108.*
Al-Nedawi et al., Intercellular transfer of the oncogenic receptor EGFRvIII by microvesicles derived from tumour cells, 10 Nature Cell Biology 1-5 (2008).
Bussard et al., Abstract 1625: Crosstalk between breast cancer and stromal cells occurs via exosomes and gap junctions in bone metastatic breast cancer, 73(8) Cancer Research Suppl. 1 1-3 (Apr. 15, 2013).
Fougère et al., NFAT3 transcription factor inhibits breast cancer cell motility by targeting the Lipocalin 2 gene, 29(15) Oncogene 2292-2301 (2010).
Harris et al., Exosomes Released from Breast Cancer Carcinomas Stimulate Cell Movement, 10(3) PLoS One 1-18 (Mar. 23, 2015).
Hendrix et al., An Ex(o)citing Machinery for Invasive Tumor Growth, 70 Cancer Res. 9533-9537 (2010).
Jauliac et al., The role of NFAT transcription factors in integrin-mediated carcinoma invasion, 4 Nat Cell Biol 540-544 (Jul. 2002).
Mancini et al. NFAT proteins: emerging roles in cancer progression, 9 Nature 810-820 (Nov. 2009).
Melo et al., Cancer Exosomes Perform Cell-Independent MicroRNA Biogenesis and Promote Tumorigenesis, 26 Cancer Cell 1-15 (Nov. 10, 2014).
Molkentin et al., A Calcineurin-Dependent Transcriptional Pathway for Cardiac Hypertrophy, 93 Cell 215-228 (Apr. 17, 1998).
Ohshima et al., Let-7 MicroRNA Family Is Selectively Secreted into the Extracellular Environment via Exosomes in a Metastatic Gastric Cancer Cell Line, 5(10) PLoS One 1-10 (Oct. 2010).
Peinado et al., Melanoma exosomes educate bone marrow progenitor cells toward a pro-metastatic phenotype through MET, 18(6) Nature Medicine 883-891 (Jun. 2012).
Shou et al., Nuclear factor of activated T cells in cancer development and treatment, 361 Cancer Letters 174-184 (2015).
Soldevilla et al., Tumor-derived exosomes are enriched in ΔNp73, which promotes oncogenic potential in acceptor cells and correlates with patient survival, 23(2) Human Molecular Genetics 467-478 (2014).
Takahashi et al., Visualization and in vivo tracking of the exosomes of murine melanoma B16-BL6 cells in mice after intravenous injection, 165 Journal of Biotechnology 77-84 (2013).
Tickner et al., Functions and therapeutic roles of exosomes in cancer, 4 Frontiers in Oncology 1-8 (May 2014).

(Continued)

*Primary Examiner* — Ileana Popa
(74) *Attorney, Agent, or Firm* — Panitch Schwarze Belisario & Nadel LLP

(57) ABSTRACT

The present invention relates to a composition comprising secreted extracellular vesicles (SEV) of cells expressing nuclear factor of activated T-cells, cytoplasmic, calcineurin-dependent 4(NFATC4), for use in the treatment of cancer or in the treatment or prevention of metastatic cancer. It further relates to in vitromethods for determining or predicting the therapeutic efficiency of a treatment with a composition comprising SEV of cells expressing NFATC4 in a cancer patient, based on the ability of the composition comprising SEV of cells expressing NFATC4 to induce an increase in TGFβ1 expression level.

20 Claims, 17 Drawing Sheets

Specification includes a Sequence Listing.

(56) References Cited

PUBLICATIONS

Van der Pol et al., Classification, Functions, and Clinical Relevance of Extracellular Vesicles, 64(3) Pharmacological Reviews A-AD (2012).
Villarroya-Beltri et al., Sorting It Out: Regulation of Exosome Loading, 28 Semin Cancer Biol. 1-24 (Oct. 2014).
Yakimchuk, Exosomes: isolation methods and specific markers, 5 Materials and Methods (Aug. 15, 2015).
Zhao et al., Increased expression of NF-AT3 and NF-AT4 in the atria correlates with procollagen I carboxyl terminal peptide and TGF-β1 levels in serum of patients with atrial fibrillation, 14 BMC Cardiovascular Disorders 1-12 (2014).
Zomer et al. In Vivo Imaging Reveals Extracellular Vesicle-Mediated Phenocopying Of Metastatic Behavior, 161 Cell 1046-1057 (2015).
De Camargo et al., Extracellular vesicles produced by NFAT3-expressing cells hinder tumor growth and metastatic dissemination, 10(8694) Scientific Reports 1-13 (2020).

* cited by examiner

COMPOSITIONS COMPRISING SECRETED EXTRACELLULAR VESICLES OF CELLS EXPRESSING NFATC4 USEFUL FOR THE TREATMENT OF CANCER

CROSS-REFERENCE TO RELATED APPLICATIONS

This application is a U.S. National Stage Application pursuant to 35 U.S.C. § 371 of International Patent Application PCT/EP2017/057374, filed on Mar. 29, 2017, and published as WO 2017/167788 on Oct. 5, 2017, which claims priority to European Patent Application 16305362.2, filed on Mar. 29, 2016, all of which are incorporated herein by reference in their entireties for all purposes.

TECHNICAL FIELD OF THE INVENTION

The present invention is in the field of oncology, and more particularly to the treatment of cancer and metastatic cancer. It relates to a composition comprising secreted extracellular vesicles (SEV) of cells expressing nuclear factor of activated T-cells, cytoplasmic, calcineurin-dependent 4 (NFATC4), for use in the treatment of cancer or in the treatment or prevention of metastatic cancer. It further relates to in vitro methods for determining or predicting the therapeutic efficiency of a treatment with a composition comprising SEV of cells expressing NFATC4 in a cancer patient, based on the ability of the composition comprising SEV of cells expressing NFATC4 to induce an increase in TGFß1 expression level.

BACKGROUND ART

Breast cancer is a leading cause of morbidity in women worldwide. The main reason of death for these patients is not the primary tumor, but distant metastases, which are directly linked to the migratory and invasive phenotype of the cancer cells. In addition, de novo and acquired resistance to anticancer agents remains a major obstacle in the treatment of breast cancer. Moreover, resistance to treatment is often associated to increased invasiveness of cancer and development of metastasis, suggesting that some treatment, while initially efficient to treat the primary cancer, at the same time promote the appearance of more invasive cells, finally resulting in metastasis combined to resistance to treatment. The same is true for other cancers. There is thus a need for new therapies that would be efficient not only on the primary cancer but that would also inhibit the development of invasiveness and metastasis.

Moreover, it is now well known that no therapy is efficient in all patients, a varying proportion of patients being resistant to any given therapy. In order to prevent long-term administration of a non-efficient treatment (which is not only costly but also detrimental to the patient's health), there is also a need for tests with the ability to predict or at least to determine efficiency of a given therapy for a given patient, before or just after treating the patient.

Different studies revealed that secreted extracellular vesicles (SEV) can be readily detected in tumor tissue and many body fluids, and are found in higher concentrations, both in tumor tissue, and in the serum and plasma of cancer patients (Tickner et al. Front Oncol 4, 127 (2014)).

Secreted extracellular vesicles (SEV), is the general term to designate cell secreted vesicles ranging approximately 40 nm to few μm in size. Among them, exosomes comprise the most prominently described classes of SEV. Exosomes have a diameter lower than about 150 nm and are derivatives of the endosomal compartment. SEV contain cytosolic and membrane proteins derived from the parental cells. The protein content of SEV depends on their cellular origin and SEV are enriched for certain molecules, especially endosome-associated proteins (e.g. CD63) and proteins involved in multivesicular bodies formation, but also contain targeting/adhesion molecules. Remarkably, SEV contain not only proteins but also functional mRNAs, long non-coding RNAs and miRNAs, and in some cases, they have been shown to deliver these genetic materials to recipient cells.

The cargo of SEV is potentially particularly interesting for targeting therapies to tumors, as SEV are secreted in the extracellular compartment, where their content is protected from degradation because of their lipid membrane, and SEV excreted from one cell are known to be able to fuse with surrounding cells, and thus have the potential to initiate signaling responses (Hendrix, A. et al. Cancer Res. 70, 9533-9537 (2010).).

However, cancer cell derived SEV have been shown by many to be involved in cancer progression and metastasis (van der Pol E. et al. Pharmacol Rev 64:A-AD, 2012). It has notably been shown that SEV function as versatile promoters in the tumorigenesis, metastasis and drug resistance of breast cancer (Yu et al. Cancer Sci 106 (2015) 959-964). Similarly, studies using tumor-derived SEV exposing a membrane-bound luciferase fused to the C1C2-domain of MFGE8/lactadherin27 show a half-life of only two minutes in blood circulation. Several hours after they had disappeared from the circulation, SEV were recovered in spleen, and melanoma-derived SEV also accumulated in lung, liver, and bone marrow—organs thought to be preferred sites of metastasis (Peinado, H. et al. Nat. Med. 18, 883-891 (2012); Takahashi, Y. et al. J. Biotechnol. 165, 77-84 (2013).). Another study has recently shown that SEV from MDA-MB-231 can be transferred in vivo to T47D cell to enhance their invasion (Zomer, A. et al. Cell 161, 1046-1057 (2015).). This is of particular relevance in tumorigenesis, as both surrounding and distant tissues are known to adopt characteristics of the primary tumor. A recent study has paved the way showing that breast cancer SEV are the site of pre-miRNA maturation to promote tumor growth (Melo, S. A. et al. Cancer Cell 26, 707-721 (2014).). The use of cancer cells derived SEV appears rather deleterious than helpful for cancer treatment.

As a result, most attempts for treating cancer using SEV have relied on the idea to prompt an immune response against cancer-specific material, using antigen presenting cells (APC)-derived SEV (in particular dendritic cells(DC)-derived exosomes, which are enriched in molecules useful for priming immune responses), loaded with tumor-specific peptides. While some immune responses have been observed, the observed treatment efficiency was generally low (van der Pol E. et al. Pharmacol Rev 64:A-AD, 2012).

The family of NFAT transcription factors comprises five genes.

Molecular pathways involving specific members of the NFAT family have been highlighted in the migratory and invasive capacities of breast cancer cells (Jauliac S, et al. (2002). Nat Cell Biol 4: 540-544). Moreover, there is growing evidence for a function of the NFAT factors in carcinogenesis (Mancini M, Toker A. (2009). Nat Rev Cancer 9: 810-820). NFATC4 (also known as NFAT3) has been shown to inhibit breast cancer cell motility by targeting the Lipocalin 2 gene. In particular, it has been shown that NFAT3 is specifically expressed in estrogen receptor a positive (ERA+) breast cancer cells of low invasive capacity, and that transduction with a vector of expression of NFAT3 inhibits invasion of both ERA+ (low invasive capacity) and ERA− (high invasive capacity) breast cancer cells (Fougère, M., et al. (2010). Oncogene, 29(15), 2292-2301).

However, while SEV composition is influenced by the cell secreting it, the molecular composition of SEV is not a mere reflection of the cell secreting it. In contrast, SEV are enriched in specific proteins, lipids and RNAs, whereas others are absent, indicating the existence of specialized mechanisms that control the sorting of molecules into SEV (Villarroya-Beltri C. et al. *Semin Cancer Biol.* 2014 October; 28: 3-13; Al-Nedawi, K. et al. Nature Publishing Group 10, 619-624 (2008); Ohshima, K. et al. PLoS ONE 5, e13247 (2010); Soldevilla, B. et al. Hum. Mol. Genet. 23, 467-478 (2014)). In particular, SEV are known to contain transmembrane receptors of the cell secreting them, and in particular oncogenic transmembrane receptors such as EGFRvIII (Al-Nedawi, K. et al. Nature Publishing Group 10, 619-624 (2008)). However, the presence in SEV of transcription factors of the cell secreting them cannot be guaranteed. For instance, Al-Nedawi, K. et al showed that while EGFRvIII+ glioma cells SEV contain oncogenic transmembrane receptor EGFRvIII and transmit it to other EGFRvIII− glioma cells, EGFRvIII effectors, such as Erk1/2 and Akt, were largely undetectable in SEV.

Moreover, it has also been shown that SEV secreted by breast cancer cell lines of both low and high invasive capacity promote cell migration (Harris D A, et al. PLoS ONE 10(3): e0117495.), suggesting that such SEV would rather promote cancer progression and invasion.

SUMMARY OF THE INVENTION

In the context of the present invention, the inventors surprisingly found that, contrary to SEV produced by human fibroblasts or by a highly invasive breast cancer cell line, SEV secreted by low invasive breast cancer cells, which express NFATC4, do not promote cancer progression and invasion but instead inhibit invasion in vitro and inhibit tumor growth and metastasis in an in vivo xeno-transplantation model. The inventors also surprisingly found that the inhibitory effect of SEV produced by low invasive breast cancer cells on the invasive capacity of highly invasive cell lines requires the expression of NFATC4 in the low invasive SEV-producing cells.

The inventors further unexpectedly found that the expression of NFATC4 in the low invasive SEV-producing cells results in de novo induction of TGFβ1 expression in highly invasive breast cancer cell lines, which is required for the SEV to modulate breast cancer cell invasion in vitro and is correlated to treatment efficiency in vivo. Increase of TGFβ1 concentration in patients administered with SEV produced by low invasive cancer cells might thus be used as a biomarker of therapeutic efficiency of the treatment.

In a first aspect, the present invention thus relates to a composition comprising secreted extracellular vesicles (SEV) of cells expressing nuclear factor of activated T-cells, cytoplasmic, calcineurin-dependent 4 (NFATC4), for use in the treatment of cancer or in the treatment or prevention of metastatic cancer.

In a second aspect, the present invention also relates to a method for preparing a composition comprising SEV of cells expressing NFATC4 from a sample of cells, comprising:

a) Inducing NFATC4 expression or activity in said cells;
b) Culturing said induced cells in SEV-free culture medium, under conditions permitting their expansion; and
c) Purifying SEV of the induced cells.

In a third aspect, the present invention also relates to an in vitro method for determining the therapeutic efficiency of a treatment with a composition comprising SEV of cells expressing NFATC4 in a treated cancer patient, from a first biological sample of said cancer patient taken before the beginning of the treatment and a second corresponding biological sample of cancer patient after the beginning of the treatment, comprising:

a) Measuring in vitro at least the Transforming growth factor beta 1 (TGFß1) expression level in said first and second biological samples;
b) Comparing the measured TGFß1 expression levels; and
c) Determining the efficiency of the treatment with a composition comprising SEV of cells expressing NFATC4 in said treated cancer patient from said comparison, wherein the treatment is considered efficient if the TGFß1 expression level measured in the biological sample after the beginning of the treatment is higher than the TGFß1 expression level in the biological sample before the beginning of the treatment.

In a fourth aspect, the present invention also relates to an in vitro method for predicting the therapeutic efficiency of a treatment with a composition comprising SEV of cells expressing NFATC4 in a cancer patient, from a cancer sample of said cancer patient, comprising:

a) Measuring in vitro at least the TGFß1 expression level in said tumor sample;
b) Incubating said cancer sample with a composition comprising SEV expressing NFATC4;
c) Measuring in vitro at least the TGFß1 expression level in said tumor sample incubated with a composition comprising SEV by cells expressing NFATC4; and
d) Predicting efficiency of a treatment with a composition comprising SEV of cells expressing NFATC4 in said cancer patient if at least the TGFß1 expression level measured in step c) is higher than at least the TGFß1 expression level measured in step a), and predicting non efficiency of a treatment with a composition comprising SEV of cells expressing NFATC4 in said cancer patient if at least the TGFß1 expression level measured in step c) is lower or equal at least to the TGFß1 expression level measured in step a).

DETAILED DESCRIPTION OF THE INVENTION

Figure 1:
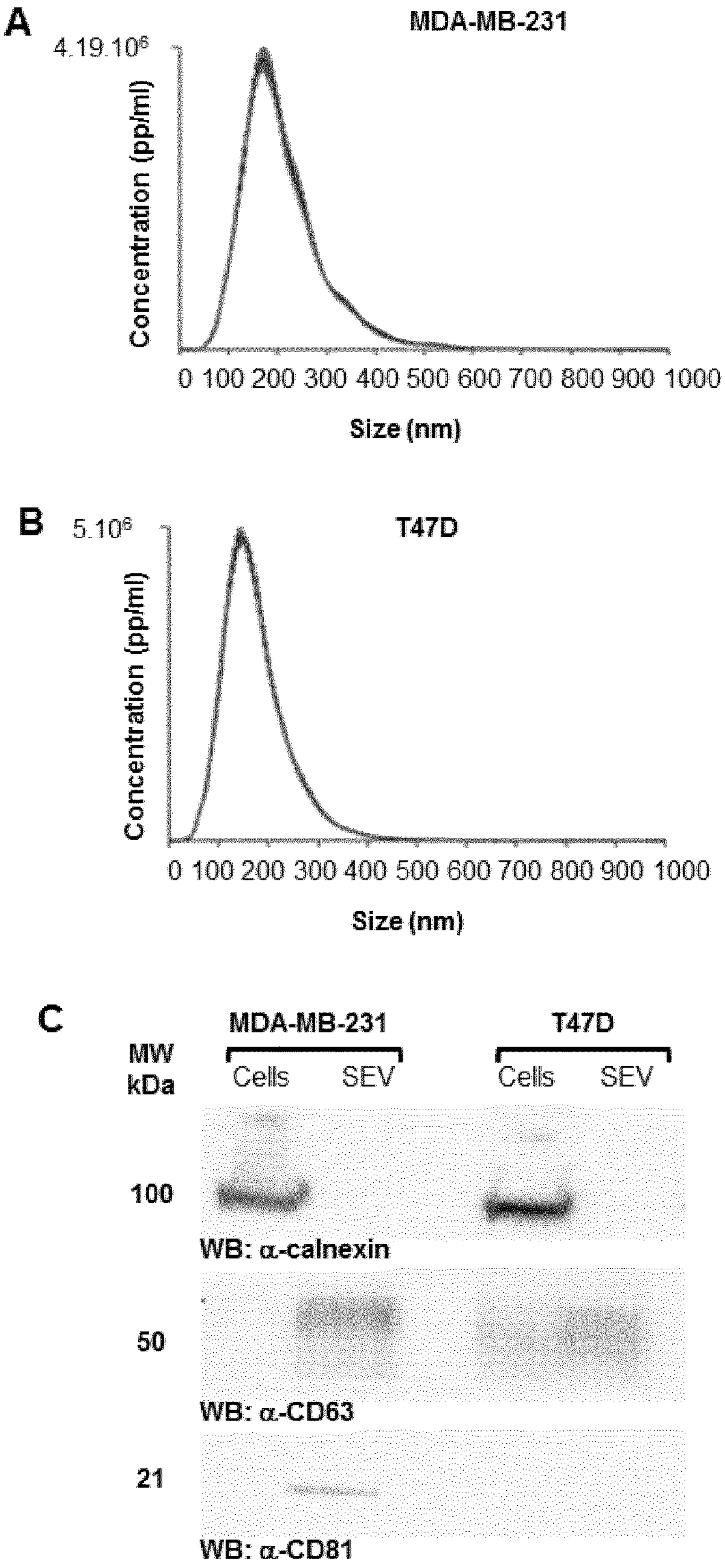
FIG. 1. Characterization by size and specific markers of SEV produced by T47D and MDA-MB-231 cells. Representative examples of size distribution of SEV produced by MDA-MB-231 (A) and T47D (B), evaluated by the NanoSight. SEV concentration (particles/ml:pp/mL) is shown in function of particle size (nm). (C) Western blot for SEV characterization: whole cells protein extract was compared to the SEV protein fraction for both cells types using antibodies against Calnexin; CD63 and CD81.

Treatment of Cancer or Treatment or Prevention of Metastatic Cancer with a Composition Comprising Secreted Extracellular Vesicles (SEV) of Cells Expressing NFATC4

In a first aspect, the present invention relates to a composition, in particular a pharmaceutical composition comprising secreted extracellular vesicles (SEV) of cells expressing nuclear factor of activated T-cells, cytoplasmic, calcineurin-dependent 4 (NFATC4), for use in the treatment of cancer or in the treatment or prevention of metastatic cancer.

The present invention also relates to a method for treating cancer or for treating or preventing metastatic cancer in a patient in need thereof, comprising administering to said patient a therapeutically efficient amount of a composition comprising SEV of cells expressing NFATC4.

The present invention also relates to the use of a composition comprising SEV of cells expressing NFATC4 for preparing a drug intended for the treatment of cancer or for the treatment or prevention of metastatic cancer.

The present invention also relates to the use of a composition comprising SEV of cells expressing NFATC4 for the treatment of cancer or for the treatment or prevention of metastatic cancer.

Secreted Extracellular Vesicles (SEV)

By "secreted extracellular vesicles" or "SEV", it is meant membranous vesicles released by cells in their microenvironment from their plasma membrane. In the context of the present invention, SEV typically have a diameter lower or equal to about 500 nm, in particular between about 30 and about 500 nm, or between about 40 and about 500 nm, or between about 50 and about 500 nm. SEV are surrounded by a phospholipid membrane, which preferably contains relatively high levels of cholesterol, sphingomyelin, and ceramide and preferably also contains detergent-resistant membrane domains (lipid rafts).

The membrane proteins of SEV have the same orientation as the cell. SEV are generally characterized by the presence of Actin B, proteins involved in membrane transport and fusion (such as Rab, GTPases, annexins, and flotillin), components of the endosomal sorting complex required for transport (ESCRT) complex (such as Alix), tumor susceptibility gene 101 (TSG101), heat shock proteins (HSPs, such as HSPA8, HSP90AA1, HSC70 and HSC90), integrins (such as CD62L, CD62E or CD62P), and tetraspanins (in particular CD63, CD81, CD82, CD53, CD9, and/or CD37).

SEV may also contain RNAs, such as mRNAs and miRNAs.

SEV may be prepared from cells secreting them by various methods, the most common and most preferred of which is differential centrifugation. Methods that may be used for preparing SEV used in the present invention include, as disclosed in Yakimchuk, K. Materials and Methods, vol. 5, 2015:

Differential Centrifugation:

As explained above, this method is one of the most common techniques and the preferred method in the present invention.

The method consists of several steps, preferably performed at about 4° C., including at least the following three steps 1) to 3):

1) a low speed centrifugation to remove cells and cellular debris, 2) a higher speed spin to eliminate larger vesicles (size over 100 nm), and finally 3) high speed centrifugation to pellet SEV.

In step 1), cells and cellular debris are removed using centrifugal accelerations of about 1300 to 3500 RPM (rounds per minute) for 5-30 minutes. Optionally, step 1) may include two low speed centrifugations, the first at very low speed (for instance about 1350 RPM) and the second at highest speed (for instance 3500 RPM).

In particular, spinning at 1350 RPM for 10 minutes at about 4° C. followed by spinning at 3500 RPM for 20 minutes at about 4° C. may be used in step 1).

In step 2), larger vesicles (size over 100 nm) are eliminated using centrifugal accelerations of about 10 000 RPM for 15-45 minutes. In particular, spinning at about 10,000 RPM for 30 minutes at about 4° C. may be used in step 2).

In step 3), which is preferably performed at least twice, SEV are pelleted using centrifugal accelerations of about 40 000 RPM (for 60-120 minutes. In particular, spinning at 40,000 RPM for 90 minutes at about 4° C. may be used in step 3).

A particularly preferred protocol is as described below:

a) Spin cultured cells at 1350 RPM for 10 minutes at 4° C. and collect supernatant;

b) Spin collected supernatant at 3500 RPM for 20 minutes at 4° C. and collect supernatant;

c) Spin collected supernatant at 10,000 RPM for 30 minutes at 4° C. and collect supernatant;

d) Ultracentrifuge collected supernatant at 40,000 RPM for 90 minutes at 4° C. and collect the pellet;

e) Resuspend the pellet in cold PBS; and f) Ultracentrifuge at 40,000 RPM for 90 minutes at 4° C. and collect the pellet.

Density Gradient Centrifugation:

This approach combines ultracentrifugation with sucrose density gradient.

More specifically, density gradient centrifugation is used to separate SEV from non-vesicular particles, such as proteins and protein/RNA aggregates. Thus, this method separates vesicles from the particles of different densities. The adequate centrifugation time is very important, otherwise contaminating particles may be still found in SEV fractions if they possess similar densities. Recent studies suggest application of the SEV pellet from ultracentrifugation to the sucrose gradient before performing centrifugation.

Size Exclusion Chromatography:

Size-exclusion chromatography is used to separate macromolecules on the base of size, not molecular weight. The technique applies a column packed with porous polymeric beads containing multiple pores and tunnels. The molecules pass through the beads depending on their diameter. It takes longer time for molecules with small radii to migrate through pores of the column, while macromolecules elute earlier from the column. Size-exclusion chromatography allows precise separation of large and small molecules. Moreover, different eluting solutions can be applied to this method.

Figure 2:
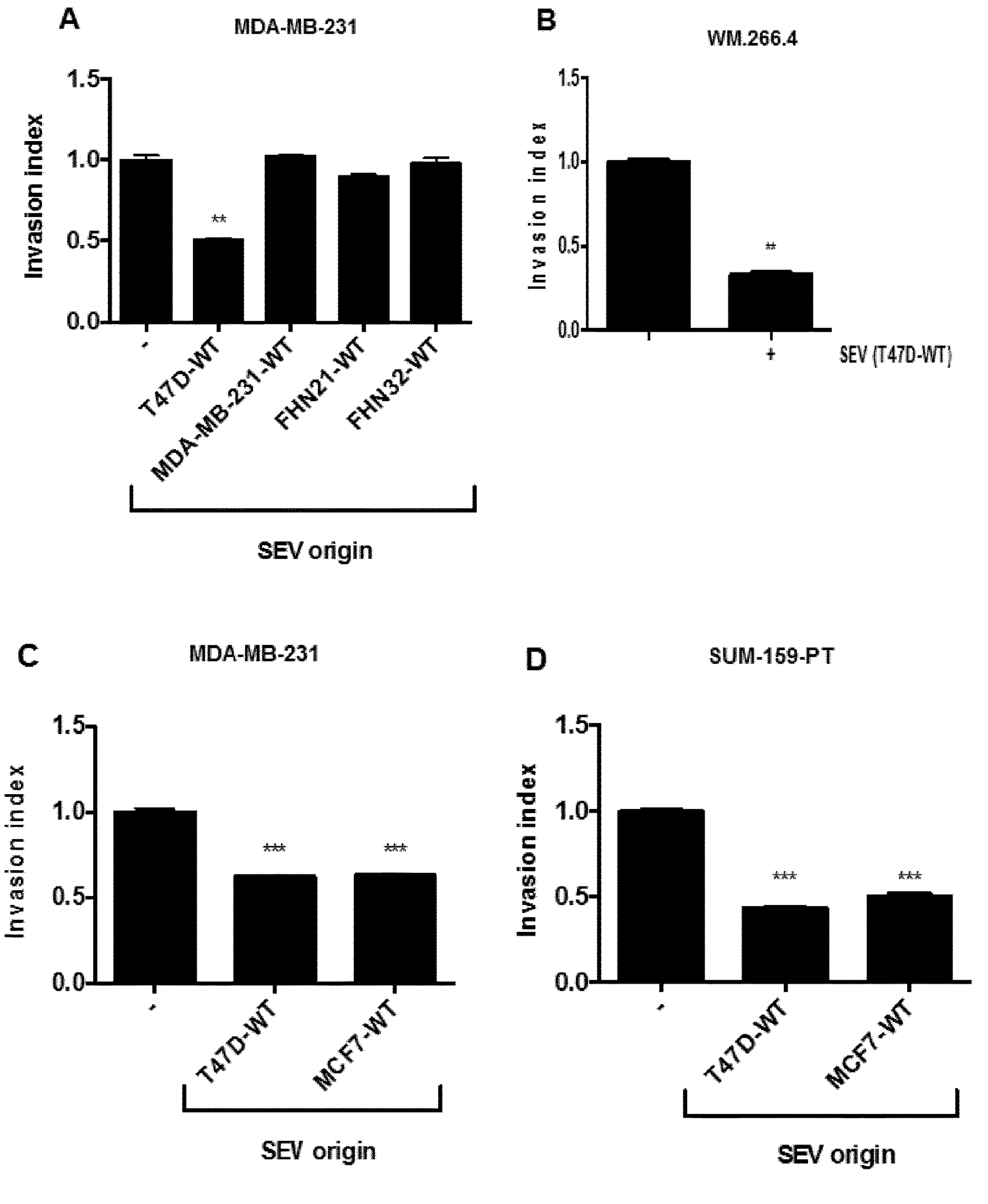
FIG. 2. SEV produced by low invasive T47D and MCF7 cells inhibit invasion of highly invasive MDA-MB-231 and SUM159PT breast cancer cells and WM.266.4 melanoma cells. (A) MDA-MB-231 were treated for 24 h with either $3.75\times10^8$ pp SEV produced by WT T47D or by WT MDA-MB-231 or by 2 different primary dermal fibroblasts (FHN21, FHN32) obtained from 2 different women skin and subjected to an in vitro invasion assay for 6 h (n=2; *p<0.05). The invasion index is calculated as a proportion of the number of invasive cells in treated wells compared to the number of invasive cells in the control well arbitrarily set to 1. (B) Melanoma cell line (WM.266.4) were treated for 24 h with $3.75\times10^8$ pp SEV produced by WT T47D and subjected to an in vitro invasion assay for 6 h (n=3; p<0.005). (C) MDA-MB-231 were treated for 24 h with either $3.75\times10^8$ pp SEV produced by WT T47D or by WT MCF7 and subjected to an in vitro invasion assay for 6 h (n=3; *p<0.0005). (D) SUM-159-PT were treated for 24 h with either $3.75\times10^8$ pp SEV produced by WT T47D or by WT MCF7 and subjected to an in vitro invasion assay for 6 h (n=3; ***p<0.0005).

Filtration:

Ultrafiltration membranes can also be used for isolation of SEV. Depending on the size of microvesicles, this method allows the separation of SEV from proteins and other macromolecules. SEV may also be isolated by trapping them via a porous structure (FIG. 2). Most common filtration membranes have pore sizes of 0.8 μm, 0.45 μm or 0.22 μm and can be used to collect SEV larger than 800 nm, 400 nm or 200 nm. In particular, a micropillar porous silicon ciliated structure was designed to isolate 40-100 nm SEV. During the initial step, the larger vesicles are removed. In the following step, the SEV population is concentrated on the filtration membrane. The isolation step is relatively short, but the method requires pre-incubation of the silicon structure with PBS buffer. In the following step, the SEV population is concentrated on the filtration membrane.

Polymer-Based Precipitation:

Polymer-based precipitation technique usually includes mixing the biological fluid with polymer-containing precipitation solution, incubation at 4° C. and centrifugation at low speed. One of the most common polymers used for polymer-based precipitation is polyethylene glycol (PEG). The precipitation with this polymer has a number of advantages, including mild effects on isolated SEV and usage of neutral pH. Several commercial kits applying PEG for isolation of SEV were generated. The most commonly used kit is ExoQuick™ (System Biosciences, Mountain View, Calif., USA). This kit is easy and fast to perform and there is no need for additional equipment. Recent studies demonstrated that the highest yield of SEV was obtained using ultracentrifugation with ExoQuick™ method.

Immunological Separation:

Several techniques of immunological separation of SEV have been developed, based on surface SEV receptors or SEV intracellular proteins. These methods are however generally applied mainly for detection, analysis and quantification of SEV proteins.

Isolation by Sieving:

This technique isolates SEV by sieving them from biological liquids via a membrane and performing filtration by pressure or electrophoresis.

NFATC4

"Nuclear factor of activated T-cells, cytoplasmic, calcineurin-dependent 4" or "NFATC4" as used herein refers to a protein encoded by the human gene with the official symbol NFATC4 in Entrez Gene database. (Gene ID: 4776) or variants thereof as defined below. The NFATC4 gene is also known as "nuclear factor of activated T-cells, cytoplasmic 4", "T-cell transcription factor NFAT3", "NFAT3", "NF-AT3", and "NF-ATC4". The gene encodes several mRNA and protein isoforms, all of which are included in the definition of NFATC4 in the context of the present invention. The cDNA and protein sequences of various isoforms of NFATC4 are mentioned in Table 1 below:

TABLE 1

| | |
|---|---|
| cDNA and protein sequences of human NFATC4 isoforms 1 to 7. | |
| Isoform 1<br>(This variant (1) represents the longest transcript and encodes isoform (1)) | |
| cDNA | GTAAACGTCTGACCTGGGGCCGTCGCTTAACCGTTTAGTTGCTGGGATGGGGCGGCGTTGGGGG<br>TGCGGCCCTGAACCGGAGGGATTTAGAGACTGGAGACGCGGCCTCTAAGAGAGGTTGAAACTGT<br>GTGTGTGTGGGAGAAAATGATAACCACCCTCCCATCTCTCCTACCCGCCAGCCTCGCCAGTATCT<br>CCCACCGAGTCACGAATCTCCCATCTAACTCCCTCTCACACAACCCAGGCCTCTCCAAGCCTGACT<br>TTCCCGGAAACTCCAGTCCAGGTCTTCCTTCCTCCTCCAGCCCAGGCCGGGACCTGGGGGCTCCT<br>GCCGGATCCATGGGGGCGGCCAGCTGCGAGGATGAGGAGCTGGAATTTAAGCTGGTGTTCGGG<br>GAGGAAAAGGAGGCCCCCCCGCTGGGCGCGGGGGGATTGGGGGAAGAACTGGACTCAGAGGAT<br>GCCCCGCCATGCTGCCGTCTGGCCTTGGGAGAGCCCCCTCCCTATGGCGCTGCACCTATCGGTAT<br>TCCCCGACCTCCACCCCCTCGGCCTGGCATGCATTCGCCACCGCCGCGACCAGCCCCCTCACCTG<br>GCACCTGGGAGAGCCAGCCCGCCAGGTCGGTGAGGCTGGGAGGACCAGGAGGGGGTGCTGGGG<br>GTGCTGGGGGTGGCCGTGTTCTCGAGTGTCCCAGCATCCGCATCACCTCCATCTCTCCCACGCCG<br>GAGCCGCCAGCAGCGCTGGAGGACAACCCTGATGCCTGGGGGGACGGCTCTCCTAGAGATTACC<br>CCCCACCAGAAGGCTTTGGGGGCTACAGAGAAGCAGGGGGCCAGGGTGGGGGGGCCTTCTTCA<br>GCCCAAGCCCTGGCAGCAGCAGCCTGTCCTCGTGGAGCTTCTTCTCCGATGCCTCTGACGAGGCA<br>GCCCTGTATGCAGCCTGCGACGAGGTGGAGTCTGAGCTAAATGAGGCGGCCTCCCGCTTTGGCC<br>TGGGCTCCCCGCTGCCCTCGCCCCGGGCCTCCCCTCGGCCATGGACCCCCGAAGATCCCTGGAGC<br>CTGTATGGTCCAAGCCCCGGAGGCCGAGGGCCAGAGGATAGCTGGCTACTCCTCAGTGCTCCTG<br>GGCCCACCCCAGCCTCCCCGCGGCCTGCCTCTCCATGTGGCAAGCGGCGCTATTCCAGCTCGGGA<br>ACCCCATCTTCAGCCTCCCCAGCTCTGTCCCGCCGTGGCAGCCTGGGGGAAGAGGGGTCTGAGC<br>CACCTCCACCACCCCCATTGCCTCTGGCCCGGGACCCGGGCTCCCCTGGTCCCTTTGACTATGTG<br>GGGGCCCCACCAGCTGAGAGCATCCCTCAGAAGACACGGCGGACTTCCAGCGAGCAGGCAGTGG<br>CTCTGCCTCGGTCTGAGGAGCCTGCCTCATGCAATGGGAAGCTGCCCTTGGGAGCAGAGGAGTC<br>TGTGGCTCCTCCAGGAGGTTCCCGGAAGGAGGTGGCTGGCATGGACTACCTGGCAGTGCCCTCC<br>CCACTCGCTTGGTCCAAGGCCCGGATTGGGGGACACAGCCCTATCTTCAGGACCTCTGCCCTACC<br>CCCACTGGACTGGCCTCTGCCCAGCCAATATGAGCAGCTGGAGCTGAGGATCGAGGTACAGCCTA<br>GAGCCCACCACCGGGCCCACTATGAGACAGAAGGCAGCCGTGGAGCTGTCAAAGCTGCCCCTGG<br>CGGTCACCCCGTAGTCAAGCTCCTAGGCTACAGTGAGAAGCCACTGACCCTACAGATGTTCATCG<br>GCACTGCAGATGAAAGGAACCTGCGGCCTCATGCCTTCTATCAGGTGCACCGTATCACAGGCAAG<br>ATGGTGGCCACGGCCAGCTATGAAGCCGTAGTCAGTGGCACCAAGGTGTTGGAGATGACTCTGC<br>TGCCTGAGAACAACATGGCGGCCAACATTGACTGCGCGGGAATCCTGAAGCTTCGGAATTCAGAC<br>ATTGAGCTTCGGAAGGGTGAGACGGACATCGGGCGCAAAAACACACGTGTACGGCTGGTGTTCC<br>GGGTACACGTGCCCCAGGGCGGCGGGAAGGTCGTCTCAGTACAGGCAGCATCGGTGCCCATCGA<br>GTGCTCCCAGCGCTCAGCCCAGGAGCTGCCCCAGGTGGAGGCCTACAGCCCCAGTGCCTGCTCT<br>GTGAGAGGAGGCGAGGAACTGGTACTGACTGGCTCCAACTTCCTGCCAGACTCCAAGGTGGTGT<br>TCATTGAGAGGGGTCCTGATGGGAAGCTGCAATGGGAGGAGGAGGCCACAGTGAACCGACTGCA<br>GAGCAACGAGGTGACGCTGACCCTGACTGTCCCCGAGTACAGCAACAAGAGGGTTTCCCGGCCA<br>GTCCAGGTCTACTTTTATGTCTCCAATGGGCGGAGGAAACGCAGTCCTACCCAGAGTTTCAGGTT<br>TCTGCCTGTGATCTGCAAAGAGGAGCCCCTACCGGACTCATCTCTGCGGGGTTTCCCTTCAGCAT<br>CGGCAACCCCCTTTGGCACTGACATGGACTTCTCACCACCCAGGCCCCCCTACCCCTCCTATCCCC<br>ATGAAGACCCTGCTTGCGAAACTCCTTACCTATCAGAAGGCTTCGGCTATGGCATGCCCCCTCTG<br>TACCCCCAGACGGGGCCCCCACCATCCTACAGACCGGGCCTGCGGATGTTCCCTGAGACTAGGG<br>GTACCACAGGTTGTGCCCAACCACCTGCAGTTTCCTTCCTTCCCCGCCCCTTCCCTAGTGACCCGT<br>ATGGAGGGCGGGGCTCCTCTTTCTCCCTGGGGCTGCCATTCTCTCCGCCAGCCCCCTTTCGGCCG<br>CCTCCTCTTCCTGCATCCCCACCGCTTGAAGGCCCCTTCCCTTCCCAGAGTGATGTGCATCCCCTA<br>CCTGCTGAGGGATACAATAAGGTAGGGCCAGGCTATGGCCCTGGGGAGGGGGCTCCGGAGCAG<br>GAGAAATCCAGGGGTGGCTACAGCAGCGGCTTCCGAGACAGTGTCCCTATCCAGGGTATCACGC<br>TGGAGGAAGGTGGGTGTGGGACTGGGGGCTGTGAGTGTGAGTGTGTGCAAGAGATTGCTCTGC<br>ATGTTTGCTGAGGGCTGGAGCTGGGCTTTTCAGAGATCGGGCATCCCTGGTCTCTCAGGGCCAG<br>TTGGAGGTTCCCAGGAGGCATGTTCTTGATGCCTGTGGCTGCCTGAATCCAATTAACTGAATTCT<br>GAAGAGTGCATGGGGTAACTGTCTCAGCCTTTCTCCTGTCTCTGCCTCTGTCCTCTGCTCCAAAT<br>CATAAAATCTCAGAGCTAGAAGCACTTTCAAGATCATTCCATCCAGCGCATTCAATTTGCAAGTTT<br>AGGCGTTGAGTTCCAGAGAGGGATGGTAGCTTGCTGAGGTCCCAGTCAAGCACACTTGCCATTG<br>CCTCAGCTTTCCCCTAAACACGGTGTCTGTGGTCAGGGTTGGTGAGGAGGAGCTTTCCTGTTTTG<br>CCTCTCCTTCTTCCCATTGGCTACACCCATCTCTGGCCCTGCTGATACCGATTCCCCTGACATTTC<br>AGGCTAAGCCAGCAGGAAAGGGCTAGGACGGGTGCCTGGGAGCCCACATGGAGGGAGTTGGGC<br>AAGATTTGATTCGGAGCAGGTGTCAAGACGTGTTGGGGAAACTGAGGCCCAGTGGAATAGAAGC<br>CAGTAGAGGAGGAATCTAGAGGCCTCCTAGATTAAGACCTGCCTGGAATGGATTGGGGGTGGGT<br>CTTTGGAAAAGGAGGGGACCCACCTCTAGCCCAGTCTCTCAACTGCCCCTCCTTTACAGTGAGTG<br>AGATCATTGGCCGAGACCTGAGTGGCTTCCCTGCACCTCCTGGAGAAGAGCCTCCTGCCTGAACC<br>ACGTGAACTGTCATCACCTGGCAACCCCAGCCCCAGCCTCAGCCCTGCCCCCTTTCCCTCCTTCCT<br>GGAGTGGTGGCTACAGAAGCTTGGGGCCAACCCTGGCTCCTCTTTCCCCAGCTTCTGTCTGTCTC<br>ACTGTCTTCCCTCCCCTCCCCCAGCTGAGGTGTGGCCCTCAGGCCTGGTGCTGCCTTGGAGGGCT |

TABLE 1-continued

| cDNA and protein sequences of human NFATC4 isoforms 1 to 7. | |
|---|---|
| | GGGGGAAGGAGTGTGTGGAGGAGGGAGGAGGGTGAAGACTGAGGCTAGGTGCCAGAATGGACT GGAGTGAAGGCGTGTCTAGAGTGTGGGCTGGCTGTTGTGCTGGAAAGCTGGGGACAGGTTGAT GGTAATAAACTGCTCAATGACCAGTGCTTCAGGCTCCAGAGCTCTTTGGAGAGATGGGTTGGGG CAGCTTACTCCAGCCCTGGCCCAAGGAGGCCCAGAAGTTGGAAAGAGATGGAATGTGGCTGGGA ACATTGCATCCCAAAGAGCTTCTCAGTGGAGGAGGCTGGGGAAGGCATGAGGGGGCTCAGAGGC TCCTTGACTGGGACCAGGATTGGGGGCCAGGGCTTGAGTAGGCCTCTCCACTCTCCTCCTTGGG GGTCCAGATTCCTTAGGAGCTTTGGGATGAGGCCCAGGAGGCTGCATTTTTCCAGGTCCTTAGTC TTGCCACCACACAGATGATTCTGATTCATAGCCAAGATGAGGACACACTGATGTAGCTGATCTCTC ATTTACAGAGGAGGATTCTAAAGTTCAGAGAGGGAAAGGGGCTTGCCTGAGGTCACGTAGATAAT CAGCAGCACATTGAACGCTGCACTCCTGGGCTCCTGTCCCCAGCCCCCATTCAGACACGCTGACT CAGGAGGTCCAGGCCTCTAAGGCTTCTCTCCCTGGAGTGAGGGTGGAGGTGAGGGAGAGCTGG CACAAGCCCTCCCTCTGGATCCTCCACTCCTGGGGATTATGAAGATATTCTGGAAAGATTTGTGC TTCAGAGGTAGACTGCAGAAAGCAAACAGTCTACCCAGCAGCTCTGAATGTCACCTGCCCTGGGG CTTACAGCACTATATGAGTTCCTGGCCTATCCTGCAAATATGCCCATGCTGGCCTTCTAAATAGCT GGTACATCCATCACCACTGACGGGCCTGGCCTGGAAACCTGGTTTGTCCCCTGTCTTGATGGCCT ACGAGAGGCCAAGTTCCACTGGGCTGGGAAAAGTCACTTTGTCTGTCTTGTTCACCTGGAGCCTG ACACACCGTAGGTACTGAGTACAAATAGCTTGATTTGGCTAGGCTTGGCTGCAGGGGGACGTGC CTAAAAGACATTCCGGGCATTTGCACTTGGGAAACTTGCCTCACCTTCAGGCTTGTGGGGCCTCT CTATGCCCAATGAGTCCAGGCAGTCCTAGCAAGTACTCAGGAGAGCAGGGGTGGGTGTGACAGA GGCTGGCTCTGGATTGGGGGACAACAGAACCAGAGTAACTCCTCGCCTGTTGCTGCTTTGCAATG AATTTCCTTTACCTTTCTGGAACACAAGCTGCTGTGAACCAAACTGATATCAAGTGATTAGCTCAC CGGGCCTTGGTTGCTTTTCAAAGATCCCCTTCAGCCCCCTGCCAGAGTCACTGCCCCATAATCACC ATGTCAGAAGGGACCCTAGGGCATTCGTGTCCTATTTATCAATCTTCAGCACCACCTCTAAGATCT CTGAGAGAGGGTGGATCAGCCTCTGTGTAAACAAAAAGCTGTTAGGACTTGTTGCCTCTCAAGGT GGACTATTCTGTTTTCTGCCAGGACACTGCCATTCATGCATTGTCAGATATTTATTAAACAGCAGC AAAGTGCCAGCCAATTTGTCCTGGAGGAATTCATAGCCTCATGGGGCAAAAGTAAATAAACAGCT TATTACAATTCAACAAAAAAAAAAAAAAAAAAAAAAAAAAAAAAAAAAAAAAAAAAAAAAAAA (NCBI Reference Sequence: NM_001136022.2; SEQ ID NO: 1) |
| Protein | MITTLPSLLPASLASISHRVTNLPSNSLSHNPGLSKPDFPGNSSPGLPSSSSPGRDLGAPAGSMGAASCEDE ELEFKLVFGEEKEAPPLGAGGLGEELDSEDAPPCCRLALGEPPPYGAAPIGIPRPPPPRPGMHSPPPRPA PSPGTWESQPARSVRLGGPGGGAGGAGGGRVLECPSIRITSISPTPEPPAALEDNPDAWGDGSPRDYPP PEGFGGYREAGGQGGGAFFSPSPGSSSLSSWSFFSDASDEAALYAACDEVESELNEAASRFGLGSPLPSP RASPRPWTPEDPWSLYGPSPGGRGPEDSWLLLSAPGPTPASPRPASPCGKRRYSSSGTPSSASPALSRR GSLGEEGSEPPPPPPLPLARDPGSPGPFDYVGAPPAESIPQKTRRTSSEQAVALPRSEEPASCNGKLPLG AEESVAPPGGSRKEVAGMDYLAVPSPLAWSKARIGGHSPIFRTSALPPLDWPLPSQYEQLELRIEVQPRA HHRAHYETEGSRGAVKAAPGGHPVVKLLGYSEKPLTLQMFIGTADERNLRPHAFYQVHRITGKMVATA SYEAVVSGTKVLEMTLLPENNMAANIDCAGILKLRNSDIELRKGETDIGRKNTRVRLVFRVHVPQGGGKV VSVQAASVPIECSQRSAQELPQVEAYSPSACSVRGGEELVLTGSNFLPDSKVVFIERGPDGKLQWEEEAT VNRLQSNEVTLTLTVPEYSNKRVSRPVQVYFYVSNGRRKRSPTQSFRFLPVICKEEPLPDSSLRGFPSASA TPFGTDMDFSPPRPPYPSYPHEDPACETPYLSEGFGYGMPPLYPQTGPPPSYRPGLRMFPETRGTTGCA QPPAVSFLPRPFPSDPYGGRGSSFSLGLPFSPPAPFRPPPLPASPPLEGPFPSQSDVHPLPAEGYNKVGP GYGPGEGAPEQEKSRGGYSSGFRDSVPIQGITLEEGGCGTGGCECECVQEIALHVC (NCBI Reference Sequence: NP_001129494.1; SEQ ID NO: 2, 964 amino acids) |
| Isoform 2<br>(This variant (2) is alternatively spliced at the 5' and 3' ends compared to transcript variant 1. This results in the use of an in-frame downstream AUG, translation termination at a downstream stop codon, and a shorter isoform (2) with a distinct C-terminus compared to isoform 1) | |
| cDNA | GAAGAGAGGACAGAGGGAGGGAGGGTGGGGGAGGACGAGGGGCGCGTGGTTTTCCCATCTCAT CCCTGGAGGAGGGGCTGGAGCATCCCCGGCAGCCAATCAGGGACAGGCTGGGGGGGGGACCGC TTTGAAGAAGTTTGGGGGAAAAAAGTTTGGAAAAGTTTCTATAATAACGAGGGGGCTTCTGGAG GGAGGCGGCAGCGACGGAGGAGGGGGCTTCTCAGAGAAAGGGAGGGAGGGAGCCACCCGGGTG AAGATACAGCAGCCTCCTGAACTCCCCCCTCCCACCCAGGCCGGGACCTGGGGGCTCCTGCCGGA TCCATGGGGGCGGCCAGCTGCGAGGATGAGGAGCTGGAATTTAAGCTGGTGTTCGGGGAGGAA AAGGAGGCCCCCCCGCTGGGCGCGGGGGGATTGGGGGAAGAACTGGACTCAGAGGATGCCCCG CCATGCTGCCGTCTGGCCTTGGGAGAGCCCCCTCCCTATGGCGCTGCACCTATCGGTATTCCCCG ACCTCCACCCCCTCGGCCTGGCATGCATTCGCCACCGCCGCGACCAGCCCCCTCACCTGGCACCT GGGAGAGCCAGCCCGCCAGGTCGGTGAGGCTGGGAGGACCAGGAGGGGGTGCTGGGGGTGCT GGGGGTGGCCGTGTTCTCGAGTGTCCCAGCATCCGCATCACCTCCATCTCTCCCACGCCGGAGCC GCCAGCAGCGCTGGAGGACAACCCTGATGCCTGGGGGGACGGCTCTCCTAGAGATTACCCCCCA CCAGAAGGCTTTGGGGGCTACAGAGAAGCAGGGGGCCAGGGTGGGGGGGCCTTCTTCAGCCCA AGCCCTGGCAGCAGCAGCCTGTCCTCGTGGAGCTTCTTCTCCGATGCCTCTGACGAGGCAGCCCT GTATGCAGCCTGCGACGAGGTGGAGTCTGAGCTAAATGAGGCGGCCTCCCGCTTTGGCCTGGGC TCCCCGCTGCCCTCGCCCCGGGCCTCCCCTCGGCCATGGACCCCCGAAGATCCCTGGAGCCTGTA TGGTCCAAGCCCCGGAGGCCGAGGGCCAGAGGATAGCTGGCTACTCCTCAGTGCTCCTGGGCCC ACCCCAGCCTCCCCGCGGCCTGCCTCTCCATGTGGCAAGCGGCGCTATTCCAGCTCGGGAACCCC ATCTTCAGCCTCCCCAGCTCTGTCCCGCCGTGGCAGCCTGGGGGAAGAGGGGTCTGAGCCACCT CCACCACCCCCATTGCCTCTGGCCCGGGACCCGGGCTCCCCTGGTCCCTTTGACTATGTGGGGGC CCCACCAGCTGAGAGCATCCCTCAGAAGACACGGCGGACTTCCAGCGAGCAGGCAGTGGCTCTG CCTCGGTCTGAGGAGCCTGCCTCATGCAATGGGAAGCTGCCCTTGGGAGCAGAGGAGTCTGTGG CTCCTCCAGGAGGTTCCCGGAAGGAGGTGGCTGGCATGGACTACCTGGCAGTGCCCTCCCCACT CGCTTGGTCCAAGGCCCGGATTGGGGGACACAGCCCTATCTTCAGGACCTCTGCCCTACCCCCAC TGGACTGGCCTCTGCCCAGCCAATATGAGCAGCTGGAGCTGAGGATCGAGGTACAGCCTAGAGC CCACCACCGGGCCCACTATGAGACAGAAGGCAGCCGTGGAGCTGTCAAAGCTGCCCCTGGCGGT CACCCCGTAGTCAAGCTCCTAGGCTACAGTGAGAAGCCACTGACCCTACAGATGTTCATCGGCAC TGCAGATGAAAGGAACCTGCGGCCTCATGCCTTCTATCAGGTGCACCGTATCACAGGCAAGATGG |

TABLE 1-continued cDNA and protein sequences of human NFATC4 isoforms 1 to 7.

TGGCCACGGCCAGCTATGAAGCCGTAGTCAGTGGCACCAAGGTGTTGGAGATGACTCTGCTGCC
TGAGAACAACATGGCGGCCAACATTGACTGCGCGGGAATCCTGAAGCTTCGGAATTCAGACATTG
AGCTTCGGAAGGGTGAGACGGACATCGGGCGCAAAAACACACGTGTACGGCTGGTGTTCCGGGT
ACACGTGCCCCAGGGCGGCGGGAAGGTCGTCTCAGTACAGGCAGCATCGGTGCCCATCGAGTGC
TCCCAGCGCTCAGCCCAGGAGCTGCCCCAGGTGGAGGCCTACAGCCCCAGTGCCTGCTCTGTGA
GAGGAGGCGAGGAACTGGTACTGACTGGCTCCAACTTCCTGCCAGACTCCAAGGTGGTGTTCATT
GAGAGGGGTCCTGATGGGAAGCTGCAATGGGAGGAGGAGGCCACAGTGAACCGACTGCAGAGC
AACGAGGTGACGCTGACCCTGACTGTCCCCGAGTACAGCAACAAGAGGGTTTCCCGGCCAGTCCA
GGTCTACTTTTATGTCTCCAATGGGCGGAGGAAACGCAGTCCTACCCAGAGTTTCAGGTTTCTGC
CTGTGATCTGCAAAGAGGAGCCCCTACCGGACTCATCTCTGCGGGGTTTCCCTTCAGCATCGGCA
ACCCCCTTTGGCACTGACATGGACTTCTCACCACCCAGGCCCCCCTACCCCTCCTATCCCCATGAA
GACCCTGCTTGCGAAACTCCTTACCTATCAGAAGGCTTCGGCTATGGCATGCCCCCTCTGTACCC
CCAGACGGGGCCCCCACCATCCTACAGACCGGGCCTGCGGATGTTCCCTGAGACTAGGGGTACC
ACAGGTTGTGCCCAACCACCTGCAGTTTCCTTCCTTCCCCGCCCCTTCCCTAGTGACCCGTATGGA
GGGCGGGGCTCCTCTTTCTCCCTGGGGCTGCCATTCTCTCCGCCAGCCCCCTTTCGGCCGCCTCC
TCTTCCTGCATCCCCACCGCTTGAAGGCCCCTTCCCTTCCCAGAGTGATGTGCATCCCCTACCTGC
TGAGGGATACAATAAGGTAGGGCCAGGCTATGGCCCTGGGGAGGGGGCTCCGGAGCAGGAGAA
ATCCAGGGGTGGCTACAGCAGCGGCTTCCGAGACAGTGTCCCTATCCAGGGTATCACGCTGGAG
GAAGTGAGTGAGATCATTGGCCGAGACCTGAGTGGCTTCCCTGCACCTCCTGGAGAAGAGCCTC
CTGCCTGAACCACGTGAACTGTCATCACCTGGCAACCCCAGCCCCAGCCTCAGCCCTGCCCCCTTT
CCCTCCTTCCTGGAGTGGTGGCTACAGAAGCTTGGGGCCAACCCTGGCTCCTCTTTCCCCAGCTT
CTGTCTGTCTCACTGTCTTCCCTCCCCTCCCCCAGCTGAGGTGTGGCCCTCAGGCCTGGTGCTGC
CTTGGAGGGCTGGGGGAAGGAGTGTGTGGAGGAGGGAGGAGGGTGAAGACTGAGGCTAGGTG
CCAGAATGGACTGGAGTGAAGGCGTGTCTAGAGTGTGGGCTGGCTGTTGTGCTGGAAAGCTGG
GGACAGGTTGATGGTAATAAACTGCTCAATGACCAGTGCTTCAGGCTCCAGAGCTCTTTGGAGAG
ATGGGTTGGGGCAGCTTACTCCAGCCCTGGCCCAAGGAGGCCCAGAAGTTGGAAAGAGATGGAA
TGTGGCTGGGAACATTGCATCCCAAAGAGCTTCTCAGTGGAGGAGGCTGGGGAAGGCATGAGGG
GGCTCAGAGGCTCCTTGACTGGGACCAGGATTGGGGGCCAGGGCTTGAGTAGGCCTCTCCACTC
TCCTCCTTGGGGGTCCAGATTCCTTAGGAGCTTTGGGATGAGGCCCAGGAGGCTGCATTTTTCCA
GGTCCTTAGTCTTGCCACCACACAGATGATTCTGATTCATAGCCAAGATGAGGACACACTGATGT
AGCTGATCTCTCATTTACAGAGGAGGATTCTAAAGTTCAGAGAGGGAAAGGGGCTTGCCTGAGG
TCACGTAGATAATCAGCAGCACATTGAACGCTGCACTCCTGGGCTCCTGTCCCCAGCCCCCATTCA
GACACGCTGACTCAGGAGGTCCAGGCCTCTAAGGCTTCTCTCCCTGGAGTGAGGGTGGAGGTGA
GGGAGAGCTGGCACAAGCCCTCCCTCTGGATCCTCCACTCCTGGGGATTATGAAGATATTCTGGA
AAGATTTGTGCTTCAGAGGTAGACTGCAGAAAGCAAACAGTCTACCCAGCAGCTCTGAATGTCAC
CTGCCCTGGGGCTTACAGCACTATATGAGTTCCTGGCCTATCCTGCAAATATGCCCATGCTGGCC
TTCTAAATAGCTGGTACATCCATCACCACTGACGGGCCTGGCCTGGAAACCTGGTTTGTCCCCTG
TCTTGATGGCCTACGAGAGGCCAAGTTCCACTGGGCTGGGAAAAGTCACTTTGTCTGTCTTGTTC
ACCTGGAGCCTGACACACCGTAGGTACTGAGTACAAATAGCTTGATTTGGCTAGGCTTGGCTGCA
GGGGGACGTGCCTAAAAGACATTCCGGGCATTTGCACTTGGGAAACTTGCCTCACCTTCAGGCTT
GTGGGGCCTCTCTATGCCCAATGAGTCCAGGCAGTCCTAGCAAGTACTCAGGAGAGCAGGGGTG
GGTGTGACAGAGGCTGGCTCTGGATTGGGGGACAACAGAACCAGAGTAACTCCTCGCCTGTTGC
TGCTTTGCAATGAATTTCCTTTACCTTTCTGGAACACAAGCTGCTGTGAACCAAACTGATATCAAG
TGATTAGCTCACCGGGCCTTGGTTGCTTTTCAAAGATCCCCTTCAGCCCCCTGCCAGAGTCACTG
CCCCATAATCACCATGTCAGAAGGGACCCTAGGGCATTCGTGTCCTATTTATCAATCTTCAGCACC
ACCTCTAAGATCTCTGAGAGAGGGTGGATCAGCCTCTGTGTAAACAAAAAGCTGTTAGGACTTGT
TGCCTCTCAAGGTGGACTATTCTGTTTTCTGCCAGGACACTGCCATTCATGCATTGTCAGATATTT
ATTAAACAGCAGCAAAGTGCCAGCCAATTTGTCCTGGAGGAATTCATAGCCTCATGGGGCAAAAG
TAAATAAACAGCTTATTACAATTCAACAAAAAAAAAAAAAAAAAAAAAAAAAAAAAAAAAAAAAAAAA
AAAAAAAAA (NCBI Reference Sequence: NM_004554.4; SEQ ID NO: 3)

Protein MGAASCEDEELEFKLVFGEEKEAPPLGAGGLGEELDSEDAPPCCRLALGEPPPYGAAPIGIPRPPPPRPG
MHSPPPRPAPSPGTWESQPARSVRLGGPGGGAGGAGGGRVLECPSIRITSISPTPEPPAALEDNPDAWG
DGSPRDYPPPEGFGGYREAGGQGGGAFFSPSPGSSSLSSWSFFSDASDEAALYAACDEVESELNEAASRF
GLGSPLPSPRASPRPWTPEDPWSLYGPSPGGRGPEDSWLLLSAPGPTPASPRPASPCGKRRYSSSGTPS
SASPALSRRGSLGEEGSEPPPPPPLPLARDPGSPGPFDYVGAPPAESIPQKTRRTSSEQAVALPRSEEPAS
CNGKLPLGAEESVAPPGGSRKEVAGMDYLAVPSPLAWSKARIGGHSPIFRTSALPPLDWPLPSQYEQLEL
RIEVQPRAHHRAHYETEGSRGAVKAAPGGHPVVKLLGYSEKPLTLQMFIGTADERNLRPHAFYQVHRIT
GKMVATASYEAVVSGTKVLEMTLLPENNMAANIDCAGILKLRNSDIELRKGETDIGRKNTRVRLVFRVHV
PQGGGKVVSVQAASVPIECSQRSAQELPQVEAYSPSACSVRGGEELVLTGSNFLPDSKVVFIERGPDGKL
QWEEEATVNRLQSNEVTLTLTVPEYSNKRVSRPVQVYFYVSNGRRKRSPTQSFRFLPVICKEEPLPDSSL
RGFPSASATPFGTDMDFSPPRPPYPSYPHEDPACETPYLSEGFGYGMPPLYPQTGPPPSYRPGLRMFPE
TRGTTGCAQPPAVSFLPRPFPSDPYGGRGSSFSLGLPFSPPAPFRPPPLPASPPLEGPFPSQSDVHPLPAE
GYNKVGPGYGPGEGAPEQEKSRGGYSSGFRDSVPIQGITLEEVSEIIGRDLSGFPAPPGEEPPA (NCBI
Reference Sequence: NP_004545.2; SEQ ID NO: 4, 902 amino acids)

Isoform 3

(This variant (3) is alternatively spliced at the 5' and 3' ends compared to transcript variant 1. This results in the use of an in-frame downstream AUG, translation termination at a downstream stop codon, and a shorter isoform (3) with a distinct C-terminus compared to isoform 1)

cDNA GAAGAGAGGACAGAGGGAGGGAGGGTGGGGGAGGACGAGGGGCGCGTGGTTTTCCCATCTCAT
CCCTGGAGGAGGGGCTGGAGCATCCCCGGCAGCCAATCAGGGACAGGCTGGGGGGGGGACCGC
TTTGAAGAAGTTTGGGGGAAAAAAGTTTGGAAAAGTTTCTATAATAACGAGGGGGCTTCTGGAG
GGAGGCGGCAGCGACGGAGGAGGGGGCTTCTCAGAGAAAGGGAGGGAGGGAGCCACCCGGGTG
AAGATACAGCAGCCTCCTGAACTCCCCCCTCCCACCCAGGCCGGGACCTGGGGGCTCCTGCCGGA
TCCATGGGGGCGGCCAGCTGCGAGGATGAGGAGCTGGAATTTAAGCTGGTGTTCGGGGAGGAA
AAGGAGGCCCCCCCGCTGGGCGCGGGGGGATTGGGGGAAGAACTGGACTCAGAGGATGCCCCG

TABLE 1-continued cDNA and protein sequences of human NFATC4 isoforms 1 to 7.

CCATGCTGCCGTCTGGCCTTGGGAGAGCCCCCTCCCTATGGCGCTGCACCTATCGGTATTCCCCG
ACCTCCACCCCCTCGGCCTGGCATGCATTCGCCACCGCCGCGACCAGCCCCCTCACCTGGCACCT
GGGAGAGCCAGCCCGCCAGGTCGGTGAGGCTGGGAGGACCAGGAGGGGGTGCTGGGGGTGCT
GGGGGTGGCCGTGTTCTCGAGTGTCCCAGCATCCGCATCACCTCCATCTCTCCCACGCCGGAGCC
GCCAGCAGCGCTGGAGGACAACCCTGATGCCTGGGGGGACGGCTCTCCTAGAGATTACCCCCCA
CCAGAAGGCTTTGGGGGCTACAGAGAAGCAGGGGGCCAGGGTGGGGGGGCCTTCTTCAGCCCA
AGCCCTGGCAGCAGCAGCCTGTCCTCGTGGAGCTTCTTCTCCGATGCCTCTGACGAGGCAGCCCT
GTATGCAGCCTGCGACGAGGTGGAGTCTGAGCTAAATGAGGCGGCCTCCCGCTTTGGCCTGGGC
TCCCCGCTGCCCTCGCCCCGGGCCTCCCCTCGGCCATGGACCCCCGAAGATCCCTGGAGCCTGTA
TGGTCCAAGCCCCGGAGGCCGAGGGCCAGAGGATAGCTGGCTACTCCTCAGTGCTCCTGGGCCC
ACCCCAGCCTCCCCGCGGCCTGCCTCTCCATGTGGCAAGCGGCGCTATTCCAGCTCGGGAACCCC
ATCTTCAGCCTCCCCAGCTCTGTCCCGCCGTGGCAGCCTGGGGGAAGAGGGGTCTGAGCCACCT
CCACCACCCCCATTGCCTCTGGCCCGGGACCCGGGCTCCCCTGGTCCCTTTGACTATGTGGGGGC
CCCACCAGCTGAGAGCATCCCTCAGAAGACACGGCGGACTTCCAGCGAGCAGGCAGTGGCTCTG
CCTCGGTCTGAGGAGCCTGCCTCATGCAATGGGAAGCTGCCCTTGGGAGCAGAGGAGTCTGTGG
CTCCTCCAGGAGGTTCCCGGAAGGAGGTGGCTGGCATGGACTACCTGGCAGTGCCCTCCCCACT
CGCTTGGTCCAAGGCCCGGATTGGGGGACACAGCCCTATCTTCAGGACCTCTGCCCTACCCCCAC
TGGACTGGCCTCTGCCCAGCCAATATGAGCAGCTGGAGCTGAGGATCGAGGTACAGCCTAGAGC
CCACCACCGGGCCCACTATGAGACAGAAGGCAGCCGTGGAGCTGTCAAAGCTGCCCCTGGCGGT
CACCCCGTAGTCAAGCTCCTAGGCTACAGTGAGAAGCCACTGACCCTACAGATGTTCATCGGCAC
TGCAGATGAAAGGAACCTGCGGCCTCATGCCTTCTATCAGGTGCACCGTATCACAGGCAAGATGG
TGGCCACGGCCAGCTATGAAGCCGTAGTCAGTGGCACCAAGGTGTTGGAGATGACTCTGCTGCC
TGAGAACAACATGGCGGCCAACATTGACTGCGCGGGAATCCTGAAGCTTCGGAATTCAGACATTG
AGCTTCGGAAGGGTGAGACGGACATCGGGCGCAAAAACACACGTGTACGGCTGGTGTTCCGGGT
ACACGTGCCCCAGGGCGGCGGGAAGGTCGTCTCAGTACAGGCAGCATCGGTGCCCATCGAGTGC
TCCCAGCGCTCAGCCCAGGAGCTGCCCCAGGTGGAGGCCTACAGCCCCAGTGCCTGCTCTGTGA
GAGGAGGCGAGGAACTGGTACTGACTGGCTCCAACTTCCTGCCAGACTCCAAGGTGGTGTTCATT
GAGAGGGGTCCTGATGGGAAGCTGCAATGGGAGGAGGAGGCCACAGTGAACCGACTGCAGAGC
AACGAGGTGACGCTGACCCTGACTGTCCCCGAGTACAGCAACAAGAGGGTTTCCCGGCCAGTCCA
GGTCTACTTTTATGTCTCCAATGGGCGGAGGAAACGCAGTCCTACCCAGAGTTTCAGGTTTCTGC
CTGTGATCTGCAAAGAGGAGCCCCTACCGGACTCATCTCTGCGGGGTTTCCCTTCAGCATCGGCA
ACCCCCTTTGGCACTGACATGGACTTCTCACCACCCAGGCCCCCCTACCCCTCCTATCCCCATGAA
GACCCTGCTTGCGAAACTCCTTACCTATCAGAAGGCTTCGGCTATGGCATGCCCCCTCTGTACCC
CCAGACGGGGCCCCCACCATCCTACAGACCGGGCCTGCGGATGTTCCCTGAGACTAGGGGTACC
ACAGTGAGTGAGATCATTGGCCGAGACCTGAGTGGCTTCCCTGCACCTCCTGGAGAAGAGCCTCC
TGCCTGAACCACGTGAACTGTCATCACCTGGCAACCCCAGCCCCAGCCTCAGCCCTGCCCCCTTTC
CCTCCTTCCTGGAGTGGTGGCTACAGAAGCTTGGGGCCAACCCTGGCTCCTCTTTCCCCAGCTTC
TGTCTGTCTCACTGTCTTCCCTCCCCTCCCCCAGCTGAGGTGTGGCCCTCAGGCCTGGTGCTGCC
TTGGAGGGCTGGGGGAAGGAGTGTGTGGAGGAGGAGGAGGAGGGTGAAGACTGAGGCTAGGTGC
CAGAATGGACTGGAGTGAAGGCGTGTCTAGAGTGTGGGCTGGCTGTTGTGCTGGAAAGCTGGG
GACAGGTTGATGGTAATAAACTGCTCAATGACCAGTGCTTCAGGCTCCAGAGCTCTTTGGAGAGA
TGGGTTGGGGCAGCTTACTCCAGCCCTGGCCCAAGGAGGCCCAGAAGTTGGAAAGAGATGGAAT
GTGGCTGGGAACATTGCATCCCAAAGAGCTTCTCAGTGGAGGAGGCTGGGGAAGGCATGAGGGG
GCTCAGAGGCTCCTTGACTGGGACCAGGATTGGGGGCCAGGGCTTGAGTAGGCCTCTCCACTCT
CCTCCTTGGGGGTCCAGATTCCTTAGGAGCTTTGGGATGAGGCCCAGGAGGCTGCATTTTTCCA
GGTCCTTAGTCTTGCCACCACACAGATGATTCTGATTCATAGCCAAGATGAGGACACACTGATGT
AGCTGATCTCTCATTTACAGAGGAGGATTCTAAAGTTCAGAGAGGGAAAGGGGCTTGCCTGAGG
TCACGTAGATAATCAGCAGCACATTGAACGCTGCACTCCTGGGCTCCTGTCCCCAGCCCCCATTCA
GACACGCTGACTCAGGAGGTCCAGGCCTCTAAGGCTTCTCTCCCTGGAGTGAGGGTGGAGGTGA
GGGAGAGCTGGCACAAGCCCTCCCTCTGGATCCTCCACTCCTGGGGATTATGAAGATATTCTGGA
AAGATTTGTGCTTCAGAGGTAGACTGCAGAAAGCAAACAGTCTACCCAGCAGCTCTGAATGTCAC
CTGCCCTGGGGCTTACAGCACTATATGAGTTCCTGGCCTATCCTGCAAATATGCCCATGCTGGCC
TTCTAAATAGCTGGTACATCCATCACCACTGACGGGCCTGGCCTGGAAACCTGGTTTGTCCCCTG
TCTTGATGGCCTACGAGAGGCCAAGTTCCACTGGGCTGGGAAAAGTCACTTTGTCTGTCTTGTTC
ACCTGGAGCCTGACACACCGTAGGTACTGAGTACAAATAGCTTGATTTGGCTAGGCTTGGCTGCA
GGGGGACGTGCCTAAAAGACATTCCGGGCATTTGCACTTGGGAAACTTGCCTCACCTTCAGGCTT
GTGGGGCCTCTCTATGCCCAATGAGTCCAGGCAGTCCTAGCAAGTACTCAGGAGAGCAGGGGTG
GGTGTGACAGAGGCTGGCTCTGGATTGGGGGACAACAGAACCAGAGTAACTCCTCGCCTGTTGC
TGCTTTGCAATGAATTTCCTTTACCTTTCTGGAACACAAGCTGCTGTGAACCAAACTGATATCAAG
TGATTAGCTCACCGGGCCTTGGTTGCTTTTCAAAGATCCCCTTCAGCCCCCTGCCAGAGTCACTG
CCCCATAATCACCATGTCAGAAGGGACCCTAGGGCATTCGTGTCCTATTTATCAATCTTCAGCACC
ACCTCTAAGATCTCTGAGAGAGGGTGGATCAGCCTCTGTGTAAACAAAAAGCTGTTAGGACTTGT
TGCCTCTCAAGGTGGACTATTCTGTTTTCTGCCAGGACACTGCCATTCATGCATTGTCAGATATTT
ATTAAACAGCAGCAAAGTGCCAGCCAATTTGTCCTGGAGGAATTCATAGCCTCATGGGGCAAAAG
TAAATAAACAGCTTATTACAATTCAACAAAAAAAAAAAAAAAAAAAAAAAAAAAAAAAAAAAAAAA
AAAAAAAAA (NCBI Reference Sequence: NM_001198965.1; SEQ ID NO: 5)

Protein MGAASCEDEELEFKLVFGEEKEAPPLGAGGLGEELDSEDAPPCCRLALGEPPPYGAAPIGIPRPPPPRPG
MHSPPPRPAPSPGTWESQPARSVRLGGPGGGAGGAGGGRVLECPSIRITSISPTPEPPAALEDNPDAWG
DGSPRDYPPPEGFGGYREAGGQGGGAFFSPSPGSSSLSSWSFFSDASDEAALYAACDEVESELNEAASRF
GLGSPLPSPRASPRPWTPEDPWSLYGPSPGGRGPEDSWLLLSAPGPTPASPRPASPCGKRRYSSSGTPS
SASPALSRRGSLGEEGSEPPPPPPLPLARDPGSPGPFDYVGAPPAESIPQKTRRTSSEQAVALPRSEEPAS
CNGKLPLGAEESVAPPGGSRKEVAGMDYLAVPSPLAWSKARIGGHSPIFRTSALPPLDWPLPSQYEQLEL
RIEVQPRAHHRAHYETEGSRGAVKAAPGGHPVVKLLGYSEKPLTLQMFIGTADERNLRPHAFYQVHRIT
GKMVATASYEAVVSGTKVLEMTLLPENNMAANIDCAGILKLRNSDIELRKGETDIGRKNTRVRLVFRVHV
PQGGGKVVSVQAASVPIECSQRSAQELPQVEAYSPSACSVRGGEELVLTGSNFLPDSKVVFIERGPDGKL TABLE 1-continued cDNA and protein sequences of human NFATC4 isoforms 1 to 7.

QWEEEATVNRLQSNEVTLTLTVPEYSNKRVSRPVQVYFYVSNGRRKRSPTQSFRFLPVICKEEPLPDSSL
RGFPSASATPFGTDMDFSPPRPPYPSYPHEDPACETPYLSEGFGYGMPPLYPQTGPPPSYRPGLRMFPE
TRGTTVSEIIGRDLSGFPAPPGEEPPA (NCBI Reference Sequence: NP_001185894.1; SEQ ID
NO: 6, 794 amino acids)

Isoform 4

(This variant (4) is alternatively spliced at the 5' and 3' ends compared to transcript variant 1. This results in the use of an in-frame downstream AUG, translation termination at a downstream stop codon, and a shorter isoform (4) with a distinct C-terminus compared to isoform 1)

cDNA
ACGGTTGCGATGGCAACTGGGGCTCCTGCCAGCGCCGTTTGGGGGTTTGGGAACCGCTGCTAAT
TGGGTTCATGTAACTGGACTCAGAGGATGCCCCGCCATGCTGCCGTCTGGCCTTGGGAGAGCCC
CCTCCCTATGGCGCTGCACCTATCGGTATTCCCCGACCTCCACCCCCTCGGCCTGGCATGCATTC
GCCACCGCCGCGACCAGCCCCCTCACCTGGCACCTGGGAGAGCCAGCCCGCCAGGTCGGTGAGG
CTGGGAGGACCAGGAGGGGGTGCTGGGGGTGCTGGGGGTGGCCGTGTTCTCGAGTGTCCCAGC
ATCCGCATCACCTCCATCTCTCCCACGCCGGAGCCGCCAGCAGCGCTGGAGGACAACCCTGATGC
CTGGGGGGACGGCTCTCCTAGAGATTACCCCCCACCAGAAGGCTTTGGGGGCTACAGAGAAGCA
GGGGGCCAGGGTGGGGGGGCCTTCTTCAGCCCAAGCCCTGGCAGCAGCAGCCTGTCCTCGTGGA
GCTTCTTCTCCGATGCCTCTGACGAGGCAGCCCTGTATGCAGCCTGCGACGAGGTGGAGTCTGA
GCTAAATGAGGCGGCCTCCCGCTTTGGCCTGGGCTCCCCGCTGCCCTCGCCCCGGGCCTCCCCTC
GGCCATGGACCCCCGAAGATCCCTGGAGCCTGTATGGTCCAAGCCCCGGAGGCCGAGGGCCAGA
GGATAGCTGGCTACTCCTCAGTGCTCCTGGGCCCACCCCAGCCTCCCCGCGGCCTGCCTCTCCAT
GTGGCAAGCGGCGCTATTCCAGCTCGGGAACCCCATCTTCAGCCTCCCCAGCTCTGTCCCGCCGT
GGCAGCCTGGGGGAAGAGGGGTCTGAGCCACCTCCACCACCCCCATTGCCTCTGGCCCGGGACC
CGGGCTCCCCTGGTCCCTTTGACTATGTGGGGGCCCCACCAGCTGAGAGCATCCCTCAGAAGACA
CGGCGGACTTCCAGCGAGCAGGCAGTGGCTCTGCCTCGGTCTGAGGAGCCTGCCTCATGCAATG
GGAAGCTGCCCTTGGGAGCAGAGGAGTCTGTGGCTCCTCCAGGAGGTTCCCGGAAGGAGGTGG
CTGGCATGGACTACCTGGCAGTGCCCTCCCCACTCGCTTGGTCCAAGGCCCGGATTGGGGGACA
CAGCCCTATCTTCAGGACCTCTGCCCTACCCCCACTGGACTGGCCTCTGCCCAGCCAATATGAGCA
GCTGGAGCTGAGGATCGAGGTACAGCCTAGAGCCCACCACCGGGCCCACTATGAGACAGAAGGC
AGCCGTGGAGCTGTCAAAGCTGCCCCTGGCGGTCACCCCGTAGTCAAGCTCCTAGGCTACAGTGA
GAAGCCACTGACCCTACAGATGTTCATCGGCACTGCAGATGAAAGGAACCTGCGGCCTCATGCCT
TCTATCAGGTGCACCGTATCACAGGCAAGATGGTGGCCACGGCCAGCTATGAAGCCGTAGTCAGT
GGCACCAAGGTGTTGGAGATGACTCTGCTGCCTGAGAACAACATGGCGGCCAACATTGACTGCG
CGGGAATCCTGAAGCTTCGGAATTCAGACATTGAGCTTCGGAAGGGTGAGACGGACATCGGGCG
CAAAAACACACGTGTACGGCTGGTGTTCCGGGTACACGTGCCCCAGGGCGGCGGGAAGGTCGTC
TCAGTACAGGCAGCATCGGTGCCCATCGAGTGCTCCCAGCGCTCAGCCCAGGAGCTGCCCCAGG
TGGAGGCCTACAGCCCCAGTGCCTGCTCTGTGAGAGGAGGCGAGGAACTGGTACTGACTGGCTC
CAACTTCCTGCCAGACTCCAAGGTGGTGTTCATTGAGAGGGGTCCTGATGGGAAGCTGCAATGG
GAGGAGGAGGCCACAGTGAACCGACTGCAGAGCAACGAGGTGACGCTGACCCTGACTGTCCCCG
AGTACAGCAACAAGAGGGTTTCCCGGCCAGTCCAGGTCTACTTTTATGTCTCCAATGGGCGGAGG
AAACGCAGTCCTACCCAGAGTTTCAGGTTTCTGCCTGTGATCTGCAAAGAGGAGCCCCTACCGGA
CTCATCTCTGCGGGGTTTCCCTTCAGCATCGGCAACCCCCTTTGGCACTGACATGGACTTCTCAC
CACCCAGGCCCCCCTACCCCTCCTATCCCCATGAAGACCCTGCTTGCGAAACTCCTTACCTATCAG
AAGGCTTCGGCTATGGCATGCCCCCTCTGTACCCCCAGACGGGGCCCCCACCATCCTACAGACCG
GGCCTGCGGATGTTCCCTGAGACTAGGGGTACCACAGGTTGTGCCCAACCACCTGCAGTTTCCTT
CCTTCCCCGCCCCTTCCCTAGTGACCCGTATGGAGGGCGGGGCTCCTCTTTCTCCCTGGGGCTGC
CATTCTCTCCGCCAGCCCCCTTTCGGCCGCCTCCTCTTCCTGCATCCCCACCGCTTGAAGGCCCCT
TCCCTTCCCAGAGTGATGTGCATCCCCTACCTGCTGAGGGATACAATAAGGTAGGGCCAGGCTAT
GGCCCTGGGGAGGGGGCTCCGGAGCAGGAGAAATCCAGGGGTGGCTACAGCAGCGGCTTCCGA
GACAGTGTCCCTATCCAGGGTATCACGCTGGAGGAAGTGAGTGAGATCATTGGCCGAGACCTGA
GTGGCTTCCCTGCACCTCCTGGAGAAGAGCCTCCTGCCTGAACCACGTGAACTGTCATCACCTGG
CAACCCCAGCCCCAGCCTCAGCCCTGCCCCCTTTCCCTCCTTCCTGGAGTGGTGGCTACAGAAGC
TTGGGGCCAACCCTGGCTCCTCTTTCCCCAGCTTCTGTCTGTCTCACTGTCTTCCCTCCCCTCCCC
CAGCTGAGGTGTGGCCCTCAGGCCTGGTGCTGCCTTGGAGGGCTGGGGGAAGGAGTGTGTGGA
GGAGGGAGGAGGGTGAAGACTGAGGCTAGGTGCCAGAATGGACTGGAGTGAAGGCGTGTCTAG
AGTGTGGGCTGGCTGTTGTGCTGGAAAGCTGGGGACAGGTTGATGGTAATAAACTGCTCAATGA
CCAGTGCTTCAGGCTCCAGAGCTCTTTGGAGAGATGGGTTGGGGCAGCTTACTCCAGCCCTGGC
CCAAGGAGGCCCAGAAGTTGGAAAGAGATGGAATGTGGCTGGGAACATTGCATCCCAAAGAGCT
TCTCAGTGGAGGAGGCTGGGGAAGGCATGAGGGGGCTCAGAGGCTCCTTGACTGGGACCAGGA
TTGGGGGCCAGGGCTTGAGTAGGCCTCTCCACTCTCCTCCTTGGGGGTCCAGATTCCTTAGGAG
CTTTGGGATGAGGCCCAGGAGGCTGCATTTTTCCAGGTCCTTAGTCTTGCCACCACACAGATGAT
TCTGATTCATAGCCAAGATGAGGACACACTGATGTAGCTGATCTCTCATTTACAGAGGAGGATTC
TAAAGTTCAGAGAGGGAAAGGGGCTTGCCTGAGGTCACGTAGATAATCAGCAGCACATTGAACGC
TGCACTCCTGGGCTCCTGTCCCCAGCCCCCATTCAGACACGCTGACTCAGGAGGTCCAGGCCTCT
AAGGCTTCTCTCCCTGGAGTGAGGGTGGAGGTGAGGGAGAGCTGGCACAAGCCCTCCCTCTGGA
TCCTCCACTCCTGGGGATTATGAAGATATTCTGGAAAGATTTGTGCTTCAGAGGTAGACTGCAGA
AAGCAAACAGTCTACCCAGCAGCTCTGAATGTCACCTGCCCTGGGGCTTACAGCACTATATGAGT
TCCTGGCCTATCCTGCAAATATGCCCATGCTGGCCTTCTAAATAGCTGGTACATCCATCACCACTG
ACGGGCCTGGCCTGGAAACCTGGTTTGTCCCCTGTCTTGATGGCCTACGAGAGGCCAAGTTCCAC
TGGGCTGGGAAAAGTCACTTTGTCTGTCTTGTTCACCTGGAGCCTGACACACCGTAGGTACTGAG
TACAAATAGCTTGATTTGGCTAGGCTTGGCTGCAGGGGGACGTGCCTAAAAGACATTCCGGGCAT
TTGCACTTGGGAAACTTGCCTCACCTTCAGGCTTGTGGGGCCTCTCTATGCCCAATGAGTCCAGG
CAGTCCTAGCAAGTACTCAGGAGAGCAGGGGTGGGTGTGACAGAGGCTGGCTCTGGATTGGGG
GACAACAGAACCAGAGTAACTCCTCGCCTGTTGCTGCTTTGCAATGAATTTCCTTTACCTTTCTGG
AACACAAGCTGCTGTGAACCAAACTGATATCAAGTGATTAGCTCACCGGGCCTTGGTTGCTTTTC
AAAGATCCCCTTCAGCCCCCTGCCAGAGTCACTGCCCCATAATCACCATGTCAGAAGGGACCCTAG
GGCATTCGTGTCCTATTTATCAATCTTCAGCACCACCTCTAAGATCTCTGAGAGAGGGTGGATCA

TABLE 1-continued

| cDNA and protein sequences of human NFATC4 isoforms 1 to 7. | |
|---|---|
| | GCCTCTGTGTAAACAAAAAGCTGTTAGGACTTGTTGCCTCTCAAGGTGGACTATTCTGTTTTCTG<br>CCAGGACACTGCCATTCATGCATTGTCAGATATTTATTAAACAGCAGCAAAGTGCCAGCCAATTTG<br>TCCTGGAGGAATTCATAGCCTCATGGGGCAAAAGTAAATAAACAGCTTATTACAATTCAACAAAAA<br>AAAAAAAAAAAAAAAAAAAAAAAAAAAAAAAAAAAAAAAAAAAA (NCBI Reference Sequence:<br>NM_001198966.2; SEQ ID NO: 7) |
| Protein | MHSPPPRPAPSPGTWESQPARSVRLGGPGGGAGGAGGGRVLECPSIRITSISPTPEPPAALEDNPDAWG<br>DGSPRDYPPPEGFGGYREAGGQGGGAFFSPSPGSSSLSSWSFFSDASDEAALYAACDEVESELNEAASRF<br>GLGSPLPSPRASPRPWTPEDPWSLYGPSPGGRGPEDSWLLLSAPGPTPASPRPASPCGKRRYSSSGTPS<br>SASPALSRRGSLGEEGSEPPPPPPLPLARDPGSPGPFDYVGAPPAESIPQKTRRTSSEQAVALPRSEEPAS<br>CNGKLPLGAEESVAPPGGSRKEVAGMDYLAVPSPLAWSKARIGGHSPIFRTSALPPLDWPLPSQYEQLEL<br>RIEVQPRAHHRAHYETEGSRGAVKAAPGGHPVVKLLGYSEKPLTLQMFIGTADERNLRPHAFYQVHRIT<br>GKMVATASYEAVVSGTKVLEMTLLPENNMAANIDCAGILKLRNSDIELRKGETDIGRKNTRVRLVFRVHV<br>PQGGGKVVSVQAASVPIECSQRSAQELPQVEAYSPSACSVRGGEELVLTGSNFLPDSKVVFIERGPDGKL<br>QWEEEATVNRLQSNEVTLTLTVPEYSNKRVSRPVQVYFYVSNGRRKRSPTQSFRFLPVICKEEPLPDSSL<br>RGFPSASATPFGTDMDFSPPRPPYPSYPHEDPACETPYLSEGFGYGMPPLYPQTGPPPSYRPGLRMFPE<br>TRGTTGCAQPPAVSFLPRPFPSDPYGGRGSSFSLGLPFSPPAPFRPPPLPASPPLEGPFPSQSDVHPLPAE<br>GYNKVGPGYGPGEGAPEQEKSRGGYSSGFRDSVPIQGITLEEVSEIIGRDLSGFPAPPGEEPPA (NCBI<br>Reference Sequence: NP_001185895.1; SEQ ID NO: 8, 832 amino acids) |
| Isoform 5<br>(This variant (5) is alternatively spliced at the 3' end compared to transcript variant 1. This results in translation termination at a downstream stop codon, and a shorter isoform (5) with a distinct C-terminus compared to isoform 1.) | |
| cDNA | GTAAACGTCTGACCTGGGGCCGTCGCTTAACCGTTTAGTTGCTGGGATGGGGCGGCGTTGGGGG<br>TGCGGCCCTGAACCGGAGGGATTTAGAGACTGGAGACGCGGCCTCTAAGAGAGGTTGAAACTGT<br>GTGTGTGTGGGAGAAAATGATAACCACCCTCCCATCTCTCCTACCCGCCAGCCTCGCCAGTATCT<br>CCCACCGAGTCACGAATCTCCCATCTAACTCCCTCTCACACAACCCAGGCCTCTCCAAGCCTGACT<br>TTCCCGGAAACTCCAGTCCAGGTCTTCCTTCCTCCTCCAGCCCAGGCCGGGACCTGGGGGCTCCT<br>GCCGGATCCATGGGGGCGGCCAGCTGCGAGGATGAGGAGCTGGAATTTAAGCTGGTGTTCGGG<br>GAGGAAAAGGAGGCCCCCCCGCTGGGCGCGGGGGGATTGGGGGAAGAACTGGACTCAGAGGAT<br>GCCCCGCCATGCTGCCGTCTGGCCTTGGGAGAGCCCCCTCCCTATGGCGCTGCACCTATCGGTAT<br>TCCCCGACCTCCACCCCCTCGGCCTGGCATGCATTCGCCACCGCCGCGACCAGCCCCCTCACCTG<br>GCACCTGGGAGAGCCAGCCCGCCAGGTCGGTGAGGCTGGGAGGACCAGGAGGGGGTGCTGGGG<br>GTGCTGGGGGTGGCCGTGTTCTCGAGTGTCCCAGCATCCGCATCACCTCCATCTCTCCCACGCCG<br>GAGCCGCCAGCAGCGCTGGAGGACAACCCTGATGCCTGGGGGGACGGCTCTCCTAGAGATTACC<br>CCCCACCAGAAGGCTTTGGGGGCTACAGAGAAGCAGGGGGCCAGGGTGGGGGGGCCTTCTTCA<br>GCCCAAGCCCTGGCAGCAGCAGCCTGTCCTCGTGGAGCTTCTTCTCCGATGCCTCTGACGAGGCA<br>GCCCTGTATGCAGCCTGCGACGAGGTGGAGTCTGAGCTAAATGAGGCGGCCTCCCGCTTTGGCC<br>TGGGCTCCCCGCTGCCCTCGCCCCGGGCCTCCCCTCGGCCATGGACCCCCGAAGATCCCTGGAGC<br>CTGTATGGTCCAAGCCCCGGAGGCCGAGGGCCAGAGGATAGCTGGCTACTCCTCAGTGCTCCTG<br>GGCCCACCCCAGCCTCCCCGCGGCCTGCCTCTCCATGTGGCAAGCGGCGCTATTCCAGCTCGGGA<br>ACCCCATCTTCAGCCTCCCCAGCTCTGTCCCGCCGTGGCAGCCTGGGGGAAGAGGGGTCTGAGC<br>CACCTCCACCACCCCCATTGCCTCTGGCCCGGGACCCGGGCTCCCCTGGTCCCTTTGACTATGTG<br>GGGGCCCCACCAGCTGAGAGCATCCCTCAGAAGACACGGCGGACTTCCAGCGAGCAGGCAGTGG<br>CTCTGCCTCGGTCTGAGGAGCCTGCCTCATGCAATGGGAAGCTGCCCTTGGGAGCAGAGGAGTC<br>TGTGGCTCCTCCAGGAGGTTCCCGGAAGGAGGTGGCTGGCATGGACTACCTGGCAGTGCCCTCC<br>CCACTCGCTTGGTCCAAGGCCCGGATTGGGGGACACAGCCCTATCTTCAGGACCTCTGCCCTACC<br>CCCACTGGACTGGCCTCTGCCCAGCCAATATGAGCAGCTGGAGCTGAGGATCGAGGTACAGCCTA<br>GAGCCCACCACCGGGCCCACTATGAGACAGAAGGCAGCCGTGGAGCTGTCAAAGCTGCCCCTGG<br>CGGTCACCCCGTAGTCAAGCTCCTAGGCTACAGTGAGAAGCCACTGACCCTACAGATGTTCATCG<br>GCACTGCAGATGAAAGGAACCTGCGGCCTCATGCCTTCTATCAGGTGCACCGTATCACAGGCAAG<br>ATGGTGGCCACGGCCAGCTATGAAGCCGTAGTCAGTGGCACCAAGGTGTTGGAGATGACTCTGC<br>TGCCTGAGAACAACATGGCGGCCAACATTGACTGCGCGGGAATCCTGAAGCTTCGGAATTCAGAC<br>ATTGAGCTTCGGAAGGGTGAGACGGACATCGGGCGCAAAAACACACGTGTACGGCTGGTGTTCC<br>GGGTACACGTGCCCCAGGGCGGCGGGAAGGTCGTCTCAGTACAGGCAGCATCGGTGCCCATCGA<br>GTGCTCCCAGCGCTCAGCCCAGGAGCTGCCCCAGGTGGAGGCCTACAGCCCCAGTGCCTGCTCT<br>GTGAGAGGAGGCGAGGAACTGGTACTGACTGGCTCCAACTTCCTGCCAGACTCCAAGGTGGTGT<br>TCATTGAGAGGGGTCCTGATGGGAAGCTGCAATGGGAGGAGGAGGCCACAGTGAACCGACTGCA<br>GAGCAACGAGGTGACGCTGACCCTGACTGTCCCCGAGTACAGCAACAAGAGGGTTTCCCGGCCA<br>GTCCAGGTCTACTTTTATGTCTCCAATGGGCGGAGGAAACGCAGTCCTACCCAGAGTTTCAGGTT<br>TCTGCCTGTGATCTGCAAAGAGGAGCCCCTACCGGACTCATCTCTGCGGGGTTTCCCTTCAGCAT<br>CGGCAACCCCCTTTGGCACTGACATGGACTTCTCACCACCCAGGCCCCCCTACCCCTCCTATCCCC<br>ATGAAGACCCTGCTTGCGAAACTCCTTACCTATCAGAAGGCTTCGGCTATGGCATGCCCCCTCTG<br>TACCCCCAGACGGGGCCCCCACCATCCTACAGACCGGGCCTGCGGATGTTCCCTGAGACTAGGG<br>GTACCACAGTGAGTGAGATCATTGGCCGAGACCTGAGTGGCTTCCCTGCACCTCCTGGAGAAGA<br>GCCTCCTGCCTGAACCACGTGAACTGTCATCACCTGGCAACCCCAGCCCCAGCCTCAGCCCTGCC<br>CCCTTTCCCTCCTTCCTGGAGTGGTGGCTACAGAAGCTTGGGGCCAACCCTGGCTCCTCTTTCCC<br>CAGCTTCTGTCTGTCTCACTGTCTTCCCTCCCCTCCCCCAGCTGAGGTGTGGCCCTCAGGCCTGG<br>TGCTGCCTTGGAGGGCTGGGGGAAGGAGTGTGTGGAGGAGGGAGGAGGGTGAAGACTGAGGCT<br>AGGTGCCAGAATGGACTGGAGTGAAGGCGTGTCTAGAGTGTGGGCTGGCTGTTGTGCTGGAAA<br>GCTGGGGACAGGTTGATGGTAATAAACTGCTCAATGACCAGTGCTTCAGGCTCCAGAGCTCTTTG<br>GAGAGATGGGTTGGGGCAGCTTACTCCAGCCCTGGCCCAAGGAGGCCCAGAAGTTGGAAAGAGA<br>TGGAATGTGGCTGGGAACATTGCATCCCAAAGAGCTTCTCAGTGGAGGAGGCTGGGGAAGGCAT<br>GAGGGGGCTCAGAGGCTCCTTGACTGGGACCAGGATTGGGGGCCAGGGCTTGAGTAGGCCTCT<br>CCACTCTCCTCCTTGGGGGTCCAGATTCCTTAGGAGCTTTGGGATGAGGCCCAGGAGGCTGCATT<br>TTTCCAGGTCCTTAGTCTTGCCACCACACAGATGATTCTGATTCATAGCCAAGATGAGGACACACT |

TABLE 1-continued cDNA and protein sequences of human NFATC4 isoforms 1 to 7.

GATGTAGCTGATCTCTCATTTACAGAGGAGGATTCTAAAGTTCAGAGAGGGAAAGGGGCTTGCCT
GAGGTCACGTAGATAATCAGCAGCACATTGAACGCTGCACTCCTGGGCTCCTGTCCCCAGCCCCC
ATTCAGACACGCTGACTCAGGAGGTCCAGGCCTCTAAGGCTTCTCTCCCTGGAGTGAGGGTGGA
GGTGAGGGAGAGCTGGCACAAGCCCTCCCTCTGGATCCTCCACTCCTGGGGATTATGAAGATATT
CTGGAAAGATTTGTGCTTCAGAGGTAGACTGCAGAAAGCAAACAGTCTACCCAGCAGCTCTGAAT
GTCACCTGCCCTGGGGCTTACAGCACTATATGAGTTCCTGGCCTATCCTGCAAATATGCCCATGC
TGGCCTTCTAAATAGCTGGTACATCCATCACCACTGACGGGCCTGGCCTGGAAACCTGGTTTGTC
CCCTGTCTTGATGGCCTACGAGAGGCCAAGTTCCACTGGGCTGGGAAAAGTCACTTTGTCTGTCT
TGTTCACCTGGAGCCTGACACACCGTAGGTACTGAGTACAAATAGCTTGATTTGGCTAGGCTTGG
CTGCAGGGGGACGTGCCTAAAAGACATTCCGGGCATTTGCACTTGGGAAACTTGCCTCACCTTCA
GGCTTGTGGGGCCTCTCTATGCCCAATGAGTCCAGGCAGTCCTAGCAAGTACTCAGGAGAGCAG
GGGTGGGTGTGACAGAGGCTGGCTCTGGATTGGGGGACAACAGAACCAGAGTAACTCCTCGCCT
GTTGCTGCTTTGCAATGAATTTCCTTTACCTTTCTGGAACACAAGCTGCTGTGAACCAAACTGATA
TCAAGTGATTAGCTCACCGGGCCTTGGTTGCTTTTCAAAGATCCCCTTCAGCCCCCTGCCAGAGT
CACTGCCCCATAATCACCATGTCAGAAGGGACCCTAGGGCATTCGTGTCCTATTTATCAATCTTCA
GCACCACCTCTAAGATCTCTGAGAGAGGGTGGATCAGCCTCTGTGTAAACAAAAAGCTGTTAGGA
CTTGTTGCCTCTCAAGGTGGACTATTCTGTTTTCTGCCAGGACACTGCCATTCATGCATTGTCAGA
TATTTATTAAACAGCAGCAAAGTGCCAGCCAATTTGTCCTGGAGGAATTCATAGCCTCATGGGGC
AAAAGTAAATAAACAGCTTATTACAATTCAACAAAAAAAAAAAAAAAAAAAAAAAAAAAAAAAAAA
AAAAAAAAAAAAAA (NCBI Reference Sequence: NM_001198967.2; SEQ ID NO: 9)

Protein MITTLPSLLPASLASISHRVTNLPSNSLSHNPGLSKPDFPGNSSPGLPSSSSPGRDLGAPAGSMGAASCEDE
ELEFKLVFGEEKEAPPLGAGGLGEELDSEDAPPCCRLALGEPPPYGAAPIGIPRPPPPRPGMHSPPPRPA
PSPGTWESQPARSVRLGGPGGGAGGAGGGRVLECPSIRITSISPTPEPPAALEDNPDAWGDGSPRDYPP
PEGFGGYREAGGQGGGAFFSPSPGSSSLSSWSFFSDASDEAALYAACDEVESELNEAASRFGLGSPLPSP
RASPRPWTPEDPWSLYGPSPGGRGPEDSWLLLSAPGPTPASPRPASPCGKRRYSSSGTPSSASPALSRR
GSLGEEGSEPPPPPPLPLARDPGSPGPFDYVGAPPAESIPQKTRRTSSEQAVALPRSEEPASCNGKLPLG
AEESVAPPGGSRKEVAGMDYLAVPSPLAWSKARIGGHSPIFRTSALPPLDWPLPSQYEQLELRIEVQPRA
HHRAHYETEGSRGAVKAAPGGHPVVKLLGYSEKPLTLQMFIGTADERNLRPHAFYQVHRITGKMVATA
SYEAVVSGTKVLEMTLLPENNMAANIDCAGILKLRNSDIELRKGETDIGRKNTRVRLVFRVHVPQGGGKV
VSVQAASVPIECSQRSAQELPQVEAYSPSACSVRGGEELVLTGSNFLPDSKVVFIERGPDGKLQWEEEAT
VNRLQSNEVTLTLTVPEYSNKRVSRPVQVYFYVSNGRRKRSPTQSFRFLPVICKEEPLPDSSLRGFPSASA
TPFGTDMDFSPPRPPYPSYPHEDPACETPYLSEGFGYGMPPLYPQTGPPPSYRPGLRMFPETRGTTVSEI
IGRDLSGFPAPPGEEPPA (NCBI Reference Sequence: NP_001185896.1; SEQ ID NO: 10, 857 amino acids)

Isoform 6

(This variant (6) lacks part of the 5' coding region, contains an alternate 5'-terminal exon, and initiates translation from an alternate start codon, compared to variant 1. The encoded isoform (6) has a shorter and distinct N-terminus, compared to isoform 1)

cDNA ATGTGTGAGTCGCCCCCAGTCCAGCCCAGTGCCTCAAGAAACACGCCTCCAGGCCCAGCCCCAGC
TCCAGCCCCTCTGGACCCACCTCTCTCACCTTAAGACCCACTGGATCGGGTACCCTCGGTCCTAG
GATCCAGGGGCCAGTGGGCAAAGGCCTGGCATGCCTGCTTCAATCTCCTCCATCTTCCCAGGTCC
AACTCTGCTTTTGTCTTGTGGCTCAGAAGAACTGGACTCAGAGGATGCCCCGCCATGCTGCCGTC
TGGCCTTGGGAGAGCCCCCTCCCTATGGCGCTGCACCTATCGGTATTCCCCGACCTCCACCCCCT
CGGCCTGGCATGCATTCGCCACCGCCGCGACCAGCCCCCTCACCTGGCACCTGGGAGAGCCAGCC
CGCCAGGTCGGTGAGGCTGGGAGGACCAGGAGGGGGTGCTGGGGGTGCTGGGGGTGGCCGTG
TTCTCGAGTGTCCCAGCATCCGCATCACCTCCATCTCTCCCACGCCGGAGCCGCCAGCAGCGCTG
GAGGACAACCCTGATGCCTGGGGGGACGGCTCTCCTAGAGATTACCCCCCACCAGAAGGCTTTG
GGGGCTACAGAGAAGCAGGGGGCCAGGGTGGGGGGGCCTTCTTCAGCCCAAGCCCTGGCAGCA
GCAGCCTGTCCTCGTGGAGCTTCTTCTCCGATGCCTCTGACGAGGCAGCCCTGTATGCAGCCTGC
GACGAGGTGGAGTCTGAGCTAAATGAGGCGGCCTCCCGCTTTGGCCTGGGCTCCCCGCTGCCCT
CGCCCCGGGCCTCCCCTCGGCCATGGACCCCCGAAGATCCCTGGAGCCTGTATGGTCCAAGCCCC
GGAGGCCGAGGGCCAGAGGATAGCTGGCTACTCCTCAGTGCTCCTGGGCCCACCCCAGCCTCCC
CGCGGCCTGCCTCTCCATGTGGCAAGCGGCGCTATTCCAGCTCGGGAACCCCATCTTCAGCCTCC
CCAGCTCTGTCCCGCCGTGGCAGCCTGGGGGAAGAGGGGTCTGAGCCACCTCCACCACCCCCAT
TGCCTCTGGCCCGGGACCCGGGCTCCCCTGGTCCCTTTGACTATGTGGGGGCCCCACCAGCTGA
GAGCATCCCTCAGAAGACACGGCGGACTTCCAGCGAGCAGGCAGTGGCTCTGCCTCGGTCTGAG
GAGCCTGCCTCATGCAATGGGAAGCTGCCCTTGGGAGCAGAGGAGTCTGTGGCTCCTCCAGGAG
GTTCCCGGAAGGAGGTGGCTGGCATGGACTACCTGGCAGTGCCCTCCCCACTCGCTTGGTCCAA
GGCCCGGATTGGGGGACACAGCCCTATCTTCAGGACCTCTGCCCTACCCCCACTGGACTGGCCTC
TGCCCAGCCAATATGAGCAGCTGGAGCTGAGGATCGAGGTACAGCCTAGAGCCCACCACCGGGC
CCACTATGAGACAGAAGGCAGCCGTGGAGCTGTCAAAGCTGCCCCTGGCGGTCACCCCGTAGTCA
AGCTCCTAGGCTACAGTGAGAAGCCACTGACCCTACAGATGTTCATCGGCACTGCAGATGAAAGG
AACCTGCGGCCTCATGCCTTCTATCAGGTGCACCGTATCACAGGCAAGATGGTGGCCACGGCCAG
CTATGAAGCCGTAGTCAGTGGCACCAAGGTGTTGGAGATGACTCTGCTGCCTGAGAACAACATGG
CGGCCAACATTGACTGCGCGGGAATCCTGAAGCTTCGGAATTCAGACATTGAGCTTCGGAAGGGT
GAGACGGACATCGGGCGCAAAAACACACGTGTACGGCTGGTGTTCCGGGTACACGTGCCCCAGG
GCGGCGGGAAGGTCGTCTCAGTACAGGCAGCATCGGTGCCCATCGAGTGCTCCCAGCGCTCAGC
CCAGGAGCTGCCCCAGGTGGAGGCCTACAGCCCCAGTGCCTGCTCTGTGAGAGGAGGCGAGGAA
CTGGTACTGACTGGCTCCAACTTCCTGCCAGACTCCAAGGTGGTGTTCATTGAGAGGGGTCCTGA
TGGGAAGCTGCAATGGGAGGAGGAGGCCACAGTGAACCGACTGCAGAGCAACGAGGTGACGCTG
ACCCTGACTGTCCCCGAGTACAGCAACAAGAGGGTTTCCCGGCCAGTCCAGGTCTACTTTTATGT
CTCCAATGGGCGGAGGAAACGCAGTCCTACCCAGAGTTTCAGGTTTCTGCCTGTGATCTGCAAAG
AGGAGCCCCTACCGGACTCATCTCTGCGGGGTTTCCCTTCAGCATCGGCAACCCCCTTTGGCACT
GACATGGACTTCTCACCACCCAGGCCCCCCTACCCCTCCTATCCCCATGAAGACCCTGCTTGCGAA
ACTCCTTACCTATCAGAAGGCTTCGGCTATGGCATGCCCCCTCTGTACCCCCAGACGGGGCCCCC

TABLE 1-continued

| cDNA and protein sequences of human NFATC4 isoforms 1 to 7. | |
|---|---|
| | ACCATCCTACAGACCGGGCCTGCGGATGTTCCCTGAGACTAGGGGTACCACAGGTTGTGCCCAAC CACCTGCAGTTTCCTTCCTTCCCCGCCCCTTCCCTAGTGACCCGTATGGAGGGCGGGGCTCCTCT TTCTCCCTGGGGCTGCCATTCTCTCCGCCAGCCCCCTTTCGGCCGCCTCCTCTTCCTGCATCCCCA CCGCTTGAAGGCCCCTTCCCTTCCCAGAGTGATGTGCATCCCCTACCTGCTGAGGGATACAATAA GGTAGGGCCAGGCTATGGCCCTGGGGAGGGGGCTCCGGAGCAGGAGAAATCCAGGGGTGGCTA CAGCAGCGGCTTCCGAGACAGTGTCCCTATCCAGGGTATCACGCTGGAGGAAGGTGGGTGTGGG ACTGGGGGCTGTGAGTGTGAGTGTGTGCAAGAGATTGCTCTGCATGTTTGCTGAGGGCTGGAGC TGGGCTTTTCAGAGATCGGGCATCCCTGGTCTCTCAGGGCCAGTTGGAGGTTCCCAGGAGGCAT GTTCTTGATGCCTGTGGCTGCCTGAATCCAATTAACTGAATTCTGAAGAGTGCATGGGGTAACTG TCTCAGCCTTTCTCCTGTCTCTGCCTCTGTCCTCTGCTCCAAATCATAAAATCTCAGAGCTAGAAG CACTTTCAAGATCATTCCATCCAGCGCATTCAATTTGCAAGTTTAGGCGTTGAGTTCCAGAGAGG GATGGTAGCTTGCTGAGGTCCCAGTCAAGCACACTTGCCATTGCCTCAGCTTTCCCCTAAACACG GTGTCTGTGGTCAGGGTTGGTGAGGAGGAGCTTTCCTGTTTTGCCTCTCCTTCTTCCCATTGGCT ACACCCATCTCTGGCCCTGCTGATACCGATTCCCCTGACATTTCAGGCTAAGCCAGCAGGAAAGG GCTAGGACGGGTGCCTGGGAGCCCACATGGAGGGAGTTGGGCAAGATTTGATTCGGAGCAGGT GTCAAGACGTGTTGGGGAAACTGAGGCCCAGTGGAATAGAAGCCAGTAGAGGAGGAATCTAGAG GCCTCCTAGATTAAGACCTGCCTGGAATGGATTGGGGGTGGGTCTTTGGAAAAGGAGGGGACCC ACCTCTAGCCCAGTCTCTCAACTGCCCCTCCCTTTACAGTGAGTGAGATCATTGGCCGAGACCTGA GTGGCTTCCCTGCACCTCCTGGAGAAGAGCCTCCTGCCTGAACCACGTGAACTGTCATCACCTGG CAACCCCAGCCCCAGCCTCAGCCCTGCCCCCTTTCCCTCCTTCCTGGAGTGGTGGCTACAGAAGC TTGGGGCCAACCCTGGCTCCTCTTTCCCCAGCTTCTGTCTGTCTCACTGTCTTCCCTCCCCTCCCC CAGCTGAGGTGTGGCCCTCAGGCCTGGTGCTGCCTTGGAGGGCTGGGGGAAGGAGTGTGTGGA GGAGGGAGGAGGGTGAAGACTGAGGCTAGGTGCCAGAATGGACTGGAGTGAAGGCGTGTCTAG AGTGTGGGCTGGCTGTTGTGCTGGAAAGCTGGGGACAGGTTGATGGTAATAAACTGCTCAATGA CCAGTGCTTCAGGCTCCAGAGCTCTTTGGAGAGATGGGTTGGGGCAGCTTACTCCAGCCCTGGC CCAAGGAGGCCCAGAAGTTGGAAAGAGATGGAATGTGGCTGGGAACATTGCATCCCAAAGAGCT TCTCAGTGGAGGAGGCTGGGGAAGGCATGAGGGGGCTCAGAGGCTCCTTGACTGGGACCAGGA TTGGGGGCCAGGGCTTGAGTAGGCCTCTCCACTCTCCTCCTTGGGGGTCCAGATTCCTTAGGAG CTTTGGGATGAGGCCCAGGAGGCTGCATTTTTCCAGGTCCTTAGTCTTGCCACCACACAGATGAT TCTGATTCATAGCCAAGATGAGGACACACTGATGTAGCTGATCTCTCATTTACAGAGGAGGATTC TAAAGTTCAGAGAGGGAAAGGGGCTTGCCTGAGGTCACGTAGATAATCAGCAGCACATTGAACGC TGCACTCCTGGGCTCCTGTCCCCAGCCCCCATTCAGACACGCTGACTCAGGAGGTCCAGGCCTCT AAGGCTTCTCTCCCTGGAGTGAGGGTGGAGGTGAGGGAGAGCTGGCACAAGCCCTCCCTCTGGA TCCTCCACTCCTGGGGATTATGAAGATATTCTGGAAAGATTTGTGCTTCAGAGGTAGACTGCAGA AAGCAAACAGTCTACCCAGCAGCTCTGAATGTCACCTGCCCTGGGGCTTACAGCACTATATGAGT TCCTGGCCTATCCTGCAAATATGCCCATGCTGGCCTTCTAAATAGCTGGTACATCCATCACCACTG ACGGGCCTGGCCTGGAAACCTGGTTTGTCCCCTGTCTTGATGGCCTACGAGAGGCCAAGTTCCAC TGGGCTGGGAAAAGTCACTTTGTCTGTCTTGTTCACCTGGAGCCTGACACACCGTAGGTACTGAG TACAAATAGCTTGATTTGGCTAGGCTTGGCTGCAGGGGGACGTGCCTAAAAGACATTCCGGGCAT TTGCACTTGGGAAACTTGCCTCACCTTCAGGCTTGTGGGGCCTCTCTATGCCCAATGAGTCCAGG CAGTCCTAGCAAGTACTCAGGAGAGCAGGGGTGGGTGTGACAGAGGCTGGCTCTGGATTGGGG GACAACAGAACCAGAGTAACTCCTCGCCTGTTGCTGCTTTGCAATGAATTTCCTTTACCTTTCTGG AACACAAGCTGCTGTGAACCAAACTGATATCAAGTGATTAGCTCACCGGGCCTTGGTTGCTTTTC AAAGATCCCCTTCAGCCCCCTGCCAGAGTCACTGCCCCATAATCACCATGTCAGAAGGGACCCTAG GGCATTCGTGTCCTATTTATCAATCTTCAGCACCACCTCTAAGATCTCTGAGAGAGGGTGGATCA GCCTCTGTGTAAACAAAAAGCTGTTAGGACTTGTTGCCTCTCAAGGTGGACTATTCTGTTTTCTG CCAGGACACTGCCATTCATGCATTGTCAGATATTTATTAAACAGCAGCAAAGTGCCAGCCAATTTG TCCTGGAGGAATTCATAGCCTCATGGGGCAAAAGTAAATAAACAGCTTATTACAATTCAACAAAAA AAAAAAAAAAAAAAAAAAAAAAAAAAAAAAAAAAAAAAAAAAAA (NCBI Reference Sequence: NM_001288802.1; SEQ ID NO: 11) |
| Protein | MPASISSIFPGPTLLLSCGSEELDSEDAPPCCRLALGEPPPYGAAPIGIPRPPPPRPGMHSPPPRPAPSPGT WESQPARSVRLGGPGGGAGGAGGRVLECPSIRITSISPTPEPPAALEDNPDAWGDGSPRDYPPPEGFG GYREAGGQGGGAFFSPSPGSSSLSSWSFFSDASDEAALYAACDEVESELNEAASRFGLGSPLPSPRASPR PWTPEDPWSLYGPSPGGRGPEDSWLLLSAPGPTPASPRPASPCGKRRYSSSGTPSSASPALSRRGSLGE EGSEPPPPPPLPLARDPGSPGPFDYVGAPPAESIPQKTRRTSSEQAVALPRSEEPASCNGKLPLGAEESVA PPGGSRKEVAGMDYLAVPSPLAWSKARIGGHSPIFRTSALPPLDWPLPSQYEQLELRIEVQPRAHHRAHY ETEGSRGAVKAAPGGHPVVKLLGYSEKPLTLQMFIGTADERNLRPHAFYQVHRITGKMVATASYEAVVS GTKVLEMTLLPENNMAANIDCAGILKLRNSDIELRKGETDIGRKNTRVRLVFRVHVPQGGGKVVSVQAAS VPIECSQRSAQELPQVEAYSPSACSVRGGEELVLTGSNFLPDSKVVFIERGPDGKLQWEEEATVNRLQSN EVTLTLTVPEYSNKRVSRPVQVYFYVSNGRRKRSPTQSFRFLPVICKEEPLPDSSLRGFPSASATPFGTDM DFSPPRPPYPSYPHEDPACETPYLSEGFGYGMPPLYPQTGPPPSYRPGLRMFPETRGTTGCAQPPAVSF LPRPFPSDPYGGRGSSFSLGLPFSPPAPFRPPPLPASPPLEGPFPSQSDVHPLPAEGYNKVGPGYGPGEG APEQEKSRGGYSSGFRDSVPIQGITLEEGGCGTGGCECECVQEIALHVC (NCBI Reference Sequence: NP_001275731.1; SEQ ID NO: 12, 889 amino acids) |

Isoform 7

(This variant (7) is alternatively spliced at the 3' end compared to transcript variant 1. This results in translation termination at a downstream stop codon, and a longer isoform (7) with a distinct C-terminus compared to isoform 1)

| | |
|---|---|
| cDNA | GTAAACGTCTGACCTGGGGCCGTCGCTTAACCGTTTAGTTGCTGGGATGGGGCGGCGTTGGGGG TGCGGCCCTGAACCGGAGGGATTTAGAGACTGGAGACGCGGCCTCTAAGAGAGGTTGAAACTGT GTGTGTGTGGGAGAAAATGATAACCACCCTCCCATCTCTCCTACCCGCCAGCCTCGCCAGTATCT CCCACCGAGTCACGAATCTCCCATCTAACTCCCTCTCACACAACCCAGGCCTCTCCAAGCCTGACT TTCCCGGAAACTCCAGTCCAGGTCTTCCTTCCTCCTCCAGCCCAGGCCGGGACCTGGGGGCTCCT GCCGGATCCATGGGGGCGGCCAGCTGCGAGGATGAGGAGCTGGAATTTAAGCTGGTGTTCGGG GAGGAAAAGGAGGCCCCCCCGCTGGGCGCGGGGGGATTGGGGGAAGAACTGGACTCAGAGGAT |

TABLE 1-continued cDNA and protein sequences of human NFATC4 isoforms 1 to 7.

GCCCCGCCATGCTGCCGTCTGGCCTTGGGAGAGCCCCCTCCCTATGGCGCTGCACCTATCGGTAT
TCCCCGACCTCCACCCCCTCGGCCTGGCATGCATTCGCCACCGCCGCGACCAGCCCCCTCACCTG
GCACCTGGGAGAGCCAGCCCGCCAGGTCGGTGAGGCTGGGAGGACCAGGAGGGGGTGCTGGGG
GTGCTGGGGGTGGCCGTGTTCTCGAGTGTCCCAGCATCCGCATCACCTCCATCTCTCCCACGCCG
GAGCCGCCAGCAGCGCTGGAGGACAACCCTGATGCCTGGGGGGACGGCTCTCCTAGAGATTACC
CCCCACCAGAAGGCTTTGGGGGCTACAGAGAAGCAGGGGGCCAGGGTGGGGGGGCCTTCTTCA
GCCCAAGCCCTGGCAGCAGCAGCCTGTCCTCGTGGAGCTTCTTCTCCGATGCCTCTGACGAGGCA
GCCCTGTATGCAGCCTGCGACGAGGTGGAGTCTGAGCTAAATGAGGCGGCCTCCCGCTTTGGCC
TGGGCTCCCCGCTGCCCTCGCCCCGGGCCTCCCCTCGGCCATGGACCCCCGAAGATCCCTGGAGC
CTGTATGGTCCAAGCCCCGGAGGCCGAGGGCCAGAGGATAGCTGGCTACTCCTCAGTGCTCCTG
GGCCCACCCCAGCCTCCCCGCGGCCTGCCTCTCCATGTGGCAAGCGGCGCTATTCCAGCTCGGGA
ACCCCATCTTCAGCCTCCCCAGCTCTGTCCCGCCGTGGCAGCCTGGGGGAAGAGGGGTCTGAGC
CACCTCCACCACCCCCATTGCCTCTGGCCCGGGACCCGGGCTCCCCTGGTCCCTTTGACTATGTG
GGGGCCCCACCAGCTGAGAGCATCCCTCAGAAGACACGGCGGACTTCCAGCGAGCAGGCAGTGG
CTCTGCCTCGGTCTGAGGAGCCTGCCTCATGCAATGGGAAGCTGCCCTTGGGAGCAGAGGAGTC
TGTGGCTCCTCCAGGAGGTTCCCGGAAGGAGGTGGCTGGCATGGACTACCTGGCAGTGCCCTCC
CCACTCGCTTGGTCCAAGGCCCGGATTGGGGGACACAGCCCTATCTTCAGGACCTCTGCCCTACC
CCCACTGGACTGGCCTCTGCCCAGCCAATATGAGCAGCTGGAGCTGAGGATCGAGGTACAGCCTA
GAGCCCACCACCGGGCCCACTATGAGACAGAAGGCAGCCGTGGAGCTGTCAAAGCTGCCCCTGG
CGGTCACCCCGTAGTCAAGCTCCTAGGCTACAGTGAGAAGCCACTGACCCTACAGATGTTCATCG
GCACTGCAGATGAAAGGAACCTGCGGCCTCATGCCTTCTATCAGGTGCACCGTATCACAGGCAAG
ATGGTGGCCACGGCCAGCTATGAAGCCGTAGTCAGTGGCACCAAGGTGTTGGAGATGACTCTGC
TGCCTGAGAACAACATGGCGGCCAACATTGACTGCGCGGGAATCCTGAAGCTTCGGAATTCAGAC
ATTGAGCTTCGGAAGGGTGAGACGGACATCGGGCGCAAAAACACACGTGTACGGCTGGTGTTCC
GGGTACACGTGCCCCAGGGCGGCGGGAAGGTCGTCTCAGTACAGGCAGCATCGGTGCCCATCGA
GTGCTCCCAGCGCTCAGCCCAGGAGCTGCCCCAGGTGGAGGCCTACAGCCCCAGTGCCTGCTCT
GTGAGAGGAGGCGAGGAACTGGTACTGACTGGCTCCAACTTCCTGCCAGACTCCAAGGTGGTGT
TCATTGAGAGGGGTCCTGATGGGAAGCTGCAATGGGAGGAGGAGGCCACAGTGAACCGACTGCA
GAGCAACGAGGTGACGCTGACCCTGACTGTCCCCGAGTACAGCAACAAGAGGGTTTCCCGGCCA
GTCCAGGTCTACTTTTATGTCTCCAATGGGCGGAGGAAACGCAGTCCTACCCAGAGTTTCAGGTT
TCTGCCTGTGATCTGCAAAGAGGAGCCCCTACCGGACTCATCTCTGCGGGGTTTCCCTTCAGCAT
CGGCAACCCCCTTTGGCACTGACATGGACTTCTCACCACCCAGGCCCCCCTACCCCTCCTATCCCC
ATGAAGACCCTGCTTGCGAAACTCCTTACCTATCAGAAGGCTTCGGCTATGGCATGCCCCCTCTG
TACCCCCAGACGGGGCCCCCACCATCCTACAGACCGGGCCTGCGGATGTTCCCTGAGACTAGGG
GTACCACAGGTTGTGCCCAACCACCTGCAGTTTCCTTCCTTCCCCGCCCCTTCCCTAGTGACCCGT
ATGGAGGGCGGGGCTCCTCTTTCTCCCTGGGGCTGCCATTCTCTCCGCCAGCCCCCTTTCGGCCG
CCTCCTCTTCCTGCATCCCCACCGCTTGAAGGCCCCTTCCCTTCCCAGAGTGATGTGCATCCCCTA
CCTGCTGAGGGATACAATAAGGTAGGGCCAGGCTATGGCCCTGGGGAGGGGGCTCCGGAGCAG
GAGAAATCCAGGGGTGGCTACAGCAGCGGCTTCCGAGACAGTGTCCCTATCCAGGGTATCACGC
TGGAGGAAGTGAGTGAGATCATTGGCCGAGACCTGAGTGGCTTCCCTGCACCTCCTGGAGAAGA
GCCTCCTGCCTGAACCACGTGAACTGTCATCACCTGGCAACCCCAGCCCCAGCCTCAGCCCTGCC
CCCTTTCCCTCCTTCCTGGAGTGGTGGCTACAGAAGCTTGGGGCCAACCCTGGCTCCTCTTTCCC
CAGCTTCTGTCTGTCTCACTGTCTTCCCTCCCCTCCCCCAGCTGAGGTGTGGCCCTCAGGCCTGG
TGCTGCCTTGGAGGGCTGGGGGAAGGAGTGTGTGGAGGAGGGAGGAGGGTGAAGACTGAGGCT
AGGTGCCAGAATGGACTGGAGTGAAGGCGTGTCTAGAGTGTGGGCTGGCTGTTGTGCTGGAAA
GCTGGGGACAGGTTGATGGTAATAAACTGCTCAATGACCAGTGCTTCAGGCTCCAGAGCTCTTTG
GAGAGATGGGTTGGGGCAGCTTACTCCAGCCCTGGCCCAAGGAGGCCCAGAAGTTGGAAAGAGA
TGGAATGTGGCTGGGAACATTGCATCCCAAAGAGCTTCTCAGTGGAGGAGGCTGGGGAAGGCAT
GAGGGGGCTCAGAGGCTCCTTGACTGGGACCAGGATTGGGGGCCAGGGCTTGAGTAGGCCTCT
CCACTCTCCTCCTTGGGGGTCCAGATTCCTTAGGAGCTTTGGGATGAGGCCCAGGAGGCTGCATT
TTTCCAGGTCCTTAGTCTTGCCACCACACAGATGATTCTGATTCATAGCCAAGATGAGGACACACT
GATGTAGCTGATCTCTCATTTACAGAGGAGGATTCTAAAGTTCAGAGAGGGAAAGGGGCTTGCCT
GAGGTCACGTAGATAATCAGCAGCACATTGAACGCTGCACTCCTGGGCTCCTGTCCCCAGCCCCC
ATTCAGACACGCTGACTCAGGAGGTCCAGGCCTCTAAGGCTTCTCTCCCTGGAGTGAGGGTGGA
GGTGAGGGAGAGCTGGCACAAGCCCTCCCTCTGGATCCTCCACTCCTGGGGATTATGAAGATATT
CTGGAAAGATTTGTGCTTCAGAGGTAGACTGCAGAAAGCAAACAGTCTACCCAGCAGCTCTGAAT
GTCACCTGCCCTGGGGCTTACAGCACTATATGAGTTCCTGGCCTATCCTGCAAATATGCCCATGC
TGGCCTTCTAAATAGCTGGTACATCCATCACCACTGACGGGCCTGGCCTGGAAACCTGGTTTGTC
CCCTGTCTTGATGGCCTACGAGAGGCCAAGTTCCACTGGGCTGGGAAAAGTCACTTTGTCTGTCT
TGTTCACCTGGAGCCTGACACACCGTAGGTACTGAGTACAAATAGCTTGATTTGGCTAGGCTTGG
CTGCAGGGGGACGTGCCTAAAAGACATTCCGGGCATTTGCACTTGGGAAACTTGCCTCACCTTCA
GGCTTGTGGGGCCTCTCTATGCCCAATGAGTCCAGGCAGTCCTAGCAAGTACTCAGGAGAGCAG
GGGTGGGTGTGACAGAGGCTGGCTCTGGATTGGGGGACAACAGAACCAGAGTAACTCCTCGCCT
GTTGCTGCTTTGCAATGAATTTCCTTTACCTTTCTGGAACACAAGCTGCTGTGAACCAAACTGATA
TCAAGTGATTAGCTCACCGGGCCTTGGTTGCTTTTCAAAGATCCCCTTCAGCCCCCTGCCAGAGT
CACTGCCCCATAATCACCATGTCAGAAGGGACCCTAGGGCATTCGTGTCCTATTTATCAATCTTCA
GCACCACCTCTAAGATCTCTGAGAGAGGGTGGATCAGCCTCTGTGTAAACAAAAAGCTGTTAGGA
CTTGTTGCCTCTCAAGGTGGACTATTCTGTTTTCTGCCAGGACACTGCCATTCATGCATTGTCAGA
TATTTATTAAACAGCAGCAAAGTGCCAGCCAATTTGTCCTGGAGGAATTCATAGCCTCATGGGGC
AAAAGTAAATAAACAGCTTATTACAATTCAACAAAAAAAAAAAAAAAAAAAAAAAAAAAAAAAAAAA
AAAAAAAAAAAAAA (NCBI Reference Sequence: NM_001320043.1; SEQ ID NO: 13)

Protein MITTLPSLLPASLASISHRVTNLPSNSLSHNPGLSKPDFPGNSSPGLPSSSSPGRDLGAPAGSMGAASCEDE
ELEFKLVFGEEKEAPPLGAGGLGEELDSEDAPPCCRLALGEPPPYGAAPIGIPRPPPPRPGMHSPPPRPA
PSPGTWESQPARSVRLGGPGGGAGGAGGGRVLECPSIRITSISPTPEPPAALEDNPDAWGDGSPRDYPP
PEGFGGYREAGGQGGGAFFSPSPGSSSLSSWSFFSDASDEAALYAACDEVESELNEAASRFGLGSPLPSP
RASPRPWTPEDPWSLYGPSPGGRGPEDSWLLLSAPGPTPASPRPASPCGKRRYSSSGTPSSASPALSRR
GSLGEEGSEPPPPPPLPLARDPGSPGPFDYVGAPPAESIPQKTRRTSSEQAVALPRSEEPASCNGKLPLG TABLE 1-continued

| cDNA and protein sequences of human NFATC4 isoforms 1 to 7. |
|---|
| AEESVAPPGGSRKEVAGMDYLAVPSPLAWSKARIGGHSPIFRTSALPPLDWPLPSQYEQLELRIEVQPRA HHRAHYETEGSRGAVKAAPGGHPVVKLLGYSEKPLTLQMFIGTADERNLRPHAFYQVHRITGKMVATA SYEAVVSGTKVLEMTLLPENNMAANIDCAGILKLRNSDIELRKGETDIGRKNTRVRLVFRVHVPQGGGKV VSVQAASVPIECSQRSAQELPQVEAYSPSACSVRGGEELVLTGSNFLPDSKVVFIERGPDGKLQWEEEAT VNRLQSNEVTLTLTVPEYSNKRVSRPVQVYFYVSNGRRKRSPTQSFRFLPVICKEEPLPDSSLRGFPSASA TPFGTDMDFSPPRPPYPSYPHEDPACETPYLSEGFGYGMPPLYPQTGPPPSYRPGLRMFPETRGTTGCA QPPAVSFLPRPFPSDPYGGRGSSFSLGLPFSPPAPFRPPPLPASPPLEGPFPSQSDVHPLPAEGYNKVGP GYGPGEGAPEQEKSRGGYSSGFRDSVPIQGITLEEVSEIIGRDLSGFPAPPGEEPPA (NCBI Reference Sequence: NP_001306972.1; SEQ ID NO: 14, 965 amino acids) |

As explained above, all isoforms of NFATC4 are included in the definition of NFATC4 in the context of the present invention. However, in a preferred embodiment, cells secreting SEV present in the composition for use according to the invention express isoform 2 of NFATC4 disclosed in Table 1 above, a 902 amino acids protein (SEQ ID NO:4), or variants thereof. Other preferred isoforms are isoforms 4 (SEQ ID NO:8, 832 amino acids) and 7 (SEQ ID NO:14, 965 amino acids) disclosed in Table 1 above, because these isoforms share with isoform 2 the sequence of variant "ΔNFATC4" described below, and because SEV of cells expressing ΔNFATC4 have been shown by the inventors as highly efficient.

In the context of the present invention, not only all isoforms of NFATC4 are included in the definition of NFATC4, but also all variants maintaining the function of NFATC4 or with increased function compared to native NFATC4. These notably include allelic variants.

A variant of particular interest is ΔNFATC4, which corresponds to isoform 2 of NFATC4 disclosed in Table 1 above, truncated of its 521 N-terminal amino acids (see Rescued NF-AT3 in FIG. 1A of Molkentin et al. (1998). Cell 93: 215-228):

ΔNFATC4 amino acid sequence is presented below:

DCAGILKLRNSDIELRKGETDIGRKNTRVRLVFRVHVPQGGGKVVSVQAA

SVPIECSQRSAQELPQVEAYSPSACSVRGGEELVLTGSNFLPDSKVVFIE

RGPDGKLQWEEEATVNRLQSNEVTLTLTVPEYSNKRVSRPVQVYFYVSNG

RRKRSPTQSFRFLPVICKEEPLPDSSLRGFPSASATPFGTDMDFSPPRPP

YPSYPHEDPACETPYLSEGFGYGMPPLYPQTGPPPSYRPGLRMFPETRGT

TGCAQPPAVSFLPRPFPSDPYGGRGSSFSLGLPFSPPAPFRPPPLPASPP

LEGPFPSQSDVHPLPAEGYNKVGPGYGPGEGAPEQEKSRGGYSSGFRDSV

PIQGITLEEVSEIIGRDLSGFPAPPGEEPPA (SEQ ID NO: 15, 381 amino acids)

In the context of the invention, a composition comprising SEV of cells expressing any NFATC4 variant comprising ΔNFATC4 amino acid sequence (SEQ ID NO:15) may be used for the treatment of cancer or for the treatment or prevention of metastatic cancer.

When cells express a variant of NFATC4, said variant preferably comprises the 85 C-terminal amino acids of isoform 2 of NFATC4 disclosed in Table 1 above (which are the same as the 85 C-terminal amino acids of isoform 2 of ΔNFATC4).

Cells Expressing NFATC4

In the context of the invention, any cell expressing NFATC4 may be used for the preparation of SEV. Non-limitative examples of cells expressing NFATC4 include:

cancer cells with low invasive capacity, and any cells that have been induced to express NFATC4.

In a preferred embodiment of the invention, SEV of cells expressing NFATC4 have been purified from cancer cells with low invasive capacity. Indeed, such cancer cells generally express NFATC4.

In the present description, "invasive capacity" or "relative invasive capacity" refers to the ability of cancer cells to move through the extracellular matrix (ECM) into neighboring tissues in a process that involves ECM degradation and proteolysis. Invasive capacity of particular cancer cells may be tested in vitro or in vivo in invasion assays. In vitro invasion assays generally rely on the use of a natural or reconstituted matrix, which is applied over a filter (also referred to as a membrane) of suitable pore size (generally 5, 8, 10, or 12 μm) depending on the tested cancer cells, located above a medium comprising chemoattractants for the cancer cells to be tested. An invasion index may then be calculated based on the number of cells able to cross the matrix and the filter to reach the chemoattractive medium. The relative invasive capacity is calculated as the ratio of the number of invasive cells relative to the number of known low (such as T47D, MCF7) or high (such as MDA-MB-231, SUM159PT) invasive cells in the same assay.

Various types of natural or reconstituted matrices may be used, including but not limited to natural matrix isolated from cells (such as "Matrigel", a gelatinous protein mixture secreted by Engelbreth-Holm-Swarm (EHS) mouse sarcoma cells), a collagen I or IV gel matrix, and a Laminin I gel matrix. The most common matrix used in in vitro invasion assays is Matrigel.

As explained above, the filter pore size should be adapted to the tested cell type, and is generally selected from 5, 8, 10, and 12 μm, depending on the cell type. For breast cancer cells, an 8-μm pore filter will generally be suitable.

Various chemoattractants may also be used in the chemoattractive medium, depending on the type of tested cells. A commonly used chemoattractant is conditioned NIH-3T3 medium.

The invasion level depends on various parameters, including the cell type, the type and thickness of the matrix, the duration of the assay, and the initial cell density over the filter. For defining the invasive capacity of a cell sample, reference cell samples of low or high invasive capacity should thus be tested in parallel with the new cell sample. The invasive capacity of the new cell sample is then assessed by comparison of its invasion index to the invasion index of reference cell samples.

For most types of cancers, cell lines of low or high invasive capacity have been defined in the prior art. In the context of the invention, cancer cells with low invasive capacity" refers to cancer cells having an invasion index in an in vitro invasion assay that is lower or equal to the invasion index of at least one cancer cell line of the same cellular type known as having low invasive capacity.

Examples of cancer cell lines of low or high invasive capacity are described in Table 2 below.

TABLE 2

Known cancer cell lines of low or high invasive capacity by cellular type.

| Cellular type | Cancer cell lines of low invasive capacity | Cancer cell lines of high invasive capacity |
|---|---|---|
| Breast cancer | breast cancer cells expressing the estrogen receptor α (ERA), such as human cell lines T-47D, MCF7, BT-474, ZR-75-1, and mouse cell line 67NR | breast cancer cells that do not express the estrogen receptor α (ERA), such as human cell lines MDA-MB-231 and SUM159PT, and mouse cell line 4T1 |
| Melanoma | SKmel23, WM164 | MV3, SKmel28, WM.266.4 |
| Pancreatic cancer | | BXPC3, AsPC-1 |
| Glioblastome | | U-87 MG |

In the case of breast cancer cells, breast cancer cells expressing the estrogen receptor a (ERA) generally have low invasive capacity, SEV of cells expressing NFATC4 may thus be purified from breast cancer cells expressing the estrogen receptor α (ERA).

Alternatively, SEV of cells expressing NFATC4 may have been purified from any other cells that have been induced to express NFATC4.

By "cells that have been induced to express NFATC4", it is meant cells that do or do not naturally express NFATC4 but that have been treated with at least one compound able to induce NFATC4 expression or to enhance NFATC4 activity in the cells. When the starting cells do not express NFATC4, then the treatment should be able to generate NFATC4 expression or to enhance NFATC4 activity in the starting cells. When the starting cells already express NFATC4, then the treatment should be able to increase NFATC4 expression or to enhance NFTAC4 activity in the starting cells.

Any type of starting cells may be used, including but not limited to:

cancer cells with low invasive capacity, as defined above, and healthy cells.

In both cases, either primary cells or cell lines may be used. The cellular type of starting cells is not particularly limited. For cancer cells with low invasive capacity, any type of cancer cells as described below may be used. In the case of healthy cells, any cellular type may be used, including fibroblasts, epithelial cells, HEK293 (Human Embryonic Kidney), dendritic cells, stem cells. By "healthy cells", it is meant cells that do not have a tumoral origin and come or are derived from normal tissue. In other words, healthy cells refer to either primary non-cancerous cells, or to cell lines derived from normal, healthy primary cells. In addition, both adherent and suspension cells may be used, although adherent cells are preferred.

For the treatment of a human patient, human cells (primary or cell lines, adherent or suspension, cancer cells with low invasive capacity or healthy cells) will preferably be used.

When healthy cells are used for induction of NFATC4 expression, in a preferred embodiment, said healthy cells are autologous cells (in particular autologous fibroblasts) from the patient to be treated. In another embodiment, said healthy cells are human embryonic cells, in particular HEK293T cells.

This indeed limits any immune response to the administered composition of SEV.

Any suitable mean for inducing NFATC4 expression may be used.

In a preferred embodiment, for induction of NFATC4 expression, cells have been transfected by an expression vector comprising a nucleic acid molecule encoding NFATC4. By "transfection", it is meant the process of deliberately introducing nucleic acids into cells by any suitable technology known to those skilled in the art. In particular, in the context of the invention, the term transfection is intended to include both viral and non-viral methods for introducing nucleic acids into cells.

An "expression vector" as used herein refers to a vector comprising a nucleic acid molecule encoding NFATC4 and elements necessary to allow expression thereof. In particular, the nucleic acid molecule encoding NFATC4 is operably linked to appropriate regulatory sequences.

As used herein, the term "regulatory elements" or "regulatory sequence" refers to any element that allows, contributes or modulates the expression of nucleic acid molecule(s) in a given host cell or subject, including replication, duplication, transcription, splicing, translation, stability and/or transport of the nucleic acid(s) or its derivative (i.e. mRNA). It will be appreciated by those skilled in the art that the choice of the regulatory sequences can depend on such factors as the vector itself and the cells to be transfected, and will be easily selected by those skilled in the art based on common general knowledge and publications on this topic. Suitable promoters for constitutive expression in eukaryotic systems include viral promoters, such as SV40 promoter, the cytomegalovirus (CMV) immediate early promoter or enhancer, the adenovirus early and late promoters, the thymidine kinase (TK) promoter of herpes simplex virus (HSV)-1 and retroviral long-terminal repeats (e.g. MoMuLV and Rous sarcoma virus (RSV) LTRs) as well as cellular promoters such as the phosphoglycero kinase (PGK) promoter. Examples of suitable promoters for a lentiviral vector include those present in pLVX-tdTomato-C1 Vector commercialized by Clontech.

The expression vector may notably be selected from plasmid and viral expression vectors. A "plasmid vector" as used herein refers to a replicable DNA construct. Representative examples of suitable plasmid vectors include, without limitation, pREP4, pCEP4 (Invitrogen), pCI (Promega), pVAX (Invitrogen) and pGWiz (Gene Therapy System Inc). For transfection, a plasmid vector may be complexed to lipids or polymers to form particulate structures such as liposomes, lipoplexes or nanoparticles.

The term "viral vector" as used herein refers to a nucleic acid vector that includes at least one element of a virus genome and may be packaged into a viral particle. The terms "virus", "virions", "viral particles" and "viral vector particle" are used interchangeably to refer to viral particles that are formed when the nucleic acid vector is transduced into an appropriate cell or cell line according to suitable conditions allowing the generation of viral particles. In the context of the present invention, the term "viral vector" has to be understood broadly as including nucleic acid vector (e.g. DNA viral vector) as well as viral particles generated thereof. The term "infectious" refers to the ability of a viral vector to infect and enter into a host cell or subject.

In a preferred embodiment, a viral expression vector comprising a nucleic acid molecule encoding NFATC4 is used.

Viral vectors can be replication-competent or -selective (e.g. engineered to replicate better or selectively in specific host cells), or can be genetically disabled so as to be replication-defective or replication-impaired. Typically, such vectors are commercially available (e.g. in Invitrogen, Stratagene, Amersham Biosciences, Promega, etc.) or available from depositary institutions such as the American Type Culture Collection (ATCC, Rockville, Md.) or have been the subject of numerous publications describing their sequence, organization and methods of producing, allowing the artisan to apply them.

Representative examples of suitable viral vectors are generated from a variety of different viruses (e.g. retrovirus, adenovirus, adenovirus-associated virus (AAV), poxvirus, herpes virus, measles virus, foamy virus, alphavirus, vesicular stomatis virus, etc). As described above, the term "viral vector" encompasses vector DNA, genomic DNA as well as viral particles generated thereof, and especially infectious viral particles.

In a preferred embodiment, a retroviral expression vector (and in particular a lentiviral expression vector) comprising a nucleic acid molecule encoding NFATC4 is used. Retroviruses have the property of infecting, and in most cases integrating into, dividing cells and in this regard are particularly appropriate for use in the context of the present invention for producing cells expressing high levels of NFATC4. A suitable retrovirus generally contains the LTR sequences, an encapsidation region and a nucleic acid molecule encoding NFATC4. The recombinant retrovirus can be derived from a retrovirus of any origin (murine, primate, feline, human, etc.) and in particular from the MoMuLV (Moloney murine leukemia virus), MVS (Murine sarcoma virus), Friend murine retrovirus (Fb29), Murine Embryonic Stem Cell Virus (MESV), LN virus or Murine Stem Cell Virus (MSCV). It is propagated in an encapsidation cell line which is able to supply in trans the viral polypeptides gag, pol and/or env which are required for constituting a viral particle. Such cell lines are described in the literature (PA317, Psi CRIP GP +Am-12, HEK 293T etc.). The retroviral (and more particularly lentiviral) expression vector used in the invention may contain modifications, in particular in the LTRs (replacement of the promoter region with a eukaryotic promoter) or the encapsidation region (replacement with a heterologous encapsidation region). Examples of commercial lentiviral vectors that may be used in the context of the present invention include pLVX-tdTomato-C1 Vector commercialized by Clontech.

However, other types of viral expression vectors comprising a nucleic acid molecule encoding NFATC4 may be used.

Examples of viral vectors that are useful in the context of the invention include adenoviral vectors, which may be derived from a variety of human or animal sources (e.g. canine, ovine, simian adenovirus, etc). Any serotype can be employed with a special preference for human adenoviruses and a specific preference for subgenus C such as Ad2, Ad5, Ad6, and subgenus B such as Ad11, Ad34 and Ad35. The cited adenovirus are available from ATCC or have been the subject of numerous publications describing their sequence, organization and methods of producing, allowing the artisan to apply them. When an adenoviral vector is used, it is preferably an E1-defective adenoviral vector with an E1 deletion extending from approximately positions 459 to 3328 or from approximately positions 459 to 3510 (by reference to the sequence of Ad5 disclosed in the GenBank under the accession number M73260.1). The cloning capacity can further be improved by deleting additional portion(s) of the adenoviral genome (all or part of the non-essential E3 region (e.g. deletion from approximately positions 27867 to 30743) or of other essential E2 and/or E4 regions. The nucleic acid molecule encoding NFATC4 can then be inserted in any location of the adenoviral genome, with a specific preference for insertion in replacement of the E1 and/or E3 region. They may be positioned in sense or antisense orientation relative to the natural transcriptional direction of the region in question.

Other examples of viral vectors that may be used in the context of the invention include poxvirus vectors such as fowlpox vectors (e.g. FP9), canarypox vectors (e.g. ALVAC) and vaccinia virus vectors, the latter being preferred. Suitable vaccinia viruses include without limitation the Copenhagen strain, the Wyeth strain, NYVAC and the modified Ankara (MVA) strain. The general conditions for constructing and producing recombinant poxvirus are well known in the art. The nucleic acid molecule encoding NFATC4 is preferably inserted within the poxviral genome in a non-essential locus. Thymidine kinase gene is particularly appropriate for insertion in Copenhagen vaccinia vectors and deletion II or III for insertion in MVA vector.

Other viral vectors suitable in the context of the invention are morbillivirus which can be obtained from the paramyxoviridae family, with a specific preference for measles virus. Insertion of the nucleic acid molecule encoding NFATC4 between P and M genes or between H and L genes is particularly appropriate.

Alternatively, instead of transfecting starting cells with an expression vector comprising a nucleic acid molecule encoding NFATC4, starting cells may be induced to express NFATC4 or to show enhanced NFATC4 activity by any other suitable mean. Notably, starting cells may be contacted with a compound or transfected by an expression vector comprising a nucleic acid molecule encoding a protein able to induce or increase NFATC4 expression or to enhance NFATC4 activity.

Cancer Treatment

A composition comprising SEV of cells expressing NFATC4 may be used in the treatment of cancer or in the treatment or prevention of metastatic cancer.

In the present description, "cancer" refers to a malignant neoplasm characterized by deregulated or uncontrolled cell growth. In particular, a "cancer cell" refers to a cell with deregulated or uncontrolled cell growth.

The term "cancer" includes primary malignant tumours (also referred to as "primary cancer", corresponding to, those whose cells have not migrated to sites in the subject's body other than the site of the original tumor) and secondary malignant tumours (also referred to as "secondary cancer" or "metastatic cancer", those arising from metastasis, the migration of tumour cells to secondary sites that are different from the site of the original tumour).

The type of cancers that may be treated or of metastatic cancer that may be treated or prevented using a composition comprising SEV of cells expressing NFATC4 is not particularly limited. Such cancer may notably be selected from the group of solid cancers. Solid cancers notably include carcinomas (cancers that begin in the lining layer (epithelial cells) of organs, glands, or body structures, also known as "epithelial cancers"), sarcomas (cancers that start in connective tissue, such as cartilage, fat, muscle, tendon, or bone), and brain cancers (cancers that start in brain cells, such as glioma, glioblastoma, and astrocytoma). A cancer is further named after the part of the body where it originated. When cancer spreads, it keeps this same name. In the context of the invention, the cancer may in particular be selected from the group of carcinomas, including but not limited to breast carcinoma, melanoma, ovarian carcinoma, digestive carcinomas (also referred as gastrointestinal carcinomas, including colorectal carcinoma, oesophageal carcinoma, gastric carcinoma, pancreatic carcinoma, hepatocellular carcinoma, cholangiocellular carcinoma and teratocarcinoma), lung carcinoma, prostate carcinoma, and throat carcinoma, particularly of human subject. In the context of the invention, the cancer may also be selected from the group of brain tumors, including but not limited to glioblastoma, particularly of human subject. In preferred embodiments, the cancer may in particular be selected from breast carcinoma, melanoma, pancreatic carcinoma, colorectal carcinoma, glioblastoma and lung carcinoma; more preferably said cancer is selected from breast carcinoma, melanoma, pancreatic carcinoma, and glioblastoma, most preferably said cancer is breast carcinoma, in particular metastatic breast carcinoma.

Such cancer may also be selected from the group of hematopoietic cancers, and in particular from the group consisting of leukaemias, lymphomas, and myelomas, particularly of human patient.

In the present description, the term "treating" or "treatment" means an improvement of the patient's disease, which may be observed at the clinical, histological, biochemical level. In particular, any alleviation of a clinical, histological or biochemical symptom of the disease is included in the terms "treating" and "treatment". In the context of primary cancer, "treating" or "treatment" thus notably relates to the fact to reduce cancer growth or spreading by metastasis. In the context of a metastatic cancer, "treating" or "treatment" thus notably relates to the fact to reduce metastatic cancer growth or further spreading by metastasis. Treatment may require administration of an agent and/or treatment more than once. Treatment also includes the possibility to combine SEV of cells expressing NFATC4 with another anticancer agent. In this case, the two anticancer agents (SEV of cells expressing NFATC4 and the other anticancer agent) may be administered sequentially or simultaneously. In the present description, the term "sequentially" refers to administration (one or more administrations) of a first anticancer agent (SEV of cells expressing NFATC4 or the other anticancer agent), followed by stopping of administration of the first anticancer agent and administration (one or more administrations) of the second anticancer agent (the other anticancer agent or SEV of cells expressing NFATC4). In the present description, the term "simultaneously" refers to administration of the two anticancer agents (SEV of cells expressing NFATC4 and the other anticancer agent) over a same period of time. This includes administration of the two anticancer agents (SEV of cells expressing NFATC4 and the other anticancer agent) in one composition containing both agents or in separate compositions containing each one of the two agents. An intermixed administration (alternation of administration of one agent and the other) over a same period of time is considered simultaneous administration.

The anticancer agent might be selected from surgical treatment, chemotherapy, radiotherapy, immunotherapy, and cell therapy.

In the present description, the term "preventing" or "prevention" means the fact to preclude or delay the onset or reduce the intensity of clinical, histological or biochemical events associated with the disease. In the context of cancer, "preventing" or "prevention" thus notably relates to the fact to inhibit, at least partially, new cancer growth or spreading. Prevention may require administration of an agent and/or treatment more than once. In the context of prevention also, SEV of cells expressing NFATC4 may be combined with another anticancer agent, either sequentially or simultaneously.

In the present description, the term "patient" refers to mammals, e. g., humans, dogs, cows, horses, kangaroos, pigs, sheep, goats, cats, mice, rabbits, rats, and transgenic non-human animals. In preferred embodiments of the present invention, a subject is a human subject.

The composition comprising SEV of cells expressing NFATC4 is administered in therapeutically efficient amounts.

As used herein, a "therapeutically efficient amount" refers to an amount sufficient for the intended use. For the anticancer composition according to the invention, it refers to an amount sufficient to reduce cancer growth or spreading.

In mice, a weekly dose of $50.10^8$ pp SEV (number of particles detected by NanoSight apparatus, commercialized by Malvern) per mouse was used successfully, and a weekly dose of $10^8$ to $10^{11}$ pp SEV may be expected to be successful, knowing that mice have a total blood volume of about 1.5 mL. Suitable doses may be extrapolated for other species based on the total blood volume. For instance, in humans (total blood volume of about 5 L), a dose of at least about $15.10^{12}$ SEV may be contemplated. In the context of the present invention, the number of SEV present in a composition is preferably determined using a NanoSight apparatus (commercialized by Malvern), in which case the number of SEV is referred to as "pp", corresponding to the number of particles detected by NanoSight apparatus. Thus, in humans (total blood volume of about 5 L), a dose of at least about $15.10^{12}$ pp SEV may be contemplated.

The administered dose may vary depending on the subject age, body surface area or body weight, or on the administration route and associated bioavailability. Such dose adaptation is well known to those skilled in the art.

The composition comprising SEV of cells expressing NFATC4 may be administered by any suitable administration route, including intravenous, intratumoral, topical, intranasal, rectal, oral, transdermal, subcutaneous, and sublingual routes. In a preferred embodiment, the composition comprising SEV of cells expressing NFATC4 is intended to be administered by intravenous or intratumoral route.

Depending on the selected route of administration, those skilled in the art will know how to formulate the above defined compounds or pharmaceutically acceptable salts thereof in order to optimize in vivo delivery and bioavailability. In particular, the above defined SEV may be formulated with suitable pharmaceutically acceptable carriers, excipients, vehicles, preservatives, solubilizing agents, stabilizers, wetting agents, emulsifiers, sweeteners, dyes, flavoring, salts intended to modify osmotic pressure, buffers, taste correctors, and antioxidants. These compounds are well-known to those skilled in the art. Details on these chemicals can be found in the latest edition of Remington's Pharmaceutical Sciences (Maack Publishing Co., Easton, Pa.). The selection of the optimal delivery formulation will be selected by those skilled in the art depending on the selected administration route.

For intravenous, intratumoral or intranasal administration, aqueous suspensions, isotonic saline solutions, or sterile, injectable solutions that contain pharmacologically compatible dispersing agents and/or wetting agents may be used. As an excipient, water, alcohols, polyols, glycerol, vegetable oils, etc., may be used.

For topical administration, compositions may be presented in the form of a gel, a paste, an ointment, a cream, a lotion, an aqueous or aqueous-alcohol liquid suspension, an oily solution, a dispersion of the lotion or serum type, an anhydrous or lipophilic gel, an emulsion with a liquid or semi-solid milk-type consistency obtained by dispersing a fatty phase in an aqueous phase or vice versa, suspensions or emulsions of a soft or semi-solid cream- or gel-type consistency, or alternatively microemulsions, microcapsules, microparticles, or vesicular dispersions of the ionic and/or nonionic type. These compositions are prepared according to standard methods. Moreover, a surfactant can be included in the composition in order to enable deeper penetration of SEV. An agent enabling an increased penetration may be selected, for example, from mineral oil, ethanol, triacetin, glycerin and propylene glycol; cohesion agents are selected, for example, from the group comprising polyisobutylene, polyvinyl acetate, polyvinyl alcohol, and thickening agents.

For rectal administration, suppositories, which are prepared with binders that melt at rectal temperatures, for example cocoa butter or semi-solid or liquid polyols such as polyethylene glycols, waxes, natural or hydrogenated oils, fats, etc., can be used. Suitable unit dose administration formulations for oral administration notably include tablets, coated tablets, pills, capsules and soft gelatin capsules, oral powders, granules, solutions and suspensions.

When a solid composition in tablet form is prepared, the principal active ingredient may be mixed with a pharmaceutical vehicle, such as gelatin, starch, lactose, stearic acid or magnesium stearate, talc, gum arabic or analogues. The tablets may be coated with saccharose or other suitable materials or even be treated so as to have a prolonged or delayed activity and to release continuously a predetermined quantity of the active ingredient.

A capsule preparation may be obtained by mixing the active ingredient with a thinner and pouring the mixture obtained into soft or hard capsules, with excipients such as vegetable oils, waxes, fats, semi-solid or liquid polyols, etc.

A preparation in syrup or elixir form can contain the active ingredient together with a sweetener, an antiseptic, as well as an agent giving taste and a suitable dye. Excipients may be used, such as water, polyols, saccharose, invert sugar, glucose, etc.

Powders or water-dispersible granules may contain the active ingredient in a mixture with dispersing agents, wetting agents, and suspending agents, together with taste correctors and sweeteners.

For subcutaneous administration, any suitable pharmaceutically acceptable vehicle may be used. In particular, a pharmaceutically acceptable oil vehicle, such as sesame oil, may be used.

Method for Preparing a Composition Comprising SEV of Cells Expressing NFATC4 from a Sample of Healthy Cells of a Cancer Patient In a second aspect, the present invention also relates to a method for preparing a composition comprising SEV of cells expressing NFATC4 from a sample of cells, comprising:

a) Inducing NFATC4 expression or activity in said cells;
b) Culturing said induced cells in SEV-free culture medium, under conditions permitting their expansion; and
c) Purifying SEV of the induced cells.

In step a), NFATC4 expression or activity is induced in starting cells, as described above. In particular, any type of starting cells disclosed above may be used (with a preference for healthy cells, in particular autologous cells and notably autologous fibroblasts of the patient to be treated, or a fibroblast cell line such as WI38, which is already approved for the production of vaccines), and any type of induction of NFATC4 expression or activity disclosed above may be used (with a preference for use of a viral, and more particularly lentiviral, vector for inducing NFATC4 expression).

In step b), induced cells are cultured in SEV-free culture medium, under conditions permitting their expansion. Some commercialized culture media are already SEV-free. However, for media containing animal driven components (e.g. serum), SEV depletion of the medium should be conducted. This may be performed by spinning the culture medium at 30,000 to 40,000 RPM for 8-16 hours (for instance, overnight) at about 4° C.

Conditions permitting expansion of induced cells vary depending on the type of starting cells (primary cells/cell line; cellular type, adherent/suspension cells) used in the method, and may be determined by skilled persons based on their common general knowledge about cell culture. The important point is that cells should be in good condition, since cell death and apoptotic bodies could lead to contamination of the SEV pellet. Conditions permitting amplification and maintenance of induced cells in exponential growth should thus be used, and SEV should be purified before the end of the exponential phase of growth, i.e. before the plateau, when cell death becomes significant.

In step c), SEV are purified from the culture supernatant, as described above. In particular, any method of purification described above may be used, with a preference for differential centrifugation, as described above.

For therapeutic purposes, the whole method should preferably be performed under sterile conditions.

In Vitro Methods for Determining or Predicting the Therapeutic Efficiency of a Treatment with a Composition Comprising SEV of Cells Expressing NFATC4 in a Cancer Patient The inventors have shown that SEV of cells expressing NFATC4 induce Transforming growth factor beta 1 (TGFß1) expression in cancer cells, and that in vivo efficiency of the treatment of cancer in animal models correlates with an increase in TGFß1 expression in the treated patient.

Therefore, in a third aspect, the present invention also relates to an in vitro method for determining the therapeutic efficiency of a treatment with a composition comprising SEV by cells expressing NFATC4 in a treated cancer patient, from a first biological sample of said cancer patient taken before the beginning of the treatment and a second corresponding biological sample of cancer patient after the beginning of the treatment, comprising:

a) Measuring in vitro at least the Transforming growth factor beta 1 (TGFß1) expression level in said first and second biological samples;
b) Comparing at least the measured TGFß1 expression levels; and
c) Determining the efficiency of the treatment with a composition comprising SEV of cells expressing NFATC4 in said treated cancer patient from said comparison, wherein the treatment is considered efficient if at least the TGFß1 expression level measured in the biological sample after the beginning of the treatment is higher than at least the TGFß1 expression level in the biological sample after the beginning of the treatment.

Since the efficiency of the treatment with SEV of cells expressing NFATC4 is correlated to an increase in TGFß1 expression in the treated patient, the above method relies on comparison of TGFß1 expression level in two successive biological samples of the patient, the first one taken before the beginning of the treatment with SEV of cells expressing NFATC4, and the second one taken after the beginning of the treatment with SEV of cells expressing NFATC4.

A "biological sample" refers to any sample of the patient in which TGFß1 expression may be measured. Such samples include notably a tumor sample, a blood sample, a serum sample, and a urine sample. For comparison purpose, the first and second samples should preferably be of the same nature (e.g. two tumor samples, two blood samples, two serum samples, or two urine samples).

"Transforming growth factor beta 1" or "TGFß1" refers to a protein encoded by the human gene with the official symbol TGFß1 in Entrez Gene database. (Gene ID: 7040). The TGFß1 gene is also known as "TGF-beta-1", "prepro-transforming growth factor beta-1", "CED", "LAP" or "latency-associated peptide", "DPD1", "TGFB", and "TGF-beta". The cDNA and protein sequences of TGFß1 are mentioned in Table 3 below:

TABLE 3

| cDNA and protein sequences of human TGFβ1. |
|---|
| TGFβ1 cDNA sequence |
| AGCCGGTCCCCGCCGCCGCCGCCCTTCGCGCCCTGGGCCATCTCCCTCCC |
| ACCTCCCTCCGCGGAGCAGCCAGACAGCGAGGGCCCCGGCCGGGGGCAGG |
| GGGGACGCCCCGTCCGGGGCACCCCCCCGGCTCTGAGCCGCCCGCGGGGC |
| CGGCCTCGGCCCGGAGCGGAGGAAGGAGTCGCCGAGGAGCAGCCTGAGGC |
| CCCAGAGTCTGAGACGAGCCGCCGCCGCCCCCGCCACTGCGGGGAGGAGG |
| GGGAGGAGGAGCGGGAGGAGGGACGAGCTGGTCGGGAGAAGAGGAAAAAA |
| ACTTTTGAGACTTTTCCGTTGCCGCTGGGAGCCGGAGGCGCGGGGACCTC |
| TTGGCGCGACGCTGCCCCGCGAGGAGGCAGGACTTGGGGACCCCAGACCG |
| CCTCCCTTTGCCGCCGGGGACGCTTGCTCCCTCCCTGCCCCCTACACGGC |
| GTCCCTCAGGCGCCCCCATTCCGGACCAGCCCTCGGGAGTCGCCGACCCG |
| GCCTCCCGCAAAGACTTTTCCCCAGACCTCGGGCGCACCCCCTGCACGCC |
| GCCTTCATCCCCGGCCTGTCTCCTGAGCCCCCGCGCATCCTAGACCCTTT |
| CTCCTCCAGGAGACGGATCTCTCTCCGACCTGCCACAGATCCCCTATTCA |
| AGACCACCCACCTTCTGGTACCAGATCGCGCCCATCTAGGTTATTTCCGT |
| GGGATACTGAGACACCCCCGGTCCAAGCCTCCCCTCCACCACTGCGCCCT |
| TCTCCCTGAGGACCTCAGCTTTCCCTCGAGGCCCTCCTACCTTTTGCCGG |
| GAGACCCCCAGCCCCTGCAGGGGCGGGGCCTCCCCACCACACCAGCCCTG |
| TTCGCGCTCTCGGCAGTGCCGGGGGGCGCCGCCTCCCCCATGCCGCCCTC |
| CGGGCTGCGGCTGCTGCCGCTGCTGCTACCGCTGCTGTGGCTACTGGTGC |
| TGACGCCTGGCCGGCCGGCCGCGGGACTATCCACCTGCAAGACTATCGAC |
| ATGGAGCTGGTGAAGCGGAAGCGCATCGAGGCCATCCGCGGCCAGATCCT |
| GTCCAAGCTGCGGCTCGCCAGCCCCCCGAGCCAGGGGGAGGTGCCGCCCG |
| GCCCGCTGCCCGAGGCCGTGCTCGCCCTGTACAACAGCACCCGCGACCGG |
| GTGGCCGGGGAGAGTGCAGAACCGGAGCCCGAGCCTGAGGCCGACTACTA |
| CGCCAAGGAGGTCACCCGCGTGCTAATGGTGGAAACCCACAACGAAATCT |
| ATGACAAGTTCAAGCAGAGTACACACAGCATATATATGTTCTTCAACACA |
| TCAGAGCTCCGAGAAGCGGTACCTGAACCCGTGTTGCTCTCCCGGGCAGA |
| GCTGCGTCTGCTGAGGCTCAAGTTAAAAGTGGAGCAGCACGTGGAGCTGT |
| ACCAGAAATACAGCAACAATTCCTGGCGATACCTCAGCAACCGGCTGCTG |
| GCACCCAGCGACTCGCCAGAGTGGTTATCTTTTGATGTCACCGGAGTTGT |
| GCGGCAGTGGTTGAGCCGTGGAGGGGAAATTGAGGGCTTTCGCCTTAGCG |
| CCCACTGCTCCTGTGACAGCAGGGATAACACACTGCAAGTGGACATCAAC |
| GGGTTCACTACCGGCCGCCGAGGTGACCTGGCCACCATTCATGGCATGAA |
| CCGGCCTTTCCTGCTTCTCATGGCCACCCCGCTGGAGAGGGCCCAGCATC |
| TGCAAAGCTCCCGGCACCGCCGAGCCCTGGACACCAACTATTGCTTCAGC |
| TCCACGGAGAAGAACTGCTGCGTGCGGCAGCTGTACATTGACTTCCGCAA |
| GGACCTCGGCTGGAAGTGGATCCACGAGCCCAAGGGCTACCATGCCAACT |
| TCTGCCTCGGGCCCTGCCCCTACATTTGGAGCCTGGACACGCAGTACAGC |
| AAGGTCCTGGCCCTGTACAACCAGCATAACCCGGGCGCCTCGGCGGCGCC |
| GTGCTGCGTGCCGCAGGCGCTGGAGCCGCTGCCCATCGTGTACTACGTGG |
| GCCGCAAGCCCAAGGTGGAGCAGCTGTCCAACATGATCGTGCGCTCCTGC |
| AAGTGCAGCTGAGGTCCCGCCCCGCCCCGCCCCGCCCCGGCAGGCCCGGC |
| CCCACCCCGCCCCGCCCCCGCTGCCTTGCCCATGGGGGCTGTATTTAAGG |
| ACACCCGTGCCCCAAGCCCACCTGGGGCCCCATTAAAGATGGAGAGAGGA |
| CTGCGGATCTCTGTGTCATTGGGCGCCTGCCTGGGGTCTCCATCCCTGAC |
| GTTCCCCCACTCCCACTCCCTCTCTCTCCCTCTCTGCCTCCTCCTGCCTG |
| TCTGCACTATTCCTTTGCCCGGCATCAAGGCACAGGGGACCAGTGGGGAA |
| CACTACTGTAGTTAGATCTATTTATTGAGCACCTTGGGCACTGTTGAAGT |
| GCCTTACATTAATGAACTCATTCAGTCACCATAGCAACACTCTGAGATGC |

TABLE 3-continued

| cDNA and protein sequences of human TGFβ1. |
|---|
| AGGGACTCTGATAACACCCATTTTAAAGGTGAGGAAACAAGCCCAGAGAG |
| GTTAAGGGAGGAGTTCCTGCCCACCAGGAACCTGCTTTAGTGGGGGATAG |
| TGAAGAAGACAATAAAAGATAGTAGTTCAGGCC (NCBI Reference Sequence: NM_000660.5; SEQ ID NO: 16) |
| TGFβ1 protein sequence |
| MPPSGLRLLPLLLPLLWLLVLTPGRPAAGLSTCKTIDMELVKRKRIEAIR |
| GQILSKLRLASPPSQGEVPPGPLPEAVLALYNSTRDRVAGESAEPEPEPE |
| ADYYAKEVTRVLMVETHNEIYDKFKQSTHSIYMFFNTSELREAVPEPVLL |
| SRAELRLLRLKLKVEQHVELYQKYSNNSWRYLSNRLLAPSDSPEWLSFDV |
| TGVVRQWLSRGGEIEGFRLSAHCSCDSRDNTLQVDINGFTTGRRGDLATI |
| HGMNRPFLLLMATPLERAQHLQSSRHRRALDTNYCFSSTEKNCCVRQLYI |
| DFRKDLGWKWIHEPKGYHANFCLGPCPYIWSLDTQYSKVLALYNQHNPGA |
| SAAPCCVPQALEPLPIVYYVGRKPKVEQLSNMIVRSCKCS (NCBI Reference Sequence: NP_000651.3; SEQ ID NO: 17) |

In a fourth aspect, the present invention also relates to an in vitro method for predicting the therapeutic efficiency of a treatment with a composition comprising SEV of cells expressing NFATC4 in a cancer patient, from a cancer sample of said cancer patient, comprising:

a) Measuring in vitro at least the TGFß1 expression level in said tumor sample;
b) Incubating said cancer sample with a composition comprising SEV expressing NFATC4;
c) Measuring in vitro at least the TGFß1 expression level in said tumor sample incubated with a composition comprising SEV by cells expressing NFATC4; and
d) Predicting efficiency of a treatment with a composition comprising SEV of cells expressing NFATC4 in said cancer patient if at least the TGFß1 expression level measured in step c) is higher than at least the TGFß1 expression level measured in step a), and predicting non efficiency of a treatment with a composition comprising SEV of cells expressing NFATC4 in said cancer patient if at least the TGFß1 expression level measured in step c) is lower or equal at least to the TGFß1 expression level measured in step a).

In the method for predicting the therapeutic efficiency of a treatment with a composition comprising SEV of cells expressing NFATC4 in a cancer patient, the ability of SEV of cells expressing NFATC4 to induce or increase TGFß1 expression by cancer cells is tested. An increase in TGFß1 expression by cancer cells after contact with SEV of cells expressing NFATC4 will predict therapeutic efficiency, while stability or decrease in TGFß1 expression by cancer cells after contact with SEV of cells expressing NFATC4 will predict therapeutic inefficiency.

By "cancer sample", it is meant any sample comprising cancer cells, including but not limited to a cancer biopsy or a complete or partial cancer surgical resection, or a blood sample. Indeed, it is well known in the art that circulating cancer cells are present in blood.

In both above described in vitro methods for determining or predicting the therapeutic efficiency of a treatment with a composition comprising SEV of cells expressing NFATC4 in a cancer patient, the expression level of TGFß1 in the two biological samples of said cancer patient may be measured by any suitable mean.

In a particular embodiment, the expression level of TGFß1 in the two biological samples of said cancer patient may be measured at the nucleic level, by measuring the amount of TGFß1 transcripts. The amount of TGFß1 transcripts can be measured by any technology known by a person skilled in the art. In particular, the measure may be carried out directly on an extracted messenger RNA (mRNA) sample, or on retrotranscribed complementary DNA (cDNA) prepared from extracted mRNA by technologies well-known in the art. From the mRNA or cDNA sample, the amount of nucleic acid transcripts may be measured using any technology known by a person skilled in the art, including nucleic microarrays, quantitative PCR, next generation sequencing and hybridization with a labelled probe.

In particular, real time quantitative RT-PCR (qRT-PCR) may be useful. Commercially available qRT-PCR based methods (e.g., Taqman® Array) may for instance be employed, the design of primers and/or probe being easily made based on the sequences of TGFß1 disclosed in Table 3 above.

Nucleic acid assays or arrays can also be used to assess in vitro the expression level of TGFB1. In some embodiments, a nucleic acid microarray can be prepared or purchased. An array typically contains a solid support and at least one nucleic acid (cDNA or oligonucleotide) contacting the support, where the oligonucleotide corresponds to at least a portion of the target gene. For example, an assay may be in the form of a membrane, a chip, a disk, a test strip, a filter, a microsphere, a multiwell plate, and the like. An assay system may have a solid support on which a nucleic acid (cDNA or oligonucleotide) corresponding to the target gene is attached. The solid support may comprise, for example, a plastic, silicon, a metal, a resin, or a glass. The assay components can be prepared and packaged together as a kit for detecting a gene. To determine the expression profile of a target nucleic sample, said sample is labelled, contacted with the microarray in hybridization conditions, leading to the formation of complexes between target nucleic acids that are complementary to probe sequences attached to the microarray surface. The presence of labelled hybridized complexes is then detected. Many variants of the microarray hybridization technology are available to the person skilled in the art.

In another particular embodiment, the expression level of TGFß1 in the two biological samples of said cancer patient may be measured at the protein level. For instance, at the protein level, the in vitro measure of the expression level of TGFß1 may be performed by any dosage method known by a person skilled in the art, including but not limited to ELISA or mass spectrometry analysis. These technologies are easily adapted to any fluid or solid sample. Indeed, proteins of the fluid or solid sample may be extracted using various technologies well known to those skilled in the art for measure by ELISA or mass spectrometry in solution. Alternatively, the expression level of a protein in a biological sample may be analyzed by using mass spectrometry directly on the tissue slice. For determination of TGFß1 expression at the protein level, ELISA is a preferred technology.

In both above described in vitro methods for determining or predicting the therapeutic efficiency of a treatment with a composition comprising SEV of cells expressing NFATC4 in a cancer patient, the tested patient may be suffering from any type of cancer, as described above.

This is particularly true for the above described in vitro methods for determining the therapeutic efficiency of a treatment with a composition comprising SEV of cells expressing NFATC4 in a cancer patient, which does not necessitate to put a cancer sample into culture. In this context, the cancer from which suffers the patient to be tested may notably be selected from solid cancers; preferably from carcinomas and brain cancers, more preferably from breast carcinoma, melanoma, pancreatic carcinoma, colorectal carcinoma, lung carcinoma, and glioblastoma; even more preferably said cancer is selected from breast carcinoma, melanoma, pancreatic carcinoma, and glioblastoma, most preferably said cancer is breast carcinoma, in particular metastatic breast carcinoma.

While the above method for predicting the therapeutic efficiency of a treatment with a composition comprising SEV of cells expressing NFATC4 in a cancer patient may be applied to any type of cancer, it is preferably applied to patients suffering from liquid cancers, such as leukemia or lymphoma. Indeed, liquid cancer samples are more easily put into culture for measure of TGFß1 expression before and after contact with SEV of cells expressing NFATC4.

The following examples merely intend to illustrate the present invention.

EXAMPLES

Example 1: SEV Produced by Low Invasive Breast Cancer Cells Inhibit Cancer Progression and Metastasis Materials and Methods Cell Culture The MDA-MB-231, T-47D, MCF7, NIH3T3, HEK293T cell lines were from the American Type Culture Collection, The SUM-159-PT cell line was provided by Alex Toker (Harvard Medical School), MDA-MB-231 D3H2 LN-Luc and 4T1-Red-FLuc cell lines were from Perkin Elmer. MDA-MB-231 D3H2 LN-Luc cell line was maintained in Eagle's MEM, 75 μg/ml Zeocin. 4T1-Red-FLuc cell line was in RPMI 1640, 10% Foetal Calf Serum. MDA-MB-231 and SUM-159-PT cells were maintained in Dulbecco Modified Eagle Medium (DMEM), low glucose (1 g/L D-glucose), 10% Foetal Calf Serum. T-47D and MCF7 were maintained in RPMI 1640, 10% Foetal Calf Serum. NIH-3T3 cells were in Dulbecco Modified Eagle Medium (DMEM), High glucose (4.5 g/L D-glucose), 10% Newborn Calf Serum. The HEK293T cell line was maintained in Dulbecco Modified Eagle Medium (DMEM), High glucose (4.5 g/L D-glucose), 10% Foetal Calf Serum. All media were supplemented with 2 mM L-Glutamine, 100 U/mL Penicillin and 100 μg/mL Streptomycin.

SEV Production

Preparation of SEV Depleted Medium

For media containing animal driven components (e.g. serum), SEV depletion of the medium should be conducted.

1. Prepare medium with up to 20% serum (higher serum concentration is not recommended).
2. Precool the ultracentrifuge and rotor to 4° c.

For SW32Ti rotor:

i. Use pollyallomer 38.5 ml tubes (326823). Fill each with 38 ml medium and balance by weight (aim for 0.01-0.02 gr differences).
ii. Spin overnight (for standardization—18 hours) at 4° c. at 30,000 RPM.

For Type 45Ti:

i. Use 65 ml reusable tubes labeled for depletion. Fill each with 65 ml medium and balance by weight (aim for 0.01-0.02 gr differences).
ii. Spin overnight (for standardization—15 hours) at 4° c. at 38,000 RPM.

3. Take supernatant carefully, do not disturb the pellet.
4. Filter 0.22 μm and save at 4° c. Use within 1 week.

Medium Change

Grow cells as optimized for SEV production for the cell type, change to SEV depleted in the time point specified.

1. Prepare medium from SEV depleted medium, dilute if necessary.

2. Vacuum medium.

3. For 150 mm dish, add 7 ml PBS.

4. Vacuum well all PBS or medium left.

5. Add SEV depleted medium.

SEV Production

Grow cells as optimized for SEV production for the cell type, change to SEV depleted medium if necessary and conduct the SEV isolation at the time point indicated (typically 24-48 hours after medium change).

Note: Cells should be in good condition—cell death and apoptotic bodies could lead to contamination of SEV pellet.

If SEV are to be used for functional assays, conduct in sterile conditions.

Precool ultracentrifuge with rotor Type 45Ti (this rotor takes a long time to cool, it is better to leave it on the fridge the night before starting the production).

1. Pass medium from dishes to 50 ml tubes.

2. Spin 1350 RPM for 10 minutes at 4° c.

In parallel: For a representative number of dishes (typically—3 for a 30 dishes production):

a. Wash with PBS and vacuum b. Add trypsin, incubate 37° c. until detachment c. Add medium with 10% serum, preferably SEV depleted d. Count cells from each dish separately and keep record of total cells used for production.

e. Add cold PBS f. Centrifuge 1350 RPM for 7 minutes at 4° c.

g. Vacuum supernatant h. Freeze −80° c. for protein/RNA.

3. Pass supernatant carefully to new 50 ml tubes. Discard tubes with pellet.

4. Spin 3500 RPM in culture room) for 20 minutes at 4° c.

5. Pass supernatant carefully to new 50 ml tubes. Discard tubes with pellet.

6. In centrifuge 5810R rotor F-34-6-38: Spin 10,000 RPM for 30 minutes at 4° c.

7. Pass supernatant carefully to sterile ultracentrifuge tubes for rotor Type 45 Ti (tubes 355622). Look carefully that tubes are not cracked. Fill tubes with 65 ml and balance by weight (aim for 0.01-0.02 gr differences). Mark the tube in the side close to rotor in order to mark pellet location.

At this step the medium can be kept in 4° c. for a few days (max 3-4) before ultracentrifugation.

8. Ultracentrifuge 40,000 RPM for 90 minutes at 4° c.

9. Carefully, as far as possible from pellet location—discard supernatant, leaving the minimal volume possible (if you can see the pellet, aspirate completely, if not, leave max 2 mL medium).

10. Using a p1000, resuspend the pellet in 2 mL cold PBS (or the remaining supernatant) and pass to another tube.

11. Add 2 ml cold PBS and wash with p1000, taking care to wash carefully the marked pellet location. Pass to the same tube.

12. Repeat wash with 2 ml PBS and pass to the same tube.

13. Repeat for all tubes, passing all to the same tube.

14. Fill tube to 65 ml with cold PBS and balance weight.

15. Ultracentrifuge 40,000 RPM for 90 minutes at 4° c.

16. Carefully, as far as possible from pellet location—discard supernatant, leaving the minimal volume possible.

17. Resuspend in remaining supernatant or add cold PBS in minimal amount to resuspend (this will depend on amount of cells used and cell type). Take care to wash carefully the marked pellet location. Pass to a sterilized siliconized tube (sigma T3281).

18. Wash tube, especially pellet location, with minimal amount of cold PBS. Pass to same siliconized tube.

19. Measure final volume and keep record.

20. Aliquot into sterile siliconized tubes and keep at −80° c.

Important Observations:

For MDA-MB 231 and SUM 159 PT cells: seed 1×10E6 cells per 150 mm diameter dish; 3 days later change the medium to SEV depleted; 2 days later start the production;

For T47-D cells: seed 6×10E6 cells per 150 mm diameter dish; 5 days later change the medium to SEV depleted; 2 days later start the production;

For MCF7 cells: seed 7×10E6 cells per 150 mm diameter dish; 5 days later change the medium to SEV depleted; 2 days later start the production;

When using 150 mm diameter dish, keep cells in 25 mL medium;

For all of the cell types listed above, a visible pellet is obtained even after the 1st ultra-centrifugation, so it is important to eliminate all supernatant both after the 1st ultra and after the PBS wash to avoid contamination with proteins that could still be in suspension in the supernatant;

SEV depleted RPMI and DMEM are prepared with 20% serum; 1% P/S (and l-glu, in the case of RPMI). The medium is filtered after the ON ultracentrifugation and can be kept in the fridge up to 1 month. When diluting 20% SEV depleted medium before changing cell medium for production, a new bottle of fresh medium should be used. The diluted medium should be re-filtered upon dilution before changing the cell medium for the production.

Antibodies and Reagents

The following antibodies were used: Anti-CD63(#clone H5C6, BD Biosciences), anti-NFAT3 (Sigma; #F1804, Thermo Scientific; #PA1-021, Santa-Cruz Biotechnology; sc-13036), anti-CD9 (#clone CBL162, Millipore), anti-Actin (Thermo Scientific; #MA5-15739), ESR1 (Santa-Cruz Biotechnology; sc-543).

Recombinant TGFß1 was from Invitrogen (#PHG9214)

SEV Characterization

Size distribution of SEV was evaluated by NanoSight.

Western Blot 400 000 T47D or MDA-MB-231 cell were used per lane in laemelli buffer. 20 ug of each SEV were used per lane in Laemelli buffer+2% SDS. Samples were boiled for 30 mins at 95° C. before loading on the gel.Gel was transferred on nitrocellulose membrane and blocked 1 h in TBS-0.05% Tween-20 at room temperature. Then membrane were incubated with the different antibodies depicted on the figure overnight. The following day membrane was washed 4 time in TBS-0.05% Tween-20 and incubate for 1 h at room temperature with horseradish-peroxydase-coupled secondary antibodies. Then the membrane was washed 4 time in TBS-0.05% Tween-20 and incubate for 1 h at room temperature and reveled with ECL to visualise the proteins.

Invasion Assays

The invasion assays were performed essentially as described, using Transwell chambers (Becton Dickinson) with 8-μm pore membranes coated with Matrigel (Becton Dickinson). Cells, non-transfected or transfected with the relevant siRNA, were starved by 4 washes during the day with medium where 10% Foetal Calf Serum was omitted, after the last wash the cells 600 ul of medium without 10% Foetal Calf Serum. The following day cell were treated with either PBS or $0.375.10^9$ particles/well in a 12 well plate for 24 h. In some cases, 5 ng/mL recombinant hTGFβ1 (#PHG9214, Invitrogen) or vehicle was added. The following day cell were trypsinized and harvested in serum-free medium containing 0.1% BSA, and cells were added to each well. Conditioned NIH-3T3 medium was added to the bottom wells of the chambers. After 6 hours, cells that had not invaded were removed from the upper face of the filters using cotton swabs, and cells that had invaded to the lower surface of the filters were fixed for 10 min in 100% methanol and then stained with crystal violet for 30 min. All cells in each Transwell were counted. The numbers of cells that invaded in each condition were compared with the PBS condition arbitrary set as a ratio of 1. When the assay was performed with cells transiently transfected by siRNA, cells were stained with crystal violet since 95% of the cells were effectively transfected. In some cases, 5 ng/mL recombinant TWEAK was added for 6 hours to the cells during the assay.

Proliferation and Apoptosis Assays

Apoptosis Test

Highly invasive MDA-MB-231 (A) were treated for 24 h and SUM-159-PT (B) for 24, with the indicated amount of SEV from T47D-WT to evaluate cell apoptosis. 24 h after SEV treatment, cell supernatant was removed and cells were trypsinized and washed twice in cold PBS. Cells were resuspended cells in cold binding buffer (10 mM HEPES pH 7.4, 140 mM NaCl, 2.5 mM CaCl2, 0.1% BSA) to a concentration of $1.10^6$ cells/mL. Then 100 μL of cells (1×105 to 1×106) was added in polypropylene FACS tubes and 10 μL of labelled Annexin V was added to the cells. Cell were incubated for 15 minutes on ice, protected from light. Then, without washing, 380 μL of cold 1× binding buffer waw added to each tube and annexin-V labelling was immediately analysed by flow cytometry to evaluated apoptosis.

Proliferation Test

Highly invasive MDA-MB-231 (A) were treated for 24 h and SUM-159-PT (B) for 24, 48 and 72 h with the indicated amount of SEV from T47D-WT to evaluate cell proliferation. MDA-MB-231 proliferation was evaluated by a BrdU Incorporation assay following the manufacturer recommendations (Roche: #11444611001).

```
shRNA
All shRNA were from Dharmacon cloned in the pGIPZ
lentiviral vector.
pGIPZ sh(hNFAT3)-3 5'-CAATGAACACCACCTTGGA-3'

(clone ID: V3LHS_383428, SEQ ID NO: 18)

pGIPZ sh(hNFAT3) 4 5'- AGTCTCAGGGAACATCCGC-3'

(clone ID: V3LHS_383431, SEQ ID NO: 19)

pGIPZ sh(hTGFB1) 1 5'- ATGCTGTGTGTACTCTGCT-3'

(clone ID: V3LHS_356824, SEQ ID NO: 20)

pGIPZ sh(hTGFB1) 2 5'- TGATGTCCACTTGCAGTGT-3'

(clone ID: V3LHS_356823, SEQ ID NO:21)
```

Production of shRNA Lentiviral Particles in HEK293T Cells

DAY 1:

Plate cells in 10% SVF/HIGH DMEM

| | Cells number | Volume medium |
|---|---|---|
| 100 cm2 | $3.5 \cdot 10^6$ | 14 ml |

DAY 2:

1—Plasmids transfection by phosphate calcium

| | Lentiviral Transfer Vector shRNA | Trans-Lentiviral Packaging Mix | Total Volume (with sterile water) |
|---|---|---|---|
| 100 cm2 | 42 ug | 30 ul | 945 ul |

2—Add the indicated volume of CaCl2 to the diluted DNA above

| | CaCl2 |
|---|---|
| 100 cm2 | 15 ul |

3—Vortex the tube at a speed sufficient to thoroughly mix reagents without spillover. While vortexing, add drop-wise the indicated volume of 2× HBSS:

| | 2x HBSS |
|---|---|
| 100 cm2 | 1050 ul |

4—Incubate at room temperature for 3 minutes. A light chalky precipitate should appear during this incubation (the precipitate may not always be obvious).

5—Add the total volume (300 μL or 2.1 mL) of transfection mix drop-wise to the cells.

(Note: The exact volume may be slightly less due to pipetting loss, but this will not negatively impact transfection effciency.)

6—Incubate cells at 37° C. with 5% CO2 for 10-16 hours

DAY 3:

1—Prepare reduced serum medium:

a. High Glucose DMEM b. 5% Fetal Bovine c. 2 mM L-glutamine d. 1× Penicillin/Streptomycin 2—Remove calcium phosphate-containing medium from cells and replace 14 ml of reduced serum medium.

3—Incubate cells at 37° C. with 5% CO2 for an additional 48 hours.

DAY 5: Viral Particle Collection and Concentration

1—Harvest viral particle-containing supernatants 48 hours after the medium change by removing medium to a 15 mL sterile, capped, conical tube.

2—Pellet non-adherent cells and debris by centrifugation at 1600×g at 4° C. for 10 minutes to pellet cell debris.

3—Filtration step in which the supernatant is passed through a sterile, 0.22-0.45 μM low protein binding filter after the low-speed centrifugation step to remove any remaining cellular debris. Filtered viral medium is directly put in ultracentrifugation tube.

4—Concentrate by ultracentrifugation in a swinging-bucket ultracentrifuge rotor. Transfer the altered supernatant to a sterile ultracentrifuge tube. Bring volume to almost fill the tube to avoid braking tube during the ultra-centrifugation with DMEM containing no serum. For an SW28 rotor, centrifuge at 23,000 rpm for 2 hours at 4° C.

5—Pipette the desired resuspension volume of DMEM (no serum) onto the pellet at the bottom of the tube.

6—The visible pellet (if visible) is made up mostly of serum proteins from the culture media of the transfected cells. The viral particles need to be dislodged from this protein pellet. After adding the DMEM to the pellet, incubate for 10 minutes at 4° C. Then gently pipette up and down about 30 times, avoiding the formation of bubbles.

7—Transfer the resuspended pellet to a sterile microfuge tube and centrifuge at full speed for 3-4 minutes. This centrifugation will pellet the serum proteins, which adhere to the bottom of the tube. After centrifugation, transfer the supernatant to a new microfuge tube and aresuspend in 100 ul pf PBS (20 ul will be used per infection. Always store lentiviral particles at −80° C.

Infection of Cells with Lentiviral Particules and Selection

DAY 1:

Plate cells in 24 well plates in 10% SVF+AB in their corresponding medium

| Cell type | Cells number | Volume medium |
|---|---|---|
| MDA-MB-231 | $2.5 \cdot 10^5$ | 1 ml DMEM low |
| SUM-159PT | $1.5 \cdot 10^5$ | 1 ml DMEM low |
| MDA-MB-231 D3H2LN | $2.5 \cdot 10^5$ | 1 ml MEM + sodum pyruvate + ZEOCINE 75 ug/ml |
| T47D | $3 \cdot 10^5$ | 1 ml RPMI |
| MCF7 | $3 \cdot 10^5$ | 1 ml RPMI |

DAY 2:

1. Replace the medium with 250 ul of the corresponding medium complemented with 4 ug/ml Polybrene
2. Infect by adding directly on the cells 20 ul of the virus
3. Let in the incubator for 4 h
4. After 4 h, add 1 ml/well of the corresponding medium complemented with polybrene

DAY 6:

1. Trypsinysed the cell to transfer them in a 25 cm flask

DAY 9:

1. Bring the cell back in the lab and tranfer them in:

| Cell type | Flask |
|---|---|
| MDA-MB-231 | 150 cm |
| SUM-159PT | 150 cm |
| MDA-MB-231 D3H2LN | 150 cm |
| T47D | 75 cm |
| MCF7 | 75 cm |

When the flask is confluent you can proceed to the sorting of FACS

CELL SORTING:

You should have a concentration for the sorting of $10.\ 10^6$ cells/ml

1. Trypsinize the cell and count them
2. Wash the cell one time in PBS
3. Resuspend the cell in the required volume of PBS completed with 2× AB
4. Pass the cell on a cell strainer to eliminate aggregate
5. Transfert the cell Polypropylene Facs tubes
6. Prepare tube to receive the sorted cells containing 100% SVF completed with 2× AB
7. Prepare 6 well plate to grow the sorted cells containing the corresponding medium without SVF but with 2× AB (when the sorted cells will be added there will be 20% SVF final)
8. Then let the cells grow until there is enough to realize the different validation tests.
9. Don't forget to frost the clone.

siRNA

All siRNA were on Target plus smartpool from Dharmacon

For human TGF□1, the siRNA were:

```
                                    (SEQ ID NO: 22)
siRNA1 5'- AUUGAGGGCUUUCGCUUA-3',

                                    (SEQ ID NO: 23)
siRNA2 5'- CCGAGAAGCGGUACCUGAA-3',

                                    (SEQ ID NO: 24)
siRNA3 5'- GCAGAGUACACAGCAUA-3',

                                    (SEQ ID NO: 25)
siRNA4 5'- GGACUAUCCACCUGCAAGA-3',
```

siRNA control was a validated non targeting smartpool from Dharmacon. Sequence was not provided by the manufacturer (reference Dharmacon: D-001810-02-20)

To transiently silence human TGFβ1, we used the specific siRNAs described above at 30 nM, and transfected cells with DharmaFECT for 48 hr according to the manufacturer's instructions. Effective downregulation of endogenous TGFβ1 was verified by ELISA.

ELISA for Human TGFβ1

In Cell Supernatant

The ELISA for TGFβ1 was performed as directed by the manufacturer on 100 μl of activated cell supernatants using a kit from R&D systems (#DY240)

In Mouse Serum

Blood was collected from mice and serum separation was achieved on BD Microtainer SSR Tubes (#365968). The ELISA for TGFβ1 was performed as directed by the manufacturer on 1 μl of activated serum using a kit from R&D systems (#DY240)

Plasmids Construction

The human TGFβ1 promoter (PGL3-hTGFß1-1670) was cloned by PCR using as a template genomic DNA isolated from MDA-MB-231 in the PGL3 basic vector (Promega). All constructions were verified by sequencing. The pCS2-(n)-βgal has been already described (Jauliac, S et al. (2002). Nature Cell Biology, 4(7), 540-544).

Cells were transiently transfected with the appropriate plasmids using Lipofectamine 2000 (Invitrogen) according to the manufacturer's instructions.

Sequences of the Different Constructions:

PGL3 basic (Promega, empty vector): SEQ ID NO:26;

PGL3-hTGFß1-1670 promoter (expression of luciferase under control of hTGFß1 promoter): SEQ ID NO:27;

Luciferase Assay

Cells were cotransfected with either the PGL3 basic plasmid or the PGL3-hTGFß1-1670 Luciferase promoter construct and the pCS2-(n)-ß-galactosidase plasmid using Lipofectamine 2000. The following day cell were treated with either PBS or $1.10^9$ particles/well in a 6 well plate for 24 h. After 24 h cell were lysed with the Reporter Lysis Buffer (Promega) and Luciferase and ß-gal activities were measured using the Luciferase Assay System (Promega) and Galacton-plus (Tropix) on a luminometer. Luciferase activities were normalized relative to the corresponding ß-gal activities.

Mice Experiments:

Xenograft and Follow-Up In Vivo

For MB-231 D3H2 LN-Luc in Hsd:AthymicNude-Foxn1nu female Mice 6 weeks old Hsd:AthymicNude-Foxn1nu female Mice were from Envigo company. Mice were hosted during 1 week in the IUH animal facility before any manipulation. When mice reached 7 weeks old, 1 to $0.5.10^6$ MDA-MB-231 D3H2 LN-Luc cells diluted in 100 μl of PBS were injected in the 2nd lower right fat-pad. 3 days later successful xeno-tranplantations were vizualised by luminescence by injecting XenoLight D-Luciferin, Potassium Salt diluted in PBS and luminescence was acquired for 30 s on the Xenogen system. Groups of 8 mice for each condition were established with equivalent luminescence. Experiments take place during 2 months. The first month, tumour size was measured by caliper on Monday and Thursday. The Tuesday of each week, mice were injected weekly with $50.10^8$ SEV T47D-WT, T47D-shCtrl, T47D-shNFAT3-3 or T47D-shNFAT3-4, either intratumoral or intravenous during 2 months as described in the different experiment. The Friday of each week blood was collected retro-orbitally. Beginning the $2n^d$ month, metastases begin to appear, therefore evaluation of metastases formation was done on Monday and Thursday when tumor size was measured. Mice were injected with XenoLight D-Luciferin, Potassium Salt diluted in PBS and bioluminescent images (where the primary tumor was shield with a black tissue) were acquired on the Xenogen system to quantify the mean photon flux produced by the metastatic MDA-MB-231 D3H2 LN-Luc cells. Metastases quantification is presented as the mean photon flux produced by the metastatic MDA-MB-231 D3H2 LN-Luc cells. At the end of the 2 months, mice were sacrificed and primary tumours and lungs, axillary lymph nodes and liver were keep at −80° C. for future immunofluorescence labelling.

Results

Characterization of SEV Produced by Low Invasive Breast Cancer T47D and MCF7 Cells Representative examples of size distribution of SEV produced by MDA-MB-231 and T47D cells are represented in FIG. 1A (MDA-MB-231) and FIG. 1B (T47D) and show that SEV produced by MDA-MB-231 and T47D cells have a similar mean size between 100 and 200 nm.

SEV produced by MDA-MB-231 and T47D cells were also characterized by Western blot and compared to whole cell extracts using antibodies against Calnexin; CD63 and CD81 (FIG. 1C). Results show that the purified sample contains only SEV because it expresses CD63 marker and not calnexin, showing that no cells are present in said sample.

SEV Produced by Low Invasive Breast Cancer T47D-WT and MCF7-WT Cells Inhibit Specifically Invasion of Highly Invasive MDA-MB-231 and SUM-159-PT Breast Cancer Cells and WM.266.4 Melanoma Cells.

SEV from different cell lines were produced with the intent to test their specific capacity to modulate invasion of highly invasive breast cancer cells (MDA-MB-231, SUM159PT) or melanoma cells (WM.266.4) in classical transwell invasion assays. Five types of cells were chosen for the production of SEV: 2 low invasive breast cancer cell lines (T47D-WT, MCF7), 1 highly invasive breast cancer cell line (MDA-MB-231), and 2 human fibroblasts obtained from young and old humans biopsies (FHN21-WT, 20 years old; FHN32-WT, 74 years old). Results are presented in FIG. 2 and show that:

SEV produced by human fibroblasts obtained from young and old humans biopsies (FHN21-WT and FHN32-WT) and by a highly invasive breast cancer cell line (MDA-MB-231) do not significantly alter the invasion index of highly invasive breast cancer cell line MDA-MB-231 (see FIG. 2A);

SEV produced by 2 low invasive breast cancer cell lines, T47D-WT and MCF7-WT cells, significantly decrease by about 50% the invasion index of highly invasive breast cancer cell lines MDA-MB-231 (see FIGS. 2A and 2C) and SUM-159-PT (see FIG. 2D). The fact that two distinct low invasive breast cancer cell lines have the same effect highlights that the inhibitory effect of SEV produced by low invasive breast cancer cell lines is not specific toward an SEV-producing cell line but is a general effect;

SEV produced by low invasive breast cancer cell lines T47D-WT and MCF7-WT cells also significantly decrease by about 60% the invasion index of highly invasive melanoma cell line WM.266.4 (see FIG. 2B). The fact that the two low invasive breast cancer cell lines have the same effect on a highly invasive melanoma cell line highlights that the inhibitory effect of SEV produced by low invasive breast cancer cell lines is not specific toward highly invasive breast cancer cell lines, but is a general effect against highly invasive cell lines, no matter what is their original cell type.

SEV from Low Invasive Breast Cancer Cells (T47D-WT) Do Not Modify the Proliferation of Highly Invasive Breast Cancer Cells (MDA-MB-231 and SUM-159-PT)

The ability of SEV from low invasive breast cancer cell line T47D-WT to alter the proliferation of highly invasive breast cancer cell lines MDA-MB-231 and SUM159PT was further assessed, as well as their ability to induce apoptosis of highly invasive breast cancer cell line MDA-MB-231.

Figure 3:
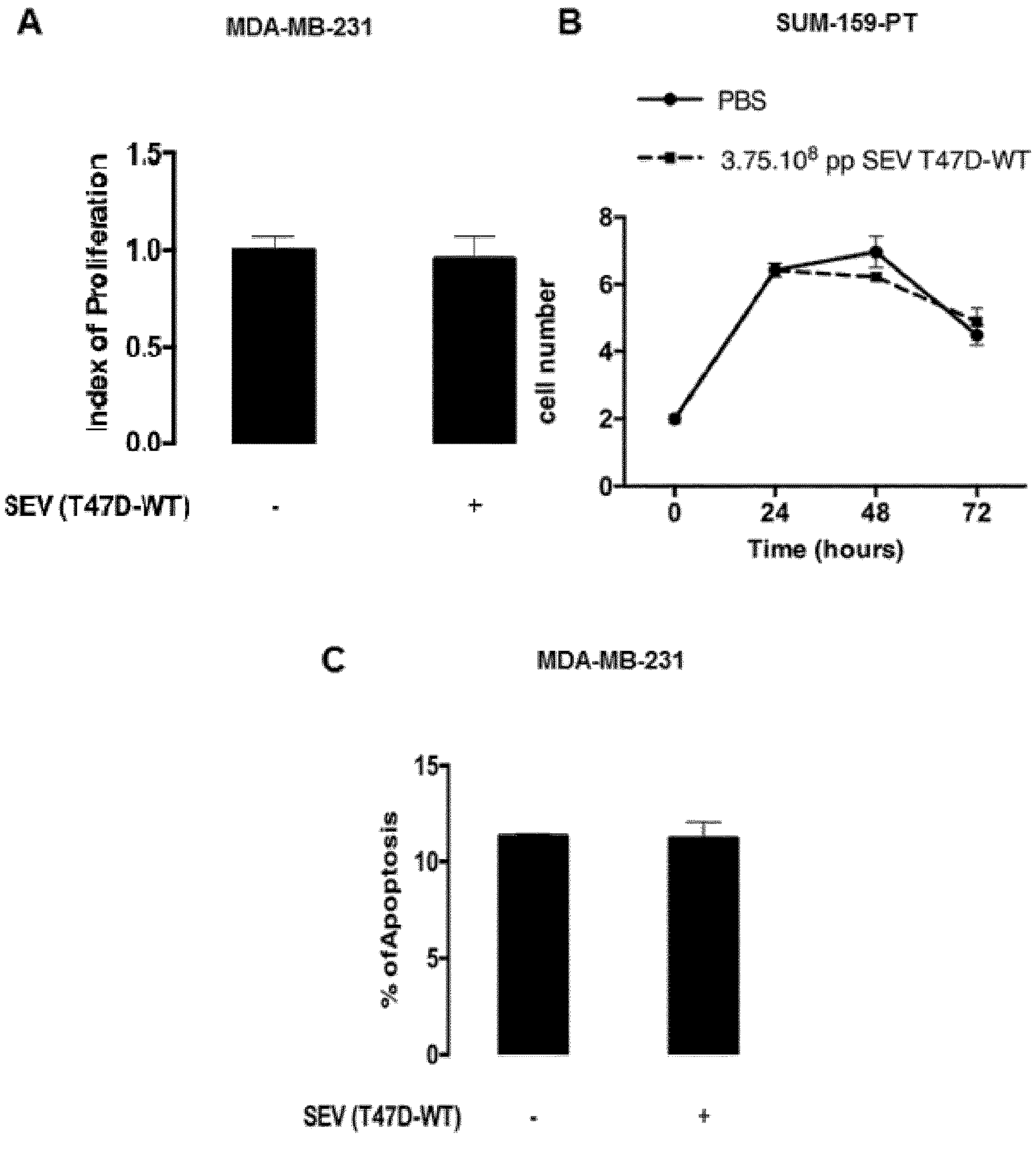
FIG. 3. SEV from low invasive breast cancer cells do not modify the proliferation of highly invasive breast cancer cells. Highly invasive MDA-MB-231 (n=2) (A) were treated for 24 h and SUM-159-PT (n=2) (B) were treated for 24, 48 and 72 h with the indicated amount of SEV from T47D-WT to evaluate cell proliferation either by BrdU incorporation (A) or direct cell counting (B). (C) Highly invasive MDA-MB-231 were treated for 48 h with SEV from T47D-WT to evaluate cell apoptosis (n=2).

Results are presented in FIG. 3 and show that SEV from low invasive breast cancer cell line T47D-WT do not modify the proliferation of highly invasive breast cancer cell lines MDA-MB-231 (see FIG. 3A) and SUM159PT(see FIG. 3B), and do not induce apoptosis of highly invasive breast cancer cell line MDA-MB-231.

The Inhibitory Effect of SEV Produced by Low Invasive Breast Cancer Cell Line T47D on the Invasive Capacity of Highly Invasive Cell Lines (MDA-MB-231 and SUM-159-PT) Requires the Expression of NFAT3 in the Low Invasive SEV-Producing Cell Line T47D-WT The inventors had previously shown that low invasive breast cancer cell lines express specifically high amount of NFAT3 compared to the high invasive breast cancer cell lines required to their low invasive capacity (Fougère, M., et al. (2010). Oncogene, 29(15), 2292-2301).

Therefore, the hypothesis was made that endogenous NFAT3 in SEV-producing cells (T47D-WT) could be required for these SEV to blunt cell invasion of high invasive cell line. To test this possibility, they generated T47D cells where endogenous NFAT3 expression was reduced by 2 shRNA that reduce to 50% the expression of endogenous NFAT3 (ShNFAT3-3, ShNFAT3-4) or unaltered by a shRNA control (shCtrl) (see FIG. 4A). SEV were produced from the shRNA expressing T47D-cell lines and tested on the invasive capacity of highly invasive cell lines MDA-MB-231 and SUM-159-PT.

Figure 4:
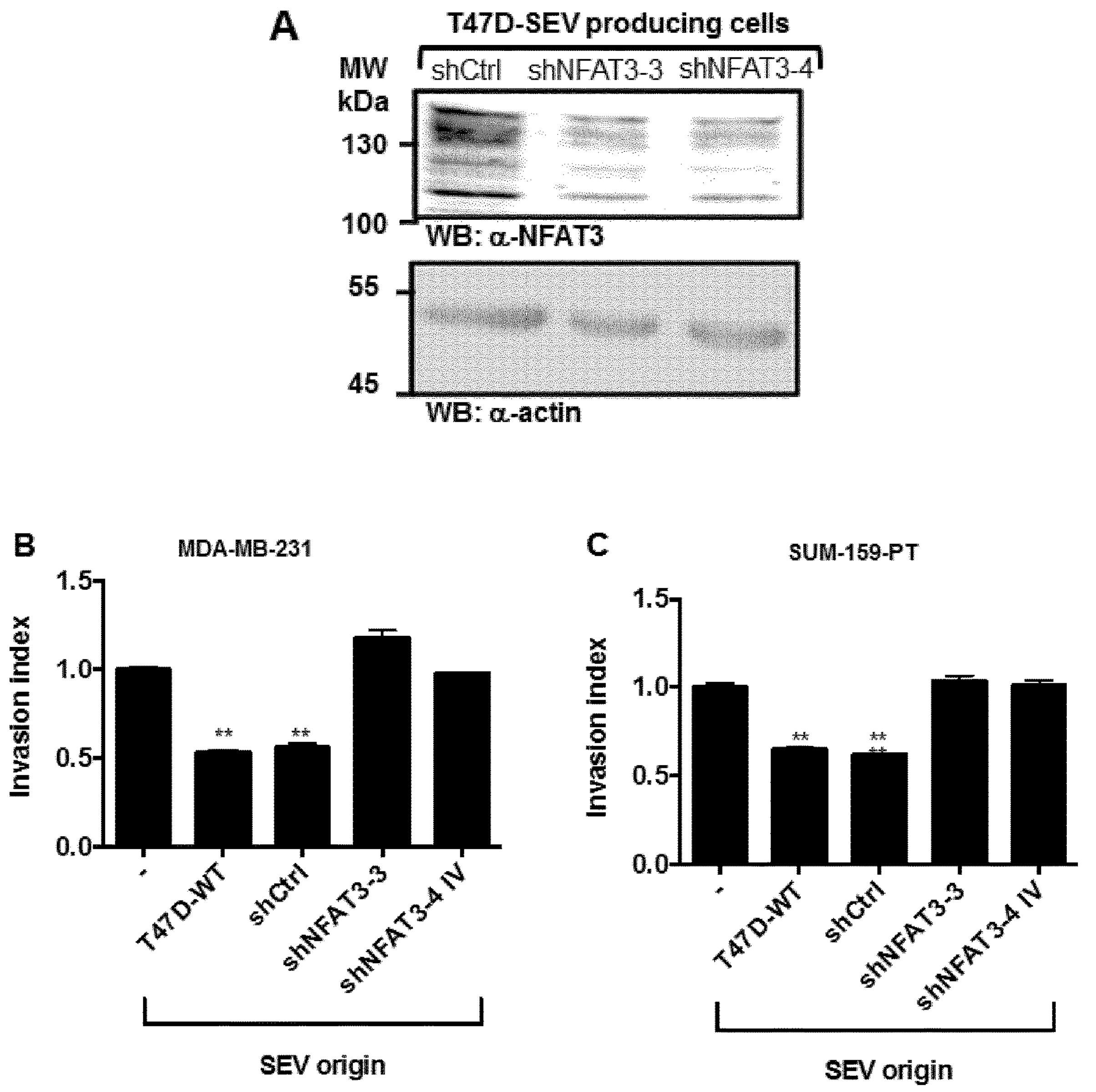
FIG. 4. The inhibitory effect of the SEV on the invasive capacity of high invasive cell lines (MDA-MB-231 and SUM-159-PT) requires the expression of NFAT3 in the low invasive SEV-producing cell line T47D. (A) Western blot of T47D cells expressing either shCtrl, shNFAT3-3 or shNFAT3-4. Whole cell lysate were revealed by an anti-NFAT3 and amount of protein was normalized by revelation with an anti-actin. Highly invasive MDA-MB-231 (B) or SUM159PT (C) cells were pre-treated or not with SEV produced by low invasive T47D breast cancer cell line WT or stably expressing shRNA that reduce to 50% the expression of endogenous NFAT3 (shNFAT3-3, shNFAT3-4) and as a control a shRNA control (shCtrl) and tested for their invasive capacity (n=3,**p<0.005). The invasion index is calculated as a proportion of the number of invasive cells in treated wells compared to the number of invasive cells in the control well arbitrarily set to 1.

Results are presented in FIG. 4B and FIG. 4C and demonstrate that expression of endogenous NFAT3 in SEV-T47D-producing cell line is absolutely required to impede breast cancer cell invasion, since SEV produced from T47D-cell lines expressing shRNA that reduce to 50% the expression of endogenous NFAT3 (ShNFAT3-3, ShNFAT3-4) do not decrease the invasion index of highly invasive cell lines MDA-MB-231 and SUM-159-PT, contrary to SEV produced from T47D-cell lines without shRNA (T47D-WT) or expressing a control shRNA (shCtrl).

These data show for the first time that NFAT3 expression in SEV producing cell line is key to the transfer the invasive inhibitory capacity to high invasive cell lines.

De Novo Induction of TGFβ1 in MDA-MB-231 Cells is Required for the SEV to Modulate Breast Cancer Cell Invasion.

To begin to elucidate by which mechanisms SEV produced by the T47D-WT cell line can impede invasion of highly invasive breast cancer cell lines, the modulation of different factors by SEV in the receiving cells (MDA-MB-231) was evaluate.

Figure 5:
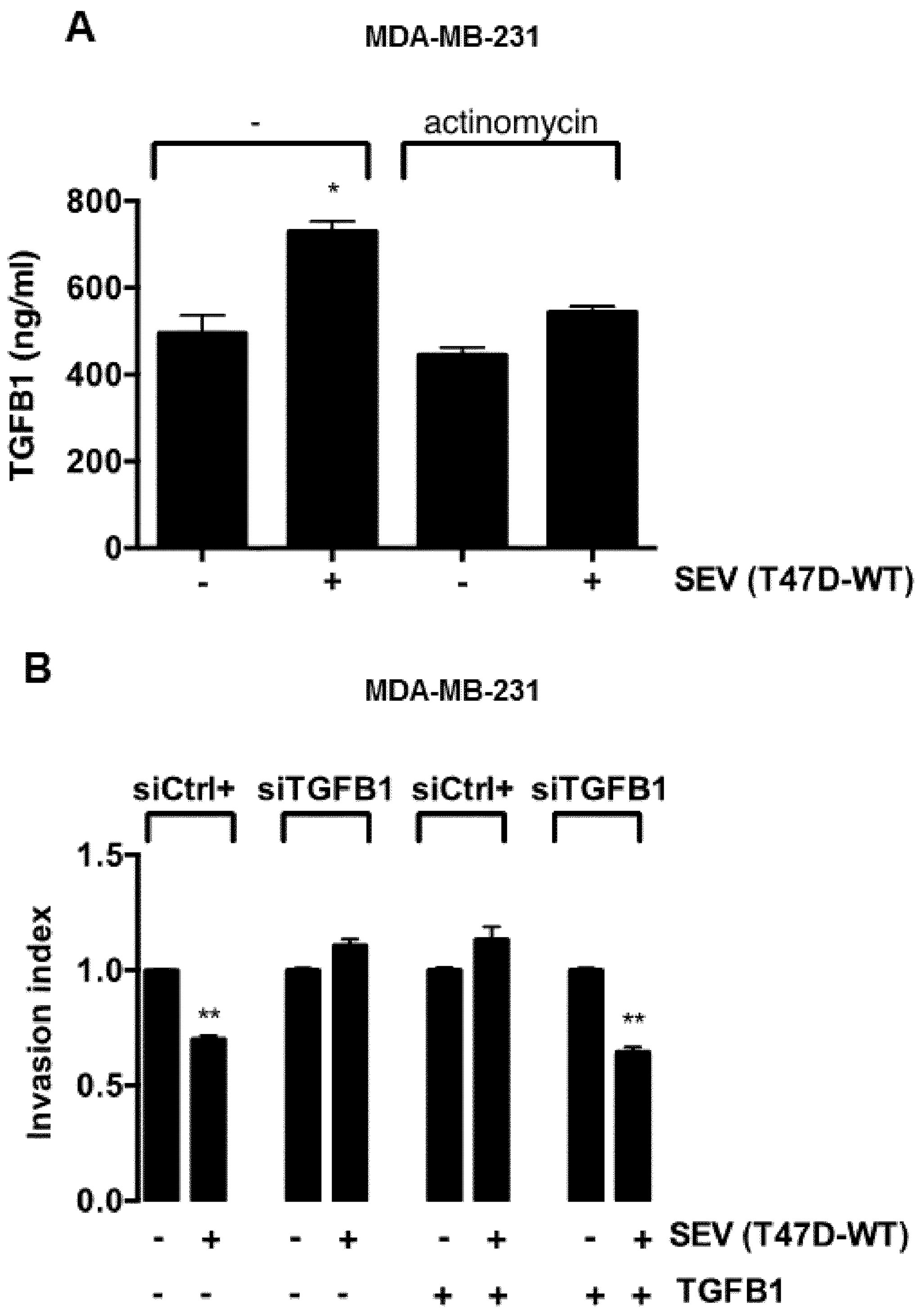
FIG. 5. De novo Induction of TGFb1 in MDA-MB-231 cells is required for the SEV to modulate breast cancer cell invasion. (A) MDA-MB-231 were incubated with SEV secreted by WT-T47D, in presence or not of actinomycin and TGFß1 was measured by ELISA (n=2; *p<0.05). (B) Highly invasive MDA-MB-231, transiently transfected with a siRNA control or a siRNA directed against endogenous TGFb1, were pre-treated or not with SEV produced by low invasive WT-T47D breast cancer cell line and tested for their invasive capacity. In some cases MDA-MB-231 were treated with exogenous TGFb1 to reverse the effect of siRNA (n=2; *p<0.005).

Data presented in FIG. 5A show that SEV from T47D-WT cells induce an increase of TGFβ1 secretion in MDA-MB-231. Moreover, this increase of TGFβ1 secretion required an active transcription since pre-treatment of the cells with an inhibitor of transcription (Actinomycin) prevents completely this increase of secretion. These results are critical because they demonstrate that the increase of TGFβ1 secretion is an active mechanism taking place in the receiving cells (MDA-MB-231) and not linked to a contribution of potential SEV TGFß1 protein.

The possibility that this increase of TGFβ1 secretion could be required for SEV to inhibit cell invasion was then tested. For this purpose, endogenous TGFβ1 was independently down regulated, in transient transfection assays, in receiving cells (MDA-MB-231) by an siRNA directed against TGFβ1 (siTGFß1) or a control siRNA (siCtrl). To rescue the loss of endogenous TGFβ1, the receiving cells were treated with exogenous TGFβ1. Results presented in FIG. 5B demonstrate that the increase in TGFβ1 secretion by SEV is absolutely required to inhibit cell invasion since, when TGFβ1 is down-regulated, SEV are no longer able to impede cell invasion (siTGFB1, +SEV) compared to the receiving shCtrl-cells (siCtrl, +SEV). Moreover, adding back exogenous TGFβ1 with SEV is sufficient to restore the capacity of SEV to inhibit cell invasion (siTGFB1, +SEV, +TGFβ1). Furthermore, adding exogenous TGFβ1 without having previously down regulated endogenous TGFb1 (siCtrl, +/−SEV, +TGFb1) is not sufficient to inhibit invasion, showing that treatment with exogenous TGFb1 alone is not enough to inhibit cell invasion. These results demonstrate that SEV from low invasive cell lines induce a transcriptional increase of TGFβ1 secretion in the receiving highly invasive cell line, which is absolutely required for the capacity of SEV to inhibit invasion.

SEV Produced by T47D-WT Cells are Competent in Up-Regulating the Activity of the hTGFB1 Promoter.

Figure 6:
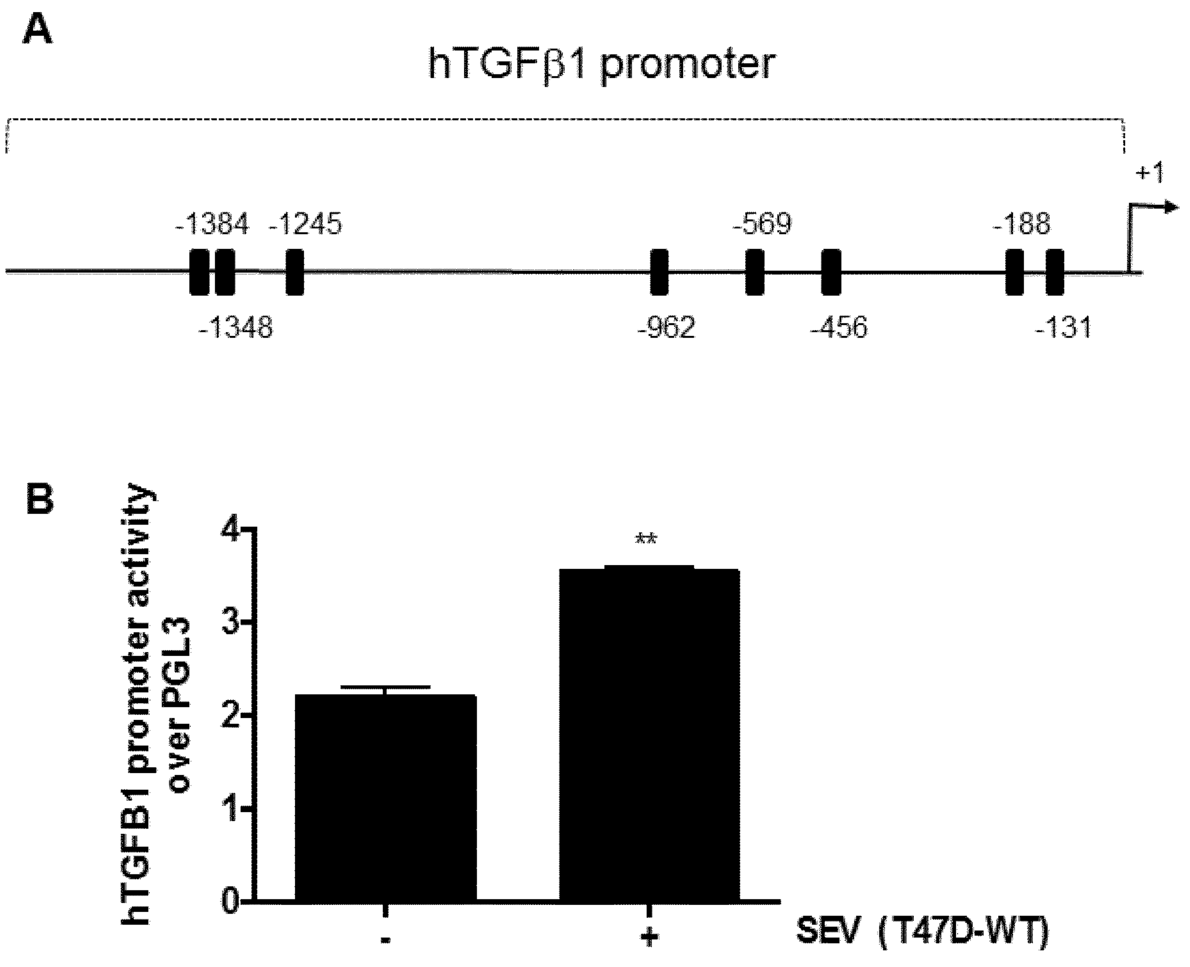
FIG. 6. SEV produced by WT-T47D cells are competent in up-regulating the activity of the hTGFB1 promoter. (A) Schematic representation of the hTGFb1 promoter. Six potential NFAT-binding sites have been found using the NFAT binding site they have developed at the address: software: http://www.fast-db.com/perl/nfat.pl; positions relative to the +1 initiation site are indicated. (B) SUM-159-PT cells were cotransfected with the pCS4-(n)-b-galactosidase and the hTGFb1 promoter plasmids or the pGL3 basic vector as a control and left untreated or treated with SEV from WT-T47D. After 24 h, cells were analysed for Luciferase and b-galactosidase activities. Quantification of hTGFb1 promoter-mediated Luciferase activity was normalized relative to that of the b-galactosidase and compare to the control luciferase activity of the pGL3 basic vector. (n=2; *p<0.005).

A schematic representation of the hTGFb1 promoter is presented in FIG. 6A. Six potential NFAT-binding sites have been found using the NFAT binding site determined using the software available at http://www.fast-db.com/perUnfat.pl. Positions relative to the +1 initiation site are indicated.

It was thus tested if SEV produced by T47D-WT cells are able to up-regulate the activity of the hTGFB1 promoter. Results are presented in FIG. 6B and show that SEV produced by T47D-WT cells do indeed up-regulate the activity of the hTGFB1 promoter.

Intravenous or Intratumoral Injection of SEV Produced by Low Invasive Breast Cancer Cell Line T47D-WT Inhibit Tumor Growth and Metastases Apparition and Correlate with an Induction of TGFβ1

It was then tested if SEV produced by low invasive breast cancer cells could induce the same inhibitory effect in in vivo model as they did in vitro. For this purpose, MDA-MB-231 cells expressing the luciferase gene (D3H2LN) were injected into the left Fat Pad of 6-week-old female mouse Athymic Nude-Foxn1nu mice. SEV produced by low invasive breast cancer cell line T47D-WT or as a control PBS were injected weekly either in the tail vein or in the tumor, one week after xenotransplation of cells.

Monitoring of tumor growth was done by caliper measuring during 10 weeks.

Figures 7A, 7B:
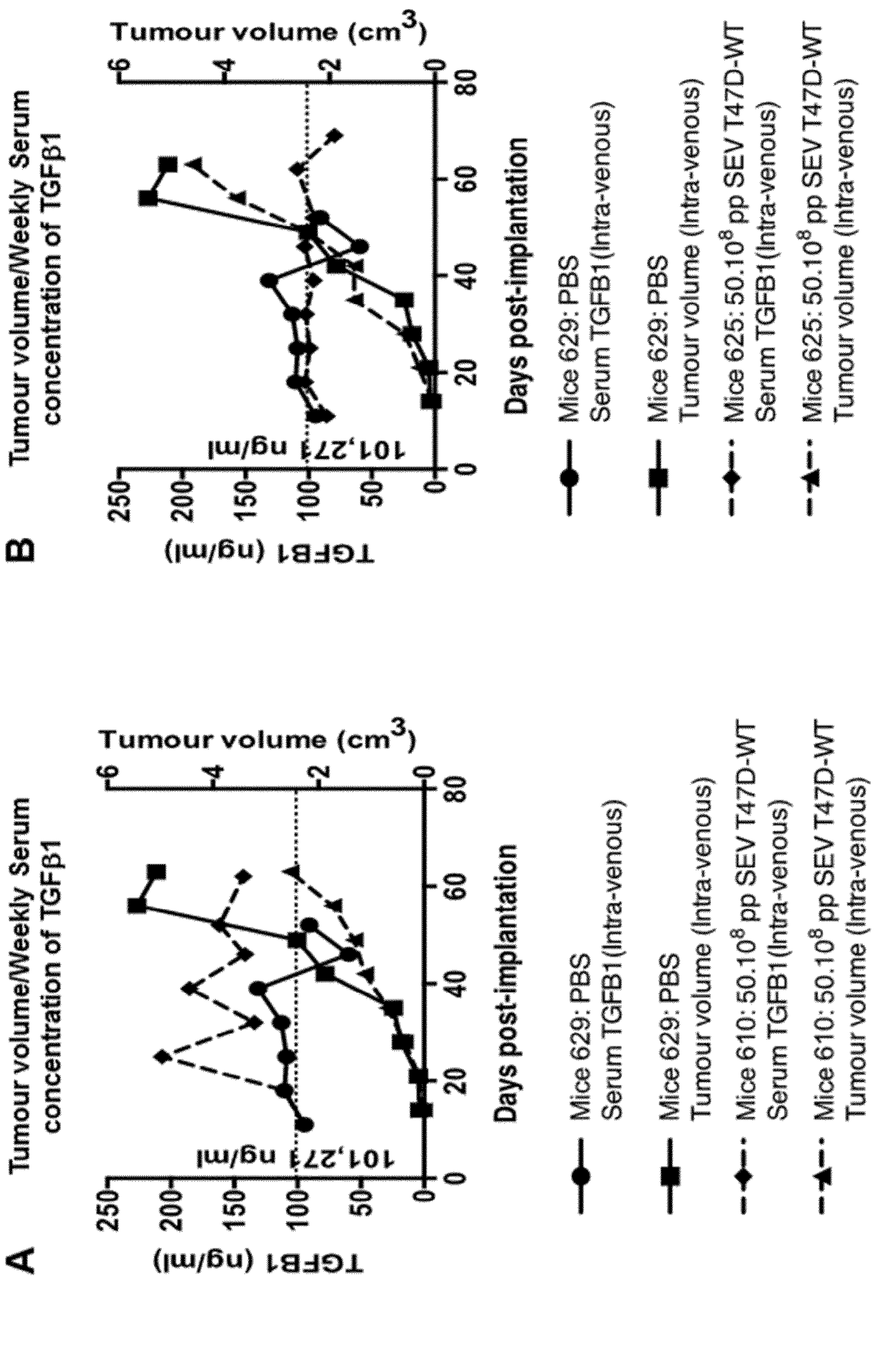
FIG. 7. Intra-venous injection of SEV produced by low invasive breast cancer cell line inhibit tumor growth and metastases apparition and correlate with an induction of TGFb1. (A) $1.10^6$ MDA-MB-231 cells (D3H2LN) in 100 ml PBS were injected into the left Fat Pad of each 6-week-old female mouse Athymic Nude-Foxn1nu mice. Tumor growth is presented as the mean tumor volume (cm3), with data from mice N° 629 (A and B) injected weekly intra-venous with PBS and data from mice N° 610 (A) or N° 625 (B) injected weekly intra-venous with $50.10^8$ pp SEV produced by WT T-47D 7 days after cell transplantation in the Fat Pad. Serum TGFb1 measurement in the blood is presented as ng/ml with data from mice N° 629 (A and B) injected weekly intra-venous with PBS and from mice N° 610 (A) or N° 625 (B) injected weekly intra-venous with $50.10^8$ pp SEV produced by WT T47D. (C and D) Beginning day 42, weekly, bioluminescent images (where the primary tumor was shield with a black tissue) were acquired on the Xenogen system to quantify the mean photon flux produced by the metastatic MDA-MB-231 cells. Metastases quantification is presented as the mean photon flux produced by the metastatic MDA-MB-231 cells, with data from mice N° 629 (C and D) injected weekly intra-venous with PBS and data from mice N° 610 (C) or N° 625 (D) injected weekly with $50.10^8$ pp SEV intra-venous produced by WT T47D. TGFb1 measurement in the blood is presented as ng/ml, with data from mice N° 629 (A and B) injected weekly intra-venous with PBS and data from mice N° 610 (C) or N° 625 (D) injected weekly $50.10^8$ pp SEV intra-venous produced by WT T47D.
Figure 7C:
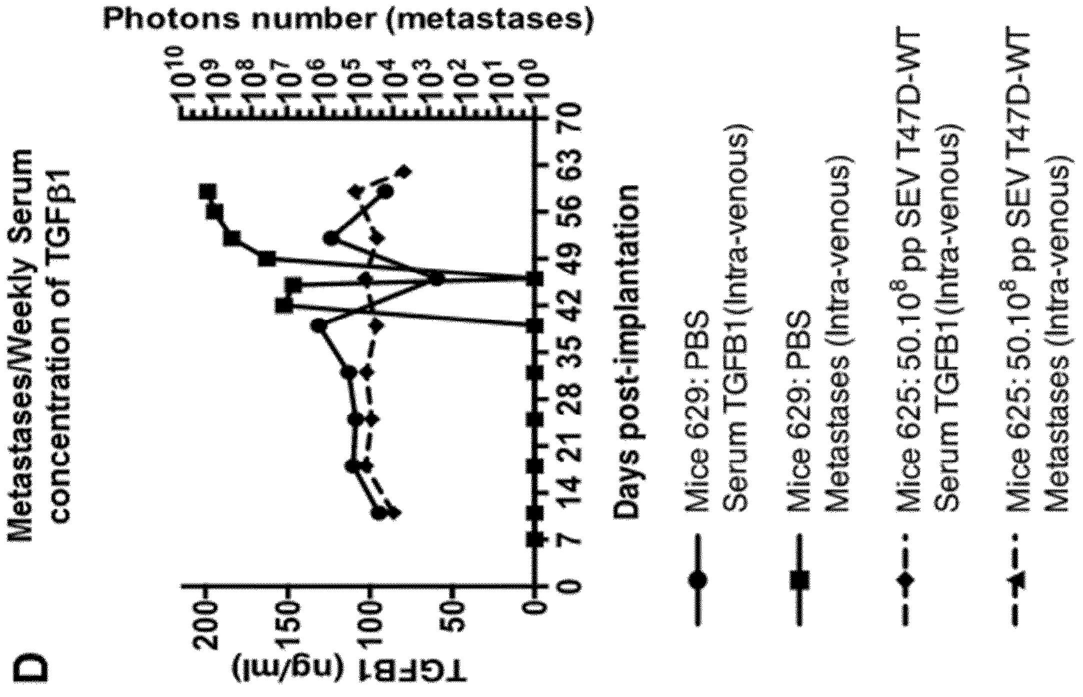
Figure 7D:
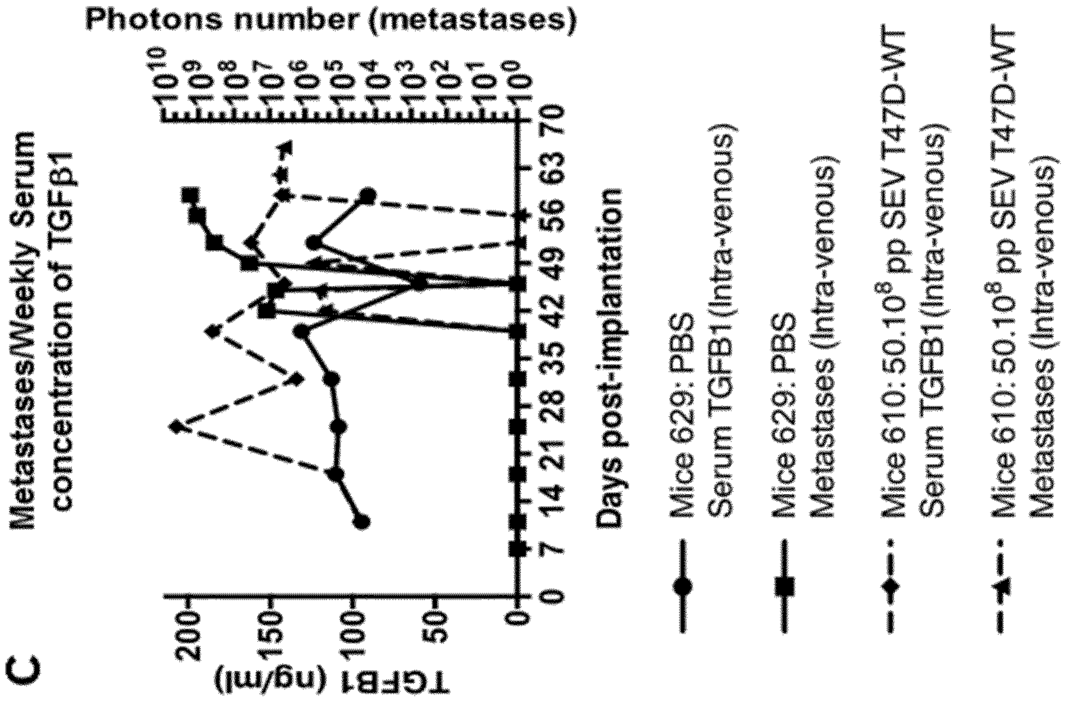
Figures 8A, 8B:
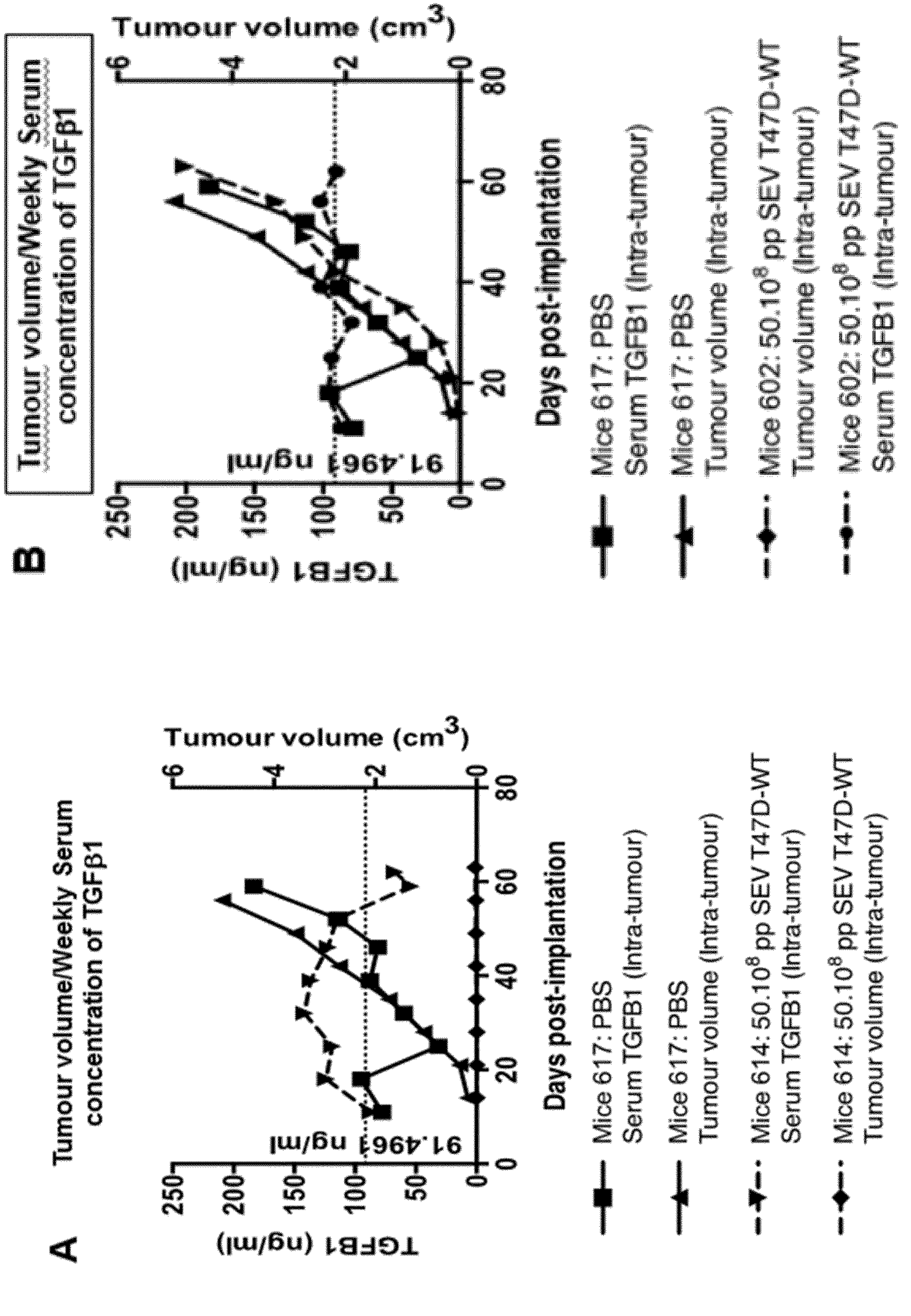
FIG. 8. Intra-tumor injection of SEV produced by low invasive breast cancer cell line inhibit tumor growth and metastases apparition and correlate with an induction of TGFb1. (A) $1.10^6$ MDA-MB-231 cells (D3H2LN) in 100 ml PBS were injected into the left Fat Pad of each 6-week-old female mouse Athymic Nude-Foxn1nu mice. Tumor growth is presented as the mean tumor volume (cm3), with data from mice N° 617 (A and B) injected weekly intratumoral with PBS and data from mice N° 614 (A) or N° 602 (B) injected weekly intratumoral with $50.10^8$ pp SEV produced by WT T-47D, 7 days after cell transplantation in the Fat Pad. Serum TGFb1 measurement in the blood is presented as ng/ml with data from mice N° 629 (A and B) injected weekly intratumoral with PBS and from mice N° 617 (A) or N° 602 (B) injected weekly intra-venous with $50.10^8$ pp SEV produced by WT T47D. (C and D) Beginning day 42, weekly, bioluminescent images (where the primary tumor was shield with a black tissue) were acquired on the Xenogen system to quantify the mean photon flux produced by the metastatic MDA-MB-231 cells. Metastases quantification is presented as the mean photon flux produced by the metastatic MDA-MB-231 cells, with data from mice N° 617 (C and D) injected weekly intratumoral with PBS and data from mice N° 614 (C) or N° 602 (D) injected weekly with $50.10^8$ pp SEV intratumoral produced by WT T47D. TGFb1 measurement in the blood is presented as ng/ml, with data from mice N° 617 (A and B) injected weekly intratumoral with PBS and data from mice N° 614 (C) or N° 602 (D) injected weekly $50.10^8$ pp SEV intratumoral produced by WT T47D.

Results are presented in FIG. 7 for intravenous injection and in FIG. 8 for intratumoral injection and show for the first time, and despite the absence of inhibition of cell proliferation in vitro (FIG. 3), that SEV from T47D-WT cells were able to significantly impede tumor growth (intravenous: FIG. 7A, mice N° 610; intratumoral: FIG. 8A, mice N° 614) in vivo compared to the mice injected with PBS (intravenous: FIG. 7A mice N° 629; intratumoral: FIG. 8A, mice N° 617).

Interestingly, in both injection types (intravenous or intratumoral) the inhibitory effect of SEV was closely correlated with an induction of TGFβ1 in the blood of treated mice. Indeed, mice in which the weekly injection of SEV did not modify the tumor growth rate did not show any increase of TGFβ1 in the blood (intravenous: FIG. 7B mice N° 625; intratumoral: FIG. 8B mice N° 602) compared to the mice injected with PBS (intravenous: FIG. 7B mice N° 629; intratumoral: FIG. 8B mice N° 617).

Figure 8C:
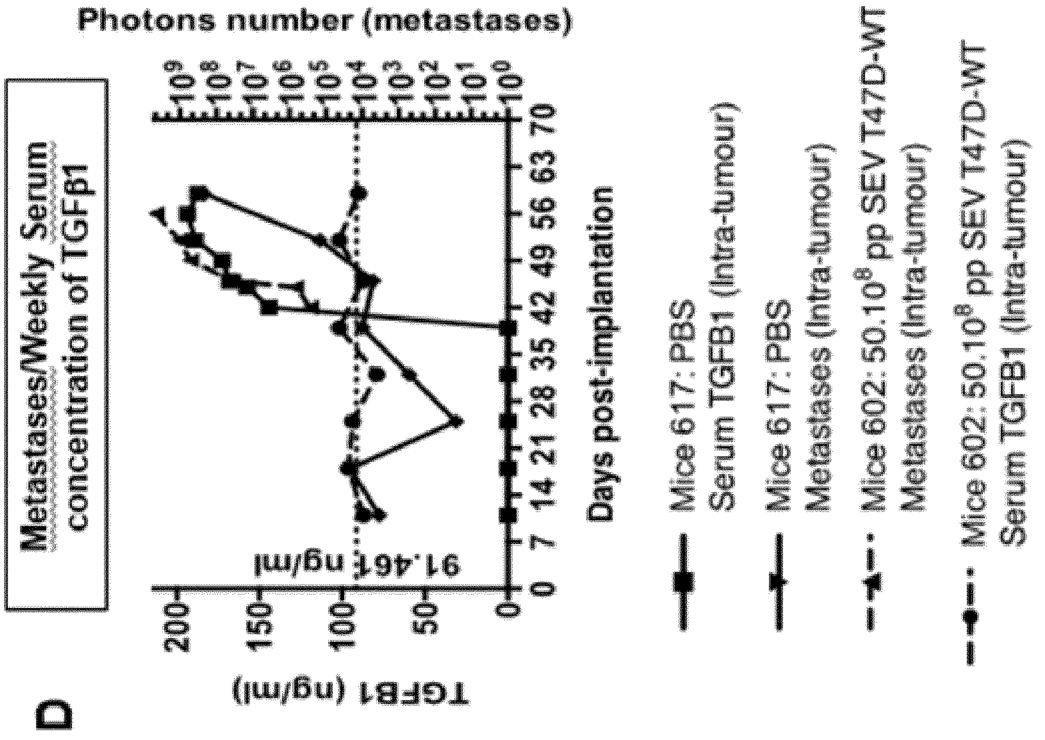

In the same group of mice, metastases formation was evaluated by bioluminescent imaging from day 42 (where the primary tumor was shield with a black tissue), on the Xenogen system, by the mean photon flux produced by the metastatic MDA-MB-231 cells. Results presented in FIG. 7 for intravenous injection and in FIG. 8 for intratumoral injection show for the first time that mice injected with SEV from T47D-WT cells have a significantly reduced unveiling and growth of metastases (intravenous: FIG. 7C, mice N° 610; intratumoral: FIG. 8C, mice N° 614) compared to mice injected with PBS (intravenous: FIG. 7C mice N° 629; intratumoral: FIG. 8C, mice N° 617) either in the tail vein or in the tumor.

Figure 8D:
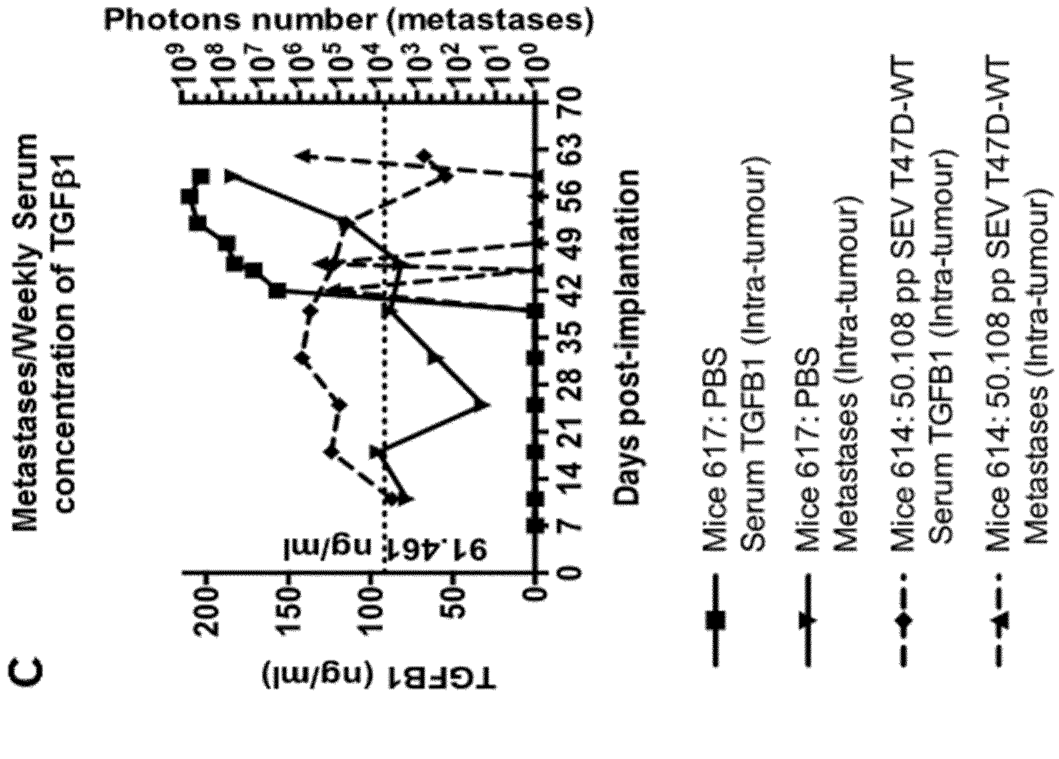

Moreover, as shown for tumor growth, the inhibitory effect of SEV on metastases was closely correlated with an induction of TGFβ1 in the blood. Indeed, mice in which the weekly injection of SEV did not modify the metastases apparition did not show any increase of TGFβ1 in the blood (intravenous: FIG. 7D mice N° 625; intratumoral: FIG. 8D mice N° 602) compared to the mice injected with PBS (intravenous: FIG. 7D mice N° 629; intratumoral: FIG. 8D mice N° 617).

These results are critical and demonstrate for the first time that SEV from low invasive breast cancer cells are able to impede tumor growth and metastases apparition in vivo and closely correlate with an increase of TGFβ1 in the blood circulation. This increase of TGFβ1 could be a good tool to evaluate the efficiency of SEV injection in cancer patients.

The inhibitory effect on the tumor growth of the intratumoral injection of SEV requires the expression of NFAT3 in the T47D-SEV producing cells and correlates with induction of TGFβ1.

It was then tested if SEV produced by low invasive breast cancer cells, in which endogenous NFAT3 was down-regulated by shRNA, could induce the same inhibitory effect in in vivo model.

Figure 9:
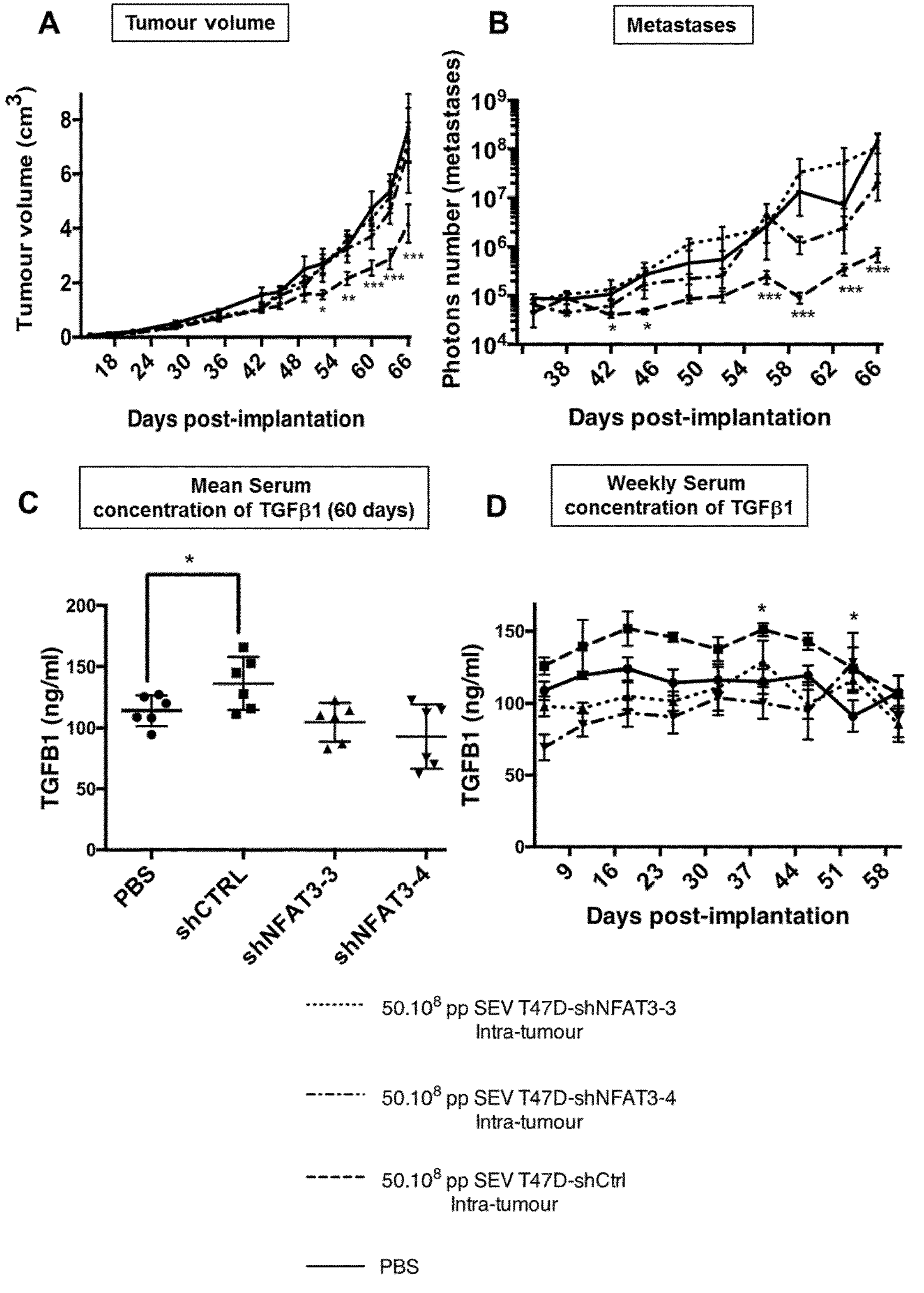
FIG. 9. The inhibitory effect on the tumor growth of the intratumoral injection of SEV requires the expression of NFAT3 in the T47D-SEV producing cells and correlates with induction of TGFb1. $1.10^6$ MDA-MB-231 cells (D3H2LN) in 100 ml PBS were injected into the left Fat Pad of each 6-week-old female mouse Athymic Nude-Foxn1nu mice. (A) Tumor growth is presented as the mean tumor volume (cm3)±SEM, from mice injected weekly intratumoral with PBS (PBS), from mice injected weekly intratumoral with $50.10^8$ pp SEV produced by shCtrl-infected T47D cells ($50.10^8$ T47D-shCtrl intratumoral), from mice injected weekly intratumoral with $50.10^8$ pp SEV produced by shNFAT3-4-infected T47D cells ($50.10^8$ T47D-shNFAT3-4 intratumoral), from mice injected weekly intratumoral with $50.10^8$ pp SEV produced by shNFAT3-3-infected T47D cells, 7 days after cell transplantation in the Fat Pad, 8 mice in each group. Comparisons were made using a two-tailed, unpaired Student's t test for each time point with the mice injected with PBS intratumoral. (B) Beginning day 42, weekly, bioluminescent images (where the primary tumor was shield with a black tissue) were acquired on the Xenogen system to quantify the mean photon flux produced by the metastatic MDA-MB-231 cells. Metastases quantification is presented as the mean photon flux produced by the metastatic MDA-MB-231 cells, with data from mice injected weekly intra-venous with PBS or $50.10^8$ pp SEV T47D-shCtrl intratumoral or $50.10^8$ pp SEV T47D-shNFAT3-4 intratumoral or $50.10^8$pp SEV produced by $50.10^8$ pp SEV shNFAT3-3-infected T47D cells. $^*p<0.05$ $^{}p<0.005$ and $^{*}p<0.0005$. (C) and (D) Serum was collected weekly from the mice of group (A) and concentration of TGFb1 present in the serum was evaluated by ELISA assay at the end of the experiment. (C) each point for each group represents the 60 days mean of TGFb1 concentration in the serum from week 1 to 9. Comparisons were made using a two-tailed, unpaired Student's t test for each time point with the mice injected with PBS intratumoral. $^*p<0.05$. (D) data are represented for each group of mice as in (A) from week 1 to 9.

For this purpose, MDA-MB-231 cells expressing the luciferase gene (D3H2LN) were injected into the left Fat Pad of 6-week-old female mouse Athymic Nude-Foxn1nu mice. SEV produced by T47D cells transfected by an shRNA that reduces to 50% the expression of endogenous NFAT3 (ShNFAT3-3, ShNFAT3-4) or by a shRNA control (shCtrl), or as a control PBS were injected in the tumor weekly, one week after xenotransplation of cells. Monitoring of tumor growth was done by caliper measuring during 10 weeks. Results presented in FIG. 9A show for the first time that, despite the absence of inhibition of cell proliferation in vitro, SEV from T47D-shCtrl cells were able to impede significantly tumor growth in vivo compared to the mice injected with PBS (around 50% diminution). Moreover, when endogenous NFAT3 was down regulated in SEV-producing cells (T47D-shNFAT3-3, T47D-shNFAT3-4), then their respective SEV were no longer able to inhibit tumor growth and growth rates were identical to the control mice treated with PBS (see FIG. 9A).

These results are critical and demonstrate for the first time that SEV from low invasive breast cancer cells require the expression of endogenous NFAT3 in the SEV producing cells to impede tumor growth in vivo.

In the same group of mice, metastases formation was evaluated by bioluminescent imaging (where the primary tumor was shield with a black tissue), on the Xenogen system, by the mean photon flux produced by the metastatic MDA-MB-231 cells. Results presented in FIG. 9B show that mice injected with SEV from T47D-shCtrl have a significantly reduced unveiling and growth of metastases compared to the mice injected with PBS. Moreover, when endogenous NFAT3 was down regulated in SEV-producing cells (T47D-shNFAT3-3, T47D-shNFAT3-4), then their respective SEV no longer impeded metastases formation and unveiling and growth rates were identical to the control mice treated with PBS (see FIG. 9B).

These results extend the in vitro data we obtained and demonstrate for the first time that SEV from low invasive breast cancer are able to impede metastases formation in vivo and require the expression of endogenous NFAT3 in the SEV producing cells.

Moreover, the anticancer effect of SEV from T47D-shCtrl cells was once more found to be correlated to an increase in TGFβ1 mean serum concentration (see FIGS. 9C and 9D).

Intravenous or Intratumoral Injection of SEV Produced by Low Invasive Breast Cancer Cell Line T47D-WT Inhibit Tumor Growth and Metastases Apparition Once Tumor is Settled.

To mimic clinical condition, it was then tested if SEV produced by low invasive breast cancer cells, could induce the same inhibitory effect in in vivo model after tumour establishment. For this purpose, MDA-MB-231 cells expressing the luciferase gene (D3H2LN) were injected into the left Fat Pad of 6-week-old female mouse Athymic Nude-Foxn1nu mice. SEV produced by T47D cells were first injected at D27 after D3H2LN injection. Monitoring of tumor growth was done by caliper measuring during 5 weeks after SEV injection. Results presented in FIGS. 10A and B show for the first time that, whatever the administration route (intravenous or intra-tumoural) and despite the absence of inhibition of cell proliferation in vitro, SEV from T47D cells were able to impede significantly tumor growth in vivo 27 days after tumour establishment compared to the mice injected with PBS (around 50% diminution).

Conclusions

The above results show that:

- Contrary to SEV produced by human fibroblasts or by a highly invasive breast cancer cell line, SEV produced by two low invasive breast cancer cell lines are able to reduce the invasion index of two highly invasive breast cancer cell lines and a highly invasive melanoma cell line. This shows that SEV produced by low invasive cancer cells may be used for reducing cancer progression and metastasis.
- Despite an absence of effect in vitro on invasive breast cancer cell lines proliferation, SEV produced by a low invasive breast cancer cell line were further found to impede both tumor growth and metastasis in an in vivo xeno-transplantation model, further demonstrating that SEV produced by low invasive cancer cells may be used for reducing cancer progression and metastasis.
- The inhibitory effect of SEV produced by a low invasive breast cancer cell line T47D on the invasive capacity of highly invasive cell lines (MDA-MB-231 and SUM-159-PT) requires the expression of NFAT3 in the low invasive SEV-producing cells.
- The expression of NFAT3 in the low invasive SEV-producing cells results in de novo induction of TGFβ1 in highly invasive breast cancer cell lines, which is required for the SEV to modulate breast cancer cell invasion in vitro. In vivo, response to SEV produced by a low invasive breast cancer cell line was found to be correlated to TGFβ1 serum concentration. Increase of TGFβ1 concentration in patients administered with SEV produced by low invasive cancer cells might thus be used as a biomarker of therapeutic efficiency of the treatment.

Example 2: SEV Produced by Modified Autologous or Not Fibroblasts Inhibit Invasion Since expression of NFAT3 by low invasive breast cancer cells has been found to be critical for SEV from these cells to inhibit cancer progression and metastasis, the ability of healthy fibroblasts induced to express NFAT3 to inhibit cancer progression and metastasis is further tested.

Figure 10:
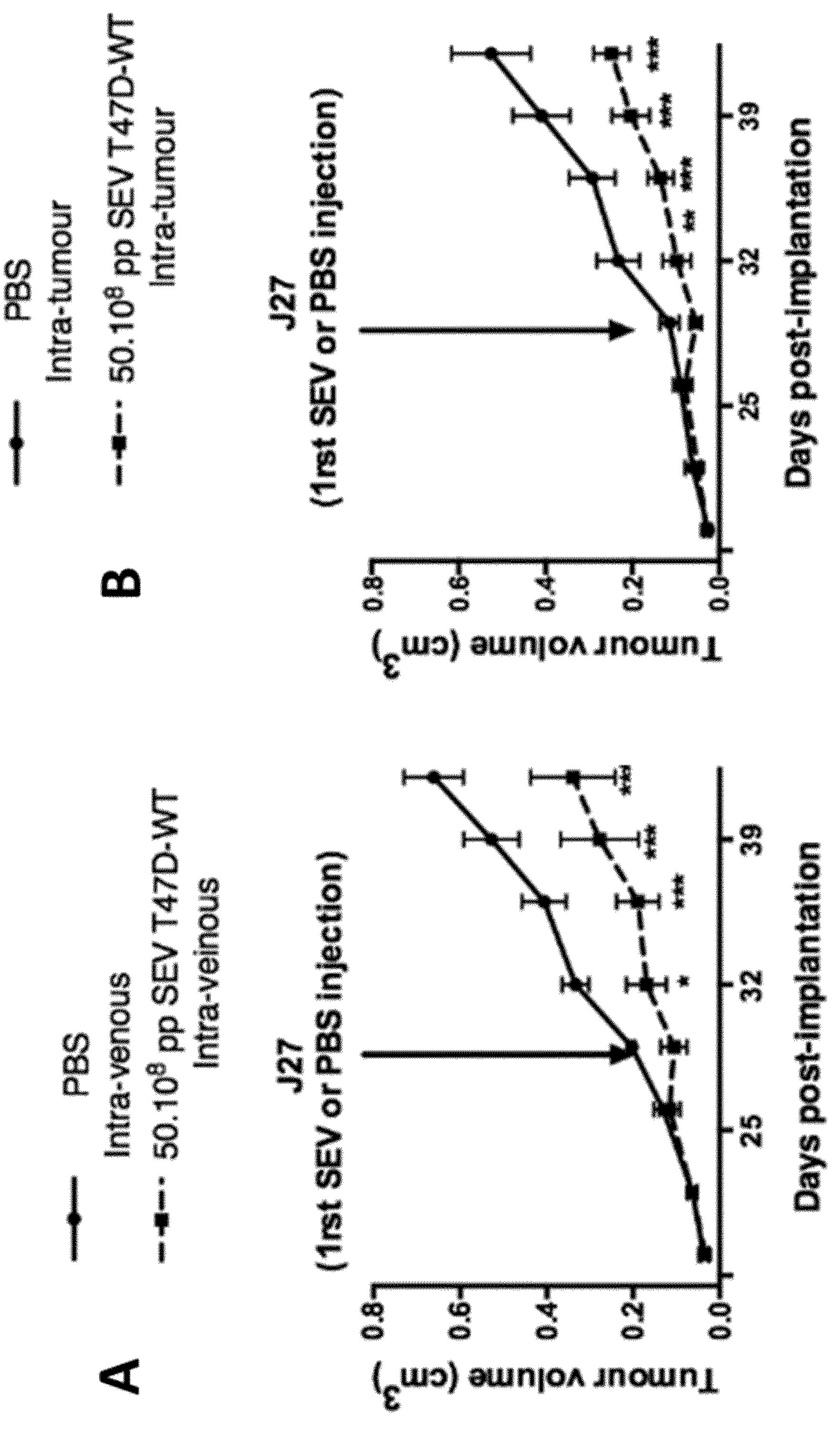
FIG. 10.: Delayed injection of SEV produced by T47D cell inhibit tumor growth. $0.5.10^6$ MDA-MB-231 cells (D3H2LN) in 100 ml PBS were injected into the left Fad Pad of each 6-week-old female Athymic Nude-Foxn1nu mouse. (A) Tumor growth is presented as the mean tumor volume (cm3)+/−SEM, from mice injected weekly, beginning day 27 intra-venous with PBS (PBS), from mice injected weekly, beginning day 27, intra-venous with $50.10^8$ ppSEV produced by T47D-WT cells. (B) Tumor growth is presented as the mean tumor volume (cm3)+/−SEM, from mice injected weekly, beginning day 27 intra-tumor with PBS (PBS), from mice injected weekly, beginning day 27, intratumoral with $50.10^8$ ppSEV produced by T47D-WT cells. Comparisons were made using a two-tailed, unpaired student's test for each time point. $^*p<0.05$, $^{}p<0.005$, $^{*}p<0.0005$. (8 mice/group).
Figure 11:
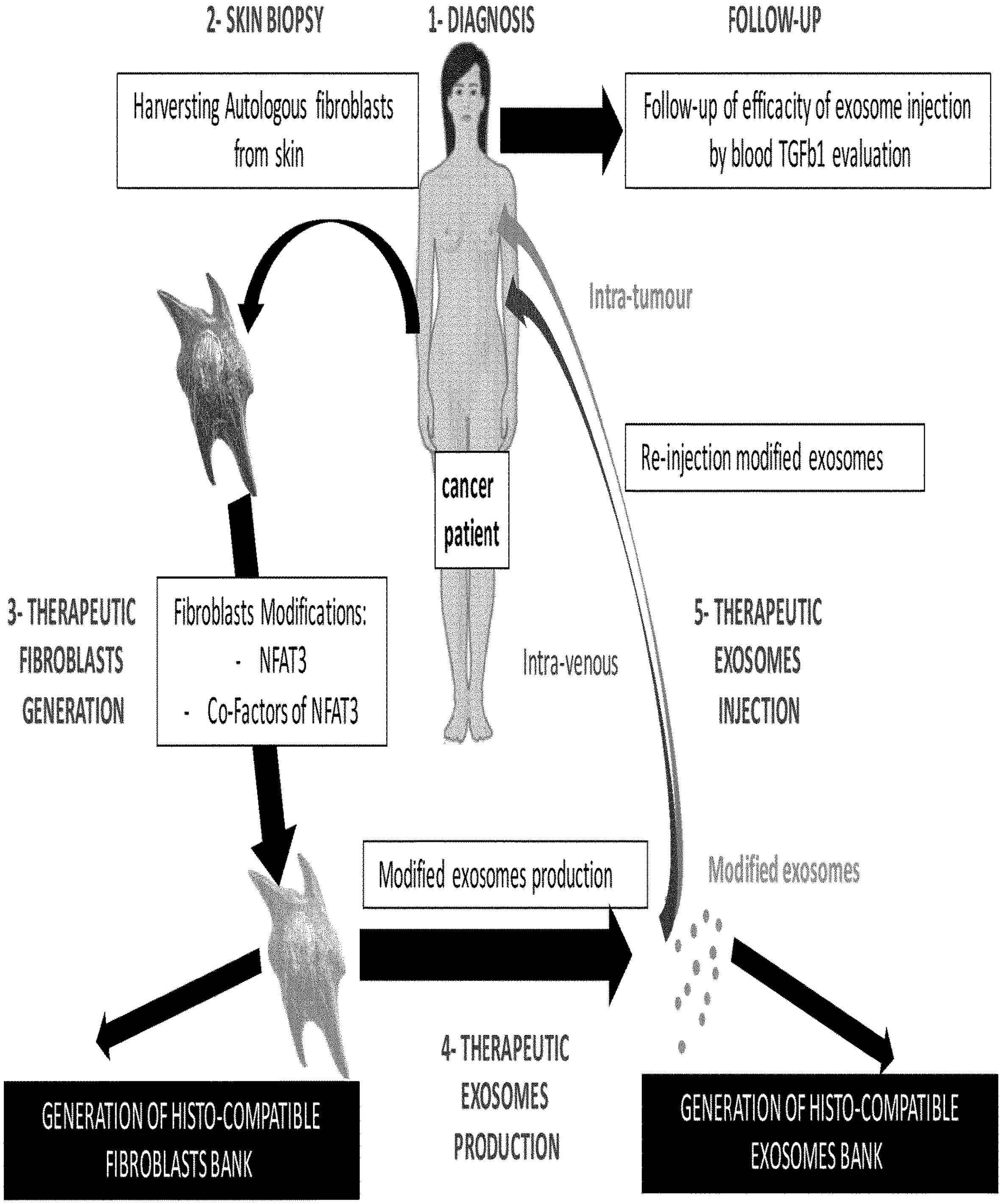
FIG. 11. Schematic diagram of the proposed therapy development.

On this basis, a schematic diagram of the proposed therapy development is represented in FIG. 10.

Materials and Methods

Unless otherwise specified, for corresponding tests, the same protocols as in Example 1 are used.

Fibroblasts Isolation from Balbc Mice Skin.

Skin from shaved Balbc mice will be put in Dispase II (Sigma; #000000004942078001) overnight at 37° C. 5% CO2. 24 h after, dermis will be separated from the epidermis and dermis will be cut in very little parts and let it stick on a plastic culture plate. Then 10 ml of Dulbecco Modified Eagle Medium (DMEM), High glucose (4.5 g/L D-glucose), 10% Foetal Calf Serum will be added. Fibroblast will appear along the culture and will be amplified to be able to infect them with the different lentiviral construct described after.

Plasmids Construction

The human NFAT3 WT, NFAT3-85C, ΔNFAT3 WT, ΔNFAT3-85C were cloned by PCR using as a template plasmids already described (Fougère, M., et al. (2010). Oncogene, 29(15), 2292-2301) in fusion with the td Tomato tag in the pLVX-tdTomato-C1 plasmid from Clontech. All constructions were verified by sequencing.

The human CD63 was cloned by PCR using as a template a plasmid given by Dr Clothilde Thery from the Curie Institute in fusion with the td Tomato tag in the pLVX-tdTomato-C1 plasmid from Clontech. All constructions were verified by sequencing.

Cells were transiently transfected with the appropriate plasmids using Lipofectamine 2000 (Invitrogen) according to the manufacturer's instructions.

Sequences of the different constructions:

pLVX-tdTomato-C1 (Clonetech, empty vector): SEQ ID NO:28, encoding protein tdTomato-C1 of sequence SEQ ID NO:34;

pLVX-tdTomato-C1-HA hNFAT3 WT (expression vector of isoform 2 of NFATC4, as defined in Table 1 above): SEQ ID NO:29, encoding protein tdTomato-C1 of sequence SEQ ID NO:35;

pLVX-tdTomato-C1-HA hNFAT3-85C (expression vector of isoform 2 of NFATC4, as defined in Table 1 above, truncated of the 85 C-terminal amino acids): SEQ ID NO:30, encoding protein tdTomato-C1 of sequence SEQ ID NO:36;

pLVX-tdTomato-C1 htNFAT3 WT (expression vector of isoform 2 of NFATC4, as defined in Table 1 above, truncated of the 521 N-terminal amino acids): SEQ ID NO:31, encoding protein tdTomato-C1 of sequence SEQ ID NO:37;

pLVX-tdTomato-C1 htNFAT3-85C (expression vector of isoform 2 of NFATC4, as defined in Table 1 above, truncated of the 521 N-terminal and 85 C-terminal amino acids): SEQ ID NO:32;

pLVX-tdTomato-C1-hCD63 (expression vector of hCD63): SEQ ID NO:33.

Production of Lentiviral Particles in HEK293T Cells

The same protocol as described in Example 1 is used, excepted in step 2 of DAY 2:

| | Lentiviral Transfer Vector DNA | pMD2G (env) | psPAX2 (gag-pol) | Total Volume (with sterile water) |
|---|---|---|---|---|
| 100 cm2 | 22.5 ug | 7.9 ug | 14.6 | 945 ul |

Example 3

Materials and Methods

Lentivirus Plasmid Construction

The following expression vectors of Example 2 has been used:

pLVX-tdTomato-C1 (Clonetech, empty vector, also referred to as "to-Ctl"): SEQ ID NO:28, encoding protein tdTomato-C1 of sequence SEQ ID NO:34;

pLVX-tdTomato-C1-HA hNFAT3 WT (expression vector of isoform 2 of NFATC4, as defined in Table 1 above, also referred to as "to-NFAT3 WT"): SEQ ID NO:29, encoding protein tdTomato-C1 of sequence SEQ ID NO:35;

pLVX-tdTomato-C1-HA hNFAT3-85C (expression vector of isoform 2 of NFATC4, as defined in Table 1 above, truncated of the 85 C-terminal amino acids, also referred to as "to-NFAT3-85C"): SEQ ID NO:30, encoding protein tdTomato-C1 of sequence SEQ ID NO:36;

pLVX-tdTomato-C1 htNFAT3 WT (expression vector of isoform 2 of NFATC4, as defined in Table 1 above, truncated of the 521 N-terminal amino acids, also referred to as "to-ΔNFAT3"): SEQ ID NO:31, encoding protein tdTomato-C1 of sequence SEQ ID NO:37;

Production of Lentiviral Particles in HEK293T Cells

❖ DAY 1:

Plate cells in 10% SVF/HIGH DMEM

| | Cells number | Volume medium |
|---|---|---|
| 100 cm2 | $3.5 \cdot 10^6$ | 14 ml |

❖ DAY 2:

1—Plasmids transfection by phosphate calcium

For Lentiviral ORF Expression Vector

| | Lentiviral Transfer Vector (PLVX-toNFAT3, PLVX-to-ΔNFAT3, PLVX-toNFAT3-85C) | Trans-Lentiviral Packaging Mix | Total Volume (with sterile water) |
|---|---|---|---|
| 100 cm2 | 42 ug | 30 ul | 945 ul |

2—Add the indicated volume of CaCl2 to the diluted DNA above

| | CaCl2 |
|---|---|
| 100 cm2 | 15 ul |

3—Vortex the tube at a speed sufficient to thoroughly mix reagents without spillover. While vortexing, add drop-wise the indicated volume of 2× HBSS:

| | 2x HBSS |
|---|---|
| 100 cm2 | 1050 ul |

4—Incubate at room temperature for 3 minutes. A light chalky precipitate should appear during this incubation (the precipitate may not always be obvious).

5—Add the total volume (300 μt or 2.1 mL) of transfection mix drop-wise to the cells. (Note: The exact volume may be slightly less due to pipetting loss, but this will not negatively impact transfection effciency.)

6—Incubate cells at 37° C. with 5% CO2 for 10-16 hours

❖ DAY 3:

1—Prepare reduced serum medium:

a. High Glucose DMEM b. 5% Fetal Bovine c. 2 mM L-glutamine d. 1× Penicillin/Streptomycin 2—Remove calcium phosphate-containing medium from cells and replace 14 ml of reduced serum medium.

3—Incubate cells at 37° C. with 5% CO2 for an additional 48 hours.

❖ DAY 5: Viral Particle Collection and Concentration

1—Harvest viral particle-containing supernatants 48 hours after the medium change by removing medium to a 15 mL sterile, capped, conical tube.

2—Pellet non-adherent cells and debris by centrifugation at 1600×g at 4° C. for 10 minutes to pellet cell debris.

3—Filtration step in which the supernatant is passed through a sterile, 0.22-0.45 μM low protein binding filter after the low-speed centrifugation step to remove any remaining cellular debris. Filtered viral medium is directly put in ultracentrifugation tube.

4—Concentrate by ultracentrifugation in a swinging-bucket ultracentrifuge rotor. Transfer the altered supernatant to a sterile ultracentrifuge tube. Bring volume to almost fill the tube to avoid braking tube during the ultra-centrifugation with DMEM containing no serum. For an SW28 rotor, centrifuge at 23,000 rpm for 2 hours at 4° C.

5—Pipette the desired resuspension volume of DMEM (no serum) onto the pellet at the bottom of the tube.

6—The visible pellet (if visible) is made up mostly of serum proteins from the culture media of the transfected cells. The viral particles need to be dislodged from this protein pellet. After adding the DMEM to the pellet, incubate for 10 minutes at 4° C. Then gently pipette up and down about 30 times, avoiding the formation of bubbles.

7—Transfer the resuspended pellet to a sterile microfuge tube and centrifuge at full speed for 3-4 minutes. This centrifugation will pellet the serum proteins, which adhere to the bottom of the tube. After centrifugation, transfer the supernatant to a new microfuge tube and aresuspend in 100 ul pf PBS (20 ul will be used per infection. Always store lentiviral particles at −80° C.

Infection of Cells with Lentiviral Particules and Selection

❖ DAY 1:

Plate cells in 24 well plates in 10% SVF+AB in their corresponding medium

| Cell type | Cells number | Volume medium |
|---|---|---|
| HEK 293T | $1.5 \cdot 10^5$ | 1 ml DMEM high |

❖ DAY 2:

1—Replace the medium with 250 ul of the corresponding medium complemented with 4 ug/ml Polybrene 2—Infect by adding directly on the cells 20 ul of the virus 3—Let in the incubator for 4 h 4—After 4 h, add 1 ml/well of the corresponding medium complemented with polybrene

❖ DAY 6:

1—Trypsinyze the cell to transfer them in a 25 cm flask

❖ DAY 9:

1. Bring the cell back in the lab and transfer them in:

| Cell type | Flask |
|---|---|
| HEK 293T | 150 cm |

When the flask is confluent you can proceed to the sorting of FACS

❖ CELL SORTING:

You should have a concentration for the sorting of 10. $10^6$ cells/ml

1. Trypsinize the cell and count them
2. Wash the cell one time in PBS
3. Resuspend the cell in the required volume of PBS completed with 2× AB
4. Pass the cell on a cell strainer to eliminate aggregate
5. Transfer the cell Polypropylene Facs tubes
6. Prepare tube to receive the sorted cells containing 100% SVF completed with 2× AB
7. Prepare 6 well plate to grow the sorted cells containing the corresponding medium without SVF but with 2× AB (when the sorted cells will be added there will be 20% SVF final)
8. Then let the cells grow until there is enough to realize the different validation tests.
9. Don't forget to frost the clone.

Antibodies and Reagents

The following antibodies were used: Anti-CD63(#clone H5C6, BD Biosciences), anti-NFAT3 (Sigma; #F1804, Thermo Scientific; #PA1-021, Santa-Cruz Biotechnology; sc-13036), anti-CD9 (#clone CBL162, Millipore), anti-Actin (Thermo Scientific; #MA5-15739), anti-tdTomato (SICGENANTIBODIES; #AB8181-200).

Cells were transiently transfected with the appropriate plasmids using Lipofectamine 2000 (Invitrogen) or DharmaFECT (Dharmacon) for siRNA according to the manufacturer's instructions.

Results

HEK Cell Line Expresses Endogenous NFAT3, Like the T47D Breast Cancer Cell Line.

Inventors wanted to evaluate the possibility of using another cell line than MCF7 and T47D to test the possibility of transferring and enhancing the inhibitory capacity of SEV by overexpressing NFAT3 WT or NFAT3 mutants in a non-breast cancer cell line. To this end inventors have chosen the HEK cell line that is an easy growing and editable cell line. Inventors first evaluated the potential expression of endogenous NFAT3 by transiently transfecting them with either a non-targeting siRNA control (siCtl) or a siRNA targeting endogenous NFAT3 (siNFAT3). As a control, inventors used the T47D breast cancer cell line that expresses endogenous NFAT3.

Figure 12:
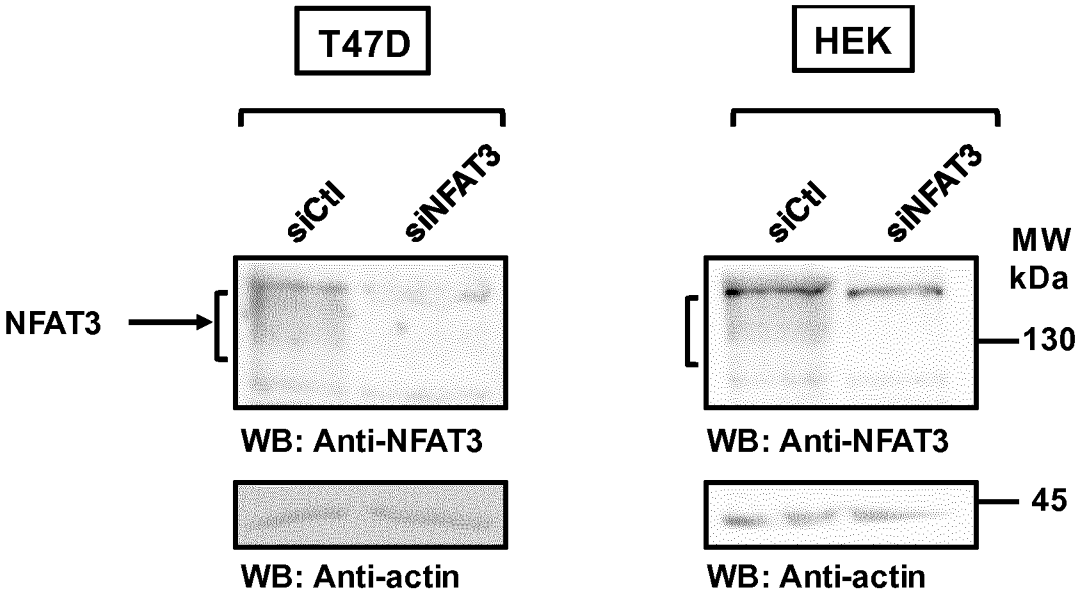
FIG. 12. NFAT3 is expressed in HEK cells as in T47D cells. T47D cells and HEK cell were transiently transfected with either a non-targeting siRNA control (siCtl) or a siRNA targeting endogenous NFAT3 (siNFAT3). 48 h after transfection, whole cells lysate were probed for endogenous NFAT3 with an antibody directed against NFAT3. Control of equal loading was evaluated by probing the membrane with an antibody directed against Actin.

Results are presented in FIG. 12 and show that HEK cell line expresses endogenous NFAT3 that is downregulated by siNFAT3 treatment as in T47D breast cancer cell line.

NFAT3 Mutants Used to Produce HEK Clone.

Figure 13:
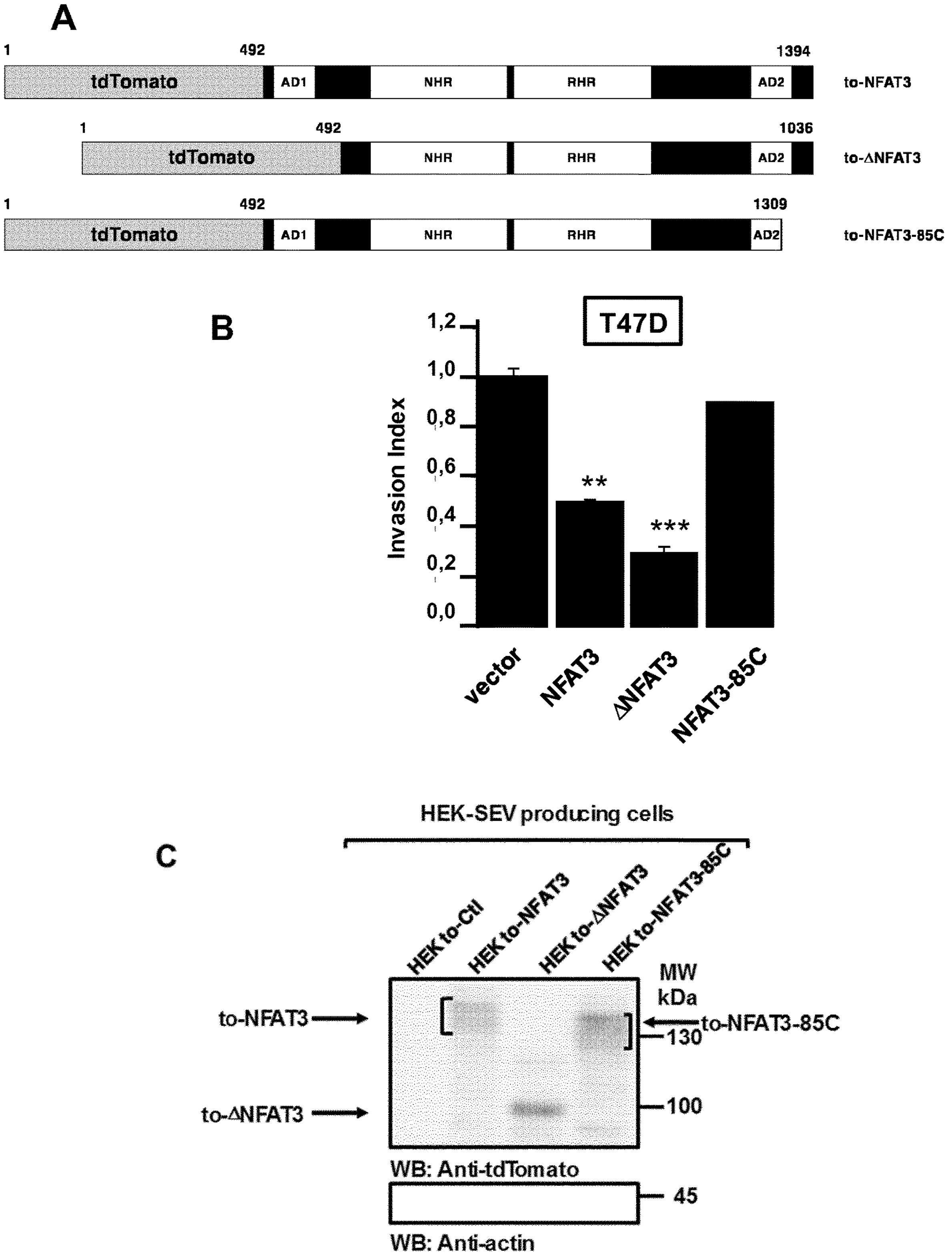
FIG. 13. Generation of NFAT3-expressing HEK cells. (A) Representation of the NFAT3 constructs used to infect HEK cells fused with the tdTomato tag. (B) T47D breast cancer cells were transiently transfected with either the vector control of NFAT3 WT, ΔNFAT3 or NFAT3 lacking the last 85 C-terminal amino acids and assess for their invasive capacity in classical transwell invasion assay. (C) Expressions the different NFAT3 constructs in the HEK-producing SEV were evaluated by western blot with the indicated antibodies.

In FIG. 13A are depicted the different NFAT3 mutants fused to the tdTomato tag used to generate HEK clones. Either the wild type NFAT3 (NFAT3 WT), or the constitutively active NFAT3 mutant (ΔNFAT3) lacking the first 342 N-terminal amino acids or the inactive mutant (NFAT3-85C) deleted from its region necessary to inhibit the invasion was used.

Characterization of NFAT3 Overexpression in T47D Breast Cancer Cell Line.

T47D breast cancer cells were transiently transfected with either the control vector or with a vector expressing NFAT3 WT, ΔNFAT3, or NFAT3 lacking the last 85 C-terminal amino acids, and assessed for their invasive capacity in classical transwell invasion assay.

Results are presented in FIG. 13B and show that:

- Overexpression of NFAT3 WT (NFAT3 WT) decreases by about 50% the invasion index of T47D breast cancer cells compared to the cells transfected with the empty vector (vector).
- Overexpression of ΔNFAT3 (ΔNFAT3), the constitutively active NFAT3 mutant, decreases to a better extent than NFAT3 WT by about 70% the invasion index of T47D breast cancer cells compared to the cells transfected with the empty vector (vector).
- Overexpression of NFAT3-85C (NFAT3-85C), the inactive mutant deleted from its region necessary to inhibit the invasion, is no longer able to decrease the invasion index compared to the vector transfected cells (vector) and the NFAT3 WT or ΔNFAT3-transfected cells.

Figure 14:
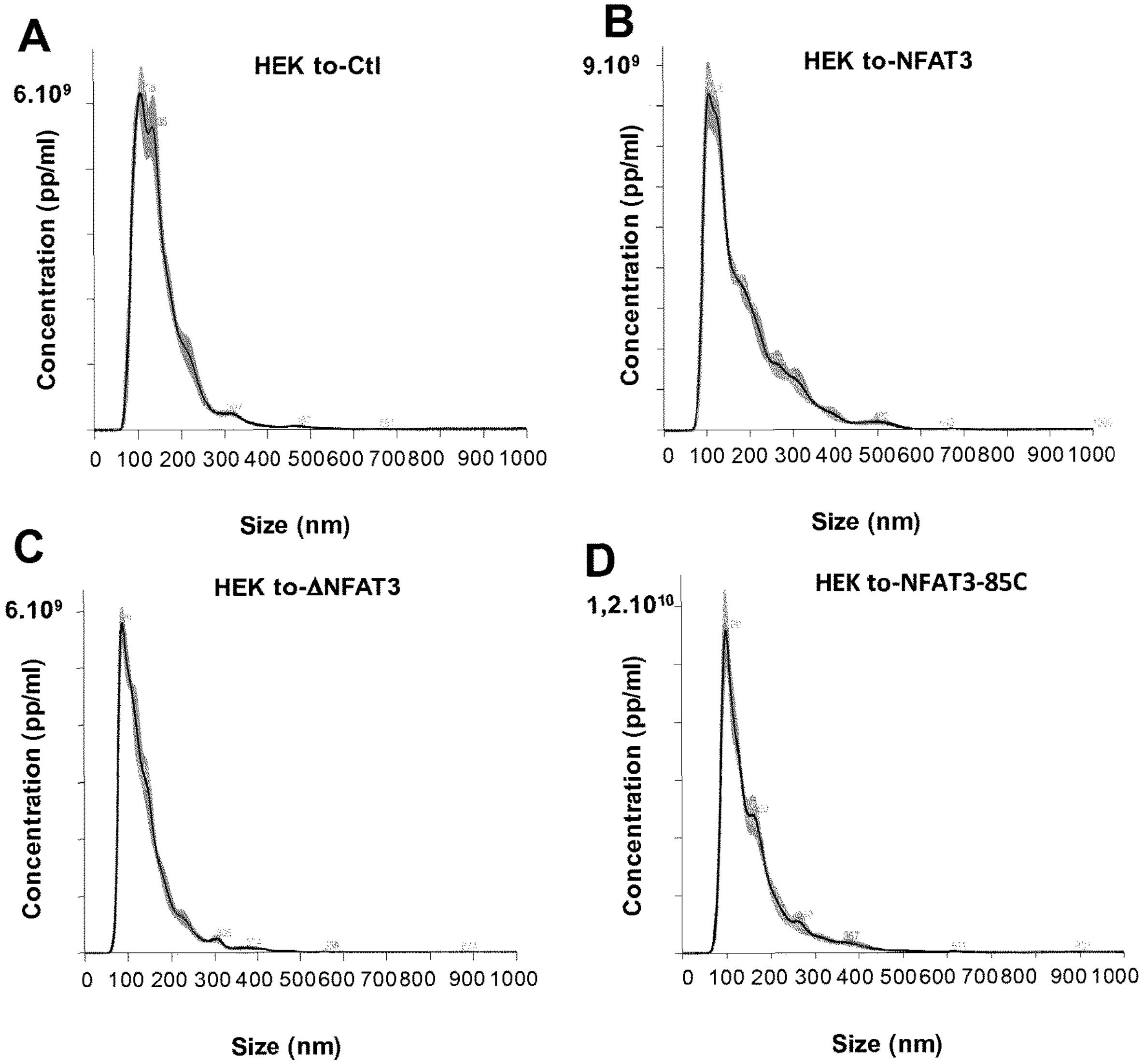
FIG. 14. Characterization by size and specific markers of SEV produced by HEK cells. Representative examples of size distribution of SEV produced by HEK to-Ctl (A), HEK to-NFAT3 (B). HEK to-ΔNFAT3 (C) and HEK to-NFAT3-85C (D), evaluated by the NanoSight. SEV concentration (particles/ml:pp/mL) is shown in function of particle size (nm).

Characterization of SEV Produced by HEK Cells Expressing to-Ctl, to-NFAT3 WT, to-ΔNFAT3 and to-NFAT3-85C Representative examples of size distribution of SEV produced by HEK cells expressing to-Ctl, to-NFAT3 WT, to-ΔNFAT3 and to-NFAT3-85c are represented in FIG. 14A (HEK to-Ctl), FIG. 14B (HEK to-NFAT3 WT), FIG. 14C (HEK to-ΔNFAT3) and FIG. 14D (HEK to-NFAT3-85c) show that the SEV produced by the HEK clone have a similar mean size between 100 and 200 nm.

Generation of HEK Cell Lines Expressing NFAT3 WT and NFAT3 Mutants.

Inventors generated by lentiviral infection and puromycin selection stable HEK clones expressing to-Ctl, to-NFAT3 WT, to-ΔNFAT3 or to-NFAT3-85C.

Results are presented in FIG. 13C and show that HEK clones stably express to-Ctl, to-NFAT3 WT or to-ΔNFAT3, or to-NFAT3-85C.

SEV Produced by NFAT3-Overexpressing HEK Cells Inhibit Invasion of Highly Invasive Breast Cancer MDA-MB-231Cells, Pancreatic Cancer BXPC3 Cells, and Glioblastoma Cancer Cell to a Higher Extend that the SEV Produced in Cells Endogenously Expressing NFAT3, such as T47D Cells and HEK Cells Stably Infected with a Control Virus (HEK to-Ctl).

SEV from HEK cells stably infected with a control virus (HEK to-Ctl) or with a virus encoding NFAT3 WT (HEK to-NFAT3) or a constitutively active mutant of NFAT3 (HEK to-ΔNFAT3) or an inactive mutant of NFAT3 deleted from its last 85 C-terminal amino acids (HEK to-NFAT3-85C) were produced with the intent to test their specific capacity to modulate invasion of highly invasive breast cancer cells (MDA-MB-231, SUM-159-PT), pancreatic cancer cells (BXPC3) and glioblastoma cancer cells (U87MG) in classical transwell invasion assays. As a control, cells were treated with either PBS or SEV produced in the T47D breast cancer cell line.

Figure 15:
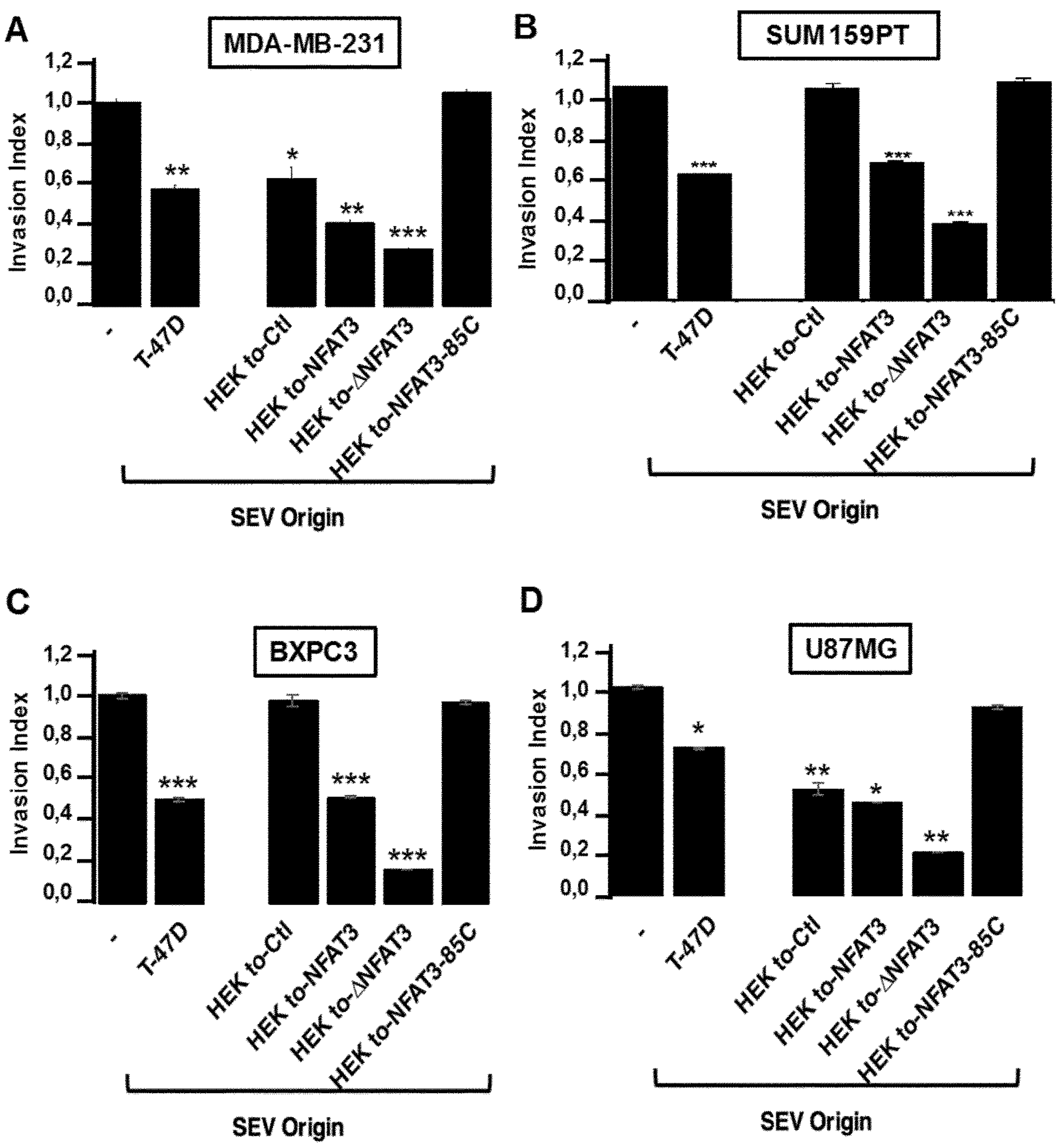
FIG. 15. Exosomes produced by NFAT3 expressing HEK cells inhibit invasion of highly invasive MDA-MB-231 cells. (A) Highly invasive breast cancer cells (MDA-MB-231) were pre-treated or not with exosomes produced by either low invasive T47D breast cancer cell line WT or HEK human embryonic cell line stably expressing either to-NFAT3 or to-ΔNFAT3 or to-NFAT3-85C) and as a control the empty vector (to-Ctl) and tested for their invasive capacity. $^*p<0.05$ $^{}p<0.005$ and $^{*}p<0.0005$, compared to the untreated cells (−). (n=2). (B) Highly invasive breast cancer cells (SUM-159-PT) were pre-treated or not with exosomes produced by either low invasive T47D breast cancer cell line WT or HEK human embryonic cell line stably expressing either to-NFAT3 or to-ΔNFAT3 or to-NFAT3-85C) and as a control the empty vector (to-Ctl) and tested for their invasive capacity. $^*p<0.05$ $^{}p<0.005$ and $^{*}p<0.0005$, compared to the untreated cells (−). (n=2) (C) Highly invasive pancreatic cancer cells (BXPC3) were pre-treated or not with exosomes produced by either low invasive T47D breast cancer cell line WT or HEK human embryonic cell line stably expressing either to-NFAT3 or to-ΔNFAT3 or to-NFAT3-85C) and as a control the empty vector (to-Ctl) and tested for their invasive capacity. $^*p<0.05$ $^{}p<0.005$ and $^{*}p<0.0005$, compared to the untreated cells (−). (n=2) (D) Highly invasive glioblastoma cancer cells (U87MG) were pre-treated or not with exosomes produced by either low invasive T47D breast cancer cell line WT or HEK human embryonic cell line stably expressing either to-NFAT3 or to-ΔNFAT3 or to-NFAT3-85C) and as a control the empty vector (to-Ctl) and tested for their invasive capacity. $^*p<0.05$ $^{}p<0.005$ and $^{*}p<0.0005$, compared to the untreated cells (−). (n=2).

Results are presented in FIG. 15 and show that:

- SEV produced by the low invasive breast cancer cell line T47D significantly decrease by about 40%-60% the invasion index of all tested cell lines: highly invasive breast cancer cell lines MDA-MB-231 (see FIG. 15A) and SUM-159-PT (see FIG. 15B), pancreatic cell line BXPC3 (see FIG. 15C), and glioblastoma cell line U87MG (see FIG. 15D).
- SEV produced by HEK cell line infected with the control virus (HEK to-Ctl) significantly decrease by about 40%-45% the invasion index of highly invasive breast cancer cell lines MDA-MB-231 (see FIG. 15A), and glioblastoma cell line U87MG (see FIG. 15D), but not the invasion index of pancreatic cell line BXPC3 (see FIG. 15C) and SUM-159-PT (see FIG. 15B).
- These results are consistent with the fact that NFAT3 is endogenously expressed by HEK cell line (see FIG. 12 showing that targeting HEK cells with a siRNA targeting the endogenous NFAT3 (siNFAT3) leads to a specific decreased of NFAT3 expression compared to HEK cells transfected with a siRNA control (siCtl)).
- SEV produced by HEK cell line infected with the virus encoding NFAT3 WT (HEK to-NFAT3) significantly decrease by about 40%-60% the invasion index of all tested cell lines: highly invasive breast cancer cell lines MDA-MB-231 (see FIG. 15A) and SUM-159-PT (see FIG. 15B), pancreatic cell line BXPC3 (see FIG. 15C), and glioblastoma cell line U87MG (see FIG. 15D).
- This decrease tends to be higher than when the cancer cells are treated with SEV produced either in the T47D cell line (see FIG. 15A for MDA-MB-231 and FIG. 15D for U87MG) or in the HEK to-Ctl cell line (see FIG. 15B for SUM-159PT and FIG. 15C for BXPC3).
- SEV produced by HEK cell line infected with the constitutively active mutant of NFAT3 (HEK to-ΔNFAT3) significantly decrease by about 60-80% the invasion index of all tested cell lines: highly invasive breast cancer cell lines MDA-MB-231 (see FIG. 15A) and SUM-159-PT (see FIG. 15B), and pancreatic cell lines BXPC3 (see FIG. 15C), and glioblastoma cell line U87MG (see FIG. 15D).
- This decrease is further higher than when the cancer cells are treated with SEV produced in the HEK to-ΔNFAT3 cell line, for all cancer cell lines in FIG. 15.
- SEV produced by HEK cell line infected with an inactive mutant of NFAT3 deleted from its last 85 C-terminal amino acids (HEK to-NFAT3-85C) is no longer able to decrease the invasion index of highly invasive breast cancer cell lines MDA-MB-231 (see FIG. 15A) and SUM-159-PT (see FIG. 15B), and pancreatic cell lines BXPC3 (see FIG. 15C), and glioblastoma cell line U87MG (see FIG. 15D).

These results demonstrate again that the expression of NFAT3 (endogenous and/or exogenous) in SEV producing cells is absolutely required for the SEV to inhibit the invasion of breast, pancreatic and glioblastoma cancer cells. The strength of this inhibition can be enhanced by ectopic expression of a WT NFAT3 (HEK to-NFAT3). Moreover, this inhibition of invasion can be further enhanced (up to 80% of inhibition of the invasion index) by ectopic expression of a constitutively active mutant of NFAT3 (HEK to-ΔNFAT3). The specificity of the role of NFAT3 in the inhibition of the invasion index in all the cancer cell lines tested is demonstrated by the absence of inhibition of the invasion by SEV produced in HEK cell expressing an inactive mutant of NFAT3 deleted from its last 85 C-terminal amino acids (HEK to-NFAT3-85C).

These results further demonstrate that ectopic expression of NFAT3 in another cell line (HEK) is sufficient to transfer the inhibitory effect of NFAT3 in the SEV produced by this other cell line.

BIBLIOGRAPHIC REFERENCES

Al-Nedawi, K. et al. Intercellular transfer of the oncogenic receptor EGFRvIII by microvesicles derived from tumour cells. Nature Publishing Group 10, 619-624 (2008).

Fougère, M., et al. (2010). NFAT3 transcription factor inhibits breast cancer cell motility by targeting the Lipocalin 2 gene. Oncogene, 29(15), 2292-2301.

Harris D A, et al. (2015) Exosomes Released from Breast Cancer Carcinomas Stimulate Cell Movement. PLoS ONE 10(3): e0117495.

Hendrix, A. et al. An Ex(o)citing Machinery for Invasive Tumor Growth. Cancer Res. 70, 9533-9537 (2010).

Jauliac S, et al. (2002). The role of NFAT transcription factors in integrin-mediated carcinoma invasion. Nat Cell Biol 4: 540-544.

Jauliac, S et al. (2002). The role of NFAT transcription factors in integrin-mediated carcinoma invasion. Nature Cell Biology, 4(7), 540-544.

Mancini M, Toker A. (2009). NFAT proteins: emerging roles in cancer progression. Nat Rev Cancer 9: 810-820.

Melo, S. A. et al. Cancer exosomes perform cell-independent microRNA biogenesis and promote tumorigenesis. *Cancer Cell* 26, 707-721 (2014).

Molkentin J D, Lu J R, Antos C L, Markham B, Richardson J, Robbins J et al. (1998). A calcineurin-dependent transcriptional pathway forcardiac hypertrophy. Cell 93: 215-228.

Ohshima, K. et al. Let-7 microRNA family is selectively secreted into the extracellular environment via exosomes in a metastatic gastric cancer cell line. PLoS ONE 5, e13247 (2010).

Peinado, H. et al. Melanoma exosomes educate bone marrow progenitor cells toward a pro-metastatic phenotype through MET. Nat. Med. 18, 883-891 (2012).

Soldevilla, B. et al. Tumor-derived exosomes are enriched in ΔNp73, which promotes oncogenic potential in acceptor cells and correlates with patient survival. Hum. Mol. Genet. 23, 467-478 (2014).

Takahashi, Y. et al. Visualization and in vivo tracking of the exosomes of murine melanoma B16-BL6 cells in mice after intravenous injection. J. Biotechnol. 165, 77-84 (2013).

Tickner, J. A., Urquhart, A. J., Stephenson, S.-A., Richard, D. J. a O'Byrne, K. J. Functions and therapeutic roles of exosomes in cancer. *Front Oncol* 4, 127 (2014).

van der Pol E. et al. Classification, Functions, and Clinical Relevance of Extracellular Vesicles. Pharmacol Rev 64:A-AD, 2012.

Villarroya-Beltri C. et al. Sorting it out: regulation of exosome loading. *Semin Cancer Biol.* 2014 October; 28: 3-13.

Yakimchuk, K. "Exosomes: isolation methods and specific markers," Materials and Methods, vol. 5, 2015.

Zomer, A. et al. In Vivo imaging reveals extracellular vesicle-mediated phenocopying of metastatic behavior. *Cell* 161, 1046-1057 (2015).

The invention claimed is:

1. A method for treating cancer or for treating metastatic cancer in a patient in need thereof, comprising administering to said patient a therapeutically efficient amount of a composition comprising secreted extracellular vesicles (SEV) of cells expressing the nuclear factor of activated T-cells, cytoplasmic, calcineurin-dependent 4 (NFATC4).

2. The method according to claim 1, wherein said SEV of cells expressing NFATC4 are purified from cancer cells with low invasive capacity.

3. The method according to claim 2, wherein said SEV of cells expressing NFATC4 are purified from breast cancer cells with low invasive capacity.

4. The method according to claim 1, wherein said SEV of cells expressing NFATC4 are purified from cells transfected with an expression vector comprising a nucleic acid molecule encoding NFATC4.

5. The method according to claim 4, wherein said cells transfected by the expression vector comprising the nucleic acid molecule encoding NFATC4 are selected from:

cancer cells with low invasive capacity, and healthy cells.

6. The method according to claim 5, wherein said healthy cells are autologous fibroblasts or human embryonic cells.

7. The method according to claim 5, wherein said healthy cells are HEK293T cells.

8. The method according to claim 1, wherein said cancer is selected from solid cancers.

9. The method according to claim 8, wherein said solid cancer is selected from breast carcinoma, pancreatic carcinoma, and glioblastoma.

10. The method according to claim 1, wherein said composition comprising SEV of cells expressing NFATC4 is administered intravenously or intratumorally.

11. An in vitro method for determining the therapeutic efficiency of treatment with a composition comprising SEV of cells expressing nuclear factor of activated T-cells, cytoplasmic, calcineurin-dependent 4 (NFATC4) in a cancer patient, said method comprising:

a) providing a first biological sample from said cancer patient taken before the beginning of the treatment and a second corresponding biological sample from said cancer patient after the beginning of the treatment;

b) measuring the transforming growth factor beta 1 (TGFβ1) expression level in said first and second biological samples;

c) comparing the measured TGFβ1 expression levels; and d) determining the efficiency of the treatment with the composition comprising SEV of cells expressing NFATC4 in said treated cancer patient from said comparison, wherein the treatment is determined efficient if the TGFβ1 expression level measured in the second biological sample is higher than the TGFβ1 expression level in the first biological sample.

12. The method according to claim 11, wherein said biological sample is a tumor sample, a blood sample, a serum sample, or a urine sample.

13. The method according to claim 11, wherein the expression level of TGFβ1 in the two biological samples of said cancer patient is measured at the nucleic acid level or at the protein level.

14. The method according to claim 11, wherein said cancer is selected from solid cancers.

15. The method according to claim 14, wherein said solid cancer is selected from breast carcinoma, pancreatic carcinoma, and glioblastoma.

16. An in vitro method for predicting the therapeutic efficiency of treatment with a composition comprising SEV of cells expressing nuclear factor of activated T-cells, cytoplasmic, calcineurin-dependent 4 (NFATC4) in a cancer patient, said method comprising:

a) providing a first biological sample and a second corresponding biological sample from said cancer patient taken before the beginning of the treatment;

b) incubating the second biological sample with the composition comprising SEV of cells expressing NFATC4;

c) measuring the transforming growth factor beta 1 (TGFβ1) expression level in said first and second biological samples;

d) comparing the measured TGFβ1 expression levels; and e) predicting the efficiency of the treatment with the composition comprising SEV of cells expressing NFATC4 in said cancer patient from said comparison, wherein the treatment is predicted efficient if the TGFβ1 expression level measured in the second biological sample is higher than the TGFβ1 expression level in the first biological sample.

17. The method according to claim 16, wherein said biological sample is a tumor sample, a blood sample, a serum sample, or a urine sample.

18. The method according to claim 16, wherein the expression level of TGFβ1 in the two biological samples of said cancer patient is measured at the nucleic acid level or at the protein level.

19. The method according to claim 16, wherein said cancer is selected from solid cancers.

20. The method according to claim 19, wherein said solid cancer is selected from breast carcinoma, pancreatic carcinoma, and glioblastoma.

* * * * *

SEQUENCE LISTING

<160> NUMBER OF SEQ ID NOS: 37

<210> SEQ ID NO 1
<211> LENGTH: 5747
<212> TYPE: DNA
<213> ORGANISM: Homo sapiens

<400> SEQUENCE: 1

```
gtaaacgtct gacctggggc cgtcgcttaa ccgtttagtt gctgggatgg ggcggcgttg     60
ggggtgcggc cctgaaccgg agggatttag agactggaga cgcggcctct aagagaggtt    120
gaaactgtgt gtgtgtggga gaaaatgata accaccctcc catctctcct acccgccagc    180
ctcgccagta tctcccaccg agtcacgaat ctcccatcta actccctctc acacaaccca    240
ggcctctcca agcctgactt tcccggaaac tccagtccag gtcttccttc ctcctccagc    300
ccaggccggg acctgggggc tcctgccgga tccatggggg cggccagctg cgaggatgag    360
gagctggaat ttaagctggt gttcggggag gaaaaggagg ccccccccgct gggcgcgggg    420
ggattggggg aagaactgga ctcagaggat gccccgccat gctgccgtct ggccttggga    480
gagccccctc cctatggcgc tgcacctatc ggtattcccc gacctccacc ccctcggcct    540
ggcatgcatt cgccaccgcc gcgaccagcc ccctcacctg gcacctggga gagccagccc    600
gccaggtcgg tgaggctggg aggaccagga gggggtgctg ggggtgctgg gggtggccgt    660
gttctcgagt gtcccagcat ccgcatcacc tccatctctc ccacgccgga gccgccagca    720
gcgctggagg acaaccctga tgcctggggg gacggctctc ctagagatta ccccccacca    780
gaaggctttg ggggctacag agaagcaggg ggccagggtg ggggggcctt cttcagccca    840
agccctggca gcagcagcct gtcctcgtgg agcttcttct ccgatgcctc tgacgaggca    900
gccctgtatg cagcctgcga cgaggtggag tctgagctaa atgaggcggc ctcccgcttt    960
ggcctgggct ccccgctgcc ctcgccccgg gcctcccctc ggccatggac ccccgaagat   1020
ccctggagcc tgtatggtcc aagccccgga ggccgagggc cagaggatag ctggctactc   1080
ctcagtgctc ctgggcccac cccagcctcc ccgcggcctg cctctccatg tggcaagcgg   1140
cgctattcca gctcgggaac ccccatcttca gcctccccag ctctgtcccg ccgtggcagc   1200
ctgggggaag aggggtctga gccacctcca ccacccccat tgcctctggc ccgggacccg   1260
ggctcccctg gtccctttga ctatgtgggg gccccaccag ctgagagcat ccctcagaag   1320
acacggcgga cttccagcga gcaggcagtg gctctgcctc ggtctgagga gcctgcctca   1380
tgcaatggga agctgccctt gggagcagag gagtctgtgg ctcctccagg aggttcccgg   1440
aaggaggtgg ctggcatgga ctacctggca gtgccctccc cactcgcttg gtccaaggcc   1500
cggattgggg gacacagccc tatcttcagg acctctgccc tacccccact ggactggcct   1560
```

-continued

```
ctgcccagcc aatatgagca gctggagctg aggatcgagg tacagcctag agcccaccac   1620
cgggcccact atgagacaga aggcagccgt ggagctgtca aagctgcccc tggcggtcac   1680
cccgtagtca agctcctagg ctacagtgag aagccactga ccctacagat gttcatcggc   1740
actgcagatg aaaggaacct gcggcctcat gccttctatc aggtgcaccg tatcacaggc   1800
aagatggtgg ccacggccag ctatgaagcc gtagtcagtg gcaccaaggt gttggagatg   1860
actctgctgc ctgagaacaa catggcggcc aacattgact gcgcgggaat cctgaagctt   1920
cggaattcag acattgagct tcggaagggt gagacggaca tcgggcgcaa aaacacacgt   1980
gtacggctgg tgttccgggt acacgtgccc cagggcggcg ggaaggtcgt ctcagtacag   2040
gcagcatcgg tgcccatcga gtgctcccag cgctcagccc aggagctgcc ccaggtggag   2100
gcctacagcc ccagtgcctg ctctgtgaga ggaggcgagg aactggtact gactggctcc   2160
aacttcctgc cagactccaa ggtggtgttc attgagaggg gtcctgatgg gaagctgcaa   2220
tgggaggagg aggccacagt gaaccgactg cagagcaacg aggtgacgct gaccctgact   2280
gtccccgagt acagcaacaa gagggtttcc cggccagtcc aggtctactt ttatgtctcc   2340
aatgggcgga ggaaacgcag tcctacccag agtttcaggt ttctgcctgt gatctgcaaa   2400
gaggagcccc taccggactc atctctgcgg ggtttccctt cagcatcggc aacccccttt   2460
ggcactgaca tggacttctc accacccagg ccccccctacc cctcctatcc ccatgaagac   2520
cctgcttgcg aaactcctta cctatcagaa ggcttcggct atggcatgcc ccctctgtac   2580
ccccagacgg ggcccccacc atcctacaga ccgggcctgc ggatgttccc tgagactagg   2640
ggtaccacag gttgtgccca accacctgca gtttccttcc ttccccgccc cttccctagt   2700
gacccgtatg gagggcgggg ctcctctttc tccctggggc tgccattctc tccgccagcc   2760
ccctttcggc cgcctcctct tcctgcatcc ccaccgcttg aaggcccctt cccttcccag   2820
agtgatgtgc atcccctacc tgctgaggga tacaataagg tagggccagg ctatggccct   2880
ggggaggggg ctccggagca ggagaaatcc aggggtggct acagcagcgg cttccgagac   2940
agtgtcccta tccagggtat cacgctggag gaaggtgggt gtgggactgg gggctgtgag   3000
tgtgagtgtg tgcaagagat tgctctgcat gtttgctgag ggctggagct gggcttttca   3060
gagatcgggc atccctggtc tctcagggcc agttggaggt tcccaggagg catgttcttg   3120
atgcctgtgg ctgcctgaat ccaattaact gaattctgaa gagtgcatgg ggtaactgtc   3180
tcagcctttc tcctgtctct gcctctgtcc tctgctccaa atcataaaat ctcagagcta   3240
gaagcacttt caagatcatt ccatccagcg cattcaattt gcaagtttag gcgttgagtt   3300
ccagagaggg atggtagctt gctgaggtcc cagtcaagca cacttgccat tgcctcagct   3360
ttcccctaaa cacggtgtct gtggtcaggg ttggtgagga ggagctttcc tgttttgcct   3420
ctccttcttc ccattggcta cacccatctc tggccctgct gataccgatt cccctgacat   3480
ttcaggctaa gccagcagga aagggctagg acgggtgcct gggagcccac atggagggag   3540
ttgggcaaga tttgattcgg agcaggtgtc aagacgtgtt ggggaaactg aggcccagtg   3600
gaatagaagc cagtagagga ggaatctaga ggcctcctag attaagacct gcctggaatg   3660
gattgggggt gggtctttgg aaaaggaggg gacccacctc tagcccagtc tctcaactgc   3720
ccctccttta cagtgagtga gatcattggc cgagacctga gtggcttccc tgcacctcct   3780
ggagaagagc ctcctgcctg aaccacgtga actgtcatca cctggcaacc ccagccccag   3840
cctcagccct gccccctttc cctccttcct ggagtggtgg ctacagaagc ttggggccaa   3900
ccctggctcc tctttcccca gcttctgtct gtctcactgt cttccctccc ctcccccagc   3960
```

```
tgaggtgtgg ccctcaggcc tggtgctgcc ttggagggct gggggaagga gtgtgtggag   4020

gagggaggag ggtgaagact gaggctaggt gccagaatgg actggagtga aggcgtgtct   4080

agagtgtggg ctggctgttg tgctggaaag ctggggacag gttgatggta ataaactgct   4140

caatgaccag tgcttcaggc tccagagctc tttggagaga tgggttgggg cagcttactc   4200

cagccctggc ccaaggaggc ccagaagttg gaaagagatg gaatgtggct gggaacattg   4260

catcccaaag agcttctcag tggaggaggc tggggaaggc atgagggggc tcagaggctc   4320

cttgactggg accaggattg gggccaggg cttgagtagg cctctccact ctcctccttg   4380

ggggtccaga ttccttagga gctttgggat gaggcccagg aggctgcatt tttccaggtc   4440

cttagtcttg ccaccacaca gatgattctg attcatagcc aagatgagga cacactgatg   4500

tagctgatct ctcatttaca gaggaggatt ctaaagttca gagagggaaa ggggcttgcc   4560

tgaggtcacg tagataatca gcagcacatt gaacgctgca ctcctgggct cctgtcccca   4620

gcccccattc agacacgctg actcaggagg tccaggcctc taaggcttct ctccctggag   4680

tgagggtgga ggtgagggag agctggcaca agccctccct ctggatcctc cactcctggg   4740

gattatgaag atattctgga aagatttgtg cttcagaggt agactgcaga aagcaaacag   4800

tctacccagc agctctgaat gtcacctgcc ctggggctta cagcactata tgagttcctg   4860

gcctatcctg caaatatgcc catgctggcc ttctaaatag ctggtacatc catcaccact   4920

gacgggcctg gcctggaaac ctggtttgtc ccctgtcttg atggcctacg agaggccaag   4980

ttccactggg ctgggaaaag tcactttgtc tgtcttgttc acctggagcc tgacacaccg   5040

taggtactga gtacaaatag cttgatttgg ctaggcttgg ctgcaggggg acgtgcctaa   5100

aagacattcc gggcatttgc acttgggaaa cttgcctcac cttcaggctt gtggggcctc   5160

tctatgccca atgagtccag gcagtcctag caagtactca ggagagcagg ggtgggtgtg   5220

acagaggctg gctctggatt gggggacaac agaaccagag taactcctcg cctgttgctg   5280

ctttgcaatg aatttccttt acctttctgg aacacaagct gctgtgaacc aaactgatat   5340

caagtgatta gctcaccggg ccttggttgc ttttcaaaga tccccttcag ccccctgcca   5400

gagtcactgc cccataatca ccatgtcaga agggacccta gggcattcgt gtcctattta   5460

tcaatcttca gcaccacctc taagatctct gagagagggt ggatcagcct ctgtgtaaac   5520

aaaaagctgt taggacttgt tgcctctcaa ggtggactat tctgttttct gccaggacac   5580

tgccattcat gcattgtcag atatttatta aacagcagca aagtgccagc caatttgtcc   5640

tggaggaatt catagcctca tggggcaaaa gtaaataaac agcttattac aattcaacaa   5700

aaaaaaaaaa aaaaaaaaaa aaaaaaaaaa aaaaaaaaaa aaaaaaa                 5747
```

<210> SEQ ID NO 2
<211> LENGTH: 964
<212> TYPE: PRT
<213> ORGANISM: Homo sapiens

<400> SEQUENCE: 2

```
Met Ile Thr Thr Leu Pro Ser Leu Leu Pro Ala Ser Leu Ala Ser Ile
1               5                   10                  15

Ser His Arg Val Thr Asn Leu Pro Ser Asn Ser Leu Ser His Asn Pro
            20                  25                  30

Gly Leu Ser Lys Pro Asp Phe Pro Gly Asn Ser Ser Pro Gly Leu Pro
        35                  40                  45

Ser Ser Ser Ser Pro Gly Arg Asp Leu Gly Ala Pro Ala Gly Ser Met
```

-continued

```
    50                  55                  60

Gly Ala Ala Ser Cys Glu Asp Glu Glu Leu Glu Phe Lys Leu Val Phe
65                  70                  75                  80

Gly Glu Glu Lys Glu Ala Pro Pro Leu Gly Ala Gly Gly Leu Gly Glu
                85                  90                  95

Glu Leu Asp Ser Glu Asp Ala Pro Pro Cys Cys Arg Leu Ala Leu Gly
            100                 105                 110

Glu Pro Pro Pro Tyr Gly Ala Ala Pro Ile Gly Ile Pro Arg Pro Pro
        115                 120                 125

Pro Pro Arg Pro Gly Met His Ser Pro Pro Pro Arg Pro Ala Pro Ser
    130                 135                 140

Pro Gly Thr Trp Glu Ser Gln Pro Ala Arg Ser Val Arg Leu Gly Gly
145                 150                 155                 160

Pro Gly Gly Gly Ala Gly Gly Ala Gly Gly Gly Arg Val Leu Glu Cys
                165                 170                 175

Pro Ser Ile Arg Ile Thr Ser Ile Ser Pro Thr Pro Glu Pro Pro Ala
            180                 185                 190

Ala Leu Glu Asp Asn Pro Asp Ala Trp Gly Asp Gly Ser Pro Arg Asp
        195                 200                 205

Tyr Pro Pro Pro Glu Gly Phe Gly Gly Tyr Arg Glu Ala Gly Gly Gln
    210                 215                 220

Gly Gly Gly Ala Phe Phe Ser Pro Ser Pro Gly Ser Ser Ser Leu Ser
225                 230                 235                 240

Ser Trp Ser Phe Phe Ser Asp Ala Ser Asp Glu Ala Ala Leu Tyr Ala
                245                 250                 255

Ala Cys Asp Glu Val Glu Ser Glu Leu Asn Glu Ala Ala Ser Arg Phe
            260                 265                 270

Gly Leu Gly Ser Pro Leu Pro Ser Pro Arg Ala Ser Pro Arg Pro Trp
        275                 280                 285

Thr Pro Glu Asp Pro Trp Ser Leu Tyr Gly Pro Ser Pro Gly Gly Arg
    290                 295                 300

Gly Pro Glu Asp Ser Trp Leu Leu Leu Ser Ala Pro Gly Pro Thr Pro
305                 310                 315                 320

Ala Ser Pro Arg Pro Ala Ser Pro Cys Gly Lys Arg Arg Tyr Ser Ser
                325                 330                 335

Ser Gly Thr Pro Ser Ser Ala Ser Pro Ala Leu Ser Arg Arg Gly Ser
            340                 345                 350

Leu Gly Glu Glu Gly Ser Glu Pro Pro Pro Pro Pro Pro Leu Pro Leu
        355                 360                 365

Ala Arg Asp Pro Gly Ser Pro Gly Pro Phe Asp Tyr Val Gly Ala Pro
    370                 375                 380

Pro Ala Glu Ser Ile Pro Gln Lys Thr Arg Arg Thr Ser Ser Glu Gln
385                 390                 395                 400

Ala Val Ala Leu Pro Arg Ser Glu Glu Pro Ala Ser Cys Asn Gly Lys
                405                 410                 415

Leu Pro Leu Gly Ala Glu Glu Ser Val Ala Pro Pro Gly Gly Ser Arg
            420                 425                 430

Lys Glu Val Ala Gly Met Asp Tyr Leu Ala Val Pro Ser Pro Leu Ala
        435                 440                 445

Trp Ser Lys Ala Arg Ile Gly Gly His Ser Pro Ile Phe Arg Thr Ser
    450                 455                 460

Ala Leu Pro Pro Leu Asp Trp Pro Leu Pro Ser Gln Tyr Glu Gln Leu
465                 470                 475                 480
```

-continued

```
Glu Leu Arg Ile Glu Val Gln Pro Arg Ala His His Arg Ala His Tyr
                485                 490                 495

Glu Thr Glu Gly Ser Arg Gly Ala Val Lys Ala Ala Pro Gly Gly His
            500                 505                 510

Pro Val Val Lys Leu Leu Gly Tyr Ser Glu Lys Pro Leu Thr Leu Gln
        515                 520                 525

Met Phe Ile Gly Thr Ala Asp Glu Arg Asn Leu Arg Pro His Ala Phe
    530                 535                 540

Tyr Gln Val His Arg Ile Thr Gly Lys Met Val Ala Thr Ala Ser Tyr
545                 550                 555                 560

Glu Ala Val Val Ser Gly Thr Lys Val Leu Glu Met Thr Leu Leu Pro
                565                 570                 575

Glu Asn Asn Met Ala Ala Asn Ile Asp Cys Ala Gly Ile Leu Lys Leu
            580                 585                 590

Arg Asn Ser Asp Ile Glu Leu Arg Lys Gly Glu Thr Asp Ile Gly Arg
        595                 600                 605

Lys Asn Thr Arg Val Arg Leu Val Phe Arg Val His Val Pro Gln Gly
    610                 615                 620

Gly Gly Lys Val Val Ser Val Gln Ala Ala Ser Val Pro Ile Glu Cys
625                 630                 635                 640

Ser Gln Arg Ser Ala Gln Glu Leu Pro Gln Val Glu Ala Tyr Ser Pro
                645                 650                 655

Ser Ala Cys Ser Val Arg Gly Gly Glu Glu Leu Val Leu Thr Gly Ser
            660                 665                 670

Asn Phe Leu Pro Asp Ser Lys Val Val Phe Ile Glu Arg Gly Pro Asp
        675                 680                 685

Gly Lys Leu Gln Trp Glu Glu Glu Ala Thr Val Asn Arg Leu Gln Ser
    690                 695                 700

Asn Glu Val Thr Leu Thr Leu Thr Val Pro Glu Tyr Ser Asn Lys Arg
705                 710                 715                 720

Val Ser Arg Pro Val Gln Val Tyr Phe Tyr Val Ser Asn Gly Arg Arg
                725                 730                 735

Lys Arg Ser Pro Thr Gln Ser Phe Arg Phe Leu Pro Val Ile Cys Lys
            740                 745                 750

Glu Glu Pro Leu Pro Asp Ser Ser Leu Arg Gly Phe Pro Ser Ala Ser
        755                 760                 765

Ala Thr Pro Phe Gly Thr Asp Met Asp Phe Ser Pro Pro Arg Pro Pro
    770                 775                 780

Tyr Pro Ser Tyr Pro His Glu Asp Pro Ala Cys Glu Thr Pro Tyr Leu
785                 790                 795                 800

Ser Glu Gly Phe Gly Tyr Gly Met Pro Pro Leu Tyr Pro Gln Thr Gly
                805                 810                 815

Pro Pro Pro Ser Tyr Arg Pro Gly Leu Arg Met Phe Pro Glu Thr Arg
            820                 825                 830

Gly Thr Thr Gly Cys Ala Gln Pro Pro Ala Val Ser Phe Leu Pro Arg
        835                 840                 845

Pro Phe Pro Ser Asp Pro Tyr Gly Gly Arg Gly Ser Ser Phe Ser Leu
    850                 855                 860

Gly Leu Pro Phe Ser Pro Pro Ala Pro Phe Arg Pro Pro Pro Leu Pro
865                 870                 875                 880

Ala Ser Pro Pro Leu Glu Gly Pro Phe Pro Ser Gln Ser Asp Val His
                885                 890                 895
```

-continued

```
Pro Leu Pro Ala Glu Gly Tyr Asn Lys Val Gly Pro Gly Tyr Gly Pro
            900                 905                 910

Gly Glu Gly Ala Pro Glu Gln Glu Lys Ser Arg Gly Gly Tyr Ser Ser
        915                 920                 925

Gly Phe Arg Asp Ser Val Pro Ile Gln Gly Ile Thr Leu Glu Glu Gly
    930                 935                 940

Gly Cys Gly Thr Gly Gly Cys Glu Cys Glu Cys Val Gln Glu Ile Ala
945                 950                 955                 960

Leu His Val Cys
```

<210> SEQ ID NO 3
<211> LENGTH: 4976
<212> TYPE: DNA
<213> ORGANISM: Homo sapiens

<400> SEQUENCE: 3

```
gaagagagga cagagggagg gagggtgggg gaggacgagg ggcgcgtggt tttcccatct      60
catccctgga ggaggggctg gagcatcccc ggcagccaat cagggacagg ctgggggggg     120
gaccgctttg aagaagtttg ggggaaaaaa gtttggaaaa gtttctataa taacgagggg     180
gcttctggag ggaggcggca gcgacggagg agggggcttc tcagagaaag ggagggaggg     240
agccacccgg gtgaagatac agcagcctcc tgaactcccc cctcccaccc aggccgggac     300
ctgggggctc ctgccggatc catgggggcg gccagctgcg aggatgagga gctggaattt     360
aagctggtgt tcggggagga aaaggaggcc cccccgctgg gcgcgggggg attgggggaa     420
gaactggact cagaggatgc cccgccatgc tgccgtctgg ccttgggaga gccccctccc     480
tatggcgctg cacctatcgg tattccccga cctccacccc ctcggcctgg catgcattcg     540
ccaccgccgc gaccagcccc ctcacctggc acctgggaga gccagcccgc caggtcggtg     600
aggctgggag gaccaggagg gggtgctggg ggtgctgggg gtggccgtgt tctcgagtgt     660
cccagcatcc gcatcacctc catctctccc acgccggagc cgccagcagc gctggaggac     720
aaccctgatg cctgggggga cggctctcct agagattacc ccccaccaga aggctttggg     780
ggctacagag aagcaggggg ccagggtggg ggggccttct tcagcccaag ccctggcagc     840
agcagcctgt cctcgtggag cttcttctcc gatgcctctg acgaggcagc cctgtatgca     900
gcctgcgacg aggtggagtc tgagctaaat gaggcggcct cccgctttgg cctgggctcc     960
ccgctgccct cgccccgggc ctcccctcgg ccatggaccc ccgaagatcc ctggagcctg    1020
tatggtccaa gccccggagg ccgagggcca gaggatagct ggctactcct cagtgctcct    1080
gggcccaccc cagcctcccc gcggcctgcc tctccatgtg gcaagcggcg ctattccagc    1140
tcgggaaccc catcttcagc ctccccagct ctgtcccgcc gtggcagcct gggggaagag    1200
gggtctgagc cacctccacc acccccattg cctctggccc gggacccggg ctcccctggt    1260
ccctttgact atgtgggggc ccccaccagct gagagcatcc ctcagaagac acggcggact    1320
tccagcgagc aggcagtggc tctgcctcgg tctgaggagc ctgcctcatg caatgggaag    1380
ctgcccttgg gagcagagga gtctgtggct cctccaggag gttcccggaa ggaggtggct    1440
ggcatggact acctggcagt gccctcccca ctcgcttggt ccaaggcccg gattggggga    1500
cacagcccta tcttcaggac ctctgcccta cccccactgg actggcctct gcccagccaa    1560
tatgagcagc tggagctgag gatcgaggta cagcctagag cccaccaccg ggcccactat    1620
gagacagaag gcagccgtgg agctgtcaaa gctgcccctg gcggtcaccc cgtagtcaag    1680
ctcctaggct acagtgagaa gccactgacc ctacagatgt tcatcggcac tgcagatgaa    1740
```

```
aggaacctgc ggcctcatgc cttctatcag gtgcaccgta tcacaggcaa gatggtggcc   1800
acggccagct atgaagccgt agtcagtggc accaaggtgt tggagatgac tctgctgcct   1860
gagaacaaca tggcggccaa cattgactgc gcgggaatcc tgaagcttcg gaattcagac   1920
attgagcttc ggaagggtga gacggacatc gggcgcaaaa acacacgtgt acggctggtg   1980
ttccgggtac acgtgcccca gggcggcggg aaggtcgtct cagtacaggc agcatcggtg   2040
cccatcgagt gctcccagcg ctcagcccag gagctgcccc aggtggaggc ctacagcccc   2100
agtgcctgct ctgtgagagg aggcgaggaa ctggtactga ctggctccaa cttcctgcca   2160
gactccaagg tggtgttcat tgagaggggt cctgatggga agctgcaatg ggaggaggag   2220
gccacagtga accgactgca gagcaacgag gtgacgctga ccctgactgt ccccgagtac   2280
agcaacaaga gggtttcccg gccagtccag gtctactttt atgtctccaa tgggcggagg   2340
aaacgcagtc ctacccagag tttcaggttt ctgcctgtga tctgcaaaga ggagcccta   2400
ccggactcat ctctgcgggg tttcccttca gcatcggcaa ccccctttgg cactgacatg   2460
gacttctcac cacccaggcc cccctacccc tcctatcccc atgaagaccc tgcttgcgaa   2520
actccttacc tatcagaagg cttcggctat ggcatgcccc ctctgtaccc ccagacgggg   2580
cccccaccat cctacagacc gggcctgcgg atgttccctg agactagggg taccacaggt   2640
tgtgcccaac cacctgcagt ttccttcctt ccccgcccct tccctagtga cccgtatgga   2700
gggcggggct cctctttctc cctggggctg ccattctctc cgccagcccc ctttcggccg   2760
cctcctcttc ctgcatcccc accgcttgaa ggccccttcc cttcccagag tgatgtgcat   2820
cccctacctg ctgagggata caataaggta gggccaggct atggccctgg ggaggggggct   2880
ccggagcagg agaaatccag ggtggctac agcagcggct tccgagacag tgtccctatc   2940
cagggtatca cgctggagga agtgagtgag atcattggcc gagacctgag tggcttccct   3000
gcacctcctg gagaagagcc tcctgcctga accacgtgaa ctgtcatcac ctggcaaccc   3060
cagccccagc ctcagccctg ccccctttcc ctccttcctg gagtggtggc tacagaagct   3120
tggggccaac cctggctcct ctttccccag cttctgtctg tctcactgtc ttccctcccc   3180
tcccccagct gaggtgtggc cctcaggcct ggtgctgcct tggagggctg ggggaaggag   3240
tgtgtggagg agggaggagg gtgaagactg aggctaggtg ccagaatgga ctggagtgaa   3300
ggcgtgtcta gagtgtgggc tggctgttgt gctggaaagc tggggacagg ttgatggtaa   3360
taaactgctc aatgaccagt gcttcaggct ccagagctct ttggagagat gggttggggc   3420
agcttactcc agccctggcc caaggaggcc cagaagttgg aaagagatgg aatgtggctg   3480
ggaacattgc atcccaaaga gcttctcagt ggaggaggct ggggaaggca tgagggggct   3540
cagaggctcc ttgactggga ccaggattgg gggccagggc ttgagtaggc ctctccactc   3600
tcctccttgg gggtccagat tccttaggag ctttgggatg aggcccagga ggctgcattt   3660
ttccaggtcc ttagtcttgc caccacacag atgattctga ttcatagcca agatgaggac   3720
acactgatgt agctgatctc tcatttacag aggaggattc taaagttcag agagggaaag   3780
gggcttgcct gaggtcacgt agataatcag cagcacattg aacgctgcac tcctgggctc   3840
ctgtccccag cccccattca gacacgctga ctcaggaggt ccaggcctct aaggcttctc   3900
tccctggagt gagggtggag gtgagggaga gctggcacaa gccctccctc tggatcctcc   3960
actcctgggg attatgaaga tattctggaa agatttgtgc ttcagaggta gactgcagaa   4020
agcaaacagt ctacccagca gctctgaatg tcacctgccc tggggcttac agcactatat   4080
```

-continued

```
gagttcctgg cctatcctgc aaatatgccc atgctggcct tctaaatagc tggtacatcc   4140

atcaccactg acgggcctgg cctggaaacc tggtttgtcc cctgtcttga tggcctacga   4200

gaggccaagt tccactgggc tgggaaaagt cactttgtct gtcttgttca cctggagcct   4260

gacacaccgt aggtactgag tacaaatagc ttgatttggc taggcttggc tgcaggggga   4320

cgtgcctaaa agacattccg ggcatttgca cttgggaaac ttgcctcacc ttcaggcttg   4380

tggggcctct ctatgcccaa tgagtccagg cagtcctagc aagtactcag gagagcaggg   4440

gtgggtgtga cagaggctgg ctctggattg gggggacaaca gaaccagagt aactcctcgc   4500

ctgttgctgc tttgcaatga atttccttta cctttctgga acacaagctg ctgtgaacca   4560

aactgatatc aagtgattag ctcaccgggc cttggttgct tttcaaagat cccccttcagc   4620

cccctgccag agtcactgcc ccataatcac catgtcagaa gggaccctag ggcattcgtg   4680

tcctatttat caatcttcag caccacctct aagatctctg agagagggtg gatcagcctc   4740

tgtgtaaaca aaaagctgtt aggacttgtt gcctctcaag gtggactatt ctgttttctg   4800

ccaggacact gccattcatg cattgtcaga tatttattaa acagcagcaa agtgccagcc   4860

aatttgtcct ggaggaattc atagcctcat ggggcaaaag taaataaaca gcttattaca   4920

attcaacaaa aaaaaaaaaa aaaaaaaaaa aaaaaaaaaa aaaaaaaaaa aaaaaa       4976


<210> SEQ ID NO 4
<211> LENGTH: 902
<212> TYPE: PRT
<213> ORGANISM: Homo sapiens

<400> SEQUENCE: 4

Met Gly Ala Ala Ser Cys Glu Asp Glu Glu Leu Glu Phe Lys Leu Val
1               5                   10                  15

Phe Gly Glu Glu Lys Glu Ala Pro Pro Leu Gly Ala Gly Gly Leu Gly
            20                  25                  30

Glu Glu Leu Asp Ser Glu Asp Ala Pro Pro Cys Cys Arg Leu Ala Leu
        35                  40                  45

Gly Glu Pro Pro Pro Tyr Gly Ala Ala Pro Ile Gly Ile Pro Arg Pro
    50                  55                  60

Pro Pro Pro Arg Pro Gly Met His Ser Pro Pro Pro Arg Pro Ala Pro
65                  70                  75                  80

Ser Pro Gly Thr Trp Glu Ser Gln Pro Ala Arg Ser Val Arg Leu Gly
                85                  90                  95

Gly Pro Gly Gly Gly Ala Gly Gly Ala Gly Gly Gly Arg Val Leu Glu
            100                 105                 110

Cys Pro Ser Ile Arg Ile Thr Ser Ile Ser Pro Thr Pro Glu Pro Pro
        115                 120                 125

Ala Ala Leu Glu Asp Asn Pro Asp Ala Trp Gly Asp Gly Ser Pro Arg
    130                 135                 140

Asp Tyr Pro Pro Pro Glu Gly Phe Gly Gly Tyr Arg Glu Ala Gly Gly
145                 150                 155                 160

Gln Gly Gly Gly Ala Phe Phe Ser Pro Ser Pro Gly Ser Ser Ser Leu
                165                 170                 175

Ser Ser Trp Ser Phe Phe Ser Asp Ala Ser Asp Glu Ala Ala Leu Tyr
            180                 185                 190

Ala Ala Cys Asp Glu Val Glu Ser Glu Leu Asn Glu Ala Ala Ser Arg
        195                 200                 205

Phe Gly Leu Gly Ser Pro Leu Pro Ser Pro Arg Ala Ser Pro Arg Pro
    210                 215                 220
```

-continued

```
Trp Thr Pro Glu Asp Pro Trp Ser Leu Tyr Gly Pro Ser Pro Gly Gly
225                 230                 235                 240

Arg Gly Pro Glu Asp Ser Trp Leu Leu Leu Ser Ala Pro Gly Pro Thr
                245                 250                 255

Pro Ala Ser Pro Arg Pro Ala Ser Pro Cys Gly Lys Arg Arg Tyr Ser
            260                 265                 270

Ser Ser Gly Thr Pro Ser Ser Ala Ser Pro Ala Leu Ser Arg Arg Gly
        275                 280                 285

Ser Leu Gly Glu Glu Gly Ser Glu Pro Pro Pro Pro Pro Pro Leu Pro
    290                 295                 300

Leu Ala Arg Asp Pro Gly Ser Pro Gly Pro Phe Asp Tyr Val Gly Ala
305                 310                 315                 320

Pro Pro Ala Glu Ser Ile Pro Gln Lys Thr Arg Arg Thr Ser Ser Glu
                325                 330                 335

Gln Ala Val Ala Leu Pro Arg Ser Glu Glu Pro Ala Ser Cys Asn Gly
            340                 345                 350

Lys Leu Pro Leu Gly Ala Glu Glu Ser Val Ala Pro Pro Gly Gly Ser
        355                 360                 365

Arg Lys Glu Val Ala Gly Met Asp Tyr Leu Ala Val Pro Ser Pro Leu
    370                 375                 380

Ala Trp Ser Lys Ala Arg Ile Gly Gly His Ser Pro Ile Phe Arg Thr
385                 390                 395                 400

Ser Ala Leu Pro Pro Leu Asp Trp Pro Leu Pro Ser Gln Tyr Glu Gln
                405                 410                 415

Leu Glu Leu Arg Ile Glu Val Gln Pro Arg Ala His His Arg Ala His
            420                 425                 430

Tyr Glu Thr Glu Gly Ser Arg Gly Ala Val Lys Ala Ala Pro Gly Gly
        435                 440                 445

His Pro Val Val Lys Leu Leu Gly Tyr Ser Glu Lys Pro Leu Thr Leu
    450                 455                 460

Gln Met Phe Ile Gly Thr Ala Asp Glu Arg Asn Leu Arg Pro His Ala
465                 470                 475                 480

Phe Tyr Gln Val His Arg Ile Thr Gly Lys Met Val Ala Thr Ala Ser
                485                 490                 495

Tyr Glu Ala Val Val Ser Gly Thr Lys Val Leu Glu Met Thr Leu Leu
            500                 505                 510

Pro Glu Asn Asn Met Ala Ala Asn Ile Asp Cys Ala Gly Ile Leu Lys
        515                 520                 525

Leu Arg Asn Ser Asp Ile Glu Leu Arg Lys Gly Glu Thr Asp Ile Gly
    530                 535                 540

Arg Lys Asn Thr Arg Val Arg Leu Val Phe Arg Val His Val Pro Gln
545                 550                 555                 560

Gly Gly Gly Lys Val Val Ser Val Gln Ala Ala Ser Val Pro Ile Glu
                565                 570                 575

Cys Ser Gln Arg Ser Ala Gln Glu Leu Pro Gln Val Glu Ala Tyr Ser
            580                 585                 590

Pro Ser Ala Cys Ser Val Arg Gly Gly Glu Glu Leu Val Leu Thr Gly
        595                 600                 605

Ser Asn Phe Leu Pro Asp Ser Lys Val Val Phe Ile Glu Arg Gly Pro
    610                 615                 620

Asp Gly Lys Leu Gln Trp Glu Glu Glu Ala Thr Val Asn Arg Leu Gln
625                 630                 635                 640
```

-continued

```
Ser Asn Glu Val Thr Leu Thr Leu Thr Val Pro Glu Tyr Ser Asn Lys
                645                 650                 655

Arg Val Ser Arg Pro Val Gln Val Tyr Phe Tyr Val Ser Asn Gly Arg
            660                 665                 670

Arg Lys Arg Ser Pro Thr Gln Ser Phe Arg Phe Leu Pro Val Ile Cys
        675                 680                 685

Lys Glu Glu Pro Leu Pro Asp Ser Ser Leu Arg Gly Phe Pro Ser Ala
    690                 695                 700

Ser Ala Thr Pro Phe Gly Thr Asp Met Asp Phe Ser Pro Pro Arg Pro
705                 710                 715                 720

Pro Tyr Pro Ser Tyr Pro His Glu Asp Pro Ala Cys Glu Thr Pro Tyr
                725                 730                 735

Leu Ser Glu Gly Phe Gly Tyr Gly Met Pro Pro Leu Tyr Pro Gln Thr
            740                 745                 750

Gly Pro Pro Pro Ser Tyr Arg Pro Gly Leu Arg Met Phe Pro Glu Thr
        755                 760                 765

Arg Gly Thr Thr Gly Cys Ala Gln Pro Pro Ala Val Ser Phe Leu Pro
    770                 775                 780

Arg Pro Phe Pro Ser Asp Pro Tyr Gly Gly Arg Gly Ser Ser Phe Ser
785                 790                 795                 800

Leu Gly Leu Pro Phe Ser Pro Pro Ala Pro Phe Arg Pro Pro Pro Leu
                805                 810                 815

Pro Ala Ser Pro Pro Leu Glu Gly Pro Phe Pro Ser Gln Ser Asp Val
            820                 825                 830

His Pro Leu Pro Ala Glu Gly Tyr Asn Lys Val Gly Pro Gly Tyr Gly
        835                 840                 845

Pro Gly Glu Gly Ala Pro Glu Gln Glu Lys Ser Arg Gly Gly Tyr Ser
    850                 855                 860

Ser Gly Phe Arg Asp Ser Val Pro Ile Gln Gly Ile Thr Leu Glu Glu
865                 870                 875                 880

Val Ser Glu Ile Ile Gly Arg Asp Leu Ser Gly Phe Pro Ala Pro Pro
                885                 890                 895

Gly Glu Glu Pro Pro Ala
            900
```

<210> SEQ ID NO 5
<211> LENGTH: 4652
<212> TYPE: DNA
<213> ORGANISM: Homo sapiens

<400> SEQUENCE: 5

```
gaagagagga cagagggagg gagggtgggg gaggacgagg ggcgcgtggt tttcccatct      60

catccctgga ggaggggctg gagcatcccc ggcagccaat cagggacagg ctgggggggg     120

gaccgctttg aagaagtttg ggggaaaaaa gtttggaaaa gtttctataa taacgagggg     180

gcttctggag ggaggcggca gcgacggagg agggggcttc tcagagaaag ggagggaggg     240

agccacccgg gtgaagatac agcagcctcc tgaactcccc cctcccaccc aggccgggac     300

ctgggggctc ctgccggatc catgggggcg gccagctgcg aggatgagga gctggaattt     360

aagctggtgt tcggggagga aaaggaggcc cccccgctgg gcgcgggggg attgggggaa     420

gaactggact cagaggatgc cccgccatgc tgccgtctgg ccttgggaga gccccctccc     480

tatggcgctg cacctatcgg tattccccga cctccacccc ctcggcctgg catgcattcg     540

ccaccgccgc gaccagcccc ctcacctggc acctgggaga gccagcccgc caggtcggtg     600
```

-continued

```
aggctgggag gaccaggagg gggtgctggg ggtgctgggg gtggccgtgt tctcgagtgt    660
cccagcatcc gcatcacctc catctctccc acgccggagc cgccagcagc gctggaggac    720
aaccctgatg cctgggggga cggctctcct agagattacc ccccaccaga aggctttggg    780
ggctacagag aagcaggggg ccagggtggg ggggccttct tcagcccaag ccctggcagc    840
agcagcctgt cctcgtggag cttcttctcc gatgcctctg acgaggcagc cctgtatgca    900
gcctgcgacg aggtggagtc tgagctaaat gaggcggcct cccgctttgg cctgggctcc    960
ccgctgccct cgccccgggc ctcccctcgg ccatggaccc ccgaagatcc ctggagcctg   1020
tatggtccaa gccccggagg ccgagggcca gaggatagct ggctactcct cagtgctcct   1080
gggcccaccc cagcctcccc gcggcctgcc tctccatgtg gcaagcggcg ctattccagc   1140
tcgggaaccc catcttcagc ctccccagct ctgtcccgcc gtggcagcct gggggaagag   1200
gggtctgagc cacctccacc acccccattg cctctggccc gggacccggg ctcccctggt   1260
ccctttgact atgtgggggc cccaccagct gagagcatcc ctcagaagac acggcggact   1320
tccagcgagc aggcagtggc tctgcctcgg tctgaggagc ctgcctcatg caatgggaag   1380
ctgcccttgg gagcagagga gtctgtggct cctccaggag gttcccggaa ggaggtggct   1440
ggcatggact acctggcagt gccctcccca ctcgcttggt ccaaggcccg gattggggga   1500
cacagcccta tcttcaggac ctctgcccta cccccactgg actggcctct gcccagccaa   1560
tatgagcagc tggagctgag gatcgaggta cagcctagag cccaccaccg ggcccactat   1620
gagacagaag gcagccgtgg agctgtcaaa gctgcccctg gcggtcaccc cgtagtcaag   1680
ctcctaggct acagtgagaa gccactgacc ctacagatgt tcatcggcac tgcagatgaa   1740
aggaacctgc ggcctcatgc cttctatcag gtgcaccgta tcacaggcaa gatggtggcc   1800
acggccagct atgaagccgt agtcagtggc accaaggtgt tggagatgac tctgctgcct   1860
gagaacaaca tggcggccaa cattgactgc gcgggaatcc tgaagcttcg gaattcagac   1920
attgagcttc ggaagggtga gacggacatc gggcgcaaaa acacacgtgt acggctggtg   1980
ttccgggtac acgtgcccca gggcggcggg aaggtcgtct cagtacaggc agcatcggtg   2040
cccatcgagt gctcccagcg ctcagcccag gagctgcccc aggtggaggc ctacagcccc   2100
agtgcctgct ctgtgagagg aggcgaggaa ctggtactga ctggctccaa cttcctgcca   2160
gactccaagg tggtgttcat tgagaggggt cctgatggga agctgcaatg ggaggaggag   2220
gccacagtga accgactgca gagcaacgag gtgacgctga ccctgactgt ccccgagtac   2280
agcaacaaga gggtttcccg gccagtccag gtctactttt atgtctccaa tgggcggagg   2340
aaacgcagtc ctacccagag tttcaggttt ctgcctgtga tctgcaaaga ggagccccta   2400
ccggactcat ctctgcgggg tttcccttca gcatcggcaa cccccctttgg cactgacatg   2460
gacttctcac cacccaggcc cccctacccc tcctatcccc atgaagaccc tgcttgcgaa   2520
actccttacc tatcagaagg cttcggctat ggcatgcccc ctctgtaccc ccagacgggg   2580
cccccaccat cctacagacc gggcctgcgg atgttccctg agactagggg taccacagtg   2640
agtgagatca ttggccgaga cctgagtggc ttccctgcac ctcctggaga agagcctcct   2700
gcctgaacca cgtgaactgt catcacctgg caaccccagc cccagcctca gccctgcccc   2760
ctttccctcc ttcctggagt ggtggctaca gaagcttggg gccaaccctg gctcctcttt   2820
ccccagcttc tgtctgtctc actgtcttcc ctcccctccc ccagctgagg tgtggccctc   2880
aggcctggtg ctgccttgga gggctggggg aaggagtgtg tggaggaggg aggagggtga   2940
agactgaggc taggtgccag aatggactgg agtgaaggcg tgtctagagt gtgggctggc   3000
```

```
tgttgtgctg gaaagctggg gacaggttga tggtaataaa ctgctcaatg accagtgctt   3060

caggctccag agctctttgg agagatgggt tggggcagct tactccagcc ctggcccaag   3120

gaggcccaga agttggaaag agatggaatg tggctgggaa cattgcatcc caaagagctt   3180

ctcagtggag gaggctgggg aaggcatgag gggctcaga ggctccttga ctgggaccag    3240

gattgggggc cagggcttga gtaggcctct ccactctcct ccttgggggt ccagattcct   3300

taggagcttt gggatgaggc ccaggaggct gcatttttcc aggtccttag tcttgccacc   3360

acacagatga ttctgattca tagccaagat gaggacacac tgatgtagct gatctctcat   3420

ttacagagga ggattctaaa gttcagagag ggaaaggggc ttgcctgagg tcacgtagat   3480

aatcagcagc acattgaacg ctgcactcct gggctcctgt ccccagcccc cattcagaca   3540

cgctgactca ggaggtccag gcctctaagg cttctctccc tggagtgagg gtggaggtga   3600

gggagagctg gcacaagccc tccctctgga tcctccactc ctggggatta tgaagatatt   3660

ctggaaagat ttgtgcttca gaggtagact gcagaaagca aacagtctac ccagcagctc   3720

tgaatgtcac ctgccctggg gcttacagca ctatatgagt tcctggccta tcctgcaaat   3780

atgcccatgc tggccttcta aatagctggt acatccatca ccactgacgg gcctggcctg   3840

gaaacctggt ttgtcccctg tcttgatggc ctacgagagg ccaagttcca ctgggctggg   3900

aaaagtcact ttgtctgtct tgttcacctg gagcctgaca caccgtaggt actgagtaca   3960

aatagcttga tttggctagg cttggctgca gggggacgtg cctaaaagac attccgggca   4020

tttgcacttg ggaaacttgc ctcaccttca ggcttgtggg gcctctctat gcccaatgag   4080

tccaggcagt cctagcaagt actcaggaga gcaggggtgg gtgtgacaga ggctggctct   4140

ggattggggg acaacagaac cagagtaact cctcgcctgt tgctgctttg caatgaattt   4200

cctttacctt tctggaacac aagctgctgt gaaccaaact gatatcaagt gattagctca   4260

ccgggccttg gttgcttttc aaagatcccc ttcagccccc tgccagagtc actgccccat   4320

aatcaccatg tcagaaggga ccctagggca ttcgtgtcct atttatcaat cttcagcacc   4380

acctctaaga tctctgagag agggtggatc agcctctgtg taaacaaaaa gctgttagga   4440

cttgttgcct ctcaaggtgg actattctgt tttctgccag gacactgcca ttcatgcatt   4500

gtcagatatt tattaaacag cagcaaagtg ccagccaatt tgtcctggag gaattcatag   4560

cctcatgggg caaaagtaaa taaacagctt attacaattc aacaaaaaaa aaaaaaaaaa   4620

aaaaaaaaaa aaaaaaaaaa aaaaaaaaaa aa                                 4652
```

<210> SEQ ID NO 6
<211> LENGTH: 794
<212> TYPE: PRT
<213> ORGANISM: Homo sapiens

<400> SEQUENCE: 6

```
Met Gly Ala Ala Ser Cys Glu Asp Glu Glu Leu Glu Phe Lys Leu Val
1               5                   10                  15

Phe Gly Glu Glu Lys Glu Ala Pro Pro Leu Gly Ala Gly Gly Leu Gly
            20                  25                  30

Glu Glu Leu Asp Ser Glu Asp Ala Pro Pro Cys Cys Arg Leu Ala Leu
        35                  40                  45

Gly Glu Pro Pro Pro Tyr Gly Ala Ala Pro Ile Gly Ile Pro Arg Pro
    50                  55                  60

Pro Pro Pro Arg Pro Gly Met His Ser Pro Pro Pro Arg Pro Ala Pro
65                  70                  75                  80
```

-continued

```
Ser Pro Gly Thr Trp Glu Ser Gln Pro Ala Arg Ser Val Arg Leu Gly
                85                  90                  95

Gly Pro Gly Gly Gly Ala Gly Gly Ala Gly Gly Gly Arg Val Leu Glu
            100                 105                 110

Cys Pro Ser Ile Arg Ile Thr Ser Ile Ser Pro Thr Pro Glu Pro Pro
        115                 120                 125

Ala Ala Leu Glu Asp Asn Pro Asp Ala Trp Gly Asp Gly Ser Pro Arg
    130                 135                 140

Asp Tyr Pro Pro Pro Glu Gly Phe Gly Gly Tyr Arg Glu Ala Gly Gly
145                 150                 155                 160

Gln Gly Gly Gly Ala Phe Phe Ser Pro Ser Pro Gly Ser Ser Ser Leu
                165                 170                 175

Ser Ser Trp Ser Phe Phe Ser Asp Ala Ser Asp Glu Ala Ala Leu Tyr
            180                 185                 190

Ala Ala Cys Asp Glu Val Glu Ser Glu Leu Asn Glu Ala Ala Ser Arg
        195                 200                 205

Phe Gly Leu Gly Ser Pro Leu Pro Ser Pro Arg Ala Ser Pro Arg Pro
    210                 215                 220

Trp Thr Pro Glu Asp Pro Trp Ser Leu Tyr Gly Pro Ser Pro Gly Gly
225                 230                 235                 240

Arg Gly Pro Glu Asp Ser Trp Leu Leu Leu Ser Ala Pro Gly Pro Thr
                245                 250                 255

Pro Ala Ser Pro Arg Pro Ala Ser Pro Cys Gly Lys Arg Arg Tyr Ser
            260                 265                 270

Ser Ser Gly Thr Pro Ser Ser Ala Ser Pro Ala Leu Ser Arg Arg Gly
        275                 280                 285

Ser Leu Gly Glu Glu Gly Ser Glu Pro Pro Pro Pro Pro Pro Leu Pro
    290                 295                 300

Leu Ala Arg Asp Pro Gly Ser Pro Gly Pro Phe Asp Tyr Val Gly Ala
305                 310                 315                 320

Pro Pro Ala Glu Ser Ile Pro Gln Lys Thr Arg Arg Thr Ser Ser Glu
                325                 330                 335

Gln Ala Val Ala Leu Pro Arg Ser Glu Glu Pro Ala Ser Cys Asn Gly
            340                 345                 350

Lys Leu Pro Leu Gly Ala Glu Glu Ser Val Ala Pro Pro Gly Gly Ser
        355                 360                 365

Arg Lys Glu Val Ala Gly Met Asp Tyr Leu Ala Val Pro Ser Pro Leu
    370                 375                 380

Ala Trp Ser Lys Ala Arg Ile Gly Gly His Ser Pro Ile Phe Arg Thr
385                 390                 395                 400

Ser Ala Leu Pro Pro Leu Asp Trp Pro Leu Pro Ser Gln Tyr Glu Gln
                405                 410                 415

Leu Glu Leu Arg Ile Glu Val Gln Pro Arg Ala His His Arg Ala His
            420                 425                 430

Tyr Glu Thr Glu Gly Ser Arg Gly Ala Val Lys Ala Ala Pro Gly Gly
        435                 440                 445

His Pro Val Val Lys Leu Leu Gly Tyr Ser Glu Lys Pro Leu Thr Leu
    450                 455                 460

Gln Met Phe Ile Gly Thr Ala Asp Glu Arg Asn Leu Arg Pro His Ala
465                 470                 475                 480

Phe Tyr Gln Val His Arg Ile Thr Gly Lys Met Val Ala Thr Ala Ser
                485                 490                 495
```

```
Tyr Glu Ala Val Val Ser Gly Thr Lys Val Leu Glu Met Thr Leu Leu
            500                 505                 510

Pro Glu Asn Asn Met Ala Ala Asn Ile Asp Cys Ala Gly Ile Leu Lys
        515                 520                 525

Leu Arg Asn Ser Asp Ile Glu Leu Arg Lys Gly Glu Thr Asp Ile Gly
    530                 535                 540

Arg Lys Asn Thr Arg Val Arg Leu Val Phe Arg Val His Val Pro Gln
545                 550                 555                 560

Gly Gly Gly Lys Val Val Ser Val Gln Ala Ala Ser Val Pro Ile Glu
                565                 570                 575

Cys Ser Gln Arg Ser Ala Gln Glu Leu Pro Gln Val Glu Ala Tyr Ser
            580                 585                 590

Pro Ser Ala Cys Ser Val Arg Gly Gly Glu Glu Leu Val Leu Thr Gly
        595                 600                 605

Ser Asn Phe Leu Pro Asp Ser Lys Val Val Phe Ile Glu Arg Gly Pro
    610                 615                 620

Asp Gly Lys Leu Gln Trp Glu Glu Glu Ala Thr Val Asn Arg Leu Gln
625                 630                 635                 640

Ser Asn Glu Val Thr Leu Thr Leu Thr Val Pro Glu Tyr Ser Asn Lys
                645                 650                 655

Arg Val Ser Arg Pro Val Gln Val Tyr Phe Tyr Val Ser Asn Gly Arg
            660                 665                 670

Arg Lys Arg Ser Pro Thr Gln Ser Phe Arg Phe Leu Pro Val Ile Cys
        675                 680                 685

Lys Glu Glu Pro Leu Pro Asp Ser Ser Leu Arg Gly Phe Pro Ser Ala
    690                 695                 700

Ser Ala Thr Pro Phe Gly Thr Asp Met Asp Phe Ser Pro Pro Arg Pro
705                 710                 715                 720

Pro Tyr Pro Ser Tyr Pro His Glu Asp Pro Ala Cys Glu Thr Pro Tyr
                725                 730                 735

Leu Ser Glu Gly Phe Gly Tyr Gly Met Pro Pro Leu Tyr Pro Gln Thr
            740                 745                 750

Gly Pro Pro Pro Ser Tyr Arg Pro Gly Leu Arg Met Phe Pro Glu Thr
        755                 760                 765

Arg Gly Thr Thr Val Ser Glu Ile Ile Gly Arg Asp Leu Ser Gly Phe
    770                 775                 780

Pro Ala Pro Pro Gly Glu Glu Pro Pro Ala
785                 790
```

<210> SEQ ID NO 7
<211> LENGTH: 4630
<212> TYPE: DNA
<213> ORGANISM: Homo sapiens

<400> SEQUENCE: 7

```
acggttgcga tggcaactgg ggctcctgcc agcgccgttt gggggtttgg gaaccgctgc      60

taattgggtt catgtaactg gactcagagg atgccccgcc atgctgccgt ctggccttgg     120

gagagccccc tccctatggc gctgcaccta tcggtattcc ccgacctcca ccccctcggc     180

ctggcatgca ttcgccaccg ccgcgaccag ccccctcacc tggcacctgg gagagccagc     240

ccgccaggtc ggtgaggctg ggaggaccag gagggggtgc tgggggtgct gggggtggcc     300

gtgttctcga gtgtcccagc atccgcatca cctccatctc tcccacgccg gagccgccag     360

cagcgctgga ggacaaccct gatgcctggg gggacggctc tcctagagat tacccccccac    420
```

-continued

```
cagaaggctt tgggggctac agagaagcag ggggccaggg tgggggggcc ttcttcagcc    480
caagccctgg cagcagcagc ctgtcctcgt ggagcttctt ctccgatgcc tctgacgagg    540
cagccctgta tgcagcctgc gacgaggtgg agtctgagct aaatgaggcg gcctcccgct    600
ttggcctggg ctccccgctg ccctcgcccc gggcctcccc tcggccatgg acccccgaag    660
atccctggag cctgtatggt ccaagccccg gaggccgagg gccagaggat agctggctac    720
tcctcagtgc tcctgggccc accccagcct ccccgcggcc tgcctctcca tgtggcaagc    780
ggcgctattc cagctcggga accccatctt cagcctcccc agctctgtcc cgccgtggca    840
gcctggggga agaggggtct gagccacctc caccaccccc attgcctctg gcccgggacc    900
cgggctcccc tggtcccttt gactatgtgg gggccccacc agctgagagc atccctcaga    960
agacacggcg gacttccagc gagcaggcag tggctctgcc tcggtctgag gagcctgcct   1020
catgcaatgg gaagctgccc ttgggagcag aggagtctgt ggctcctcca ggaggttccc   1080
ggaaggaggt ggctggcatg gactacctgg cagtgccctc cccactcgct tggtccaagg   1140
cccggattgg gggacacagc cctatcttca ggacctctgc cctaccccca ctggactggc   1200
ctctgcccag ccaatatgag cagctggagc tgaggatcga ggtacagcct agagcccacc   1260
accgggccca ctatgagaca gaaggcagcc gtggagctgt caaagctgcc cctggcggtc   1320
accccgtagt caagctccta ggctacagtg agaagccact gaccctacag atgttcatcg   1380
gcactgcaga tgaaaggaac ctgcggcctc atgccttcta tcaggtgcac cgtatcacag   1440
gcaagatggt ggccacggcc agctatgaag ccgtagtcag tggcaccaag gtgttggaga   1500
tgactctgct gcctgagaac aacatggcgg ccaacattga ctgcgcggga atcctgaagc   1560
ttcggaattc agacattgag cttcggaagg gtgagacgga catcgggcgc aaaaacacac   1620
gtgtacggct ggtgttccgg gtacacgtgc cccagggcgg cgggaaggtc gtctcagtac   1680
aggcagcatc ggtgcccatc gagtgctccc agcgctcagc ccaggagctg ccccaggtgg   1740
aggcctacag ccccagtgcc tgctctgtga gaggaggcga ggaactggta ctgactggct   1800
ccaacttcct gccagactcc aaggtggtgt tcattgagag ggtcctgat gggaagctgc    1860
aatgggagga ggaggccaca gtgaaccgac tgcagagcaa cgaggtgacg ctgaccctga   1920
ctgtccccga gtacagcaac aagagggttt cccggccagt ccaggtctac ttttatgtct   1980
ccaatgggcg gaggaaacgc agtcctaccc agagtttcag gtttctgcct gtgatctgca   2040
aagaggagcc cctaccggac tcatctctgc ggggtttccc ttcagcatcg gcaaccccct   2100
ttggcactga catggacttc tcaccaccca ggcccccta cccctcctat ccccatgaag    2160
accctgcttg cgaaactcct tacctatcag aaggcttcgg ctatggcatg ccccctctgt   2220
acccccagac ggggcccccca ccatcctaca gaccgggcct gcggatgttc cctgagacta  2280
ggggtaccac aggttgtgcc caaccacctg cagtttcctt ccttccccgc cccttcccta   2340
gtgacccgta tggagggcgg ggctcctctt tctccctggg gctgccattc tctccgccag   2400
cccccttcg gccgcctcct cttcctgcat ccccaccgct tgaaggcccc ttcccttccc    2460
agagtgatgt gcatccccta cctgctgagg gatacaataa ggtagggcca ggctatggcc   2520
ctggggaggg ggctccggag caggagaaat ccaggggtgg ctacagcagc ggcttccgag   2580
acagtgtccc tatccagggt atcacgctgg aggaagtgag tgagatcatt ggccgagacc   2640
tgagtggctt ccctgcacct cctggagaag agcctcctgc ctgaaccacg tgaactgtca   2700
tcacctggca accccagccc cagcctcagc cctgccccct ttccctcctt cctggagtgg   2760
tggctacaga agcttggggc caaccctggc tcctctttcc ccagcttctg tctgtctcac   2820
```

tgtcttccct cccctccccc agctgaggtg tggccctcag gcctggtgct gccttggagg 2880
gctgggggaa ggagtgtgtg gaggagggag gagggtgaag actgaggcta ggtgccagaa 2940
tggactggag tgaaggcgtg tctagagtgt gggctggctg ttgtgctgga aagctgggga 3000
caggttgatg gtaataaact gctcaatgac cagtgcttca ggctccagag ctctttggag 3060
agatgggttg gggcagctta ctccagccct ggcccaagga ggcccagaag ttggaaagag 3120
atggaatgtg gctgggaaca ttgcatccca aagagcttct cagtggagga ggctggggaa 3180
ggcatgaggg ggctcagagg ctccttgact gggaccagga ttgggggcca gggcttgagt 3240
aggcctctcc actctcctcc ttgggggtcc agattcctta ggagctttgg gatgaggccc 3300
aggaggctgc atttttccag gtccttagtc ttgccaccac acagatgatt ctgattcata 3360
gccaagatga ggacacactg atgtagctga tctctcattt acagaggagg attctaaagt 3420
tcagagaggg aaaggggctt gcctgaggtc acgtagataa tcagcagcac attgaacgct 3480
gcactcctgg gctcctgtcc ccagccccca ttcagacacg ctgactcagg aggtccaggc 3540
ctctaaggct tctctccctg gagtgagggt ggaggtgagg gagagctggc acaagccctc 3600
cctctggatc ctccactcct ggggattatg aagatattct ggaaagattt gtgcttcaga 3660
ggtagactgc agaaagcaaa cagtctaccc agcagctctg aatgtcacct gccctggggc 3720
ttacagcact atatgagttc ctggcctatc ctgcaaatat gcccatgctg gccttctaaa 3780
tagctggtac atccatcacc actgacgggc ctggcctgga aacctggttt gtcccctgtc 3840
ttgatggcct acgagaggcc aagttccact gggctgggaa aagtcacttt gtctgtcttg 3900
ttcacctgga gcctgacaca ccgtaggtac tgagtacaaa tagcttgatt tggctaggct 3960
tggctgcagg gggacgtgcc taaaagacat tccgggcatt tgcacttggg aaacttgcct 4020
caccttcagg cttgtggggc ctctctatgc ccaatgagtc caggcagtcc tagcaagtac 4080
tcaggagagc aggggtgggt gtgacagagg ctggctctgg attgggggac aacagaacca 4140
gagtaactcc tcgcctgttg ctgctttgca atgaatttcc tttacctttc tggaacacaa 4200
gctgctgtga accaaactga tatcaagtga ttagctcacc gggccttggt tgcttttcaa 4260
agatcccctt cagccccctg ccagagtcac tgccccataa tcaccatgtc agaagggacc 4320
ctagggcatt cgtgtcctat ttatcaatct tcagcaccac ctctaagatc tctgagagag 4380
ggtggatcag cctctgtgta aacaaaaagc tgttaggact tgttgcctct caaggtggac 4440
tattctgttt tctgccagga cactgccatt catgcattgt cagatattta ttaaacagca 4500
gcaaagtgcc agccaatttg tcctggagga attcatagcc tcatggggca aaagtaaata 4560
aacagcttat tacaattcaa caaaaaaaaa aaaaaaaaaa aaaaaaaaaa aaaaaaaaaa 4620
aaaaaaaaaa 4630

<210> SEQ ID NO 8
<211> LENGTH: 832
<212> TYPE: PRT
<213> ORGANISM: Homo sapiens

<400> SEQUENCE: 8

Met His Ser Pro Pro Pro Arg Pro Ala Pro Ser Pro Gly Thr Trp Glu
1 5 10 15

Ser Gln Pro Ala Arg Ser Val Arg Leu Gly Gly Pro Gly Gly Gly Ala
20 25 30

Gly Gly Ala Gly Gly Gly Arg Val Leu Glu Cys Pro Ser Ile Arg Ile
35 40 45

```
Thr Ser Ile Ser Pro Thr Pro Glu Pro Pro Ala Ala Leu Glu Asp Asn
    50                  55                  60

Pro Asp Ala Trp Gly Asp Gly Ser Pro Arg Asp Tyr Pro Pro Pro Glu
65                  70                  75                  80

Gly Phe Gly Gly Tyr Arg Glu Ala Gly Gly Gln Gly Gly Gly Ala Phe
                85                  90                  95

Phe Ser Pro Ser Pro Gly Ser Ser Ser Leu Ser Ser Trp Ser Phe Phe
            100                 105                 110

Ser Asp Ala Ser Asp Glu Ala Ala Leu Tyr Ala Ala Cys Asp Glu Val
        115                 120                 125

Glu Ser Glu Leu Asn Glu Ala Ala Ser Arg Phe Gly Leu Gly Ser Pro
    130                 135                 140

Leu Pro Ser Pro Arg Ala Ser Pro Arg Pro Trp Thr Pro Glu Asp Pro
145                 150                 155                 160

Trp Ser Leu Tyr Gly Pro Ser Pro Gly Gly Arg Gly Pro Glu Asp Ser
                165                 170                 175

Trp Leu Leu Leu Ser Ala Pro Gly Pro Thr Pro Ala Ser Pro Arg Pro
            180                 185                 190

Ala Ser Pro Cys Gly Lys Arg Arg Tyr Ser Ser Ser Gly Thr Pro Ser
        195                 200                 205

Ser Ala Ser Pro Ala Leu Ser Arg Arg Gly Ser Leu Gly Glu Glu Gly
    210                 215                 220

Ser Glu Pro Pro Pro Pro Pro Pro Leu Pro Leu Ala Arg Asp Pro Gly
225                 230                 235                 240

Ser Pro Gly Pro Phe Asp Tyr Val Gly Ala Pro Pro Ala Glu Ser Ile
                245                 250                 255

Pro Gln Lys Thr Arg Arg Thr Ser Ser Glu Gln Ala Val Ala Leu Pro
            260                 265                 270

Arg Ser Glu Glu Pro Ala Ser Cys Asn Gly Lys Leu Pro Leu Gly Ala
        275                 280                 285

Glu Glu Ser Val Ala Pro Pro Gly Gly Ser Arg Lys Glu Val Ala Gly
    290                 295                 300

Met Asp Tyr Leu Ala Val Pro Ser Pro Leu Ala Trp Ser Lys Ala Arg
305                 310                 315                 320

Ile Gly Gly His Ser Pro Ile Phe Arg Thr Ser Ala Leu Pro Pro Leu
                325                 330                 335

Asp Trp Pro Leu Pro Ser Gln Tyr Glu Gln Leu Glu Leu Arg Ile Glu
            340                 345                 350

Val Gln Pro Arg Ala His His Arg Ala His Tyr Glu Thr Glu Gly Ser
        355                 360                 365

Arg Gly Ala Val Lys Ala Ala Pro Gly Gly His Pro Val Val Lys Leu
    370                 375                 380

Leu Gly Tyr Ser Glu Lys Pro Leu Thr Leu Gln Met Phe Ile Gly Thr
385                 390                 395                 400

Ala Asp Glu Arg Asn Leu Arg Pro His Ala Phe Tyr Gln Val His Arg
                405                 410                 415

Ile Thr Gly Lys Met Val Ala Thr Ala Ser Tyr Glu Ala Val Val Ser
            420                 425                 430

Gly Thr Lys Val Leu Glu Met Thr Leu Leu Pro Glu Asn Asn Met Ala
        435                 440                 445

Ala Asn Ile Asp Cys Ala Gly Ile Leu Lys Leu Arg Asn Ser Asp Ile
    450                 455                 460
```

-continued

```
Glu Leu Arg Lys Gly Glu Thr Asp Ile Gly Arg Lys Asn Thr Arg Val
465                 470                 475                 480

Arg Leu Val Phe Arg Val His Val Pro Gln Gly Gly Gly Lys Val Val
                485                 490                 495

Ser Val Gln Ala Ala Ser Val Pro Ile Glu Cys Ser Gln Arg Ser Ala
            500                 505                 510

Gln Glu Leu Pro Gln Val Glu Ala Tyr Ser Pro Ser Ala Cys Ser Val
        515                 520                 525

Arg Gly Gly Glu Glu Leu Val Leu Thr Gly Ser Asn Phe Leu Pro Asp
    530                 535                 540

Ser Lys Val Val Phe Ile Glu Arg Gly Pro Asp Gly Lys Leu Gln Trp
545                 550                 555                 560

Glu Glu Glu Ala Thr Val Asn Arg Leu Gln Ser Asn Glu Val Thr Leu
                565                 570                 575

Thr Leu Thr Val Pro Glu Tyr Ser Asn Lys Arg Val Ser Arg Pro Val
            580                 585                 590

Gln Val Tyr Phe Tyr Val Ser Asn Gly Arg Arg Lys Arg Ser Pro Thr
        595                 600                 605

Gln Ser Phe Arg Phe Leu Pro Val Ile Cys Lys Glu Glu Pro Leu Pro
    610                 615                 620

Asp Ser Ser Leu Arg Gly Phe Pro Ser Ala Ser Ala Thr Pro Phe Gly
625                 630                 635                 640

Thr Asp Met Asp Phe Ser Pro Pro Arg Pro Pro Tyr Pro Ser Tyr Pro
                645                 650                 655

His Glu Asp Pro Ala Cys Glu Thr Pro Tyr Leu Ser Glu Gly Phe Gly
            660                 665                 670

Tyr Gly Met Pro Pro Leu Tyr Pro Gln Thr Gly Pro Pro Pro Ser Tyr
        675                 680                 685

Arg Pro Gly Leu Arg Met Phe Pro Glu Thr Arg Gly Thr Thr Gly Cys
    690                 695                 700

Ala Gln Pro Pro Ala Val Ser Phe Leu Pro Arg Pro Phe Pro Ser Asp
705                 710                 715                 720

Pro Tyr Gly Gly Arg Gly Ser Ser Phe Ser Leu Gly Leu Pro Phe Ser
                725                 730                 735

Pro Pro Ala Pro Phe Arg Pro Pro Pro Leu Pro Ala Ser Pro Pro Leu
            740                 745                 750

Glu Gly Pro Phe Pro Ser Gln Ser Asp Val His Pro Leu Pro Ala Glu
        755                 760                 765

Gly Tyr Asn Lys Val Gly Pro Gly Tyr Gly Pro Gly Glu Gly Ala Pro
    770                 775                 780

Glu Gln Glu Lys Ser Arg Gly Gly Tyr Ser Ser Gly Phe Arg Asp Ser
785                 790                 795                 800

Val Pro Ile Gln Gly Ile Thr Leu Glu Glu Val Ser Glu Ile Ile Gly
                805                 810                 815

Arg Asp Leu Ser Gly Phe Pro Ala Pro Pro Gly Glu Glu Pro Pro Ala
            820                 825                 830


<210> SEQ ID NO 9
<211> LENGTH: 4664
<212> TYPE: DNA
<213> ORGANISM: Homo sapiens

<400> SEQUENCE: 9

gtaaacgtct gacctggggc cgtcgcttaa ccgtttagtt gctgggatgg ggcggcgttg      60
```

-continued

```
ggggtgcggc cctgaaccgg agggatttag agactggaga cgcggcctct aagagaggtt    120
gaaactgtgt gtgtgtggga gaaaatgata accaccctcc catctctcct acccgccagc    180
ctcgccagta tctcccaccg agtcacgaat ctcccatcta actccctctc acacaaccca    240
ggcctctcca agcctgactt tcccggaaac tccagtccag gtcttccttc ctcctccagc    300
ccaggccggg acctgggggc tcctgccgga tccatggggg cggccagctg cgaggatgag    360
gagctggaat ttaagctggt gttcggggag gaaaaggagg cccccccgct gggcgcgggg    420
ggattggggg aagaactgga ctcagaggat gccccgccat gctgccgtct ggccttggga    480
gagcccccctc cctatggcgc tgcacctatc ggtattcccc gacctccacc ccctcggcct    540
ggcatgcatt cgccaccgcc gcgaccagcc ccctcacctg gcacctggga gagccagccc    600
gccaggtcgg tgaggctggg aggaccagga gggggtgctg ggggtgctgg gggtggccgt    660
gttctcgagt gtcccagcat ccgcatcacc tccatctctc ccacgccgga gccgccagca    720
gcgctggagg acaaccctga tgcctggggg gacggctctc ctagagatta ccccccacca    780
gaaggctttg gggctacag agaagcaggg ggccagggtg ggggggcctt cttcagccca    840
agccctggca gcagcagcct gtcctcgtgg agcttcttct ccgatgcctc tgacgaggca    900
gccctgtatg cagcctgcga cgaggtggag tctgagctaa atgaggcggc ctcccgcttt    960
ggcctgggct ccccgctgcc ctcgccccgg gcctcccctc ggccatggac ccccgaagat   1020
ccctggagcc tgtatggtcc aagccccgga ggccgagggc cagaggatag ctggctactc   1080
ctcagtgctc ctgggcccac cccagcctcc ccgcggcctg cctctccatg tggcaagcgg   1140
cgctattcca gctcgggaac cccatcttca gcctccccag ctctgtcccg ccgtggcagc   1200
ctgggggaag aggggtctga gccacctcca ccaccccccat tgcctctggc ccgggacccg   1260
ggctcccctg gtccctttga ctatgtgggg gccccaccag ctgagagcat ccctcagaag   1320
acacggcgga cttccagcga gcaggcagtg gctctgcctc ggtctgagga gcctgcctca   1380
tgcaatggga agctgccctt gggagcagag gagtctgtgg ctcctccagg aggttcccgg   1440
aaggaggtgg ctggcatgga ctacctggca gtgccctccc cactcgcttg gtccaaggcc   1500
cggattgggg gacacagccc tatcttcagg acctctgccc taccccccact ggactggcct   1560
ctgcccagcc aatatgagca gctggagctg aggatcgagg tacagcctag agcccaccac   1620
cgggcccact atgagacaga aggcagccgt ggagctgtca aagctgcccc tggcggtcac   1680
cccgtagtca agctcctagg ctacagtgag aagccactga ccctacagat gttcatcggc   1740
actgcagatg aaaggaacct gcggcctcat gccttctatc aggtgcaccg tatcacaggc   1800
aagatggtgg ccacggccag ctatgaagcc gtagtcagtg gcaccaaggt gttggagatg   1860
actctgctgc ctgagaacaa catggcggcc aacattgact gcgcgggaat cctgaagctt   1920
cggaattcag acattgagct tcggaagggt gagacggaca tcgggcgcaa aaacacacgt   1980
gtacggctgg tgttccgggt acacgtgccc cagggcggcg ggaaggtcgt ctcagtacag   2040
gcagcatcgg tgcccatcga gtgctcccag cgctcagccc aggagctgcc ccaggtggag   2100
gcctacagcc ccagtgcctg ctctgtgaga ggaggcgagg aactggtact gactggctcc   2160
aacttcctgc cagactccaa ggtggtgttc attgagaggg gtcctgatgg gaagctgcaa   2220
tgggaggagg aggccacagt gaaccgactg cagagcaacg aggtgacgct gaccctgact   2280
gtccccgagt acagcaacaa gagggtttcc cggccagtcc aggtctactt ttatgtctcc   2340
aatgggcgga ggaaacgcag tcctacccag agtttcaggt ttctgcctgt gatctgcaaa   2400
gaggagcccc taccggactc atctctgcgg ggtttccctt cagcatcggc aaccccccttt   2460
```

```
ggcactgaca tggacttctc accacccagg ccccccctacc cctcctatcc ccatgaagac   2520
cctgcttgcg aaactcctta cctatcagaa ggcttcggct atggcatgcc ccctctgtac   2580
ccccagacgg ggcccccacc atcctacaga ccgggcctgc ggatgttccc tgagactagg   2640
ggtaccacag tgagtgagat cattggccga gacctgagtg gcttccctgc acctcctgga   2700
gaagagcctc ctgcctgaac cacgtgaact gtcatcacct ggcaacccca gccccagcct   2760
cagccctgcc ccctttccct ccttcctgga gtggtggcta cagaagcttg gggccaaccc   2820
tggctcctct ttccccagct tctgtctgtc tcactgtctt ccctcccctc ccccagctga   2880
ggtgtggccc tcaggcctgg tgctgccttg gagggctggg ggaaggagtg tgtggaggag   2940
ggaggagggt gaagactgag gctaggtgcc agaatggact ggagtgaagg cgtgtctaga   3000
gtgtgggctg gctgttgtgc tggaaagctg gggacaggtt gatggtaata aactgctcaa   3060
tgaccagtgc ttcaggctcc agagctcttt ggagagatgg gttggggcag cttactccag   3120
ccctggccca aggaggccca gaagttggaa agagatggaa tgtggctggg aacattgcat   3180
cccaaagagc ttctcagtgg aggaggctgg ggaaggcatg agggggctca gaggctcctt   3240
gactgggacc aggattgggg gccagggctt gagtaggcct ctccactctc ctccttgggg   3300
gtccagattc cttaggagct ttgggatgag gcccaggagg ctgcattttt ccaggtcctt   3360
agtcttgcca ccacacagat gattctgatt catagccaag atgaggacac actgatgtag   3420
ctgatctctc atttacagag gaggattcta aagttcagag agggaaaggg gcttgcctga   3480
ggtcacgtag ataatcagca gcacattgaa cgctgcactc ctgggctcct gtccccagcc   3540
cccattcaga cacgctgact caggaggtcc aggcctctaa ggcttctctc cctggagtga   3600
gggtggaggt gagggagagc tggcacaagc cctccctctg gatcctccac tcctggggat   3660
tatgaagata ttctggaaag atttgtgctt cagaggtaga ctgcagaaag caaacagtct   3720
acccagcagc tctgaatgtc acctgccctg gggcttacag cactatatga gttcctggcc   3780
tatcctgcaa atatgcccat gctggccttc taaatagctg gtacatccat caccactgac   3840
gggcctggcc tggaaacctg gtttgtcccc tgtcttgatg gcctacgaga ggccaagttc   3900
cactgggctg ggaaaagtca ctttgtctgt cttgttcacc tggagcctga cacaccgtag   3960
gtactgagta caaatagctt gatttggcta ggcttggctg cagggggacg tgcctaaaag   4020
acattccggg catttgcact tgggaaactt gcctcacctt caggcttgtg gggcctctct   4080
atgcccaatg agtccaggca gtcctagcaa gtactcagga gagcaggggt gggtgtgaca   4140
gaggctggct ctggattggg ggacaacaga accagagtaa ctcctcgcct gttgctgctt   4200
tgcaatgaat ttcctttacc tttctggaac acaagctgct gtgaaccaaa ctgatatcaa   4260
gtgattagct caccgggcct tggttgcttt tcaaagatcc ccttcagccc cctgccagag   4320
tcactgcccc ataatcacca tgtcagaagg gaccctaggg cattcgtgtc ctatttatca   4380
atcttcagca ccacctctaa gatctctgag agagggtgga tcagcctctg tgtaaacaaa   4440
aagctgttag gacttgttgc ctctcaaggt ggactattct gttttctgcc aggacactgc   4500
cattcatgca ttgtcagata tttattaaac agcagcaaag tgccagccaa tttgtcctgg   4560
aggaattcat agcctcatgg ggcaaaagta aataaacagc ttattacaat tcaacaaaaa   4620
aaaaaaaaaa aaaaaaaaaa aaaaaaaaaa aaaaaaaaaa aaaa                  4664
```

<210> SEQ ID NO 10
<211> LENGTH: 857
<212> TYPE: PRT

<213> ORGANISM: Homo sapiens

<400> SEQUENCE: 10

```
Met Ile Thr Thr Leu Pro Ser Leu Leu Pro Ala Ser Leu Ala Ser Ile
1               5                   10                  15

Ser His Arg Val Thr Asn Leu Pro Ser Asn Ser Leu Ser His Asn Pro
            20                  25                  30

Gly Leu Ser Lys Pro Asp Phe Pro Gly Asn Ser Ser Pro Gly Leu Pro
        35                  40                  45

Ser Ser Ser Ser Pro Gly Arg Asp Leu Gly Ala Pro Ala Gly Ser Met
    50                  55                  60

Gly Ala Ala Ser Cys Glu Asp Glu Glu Leu Glu Phe Lys Leu Val Phe
65                  70                  75                  80

Gly Glu Glu Lys Glu Ala Pro Pro Leu Gly Ala Gly Gly Leu Gly Glu
                85                  90                  95

Glu Leu Asp Ser Glu Asp Ala Pro Pro Cys Cys Arg Leu Ala Leu Gly
            100                 105                 110

Glu Pro Pro Pro Tyr Gly Ala Ala Pro Ile Gly Ile Pro Arg Pro Pro
        115                 120                 125

Pro Pro Arg Pro Gly Met His Ser Pro Pro Pro Arg Pro Ala Pro Ser
    130                 135                 140

Pro Gly Thr Trp Glu Ser Gln Pro Ala Arg Ser Val Arg Leu Gly Gly
145                 150                 155                 160

Pro Gly Gly Gly Ala Gly Gly Ala Gly Gly Gly Arg Val Leu Glu Cys
                165                 170                 175

Pro Ser Ile Arg Ile Thr Ser Ile Ser Pro Thr Pro Glu Pro Pro Ala
            180                 185                 190

Ala Leu Glu Asp Asn Pro Asp Ala Trp Gly Asp Gly Ser Pro Arg Asp
        195                 200                 205

Tyr Pro Pro Pro Glu Gly Phe Gly Gly Tyr Arg Glu Ala Gly Gly Gln
    210                 215                 220

Gly Gly Gly Ala Phe Phe Ser Pro Ser Pro Gly Ser Ser Ser Leu Ser
225                 230                 235                 240

Ser Trp Ser Phe Phe Ser Asp Ala Ser Asp Glu Ala Ala Leu Tyr Ala
                245                 250                 255

Ala Cys Asp Glu Val Glu Ser Glu Leu Asn Glu Ala Ala Ser Arg Phe
            260                 265                 270

Gly Leu Gly Ser Pro Leu Pro Ser Pro Arg Ala Ser Pro Arg Pro Trp
        275                 280                 285

Thr Pro Glu Asp Pro Trp Ser Leu Tyr Gly Pro Ser Pro Gly Gly Arg
    290                 295                 300

Gly Pro Glu Asp Ser Trp Leu Leu Leu Ser Ala Pro Gly Pro Thr Pro
305                 310                 315                 320

Ala Ser Pro Arg Pro Ala Ser Pro Cys Gly Lys Arg Arg Tyr Ser Ser
                325                 330                 335

Ser Gly Thr Pro Ser Ser Ala Ser Pro Ala Leu Ser Arg Arg Gly Ser
            340                 345                 350

Leu Gly Glu Glu Gly Ser Glu Pro Pro Pro Pro Pro Pro Leu Pro Leu
        355                 360                 365

Ala Arg Asp Pro Gly Ser Pro Gly Pro Phe Asp Tyr Val Gly Ala Pro
    370                 375                 380

Pro Ala Glu Ser Ile Pro Gln Lys Thr Arg Arg Thr Ser Ser Glu Gln
385                 390                 395                 400
```

-continued

```
Ala Val Ala Leu Pro Arg Ser Glu Glu Pro Ala Ser Cys Asn Gly Lys
                405                 410                 415

Leu Pro Leu Gly Ala Glu Glu Ser Val Ala Pro Pro Gly Gly Ser Arg
            420                 425                 430

Lys Glu Val Ala Gly Met Asp Tyr Leu Ala Val Pro Ser Pro Leu Ala
        435                 440                 445

Trp Ser Lys Ala Arg Ile Gly Gly His Ser Pro Ile Phe Arg Thr Ser
    450                 455                 460

Ala Leu Pro Pro Leu Asp Trp Pro Leu Pro Ser Gln Tyr Glu Gln Leu
465                 470                 475                 480

Glu Leu Arg Ile Glu Val Gln Pro Arg Ala His His Arg Ala His Tyr
                485                 490                 495

Glu Thr Glu Gly Ser Arg Gly Ala Val Lys Ala Ala Pro Gly Gly His
            500                 505                 510

Pro Val Val Lys Leu Leu Gly Tyr Ser Glu Lys Pro Leu Thr Leu Gln
        515                 520                 525

Met Phe Ile Gly Thr Ala Asp Glu Arg Asn Leu Arg Pro His Ala Phe
    530                 535                 540

Tyr Gln Val His Arg Ile Thr Gly Lys Met Val Ala Thr Ala Ser Tyr
545                 550                 555                 560

Glu Ala Val Val Ser Gly Thr Lys Val Leu Glu Met Thr Leu Leu Pro
                565                 570                 575

Glu Asn Asn Met Ala Ala Asn Ile Asp Cys Ala Gly Ile Leu Lys Leu
            580                 585                 590

Arg Asn Ser Asp Ile Glu Leu Arg Lys Gly Glu Thr Asp Ile Gly Arg
        595                 600                 605

Lys Asn Thr Arg Val Arg Leu Val Phe Arg Val His Val Pro Gln Gly
    610                 615                 620

Gly Gly Lys Val Val Ser Val Gln Ala Ala Ser Val Pro Ile Glu Cys
625                 630                 635                 640

Ser Gln Arg Ser Ala Gln Glu Leu Pro Gln Val Glu Ala Tyr Ser Pro
                645                 650                 655

Ser Ala Cys Ser Val Arg Gly Gly Glu Glu Leu Val Leu Thr Gly Ser
            660                 665                 670

Asn Phe Leu Pro Asp Ser Lys Val Val Phe Ile Glu Arg Gly Pro Asp
        675                 680                 685

Gly Lys Leu Gln Trp Glu Glu Glu Ala Thr Val Asn Arg Leu Gln Ser
    690                 695                 700

Asn Glu Val Thr Leu Thr Leu Thr Val Pro Glu Tyr Ser Asn Lys Arg
705                 710                 715                 720

Val Ser Arg Pro Val Gln Val Tyr Phe Tyr Val Ser Asn Gly Arg Arg
                725                 730                 735

Lys Arg Ser Pro Thr Gln Ser Phe Arg Phe Leu Pro Val Ile Cys Lys
            740                 745                 750

Glu Glu Pro Leu Pro Asp Ser Ser Leu Arg Gly Phe Pro Ser Ala Ser
        755                 760                 765

Ala Thr Pro Phe Gly Thr Asp Met Asp Phe Ser Pro Pro Arg Pro Pro
    770                 775                 780

Tyr Pro Ser Tyr Pro His Glu Asp Pro Ala Cys Glu Thr Pro Tyr Leu
785                 790                 795                 800

Ser Glu Gly Phe Gly Tyr Gly Met Pro Pro Leu Tyr Pro Gln Thr Gly
                805                 810                 815

Pro Pro Pro Ser Tyr Arg Pro Gly Leu Arg Met Phe Pro Glu Thr Arg
```

```
            820                 825                 830

Gly Thr Thr Val Ser Glu Ile Ile Gly Arg Asp Leu Ser Gly Phe Pro
        835                 840                 845

Ala Pro Pro Gly Glu Glu Pro Pro Ala
    850                 855


<210> SEQ ID NO 11
<211> LENGTH: 5538
<212> TYPE: DNA
<213> ORGANISM: Homo sapiens

<400> SEQUENCE: 11

atgtgtgagt cgcccccagt ccagcccagt gcctcaagaa acacgcctcc aggcccagcc     60

ccagctccag cccctctgga cccacctctc tcaccttaag acccactgga tcgggtaccc    120

tcggtcctag gatccagggg ccagtgggca aaggcctggc atgcctgctt caatctcctc    180

catcttccca ggtccaactc tgcttttgtc ttgtggctca gaagaactgg actcagagga    240

tgccccgcca tgctgccgtc tggccttggg agagccccct ccctatggcg ctgcacctat    300

cggtattccc cgacctccac cccctcggcc tggcatgcat tcgccaccgc cgcgaccagc    360

cccctcacct ggcacctggg agagccagcc cgccaggtcg gtgaggctgg gaggaccagg    420

agggggtgct gggggtgctg ggggtggccg tgttctcgag tgtcccagca tccgcatcac    480

ctccatctct cccacgccgg agccgccagc agcgctggag gacaaccctg atgcctgggg    540

ggacggctct cctagagatt accccccacc agaaggcttt gggggctaca gagaagcagg    600

gggccagggt ggggggggcct tcttcagccc aagccctggc agcagcagcc tgtcctcgtg    660

gagcttcttc tccgatgcct ctgacgaggc agccctgtat gcagcctgcg acgaggtgga    720

gtctgagcta aatgaggcgg cctcccgctt tggcctgggc tccccgctgc cctcgccccg    780

ggcctcccct cggccatgga cccccgaaga tccctggagc ctgtatggtc caagccccgg    840

aggccgaggg ccagaggata gctggctact cctcagtgct cctgggccca ccccagcctc    900

cccgcggcct gcctctccat gtggcaagcg gcgctattcc agctcgggaa ccccatcttc    960

agcctcccca gctctgtccc gccgtggcag cctgggggaa gaggggtctg agccacctcc   1020

accaccccca ttgcctctgg cccgggaccc gggctcccct ggtccctttg actatgtggg   1080

ggccccacca gctgagagca tccctcagaa gacacggcgg acttccagcg agcaggcagt   1140

ggctctgcct cggtctgagg agcctgcctc atgcaatggg aagctgccct tgggagcaga   1200

ggagtctgtg gctcctccag gaggttcccg gaaggaggtg gctggcatgg actacctggc   1260

agtgccctcc ccactcgctt ggtccaaggc ccggattggg ggacacagcc ctatcttcag   1320

gacctctgcc ctacccccac tggactggcc tctgcccagc caatatgagc agctggagct   1380

gaggatcgag gtacagccta gagcccacca ccgggcccac tatgagacag aaggcagccg   1440

tggagctgtc aaagctgccc ctggcggtca ccccgtagtc aagctcctag gctacagtga   1500

gaagccactg accctacaga tgttcatcgg cactgcagat gaaaggaacc tgcggcctca   1560

tgccttctat caggtgcacc gtatcacagg caagatggtg gccacggcca gctatgaagc   1620

cgtagtcagt ggcaccaagg tgttggagat gactctgctg cctgagaaca acatggcggc   1680

caacattgac tgcgcgggaa tcctgaagct tcggaattca gacattgagc ttcggaaggg   1740

tgagacggac atcgggcgca aaaacacacg tgtacggctg gtgttccggg tacacgtgcc   1800

ccagggcggc gggaaggtcg tctcagtaca ggcagcatcg gtgcccatcg agtgctccca   1860

gcgctcagcc caggagctgc cccaggtgga ggcctacagc cccagtgcct gctctgtgag   1920
```

aggaggcgag gaactggtac tgactggctc caacttcctg ccagactcca aggtggtgtt 1980
cattgagagg ggtcctgatg ggaagctgca atgggaggag gaggccacag tgaaccgact 2040
gcagagcaac gaggtgacgc tgaccctgac tgtccccgag tacagcaaca agagggtttc 2100
ccggccagtc caggtctact tttatgtctc caatgggcgg aggaaacgca gtcctaccca 2160
gagtttcagg tttctgcctg tgatctgcaa agaggagccc ctaccggact catctctgcg 2220
gggtttccct tcagcatcgg caacccccttt tggcactgac atggacttct caccacccag 2280
gcccccctac ccctcctatc cccatgaaga ccctgcttgc gaaactcctt acctatcaga 2340
aggcttcggc tatggcatgc cccctctgta cccccagacg gggcccccac catcctacag 2400
accgggcctg cggatgttcc ctgagactag ggtaccaca ggttgtgccc aaccacctgc 2460
agtttccttc cttccccgcc ccttccctag tgacccgtat ggagggcggg gctcctcttt 2520
ctccctgggg ctgccattct ctccgccagc cccctttcgg ccgcctcctc ttcctgcatc 2580
cccaccgctt gaaggcccct tcccttccca gagtgatgtg catcccctac ctgctgaggg 2640
atacaataag gtagggccag gctatggccc tggggagggg gctccggagc aggagaaatc 2700
caggggtggc tacagcagcg gcttccgaga cagtgtccct atccagggta tcacgctgga 2760
ggaaggtggg tgtgggactg gggctgtga gtgtgagtgt gtgcaagaga ttgctctgca 2820
tgtttgctga gggctggagc tgggcttttc agagatcggg catccctggt ctctcagggc 2880
cagttggagg ttcccaggag gcatgttctt gatgcctgtg gctgcctgaa tccaattaac 2940
tgaattctga agagtgcatg gggtaactgt ctcagccttt ctcctgtctc tgcctctgtc 3000
ctctgctcca aatcataaaa tctcagagct agaagcactt tcaagatcat tccatccagc 3060
gcattcaatt tgcaagttta ggcgttgagt tccagagagg gatggtagct tgctgaggtc 3120
ccagtcaagc acacttgcca ttgcctcagc tttcccctaa acacggtgtc tgtggtcagg 3180
gttggtgagg aggagctttc ctgttttgcc tctccttctt cccattggct acacccatct 3240
ctggccctgc tgataccgat tcccctgaca tttcaggcta agccagcagg aaagggctag 3300
gacgggtgcc tgggagccca catggaggga gttgggcaag atttgattcg gagcaggtgt 3360
caagacgtgt tggggaaact gaggcccagt ggaatagaag ccagtagagg aggaatctag 3420
aggcctccta gattaagacc tgcctggaat ggattggggg tgggtctttg gaaaaggagg 3480
ggacccacct ctagcccagt ctctcaactg cccctccttt acagtgagtg agatcattgg 3540
ccgagacctg agtggcttcc ctgcacctcc tggagaagag cctcctgcct gaaccacgtg 3600
aactgtcatc acctggcaac cccagcccca gcctcagccc tgcccccttt ccctccttcc 3660
tggagtggtg gctacagaag cttggggcca accctggctc ctctttcccc agcttctgtc 3720
tgtctcactg tcttccctcc cctcccccag ctgaggtgtg gccctcaggc ctggtgctgc 3780
cttggagggc tgggggaagg agtgtgtgga ggagggagga gggtgaagac tgaggctagg 3840
tgccagaatg gactggagtg aaggcgtgtc tagagtgtgg gctggctgtt gtgctggaaa 3900
gctggggaca ggttgatggt aataaactgc tcaatgacca gtgcttcagg ctccagagct 3960
ctttggagag atgggttggg gcagcttact ccagccctgg cccaaggagg cccagaagtt 4020
ggaaagagat ggaatgtggc tgggaacatt gcatcccaaa gagcttctca gtggaggagg 4080
ctggggaagg catgaggggg ctcagaggct ccttgactgg gaccaggatt gggggccagg 4140
gcttgagtag gcctctccac tctcctcctt gggggtccag attccttagg agctttggga 4200
tgaggcccag gaggctgcat tttccaggt ccttagtctt gccaccacac agatgattct 4260

-continued

```
gattcatagc caagatgagg acacactgat gtagctgatc tctcatttac agaggaggat   4320

tctaaagttc agagagggaa aggggcttgc ctgaggtcac gtagataatc agcagcacat   4380

tgaacgctgc actcctgggc tcctgtcccc agcccccatt cagacacgct gactcaggag   4440

gtccaggcct ctaaggcttc tctccctgga gtgagggtgg aggtgaggga gagctggcac   4500

aagccctccc tctggatcct ccactcctgg ggattatgaa gatattctgg aaagatttgt   4560

gcttcagagg tagactgcag aaagcaaaca gtctacccag cagctctgaa tgtcacctgc   4620

cctggggctt acagcactat atgagttcct ggcctatcct gcaaatatgc ccatgctggc   4680

cttctaaata gctggtacat ccatcaccac tgacgggcct ggcctggaaa cctggtttgt   4740

cccctgtctt gatggcctac gagaggccaa gttccactgg gctgggaaaa gtcactttgt   4800

ctgtcttgtt cacctggagc ctgacacacc gtaggtactg agtacaaata gcttgatttg   4860

gctaggcttg gctgcagggg gacgtgccta aaagacattc cgggcatttg cacttgggaa   4920

acttgcctca ccttcaggct tgtggggcct ctctatgccc aatgagtcca ggcagtccta   4980

gcaagtactc aggagagcag gggtgggtgt gacagaggct ggctctggat tgggggacaa   5040

cagaaccaga gtaactcctc gcctgttgct gctttgcaat gaatttcctt tacctttctg   5100

gaacacaagc tgctgtgaac caaactgata tcaagtgatt agctcaccgg gccttggttg   5160

cttttcaaag atccccttca gccccctgcc agagtcactg ccccataatc accatgtcag   5220

aagggaccct agggcattcg tgtcctattt atcaatcttc agcaccacct ctaagatctc   5280

tgagagaggg tggatcagcc tctgtgtaaa caaaaagctg ttaggacttg ttgcctctca   5340

aggtggacta ttctgttttc tgccaggaca ctgccattca tgcattgtca gatatttatt   5400

aaacagcagc aaagtgccag ccaatttgtc ctggaggaat tcatagcctc atggggcaaa   5460

agtaaataaa cagcttatta caattcaaca aaaaaaaaaa aaaaaaaaaa aaaaaaaaaa   5520

aaaaaaaaaa aaaaaaaa                                                 5538
```

<210> SEQ ID NO 12
<211> LENGTH: 889
<212> TYPE: PRT
<213> ORGANISM: Homo sapiens

<400> SEQUENCE: 12

```
Met Pro Ala Ser Ile Ser Ser Ile Phe Pro Gly Pro Thr Leu Leu Leu
1               5                   10                  15

Ser Cys Gly Ser Glu Glu Leu Asp Ser Glu Asp Ala Pro Pro Cys Cys
            20                  25                  30

Arg Leu Ala Leu Gly Glu Pro Pro Pro Tyr Gly Ala Ala Pro Ile Gly
        35                  40                  45

Ile Pro Arg Pro Pro Pro Pro Arg Pro Gly Met His Ser Pro Pro Pro
    50                  55                  60

Arg Pro Ala Pro Ser Pro Gly Thr Trp Glu Ser Gln Pro Ala Arg Ser
65                  70                  75                  80

Val Arg Leu Gly Gly Pro Gly Gly Gly Ala Gly Gly Ala Gly Gly Gly
                85                  90                  95

Arg Val Leu Glu Cys Pro Ser Ile Arg Ile Thr Ser Ile Ser Pro Thr
            100                 105                 110

Pro Glu Pro Pro Ala Ala Leu Glu Asp Asn Pro Asp Ala Trp Gly Asp
        115                 120                 125

Gly Ser Pro Arg Asp Tyr Pro Pro Pro Glu Gly Phe Gly Gly Tyr Arg
    130                 135                 140
```

-continued

```
Glu Ala Gly Gly Gln Gly Gly Gly Ala Phe Phe Ser Pro Ser Pro Gly
145                 150                 155                 160

Ser Ser Ser Leu Ser Ser Trp Ser Phe Phe Ser Asp Ala Ser Asp Glu
                165                 170                 175

Ala Ala Leu Tyr Ala Ala Cys Asp Glu Val Glu Ser Glu Leu Asn Glu
            180                 185                 190

Ala Ala Ser Arg Phe Gly Leu Gly Ser Pro Leu Pro Ser Pro Arg Ala
        195                 200                 205

Ser Pro Arg Pro Trp Thr Pro Glu Asp Pro Trp Ser Leu Tyr Gly Pro
    210                 215                 220

Ser Pro Gly Gly Arg Gly Pro Glu Asp Ser Trp Leu Leu Leu Ser Ala
225                 230                 235                 240

Pro Gly Pro Thr Pro Ala Ser Pro Arg Pro Ala Ser Pro Cys Gly Lys
                245                 250                 255

Arg Arg Tyr Ser Ser Ser Gly Thr Pro Ser Ser Ala Ser Pro Ala Leu
            260                 265                 270

Ser Arg Arg Gly Ser Leu Gly Glu Glu Gly Ser Glu Pro Pro Pro Pro
        275                 280                 285

Pro Pro Leu Pro Leu Ala Arg Asp Pro Gly Ser Pro Gly Pro Phe Asp
    290                 295                 300

Tyr Val Gly Ala Pro Pro Ala Glu Ser Ile Pro Gln Lys Thr Arg Arg
305                 310                 315                 320

Thr Ser Ser Glu Gln Ala Val Ala Leu Pro Arg Ser Glu Glu Pro Ala
                325                 330                 335

Ser Cys Asn Gly Lys Leu Pro Leu Gly Ala Glu Glu Ser Val Ala Pro
            340                 345                 350

Pro Gly Gly Ser Arg Lys Glu Val Ala Gly Met Asp Tyr Leu Ala Val
        355                 360                 365

Pro Ser Pro Leu Ala Trp Ser Lys Ala Arg Ile Gly Gly His Ser Pro
    370                 375                 380

Ile Phe Arg Thr Ser Ala Leu Pro Pro Leu Asp Trp Pro Leu Pro Ser
385                 390                 395                 400

Gln Tyr Glu Gln Leu Glu Leu Arg Ile Glu Val Gln Pro Arg Ala His
                405                 410                 415

His Arg Ala His Tyr Glu Thr Glu Gly Ser Arg Gly Ala Val Lys Ala
            420                 425                 430

Ala Pro Gly Gly His Pro Val Val Lys Leu Leu Gly Tyr Ser Glu Lys
        435                 440                 445

Pro Leu Thr Leu Gln Met Phe Ile Gly Thr Ala Asp Glu Arg Asn Leu
    450                 455                 460

Arg Pro His Ala Phe Tyr Gln Val His Arg Ile Thr Gly Lys Met Val
465                 470                 475                 480

Ala Thr Ala Ser Tyr Glu Ala Val Val Ser Gly Thr Lys Val Leu Glu
                485                 490                 495

Met Thr Leu Leu Pro Glu Asn Asn Met Ala Ala Asn Ile Asp Cys Ala
            500                 505                 510

Gly Ile Leu Lys Leu Arg Asn Ser Asp Ile Glu Leu Arg Lys Gly Glu
        515                 520                 525

Thr Asp Ile Gly Arg Lys Asn Thr Arg Val Arg Leu Val Phe Arg Val
    530                 535                 540

His Val Pro Gln Gly Gly Gly Lys Val Val Ser Val Gln Ala Ala Ser
545                 550                 555                 560

Val Pro Ile Glu Cys Ser Gln Arg Ser Ala Gln Glu Leu Pro Gln Val
```

-continued

```
                565                 570                 575

Glu Ala Tyr Ser Pro Ser Ala Cys Ser Val Arg Gly Gly Glu Glu Leu
            580                 585                 590

Val Leu Thr Gly Ser Asn Phe Leu Pro Asp Ser Lys Val Val Phe Ile
        595                 600                 605

Glu Arg Gly Pro Asp Gly Lys Leu Gln Trp Glu Glu Glu Ala Thr Val
    610                 615                 620

Asn Arg Leu Gln Ser Asn Glu Val Thr Leu Thr Leu Thr Val Pro Glu
625                 630                 635                 640

Tyr Ser Asn Lys Arg Val Ser Arg Pro Val Gln Val Tyr Phe Tyr Val
                645                 650                 655

Ser Asn Gly Arg Arg Lys Arg Ser Pro Thr Gln Ser Phe Arg Phe Leu
            660                 665                 670

Pro Val Ile Cys Lys Glu Glu Pro Leu Pro Asp Ser Ser Leu Arg Gly
        675                 680                 685

Phe Pro Ser Ala Ser Ala Thr Pro Phe Gly Thr Asp Met Asp Phe Ser
    690                 695                 700

Pro Pro Arg Pro Pro Tyr Pro Ser Tyr Pro His Glu Asp Pro Ala Cys
705                 710                 715                 720

Glu Thr Pro Tyr Leu Ser Glu Gly Phe Gly Tyr Gly Met Pro Pro Leu
                725                 730                 735

Tyr Pro Gln Thr Gly Pro Pro Pro Ser Tyr Arg Pro Gly Leu Arg Met
            740                 745                 750

Phe Pro Glu Thr Arg Gly Thr Thr Gly Cys Ala Gln Pro Pro Ala Val
        755                 760                 765

Ser Phe Leu Pro Arg Pro Phe Pro Ser Asp Pro Tyr Gly Gly Arg Gly
    770                 775                 780

Ser Ser Phe Ser Leu Gly Leu Pro Phe Ser Pro Pro Ala Pro Phe Arg
785                 790                 795                 800

Pro Pro Pro Leu Pro Ala Ser Pro Pro Leu Glu Gly Pro Phe Pro Ser
                805                 810                 815

Gln Ser Asp Val His Pro Leu Pro Ala Glu Gly Tyr Asn Lys Val Gly
            820                 825                 830

Pro Gly Tyr Gly Pro Gly Glu Gly Ala Pro Glu Gln Glu Lys Ser Arg
        835                 840                 845

Gly Gly Tyr Ser Ser Gly Phe Arg Asp Ser Val Pro Ile Gln Gly Ile
    850                 855                 860

Thr Leu Glu Glu Gly Gly Cys Gly Thr Gly Gly Cys Glu Cys Glu Cys
865                 870                 875                 880

Val Gln Glu Ile Ala Leu His Val Cys
                885
```

<210> SEQ ID NO 13
<211> LENGTH: 4988
<212> TYPE: DNA
<213> ORGANISM: Homo sapiens

<400> SEQUENCE: 13

```
gtaaacgtct gacctggggc cgtcgcttaa ccgtttagtt gctgggatgg ggcggcgttg      60

ggggtgcggc cctgaaccgg agggatttag agactggaga cgcggcctct aagagaggtt     120

gaaactgtgt gtgtgtggga gaaaatgata accaccctcc catctctcct acccgccagc     180

ctcgccagta tctcccaccg agtcacgaat ctcccatcta actccctctc acacaaccca     240

ggcctctcca agcctgactt tcccggaaac tccagtccag gtcttccttc ctcctccagc     300
```

-continued

```
ccaggccggg acctgggggc tcctgccgga tccatggggg cggccagctg cgaggatgag    360
gagctggaat ttaagctggt gttcggggag gaaaaggagg cccccccgct gggcgcgggg    420
ggattggggg aagaactgga ctcagaggat gccccgccat gctgccgtct ggccttggga    480
gagcccccctc cctatggcgc tgcacctatc ggtattcccc gacctccacc ccctcggcct    540
ggcatgcatt cgccaccgcc gcgaccagcc ccctcacctg gcacctggga gagccagccc    600
gccaggtcgg tgaggctggg aggaccagga gggggtgctg ggggtgctgg gggtggccgt    660
gttctcgagt gtcccagcat ccgcatcacc tccatctctc ccacgccgga gccgccagca    720
gcgctggagg acaaccctga tgcctggggg gacggctctc ctagagatta ccccccacca    780
gaaggctttg gggctacag agaagcaggg ggccagggtg ggggggcctt cttcagccca    840
agccctggca gcagcagcct gtcctcgtgg agcttcttct ccgatgcctc tgacgaggca    900
gccctgtatg cagcctgcga cgaggtggag tctgagctaa atgaggcggc ctcccgcttt    960
ggcctgggct ccccgctgcc ctcgccccgg gcctcccctc ggccatggac cccgaagat   1020
ccctggagcc tgtatggtcc aagccccgga ggccgagggc cagaggatag ctggctactc   1080
ctcagtgctc ctgggcccac cccagcctcc ccgcggcctg cctctccatg tggcaagcgg   1140
cgctattcca gctcgggaac ccccatcttca gcctccccag ctctgtcccg ccgtggcagc   1200
ctgggggaag aggggtctga gccacctcca ccacccccat tgcctctggc ccgggacccg   1260
ggctcccctg gtccctttga ctatgtgggg gccccaccag ctgagagcat ccctcagaag   1320
acacggcgga cttccagcga gcaggcagtg gctctgcctc ggtctgagga gcctgcctca   1380
tgcaatggga agctgccctt gggagcagag gagtctgtgg ctcctccagg aggttcccgg   1440
aaggaggtgg ctggcatgga ctacctggca gtgccctccc cactcgcttg gtccaaggcc   1500
cggattgggg gacacagccc tatcttcagg acctctgccc tacccccact ggactggcct   1560
ctgcccagcc aatatgagca gctggagctg aggatcgagg tacagcctag agcccaccac   1620
cgggcccact atgagacaga aggcagccgt ggagctgtca aagctgcccc tggcggtcac   1680
cccgtagtca agctcctagg ctacagtgag aagccactga ccctacagat gttcatcggc   1740
actgcagatg aaaggaacct gcggcctcat gccttctatc aggtgcaccg tatcacaggc   1800
aagatggtgg ccacggccag ctatgaagcc gtagtcagtg gcaccaaggt gttggagatg   1860
actctgctgc ctgagaacaa catggcggcc aacattgact gcgcgggaat cctgaagctt   1920
cggaattcag acattgagct tcggaagggt gagacggaca tcgggcgcaa aaacacacgt   1980
gtacggctgg tgttccgggt acacgtgccc cagggcggcg ggaaggtcgt ctcagtacag   2040
gcagcatcgg tgcccatcga gtgctcccag cgctcagccc aggagctgcc ccaggtggag   2100
gcctacagcc ccagtgcctg ctctgtgaga ggaggcgagg aactggtact gactggctcc   2160
aacttcctgc cagactccaa ggtggtgttc attgagaggg gtcctgatgg gaagctgcaa   2220
tgggaggagg aggccacagt gaaccgactg cagagcaacg aggtgacgct gaccctgact   2280
gtccccgagt acagcaacaa gagggtttcc cggccagtcc aggtctactt ttatgtctcc   2340
aatgggcgga ggaaacgcag tcctacccag agtttcaggt ttctgcctgt gatctgcaaa   2400
gaggagcccc taccggactc atctctgcgg ggtttccctt cagcatcggc aaccccccttt   2460
ggcactgaca tggacttctc accacccagg cccccctacc cctcctatcc ccatgaagac   2520
cctgcttgcg aaactcctta cctatcagaa ggcttcggct atggcatgcc ccctctgtac   2580
ccccagacgg ggcccccacc atcctacaga ccgggcctgc ggatgttccc tgagactagg   2640
```

-continued

```
ggtaccacag gttgtgccca accacctgca gtttccttcc ttccccgccc cttccctagt   2700
gacccgtatg gagggcgggg ctcctctttc tccctggggc tgccattctc tccgccagcc   2760
ccctttcggc cgcctcctct tcctgcatcc ccaccgcttg aaggcccctt cccttcccag   2820
agtgatgtgc atcccctacc tgctgaggga tacaataagg tagggccagg ctatggccct   2880
ggggaggggg ctccggagca ggagaaatcc aggggtggct acagcagcgg cttccgagac   2940
agtgtcccta tccagggtat cacgctggag gaagtgagtg agatcattgg ccgagacctg   3000
agtggcttcc ctgcacctcc tggagaagag cctcctgcct gaaccacgtg aactgtcatc   3060
acctggcaac cccagcccca gcctcagccc tgccccttt ccctccttcc tggagtggtg    3120
gctacagaag cttggggcca accctggctc ctctttcccc agcttctgtc tgtctcactg   3180
tcttccctcc cctcccccag ctgaggtgtg gccctcaggc ctggtgctgc cttggagggc   3240
tgggggaagg agtgtgtgga ggagggagga gggtgaagac tgaggctagg tgccagaatg   3300
gactggagtg aaggcgtgtc tagagtgtgg gctggctgtt gtgctggaaa gctggggaca   3360
ggttgatggt aataaactgc tcaatgacca gtgcttcagg ctccagagct ctttggagag   3420
atgggttggg gcagcttact ccagccctgg cccaaggagg cccagaagtt ggaaagagat   3480
ggaatgtggc tgggaacatt gcatcccaaa gagcttctca gtggaggagg ctggggaagg   3540
catgaggggg ctcagaggct ccttgactgg gaccaggatt gggggccagg gcttgagtag   3600
gcctctccac tctcctcctt gggggtccag attccttagg agctttggga tgaggcccag   3660
gaggctgcat ttttccaggt ccttagtctt gccaccacac agatgattct gattcatagc   3720
caagatgagg acacactgat gtagctgatc tctcatttac agaggaggat tctaaagttc   3780
agagagggaa aggggcttgc ctgaggtcac gtagataatc agcagcacat tgaacgctgc   3840
actcctgggc tcctgtcccc agcccccatt cagacacgct gactcaggag gtccaggcct   3900
ctaaggcttc tctccctgga gtgagggtgg aggtgaggga gagctggcac aagccctccc   3960
tctggatcct ccactcctgg ggattatgaa gatattctgg aaagatttgt gcttcagagg   4020
tagactgcag aaagcaaaca gtctacccag cagctctgaa tgtcacctgc cctggggctt   4080
acagcactat atgagttcct ggcctatcct gcaaatatgc ccatgctggc cttctaaata   4140
gctggtacat ccatcaccac tgacgggcct ggcctggaaa cctggtttgt cccctgtctt   4200
gatggcctac gagaggccaa gttccactgg gctgggaaaa gtcactttgt ctgtcttgtt   4260
cacctggagc ctgacacacc gtaggtactg agtacaaata gcttgatttg gctaggcttg   4320
gctgcagggg gacgtgccta aaagacattc cgggcatttg cacttgggaa acttgcctca   4380
ccttcaggct tgtggggcct ctctatgccc aatgagtcca ggcagtccta gcaagtactc   4440
aggagagcag gggtgggtgt gacagaggct ggctctggat tgggggacaa cagaaccaga   4500
gtaactcctc gcctgttgct gctttgcaat gaatttcctt tacctttctg gaacacaagc   4560
tgctgtgaac caaactgata tcaagtgatt agctcaccgg gccttggttg cttttcaaag   4620
atccccttca gccccctgcc agagtcactg ccccataatc accatgtcag aagggaccct   4680
agggcattcg tgtcctattt atcaatcttc agcaccacct ctaagatctc tgagagaggg   4740
tggatcagcc tctgtgtaaa caaaaagctg ttaggacttg ttgcctctca aggtggacta   4800
ttctgttttc tgccaggaca ctgccattca tgcattgtca gatatttatt aaacagcagc   4860
aaagtgccag ccaatttgtc ctggaggaat tcatagcctc atggggcaaa agtaaataaa   4920
cagcttatta caattcaaca aaaaaaaaaa aaaaaaaaaa aaaaaaaaaa aaaaaaaaaa   4980
aaaaaaaa                                                            4988
```

<210> SEQ ID NO 14
<211> LENGTH: 965
<212> TYPE: PRT
<213> ORGANISM: Homo sapiens

<400> SEQUENCE: 14

```
Met Ile Thr Thr Leu Pro Ser Leu Leu Pro Ala Ser Leu Ala Ser Ile
1               5                   10                  15

Ser His Arg Val Thr Asn Leu Pro Ser Asn Ser Leu Ser His Asn Pro
            20                  25                  30

Gly Leu Ser Lys Pro Asp Phe Pro Gly Asn Ser Ser Pro Gly Leu Pro
        35                  40                  45

Ser Ser Ser Ser Pro Gly Arg Asp Leu Gly Ala Pro Ala Gly Ser Met
    50                  55                  60

Gly Ala Ala Ser Cys Glu Asp Glu Glu Leu Glu Phe Lys Leu Val Phe
65                  70                  75                  80

Gly Glu Glu Lys Glu Ala Pro Pro Leu Gly Ala Gly Gly Leu Gly Glu
                85                  90                  95

Glu Leu Asp Ser Glu Asp Ala Pro Pro Cys Cys Arg Leu Ala Leu Gly
            100                 105                 110

Glu Pro Pro Pro Tyr Gly Ala Ala Pro Ile Gly Ile Pro Arg Pro Pro
        115                 120                 125

Pro Pro Arg Pro Gly Met His Ser Pro Pro Pro Arg Pro Ala Pro Ser
    130                 135                 140

Pro Gly Thr Trp Glu Ser Gln Pro Ala Arg Ser Val Arg Leu Gly Gly
145                 150                 155                 160

Pro Gly Gly Gly Ala Gly Gly Ala Gly Gly Gly Arg Val Leu Glu Cys
                165                 170                 175

Pro Ser Ile Arg Ile Thr Ser Ile Ser Pro Thr Pro Glu Pro Pro Ala
            180                 185                 190

Ala Leu Glu Asp Asn Pro Asp Ala Trp Gly Asp Gly Ser Pro Arg Asp
        195                 200                 205

Tyr Pro Pro Pro Glu Gly Phe Gly Gly Tyr Arg Glu Ala Gly Gly Gln
    210                 215                 220

Gly Gly Gly Ala Phe Phe Ser Pro Ser Pro Gly Ser Ser Ser Leu Ser
225                 230                 235                 240

Ser Trp Ser Phe Phe Ser Asp Ala Ser Asp Glu Ala Ala Leu Tyr Ala
                245                 250                 255

Ala Cys Asp Glu Val Glu Ser Glu Leu Asn Glu Ala Ala Ser Arg Phe
            260                 265                 270

Gly Leu Gly Ser Pro Leu Pro Ser Pro Arg Ala Ser Pro Arg Pro Trp
        275                 280                 285

Thr Pro Glu Asp Pro Trp Ser Leu Tyr Gly Pro Ser Pro Gly Gly Arg
    290                 295                 300

Gly Pro Glu Asp Ser Trp Leu Leu Leu Ser Ala Pro Gly Pro Thr Pro
305                 310                 315                 320

Ala Ser Pro Arg Pro Ala Ser Pro Cys Gly Lys Arg Arg Tyr Ser Ser
                325                 330                 335

Ser Gly Thr Pro Ser Ser Ala Ser Pro Ala Leu Ser Arg Arg Gly Ser
            340                 345                 350

Leu Gly Glu Glu Gly Ser Glu Pro Pro Pro Pro Pro Pro Leu Pro Leu
        355                 360                 365

Ala Arg Asp Pro Gly Ser Pro Gly Pro Phe Asp Tyr Val Gly Ala Pro
```

-continued

```
    370                 375                 380

Pro Ala Glu Ser Ile Pro Gln Lys Thr Arg Arg Thr Ser Ser Glu Gln
385                 390                 395                 400

Ala Val Ala Leu Pro Arg Ser Glu Glu Pro Ala Ser Cys Asn Gly Lys
                405                 410                 415

Leu Pro Leu Gly Ala Glu Glu Ser Val Ala Pro Pro Gly Gly Ser Arg
            420                 425                 430

Lys Glu Val Ala Gly Met Asp Tyr Leu Ala Val Pro Ser Pro Leu Ala
        435                 440                 445

Trp Ser Lys Ala Arg Ile Gly Gly His Ser Pro Ile Phe Arg Thr Ser
    450                 455                 460

Ala Leu Pro Pro Leu Asp Trp Pro Leu Pro Ser Gln Tyr Glu Gln Leu
465                 470                 475                 480

Glu Leu Arg Ile Glu Val Gln Pro Arg Ala His His Arg Ala His Tyr
                485                 490                 495

Glu Thr Glu Gly Ser Arg Gly Ala Val Lys Ala Ala Pro Gly Gly His
            500                 505                 510

Pro Val Val Lys Leu Leu Gly Tyr Ser Glu Lys Pro Leu Thr Leu Gln
        515                 520                 525

Met Phe Ile Gly Thr Ala Asp Glu Arg Asn Leu Arg Pro His Ala Phe
    530                 535                 540

Tyr Gln Val His Arg Ile Thr Gly Lys Met Val Ala Thr Ala Ser Tyr
545                 550                 555                 560

Glu Ala Val Val Ser Gly Thr Lys Val Leu Glu Met Thr Leu Leu Pro
                565                 570                 575

Glu Asn Asn Met Ala Ala Asn Ile Asp Cys Ala Gly Ile Leu Lys Leu
            580                 585                 590

Arg Asn Ser Asp Ile Glu Leu Arg Lys Gly Glu Thr Asp Ile Gly Arg
        595                 600                 605

Lys Asn Thr Arg Val Arg Leu Val Phe Arg Val His Val Pro Gln Gly
    610                 615                 620

Gly Gly Lys Val Val Ser Val Gln Ala Ala Ser Val Pro Ile Glu Cys
625                 630                 635                 640

Ser Gln Arg Ser Ala Gln Glu Leu Pro Gln Val Glu Ala Tyr Ser Pro
                645                 650                 655

Ser Ala Cys Ser Val Arg Gly Gly Glu Glu Leu Val Leu Thr Gly Ser
            660                 665                 670

Asn Phe Leu Pro Asp Ser Lys Val Val Phe Ile Glu Arg Gly Pro Asp
        675                 680                 685

Gly Lys Leu Gln Trp Glu Glu Glu Ala Thr Val Asn Arg Leu Gln Ser
    690                 695                 700

Asn Glu Val Thr Leu Thr Leu Thr Val Pro Glu Tyr Ser Asn Lys Arg
705                 710                 715                 720

Val Ser Arg Pro Val Gln Val Tyr Phe Tyr Val Ser Asn Gly Arg Arg
                725                 730                 735

Lys Arg Ser Pro Thr Gln Ser Phe Arg Phe Leu Pro Val Ile Cys Lys
            740                 745                 750

Glu Glu Pro Leu Pro Asp Ser Ser Leu Arg Gly Phe Pro Ser Ala Ser
        755                 760                 765

Ala Thr Pro Phe Gly Thr Asp Met Asp Phe Ser Pro Pro Arg Pro Pro
    770                 775                 780

Tyr Pro Ser Tyr Pro His Glu Asp Pro Ala Cys Glu Thr Pro Tyr Leu
785                 790                 795                 800
```

Ser Glu Gly Phe Gly Tyr Gly Met Pro Pro Leu Tyr Pro Gln Thr Gly
805 810 815

Pro Pro Pro Ser Tyr Arg Pro Gly Leu Arg Met Phe Pro Glu Thr Arg
820 825 830

Gly Thr Thr Gly Cys Ala Gln Pro Pro Ala Val Ser Phe Leu Pro Arg
835 840 845

Pro Phe Pro Ser Asp Pro Tyr Gly Gly Arg Gly Ser Ser Phe Ser Leu
850 855 860

Gly Leu Pro Phe Ser Pro Pro Ala Pro Phe Arg Pro Pro Pro Leu Pro
865 870 875 880

Ala Ser Pro Pro Leu Glu Gly Pro Phe Pro Ser Gln Ser Asp Val His
885 890 895

Pro Leu Pro Ala Glu Gly Tyr Asn Lys Val Gly Pro Gly Tyr Gly Pro
900 905 910

Gly Glu Gly Ala Pro Glu Gln Glu Lys Ser Arg Gly Gly Tyr Ser Ser
915 920 925

Gly Phe Arg Asp Ser Val Pro Ile Gln Gly Ile Thr Leu Glu Glu Val
930 935 940

Ser Glu Ile Ile Gly Arg Asp Leu Ser Gly Phe Pro Ala Pro Pro Gly
945 950 955 960

Glu Glu Pro Pro Ala
965

<210> SEQ ID NO 15
<211> LENGTH: 381
<212> TYPE: PRT
<213> ORGANISM: Artificial sequence
<220> FEATURE:
<223> OTHER INFORMATION: Isoform 2 of NFATC4 truncated of the 521
N-terminal amino acids (dNFATC4)

<400> SEQUENCE: 15

Asp Cys Ala Gly Ile Leu Lys Leu Arg Asn Ser Asp Ile Glu Leu Arg
1 5 10 15

Lys Gly Glu Thr Asp Ile Gly Arg Lys Asn Thr Arg Val Arg Leu Val
20 25 30

Phe Arg Val His Val Pro Gln Gly Gly Gly Lys Val Val Ser Val Gln
35 40 45

Ala Ala Ser Val Pro Ile Glu Cys Ser Gln Arg Ser Ala Gln Glu Leu
50 55 60

Pro Gln Val Glu Ala Tyr Ser Pro Ser Ala Cys Ser Val Arg Gly Gly
65 70 75 80

Glu Glu Leu Val Leu Thr Gly Ser Asn Phe Leu Pro Asp Ser Lys Val
85 90 95

Val Phe Ile Glu Arg Gly Pro Asp Gly Lys Leu Gln Trp Glu Glu Glu
100 105 110

Ala Thr Val Asn Arg Leu Gln Ser Asn Glu Val Thr Leu Thr Leu Thr
115 120 125

Val Pro Glu Tyr Ser Asn Lys Arg Val Ser Arg Pro Val Gln Val Tyr
130 135 140

Phe Tyr Val Ser Asn Gly Arg Arg Lys Arg Ser Pro Thr Gln Ser Phe
145 150 155 160

Arg Phe Leu Pro Val Ile Cys Lys Glu Glu Pro Leu Pro Asp Ser Ser
165 170 175

Leu Arg Gly Phe Pro Ser Ala Ser Ala Thr Pro Phe Gly Thr Asp Met

-continued

```
            180                 185                 190

Asp Phe Ser Pro Pro Arg Pro Pro Tyr Pro Ser Tyr Pro His Glu Asp
        195                 200                 205

Pro Ala Cys Glu Thr Pro Tyr Leu Ser Glu Gly Phe Gly Tyr Gly Met
    210                 215                 220

Pro Pro Leu Tyr Pro Gln Thr Gly Pro Pro Pro Ser Tyr Arg Pro Gly
225                 230                 235                 240

Leu Arg Met Phe Pro Glu Thr Arg Gly Thr Thr Gly Cys Ala Gln Pro
                245                 250                 255

Pro Ala Val Ser Phe Leu Pro Arg Pro Phe Pro Ser Asp Pro Tyr Gly
            260                 265                 270

Gly Arg Gly Ser Ser Phe Ser Leu Gly Leu Pro Phe Ser Pro Pro Ala
        275                 280                 285

Pro Phe Arg Pro Pro Pro Leu Pro Ala Ser Pro Pro Leu Glu Gly Pro
    290                 295                 300

Phe Pro Ser Gln Ser Asp Val His Pro Leu Pro Ala Glu Gly Tyr Asn
305                 310                 315                 320

Lys Val Gly Pro Gly Tyr Gly Pro Gly Glu Gly Ala Pro Glu Gln Glu
                325                 330                 335

Lys Ser Arg Gly Gly Tyr Ser Ser Gly Phe Arg Asp Ser Val Pro Ile
            340                 345                 350

Gln Gly Ile Thr Leu Glu Glu Val Ser Glu Ile Ile Gly Arg Asp Leu
        355                 360                 365

Ser Gly Phe Pro Ala Pro Pro Gly Glu Glu Pro Pro Ala
    370                 375                 380


<210> SEQ ID NO 16
<211> LENGTH: 2583
<212> TYPE: DNA
<213> ORGANISM: Homo sapiens

<400> SEQUENCE: 16

agccggtccc cgccgccgcc gcccttcgcg ccctgggcca tctccctccc acctccctcc     60

gcggagcagc cagacagcga gggccccggc cgggggcagg ggggacgccc cgtccggggc    120

acccccccgg ctctgagccg cccgcggggc cggcctcggc ccggagcgga ggaaggagtc    180

gccgaggagc agcctgaggc cccagagtct gagacgagcc gccgccgccc ccgccactgc    240

ggggaggagg gggaggagga gcgggaggag ggacgagctg gtcgggagaa gaggaaaaaa    300

acttttgaga cttttccgtt gccgctggga gccggaggcg cggggacctc ttggcgcgac    360

gctgccccgc gaggaggcag gacttgggga ccccagaccg cctccctttg ccgccgggga    420

cgcttgctcc ctccctgccc cctacacggc gtccctcagg cgcccccatt ccggaccagc    480

cctcgggagt cgccgacccg gcctcccgca aagacttttc cccagacctc gggcgcaccc    540

cctgcacgcc gccttcatcc ccggcctgtc tcctgagccc ccgcgcatcc tagacccttt    600

ctcctccagg agacggatct ctctccgacc tgccacagat cccctattca agaccaccca    660

ccttctggta ccagatcgcg cccatctagg ttatttccgt gggatactga gacacccccg    720

gtccaagcct cccctccacc actgcgccct tctccctgag gacctcagct ttccctcgag    780

gccctcctac cttttgccgg gagaccccca gcccctgcag gggcggggcc tccccaccac    840

accagccctg ttcgcgctct cggcagtgcc ggggggcgcc gcctccccca tgccgccctc    900

cgggctgcgg ctgctgccgc tgctgctacc gctgctgtgg ctactggtgc tgacgcctgg    960

ccggccggcc gcgggactat ccacctgcaa gactatcgac atggagctgg tgaagcggaa   1020
```

```
gcgcatcgag gccatccgcg gccagatcct gtccaagctg cggctcgcca gccccccgag   1080

ccagggggag gtgccgcccg gcccgctgcc cgaggccgtg ctcgccctgt acaacagcac   1140

ccgcgaccgg gtggccgggg agagtgcaga accggagccc gagcctgagg ccgactacta   1200

cgccaaggag gtcacccgcg tgctaatggt ggaaacccac aacgaaatct atgacaagtt   1260

caagcagagt acacacagca tatatatgtt cttcaacaca tcagagctcc gagaagcggt   1320

acctgaaccc gtgttgctct cccgggcaga gctgcgtctg ctgaggctca agttaaaagt   1380

ggagcagcac gtggagctgt accagaaata cagcaacaat tcctggcgat acctcagcaa   1440

ccggctgctg gcacccagcg actcgccaga gtggttatct tttgatgtca ccggagttgt   1500

gcggcagtgg ttgagccgtg gaggggaaat tgagggcttt cgccttagcg cccactgctc   1560

ctgtgacagc agggataaca cactgcaagt ggacatcaac gggttcacta ccggccgccg   1620

aggtgacctg gccaccattc atggcatgaa ccggcctttc ctgcttctca tggccacccc   1680

gctggagagg gcccagcatc tgcaaagctc ccggcaccgc cgagccctgg acaccaacta   1740

ttgcttcagc tccacggaga agaactgctg cgtgcggcag ctgtacattg acttccgcaa   1800

ggacctcggc tggaagtgga tccacgagcc caagggctac catgccaact tctgcctcgg   1860

gccctgcccc tacatttgga gcctggacac gcagtacagc aaggtcctgg ccctgtacaa   1920

ccagcataac ccgggcgcct cggcggcgcc gtgctgcgtg ccgcaggcgc tggagccgct   1980

gcccatcgtg tactacgtgg gccgcaagcc caaggtggag cagctgtcca acatgatcgt   2040

gcgctcctgc aagtgcagct gaggtcccgc cccgccccgc cccgccccgg caggcccggc   2100

cccaccccgc cccgcccccg ctgccttgcc catgggggct gtatttaagg acacccgtgc   2160

cccaagccca cctggggccc cattaaagat ggagagagga ctgcggatct ctgtgtcatt   2220

gggcgcctgc ctggggtctc catccctgac gttcccccac tcccactccc tctctctccc   2280

tctctgcctc ctcctgcctg tctgcactat tcctttgccc ggcatcaagg cacaggggac   2340

cagtggggaa cactactgta gttagatcta tttattgagc accttgggca ctgttgaagt   2400

gccttacatt aatgaactca ttcagtcacc atagcaacac tctgagatgc agggactctg   2460

ataacaccca ttttaaaggt gaggaaacaa gcccagagag gttaagggag gagttcctgc   2520

ccaccaggaa cctgctttag tgggggatag tgaagaagac aataaaagat agtagttcag   2580

gcc                                                                  2583
```

<210> SEQ ID NO 17
<211> LENGTH: 390
<212> TYPE: PRT
<213> ORGANISM: Homo sapiens

<400> SEQUENCE: 17

```
Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
```

-continued

```
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390
```

<210> SEQ ID NO 18
<211> LENGTH: 19
<212> TYPE: DNA
<213> ORGANISM: Artificial sequence
<220> FEATURE:
<223> OTHER INFORMATION: human NFATC4 shRNA3

<400> SEQUENCE: 18
caatgaacac caccttgga 19

<210> SEQ ID NO 19
<211> LENGTH: 19
<212> TYPE: DNA
<213> ORGANISM: Artificial sequence
<220> FEATURE:
<223> OTHER INFORMATION: human NFATC4 shRNA4

<400> SEQUENCE: 19
agtctcaggg aacatccgc 19

<210> SEQ ID NO 20
<211> LENGTH: 19
<212> TYPE: DNA
<213> ORGANISM: Artificial sequence
<220> FEATURE:
<223> OTHER INFORMATION: human TGFbeta1 shRNA1

<400> SEQUENCE: 20
atgctgtgtg tactctgct 19

<210> SEQ ID NO 21
<211> LENGTH: 19
<212> TYPE: DNA
<213> ORGANISM: Artificial sequence
<220> FEATURE:
<223> OTHER INFORMATION: human TGFbeta1 shRNA2

<400> SEQUENCE: 21
tgatgtccac ttgcagtgt 19

<210> SEQ ID NO 22
<211> LENGTH: 18
<212> TYPE: RNA
<213> ORGANISM: Artificial sequence
<220> FEATURE:
<223> OTHER INFORMATION: human TGFbeta1 siRNA1

<400> SEQUENCE: 22
auugagggcu uucgcuua 18

<210> SEQ ID NO 23
<211> LENGTH: 19
<212> TYPE: RNA
<213> ORGANISM: Artificial sequence
<220> FEATURE:
<223> OTHER INFORMATION: human TGFbeta1 siRNA2

<400> SEQUENCE: 23
ccgagaagcg guaccugaa 19

<210> SEQ ID NO 24
<211> LENGTH: 17
<212> TYPE: RNA
<213> ORGANISM: Artificial sequence
<220> FEATURE:
<223> OTHER INFORMATION: human TGFbeta1 siRNA3

<400> SEQUENCE: 24
gcagaguaca cagcaua 17

<210> SEQ ID NO 25
<211> LENGTH: 19
<212> TYPE: RNA
<213> ORGANISM: Artificial sequence
<220> FEATURE:
<223> OTHER INFORMATION: human TGFbeta1 siRNA4

<400> SEQUENCE: 25
ggacuaucca ccugcaaga 19

<210> SEQ ID NO 26
<211> LENGTH: 4818

-continued

<212> TYPE: DNA
<213> ORGANISM: Artificial sequence
<220> FEATURE:
<223> OTHER INFORMATION: Promega PGL3 basic, empty vector

<400> SEQUENCE: 26
ggtaccgagc tcttacgcgt gctagcccgg gctcgagatc tgcgatctaa gtaagcttgg 60
cattccggta ctgttggtaa agccaccatg gaagacgcca aaaacataaa gaaaggcccg 120
gcgccattct atccgctgga agatggaacc gctggagagc aactgcataa ggctatgaag 180
agatacgccc tggttcctgg aacaattgct tttacagatg cacatatcga ggtggacatc 240
acttacgctg agtacttcga aatgtccgtt cggttggcag aagctatgaa acgatatggg 300
ctgaatacaa atcacagaat cgtcgtatgc agtgaaaact ctcttcaatt ctttatgccg 360
gtgttgggcg cgttatttat cggagttgca gttgcgcccg cgaacgacat ttataatgaa 420
cgtgaattgc tcaacagtat gggcatttcg cagcctaccg tggtgttcgt ttccaaaaag 480
gggttgcaaa aaattttgaa cgtgcaaaaa aagctcccaa tcatccaaaa aattattatc 540
atggattcta aaacggatta ccagggattt cagtcgatgt acacgttcgt cacatctcat 600
ctacctcccg gttttaatga atacgatttt gtgccagagt ccttcgatag ggacaagaca 660
attgcactga tcatgaactc ctctggatct actggtctgc ctaaaggtgt cgctctgcct 720
catagaactg cctgcgtgag attctcgcat gccagagatc ctatttttgg caatcaaatc 780
attccggata ctgcgatttt aagtgttgtt ccattccatc acggttttgg aatgtttact 840
acactcggat atttgatatg tggatttcga gtcgtcttaa tgtatagatt tgaagaagag 900
ctgtttctga ggagccttca ggattacaag attcaaagtg cgctgctggt gccaacccta 960
ttctccttct tcgccaaaag cactctgatt gacaaatacg atttatctaa tttacacgaa 1020
attgcttctg gtggcgctcc cctctctaag gaagtcgggg aagcggttgc caagaggttc 1080
catctgccag gtatcaggca aggatatggg ctcactgaga ctacatcagc tattctgatt 1140
acacccgagg gggatgataa accgggcgcg gtcggtaaag ttgttccatt ttttgaagcg 1200
aaggttgtgg atctggatac cgggaaaacg ctgggcgtta atcaaagagg cgaactgtgt 1260
gtgagaggtc ctatgattat gtccggttat gtaaacaatc cggaagcgac caacgccttg 1320
attgacaagg atggatggct acattctgga gacatagctt actgggacga agacgaacac 1380
ttcttcatcg ttgaccgcct gaagtctctg attaagtaca aaggctatca ggtggctccc 1440
gctgaattgg aatccatctt gctccaacac cccaacatct tcgacgcagg tgtcgcaggt 1500
cttcccgacg atgacgccgg tgaacttccc gccgccgttg ttgttttgga gcacggaaag 1560
acgatgacgg aaaaagagat cgtggattac gtcgccagtc aagtaacaac cgcgaaaaag 1620
ttgcgcggag gagttgtgtt tgtggacgaa gtaccgaaag gtcttaccgg aaaactcgac 1680
gcaagaaaaa tcagagagat cctcataaag gccaagaagg gcggaaagat cgccgtgtaa 1740
ttctagagtc ggggcggccg gccgcttcga gcagacatga taagatacat tgatgagttt 1800
ggacaaacca caactagaat gcagtgaaaa aaatgcttta tttgtgaaat ttgtgatgct 1860
attgctttat ttgtaaccat tataagctgc aataaacaag ttaacaacaa caattgcatt 1920
cattttatgt ttcaggttca gggggaggtg tgggaggttt tttaaagcaa gtaaaacctc 1980
tacaaatgtg gtaaaatcga taaggatccg tcgaccgatg cccttgagag ccttcaaccc 2040
agtcagctcc ttccggtggg cgcggggcat gactatcgtc gccgcactta tgactgtctt 2100
ctttatcatg caactcgtag gacaggtgcc ggcagcgctc ttccgcttcc tcgctcactg 2160

-continued

```
actcgctgcg ctcggtcgtt cggctgcggc gagcggtatc agctcactca aaggcggtaa   2220
tacggttatc cacagaatca ggggataacg caggaaagaa catgtgagca aaaggccagc   2280
aaaaggccag gaaccgtaaa aaggccgcgt tgctggcgtt tttccatagg ctccgccccc   2340
ctgacgagca tcacaaaaat cgacgctcaa gtcagaggtg gcgaaacccg acaggactat   2400
aaagatacca ggcgtttccc cctggaagct ccctcgtgcg ctctcctgtt ccgaccctgc   2460
cgcttaccgg atacctgtcc gcctttctcc cttcgggaag cgtggcgctt tctcatagct   2520
cacgctgtag gtatctcagt tcggtgtagg tcgttcgctc caagctgggc tgtgtgcacg   2580
aaccccccgt tcagcccgac cgctgcgcct tatccggtaa ctatcgtctt gagtccaacc   2640
cggtaagaca cgacttatcg ccactggcag cagccactgg taacaggatt agcagagcga   2700
ggtatgtagg cggtgctaca gagttcttga agtggtggcc taactacggc tacactagaa   2760
gaacagtatt tggtatctgc gctctgctga agccagttac cttcggaaaa agagttggta   2820
gctcttgatc cggcaaacaa accaccgctg gtagcggtgg tttttttgtt tgcaagcagc   2880
agattacgcg cagaaaaaaa ggatctcaag aagatccttt gatcttttct acggggtctg   2940
acgctcagtg gaacgaaaac tcacgttaag ggattttggt catgagatta tcaaaaagga   3000
tcttcaccta gatcctttta aattaaaaat gaagttttaa atcaatctaa agtatatatg   3060
agtaaacttg gtctgacagt taccaatgct taatcagtga ggcacctatc tcagcgatct   3120
gtctatttcg ttcatccata gttgcctgac tccccgtcgt gtagataact acgatacggg   3180
agggcttacc atctggcccc agtgctgcaa tgataccgcg agacccacgc tcaccggctc   3240
cagatttatc agcaataaac cagccagccg gaagggccga gcgcagaagt ggtcctgcaa   3300
ctttatccgc ctccatccag tctattaatt gttgccggga agctagagta agtagttcgc   3360
cagttaatag tttgcgcaac gttgttgcca ttgctacagg catcgtggtg tcacgctcgt   3420
cgtttggtat ggcttcattc agctccggtt cccaacgatc aaggcgagtt acatgatccc   3480
ccatgttgtg caaaaaagcg gttagctcct tcggtcctcc gatcgttgtc agaagtaagt   3540
tggccgcagt gttatcactc atggttatgg cagcactgca taattctctt actgtcatgc   3600
catccgtaag atgcttttct gtgactggtg agtactcaac caagtcattc tgagaatagt   3660
gtatgcggcg accgagttgc tcttgcccgg cgtcaatacg ggataatacc gcgccacata   3720
gcagaacttt aaaagtgctc atcattggaa aacgttcttc ggggcgaaaa ctctcaagga   3780
tcttaccgct gttgagatcc agttcgatgt aacccactcg tgcacccaac tgatcttcag   3840
catcttttac tttcaccagc gtttctgggt gagcaaaaac aggaaggcaa aatgccgcaa   3900
aaaagggaat aagggcgaca cggaaatgtt gaatactcat actcttcctt tttcaatatt   3960
attgaagcat ttatcagggt tattgtctca tgagcggata catatttgaa tgtatttaga   4020
aaaataaaca aataggggtt ccgcgcacat ttccccgaaa agtgccacct gacgcgccct   4080
gtagcggcgc attaagcgcg gcgggtgtgg tggttacgcg cagcgtgacc gctacacttg   4140
ccagcgccct agcgcccgct cctttcgctt tcttcccttc ctttctcgcc acgttcgccg   4200
gctttccccg tcaagctcta aatcgggggc tccctttagg gttccgattt agtgctttac   4260
ggcacctcga ccccaaaaaa cttgattagg gtgatggttc acgtagtggg ccatcgccct   4320
gatagacggt ttttcgccct ttgacgttgg agtccacgtt ctttaatagt ggactcttgt   4380
tccaaactgg aacaacactc aaccctatct cggtctattc ttttgattta taagggattt   4440
tgccgatttc ggcctattgg ttaaaaaatg agctgattta acaaaaattt aacgcgaatt   4500
ttaacaaaat attaacgctt acaatttgcc attcgccatt caggctgcgc aactgttggg   4560
```

aagggcgatc ggtgcgggcc tcttcgctat tacgccagcc caagctacca tgataagtaa 4620
gtaatattaa ggtacgggag gtacttggag cggccgcaat aaaatatctt tattttcatt 4680
acatctgtgt gttggttttt tgtgtgaatc gatagtacta acatacgctc tccatcaaaa 4740
caaaacgaaa caaaacaaac tagcaaaata ggctgtcccc agtgcaagtg caggtgccag 4800
aacatttctc tatcgata 4818

<210> SEQ ID NO 27
<211> LENGTH: 6494
<212> TYPE: DNA
<213> ORGANISM: Artificial sequence
<220> FEATURE:
<223> OTHER INFORMATION: PGL3-hTGFb1-1670 promoter

<400> SEQUENCE: 27
ggtaccgagc tcttacgcgt gctagcccgg gctcgagatc tgcgatctaa gtaagcttgg 60
cattccggta ctgttggtaa agccaccatg gaagacgcca aaaacataaa gaaaggcccg 120
gcgccattct atccgctgga agatggaacc gctggagagc aactgcataa ggctatgaag 180
agatacgccc tggttcctgg aacaattgct tttacagatg cacatatcga ggtggacatc 240
acttacgctg agtacttcga aatgtccgtt cggttggcag aagctatgaa acgatatggg 300
ctgaatacaa atcacagaat cgtcgtatgc agtgaaaact ctcttcaatt ctttatgccg 360
gtgttgggcg cgttatttat cggagttgca gttgcgcccg cgaacgacat ttataatgaa 420
cgtgaattgc tcaacagtat gggcatttcg cagcctaccg tggtgttcgt ttccaaaaag 480
gggttgcaaa aaattttgaa cgtgcaaaaa aagctcccaa tcatccaaaa aattattatc 540
atggattcta aaacggatta ccagggattt cagtcgatgt acacgttcgt cacatctcat 600
ctacctcccg gttttaatga atacgatttt gtgccagagt ccttcgatag ggacaagaca 660
attgcactga tcatgaactc ctctggatct actggtctgc ctaaaggtgt cgctctgcct 720
catagaactg cctgcgtgag attctcgcat gccagagatc ctatttttgg caatcaaatc 780
attccggata ctgcgatttt aagtgttgtt ccattccatc acggttttgg aatgtttact 840
acactcggat atttgatatg tggatttcga gtcgtcttaa tgtatagatt tgaagaagag 900
ctgtttctga ggagccttca ggattacaag attcaaagtg cgctgctggt gccaacccta 960
ttctccttct tcgccaaaag cactctgatt gacaaatacg atttatctaa tttacacgaa 1020
attgcttctg gtggcgctcc cctctctaag gaagtcgggg aagcggttgc caagaggttc 1080
catctgccag gtatcaggca aggatatggg ctcactgaga ctacatcagc tattctgatt 1140
acacccgagg gggatgataa accgggcgcg gtcggtaaag ttgttccatt ttttgaagcg 1200
aaggttgtgg atctggatac cgggaaaacg ctgggcgtta atcaaagagg cgaactgtgt 1260
gtgagaggtc ctatgattat gtccggttat gtaaacaatc cggaagcgac caacgccttg 1320
attgacaagg atggatggct acattctgga gacatagctt actgggacga agacgaacac 1380
ttcttcatcg ttgaccgcct gaagtctctg attaagtaca aaggctatca ggtggctccc 1440
gctgaattgg aatccatctt gctccaacac cccaacatct tcgacgcagg tgtcgcaggt 1500
cttcccgacg atgacgccgg tgaacttccc gccgccgttg ttgttttgga gcacggaaag 1560
acgatgacgg aaaaagagat cgtggattac gtcgccagtc aagtaacaac cgcgaaaaag 1620
ttgcgcggag gagttgtgtt tgtggacgaa gtaccgaaag gtcttaccgg aaaactcgac 1680
gcaagaaaaa tcagagagat cctcataaag gccaagaagg gcggaaagat cgccgtgtaa 1740

```
ttctagagtc ggggcggccg gccgcttcga gcagacatga taagatacat tgatgagttt   1800
ggacaaacca caactagaat gcagtgaaaa aaatgcttta tttgtgaaat ttgtgatgct   1860
attgctttat ttgtaaccat tataagctgc aataaacaag ttaacaacaa caattgcatt   1920
cattttatgt ttcaggttca gggggaggtg tgggaggttt tttaaagcaa gtaaaacctc   1980
tacaaatgtg gtaaaatcga taaggatccg tcgaccgatg cccttgagag ccttcaaccc   2040
agtcagctcc ttccggtggg cgcggggcat gactatcgtc gccgcactta tgactgtctt   2100
ctttatcatg caactcgtag gacaggtgcc ggcagcgctc ttccgcttcc tcgctcactg   2160
actcgctgcg ctcggtcgtt cggctgcggc gagcggtatc agctcactca aaggcggtaa   2220
tacggttatc cacagaatca ggggataacg caggaaagaa catgtgagca aaaggccagc   2280
aaaaggccag gaaccgtaaa aaggccgcgt tgctggcgtt tttccatagg ctccgccccc   2340
ctgacgagca tcacaaaaat cgacgctcaa gtcagaggtg gcgaaacccg acaggactat   2400
aaagatacca ggcgtttccc cctggaagct ccctcgtgcg ctctcctgtt ccgaccctgc   2460
cgcttaccgg atacctgtcc gcctttctcc cttcgggaag cgtggcgctt tctcatagct   2520
cacgctgtag gtatctcagt tcggtgtagg tcgttcgctc caagctgggc tgtgtgcacg   2580
aaccccccgt tcagcccgac cgctgcgcct tatccggtaa ctatcgtctt gagtccaacc   2640
cggtaagaca cgacttatcg ccactggcag cagccactgg taacaggatt agcagagcga   2700
ggtatgtagg cggtgctaca gagttcttga agtggtggcc taactacggc tacactagaa   2760
gaacagtatt tggtatctgc gctctgctga agccagttac cttcggaaaa agagttggta   2820
gctcttgatc cggcaaacaa accaccgctg gtagcggtgg tttttttgtt tgcaagcagc   2880
agattacgcg cagaaaaaaa ggatctcaag aagatccttt gatcttttct acggggtctg   2940
acgctcagtg gaacgaaaac tcacgttaag ggattttggt catgagatta tcaaaaagga   3000
tcttcaccta gatcctttta aattaaaaat gaagttttaa atcaatctaa agtatatatg   3060
agtaaacttg gtctgacagt taccaatgct taatcagtga ggcacctatc tcagcgatct   3120
gtctatttcg ttcatccata gttgcctgac tccccgtcgt gtagataact acgatacggg   3180
agggcttacc atctggcccc agtgctgcaa tgataccgcg agacccacgc tcaccggctc   3240
cagatttatc agcaataaac cagccagccg gaagggccga gcgcagaagt ggtcctgcaa   3300
ctttatccgc ctccatccag tctattaatt gttgccggga agctagagta agtagttcgc   3360
cagttaatag tttgcgcaac gttgttgcca ttgctacagg catcgtggtg tcacgctcgt   3420
cgtttggtat ggcttcattc agctccggtt cccaacgatc aaggcgagtt acatgatccc   3480
ccatgttgtg caaaaaagcg gttagctcct tcggtcctcc gatcgttgtc agaagtaagt   3540
tggccgcagt gttatcactc atggttatgg cagcactgca taattctctt actgtcatgc   3600
catccgtaag atgcttttct gtgactggtg agtactcaac caagtcattc tgagaatagt   3660
gtatgcggcg accgagttgc tcttgcccgg cgtcaatacg ggataatacc gcgccacata   3720
gcagaacttt aaaagtgctc atcattggaa aacgttcttc ggggcgaaaa ctctcaagga   3780
tcttaccgct gttgagatcc agttcgatgt aacccactcg tgcacccaac tgatcttcag   3840
catcttttac tttcaccagc gtttctgggt gagcaaaaac aggaaggcaa aatgccgcaa   3900
aaaagggaat aagggcgaca cggaaatgtt gaatactcat actcttcctt tttcaatatt   3960
attgaagcat ttatcagggt tattgtctca tgagcggata catatttgaa tgtatttaga   4020
aaaataaaca aataggggtt ccgcgcacat ttccccgaaa agtgccacct gacgcgccct   4080
gtagcggcgc attaagcgcg gcgggtgtgg tggttacgcg cagcgtgacc gctacacttg   4140
```

ccagcgccct agcgcccgct cctttcgctt tcttcccttc ctttctcgcc acgttcgccg 4200
gctttccccg tcaagctcta aatcgggggc tccctttagg gttccgattt agtgctttac 4260
ggcacctcga ccccaaaaaa cttgattagg gtgatggttc acgtagtggg ccatcgccct 4320
gatagacggt ttttcgccct ttgacgttgg agtccacgtt ctttaatagt ggactcttgt 4380
tccaaactgg aacaacactc aaccctatct cggtctattc ttttgattta taagggattt 4440
tgccgatttc ggcctattgg ttaaaaaatg agctgattta acaaaaattt aacgcgaatt 4500
ttaacaaaat attaacgctt acaatttgcc attcgccatt caggctgcgc aactgttggg 4560
aagggcgatc ggtgcgggcc tcttcgctat tacgccagcc caagctacca tgataagtaa 4620
gtaatattaa ggtacgggag gtacttggag cggccgcaat aaaatatctt tattttcatt 4680
acatctgtgt gttggttttt tgtgtgaatc gatagtacta acatacgctc tccatcaaaa 4740
caaaacgaaa caaaacaaac tagcaaaata ggctgtcccc agtgcaagtg caggtgccag 4800
aacatttctc tatcgatagg taccggcgtg gagtgctgag ggactctgcc tccaacgtca 4860
ccaccatcca caccccggac acccagtgat gggggaggat ggcacagtgg tcaagagcac 4920
agactctaga gactgtcaga gctgacccca gctaaggcat ggcaccgctt ctgtcctttc 4980
taggacctcg gggtccctct gggcccagtt tccctatctg taaattgggg acagtaaatg 5040
tatggggtcg cagggtgttg agtgacagga ggctgcttag ccacatggga ggtgctcagt 5100
aaaggagagc aattcttaca ggtgtctgcc tcctgaccct tccatccttc aggtgtcctg 5160
ttgcccccctc ctcccactga caccctccgg aggcccccat gttgacagac cctcttctcc 5220
taccttgttt cccagcctga ctctccttcc gttctgggtc cccctcctct ggtcggctcc 5280
cctgtgtctc atcccccgga ttaagccttc tccgcctggt cctctttctc tggtgaccca 5340
caccgcccgc aaagccacag cgcatctgga tcacccgctt tggtggcgct tggccgccag 5400
gaggcagcac cctgtttgcg gggcggagcc ggggtgcccg cccccctttcc cccagggctg 5460
aagggacccc cctcggagcc cgcccacgcg agatgaggac ggtggcccag cccccccatg 5520
ccctcccccct gggggccgcc cccgctcccg ccccgtgcgc ttcctgggtg gggccggggg 5580
cggcttcaaa acccccctgcc gacccagccg gtccccgccg ccgccgccct tcgcgccctg 5640
ggccatctcc ctcccacctc cctccgcgga gcagccagac agcgagggcc ccggccgggg 5700
gcaggggggga cgccccgtcc ggggcacccc cccggctctg agccgcccgc ggggccggcc 5760
tcggcccgga gcggaggaag gagtcgccga ggagcagcct gaggccccag agtctgagac 5820
gagccgccgc cgcccccgcc actgcgggga ggaggggggag gaggagcggg aggagggacg 5880
agctggtcgg gagaagagga aaaaaacttt tgagactttt ccgttgccgc tgggagccgg 5940
aggcgcgggg acctcttggc gcgacgctgc ccccgcgagga ggcaggactt ggggacccca 6000
gaccgcctcc ctttgccgcc ggggacgctt gctccctccc tgccccctac acggcgtccc 6060
tcaggcgccc ccattccgga ccagccctcg ggagtcgccg acccggcctc ccgcaaagac 6120
ttttccccag acctcgggcg caccccctgc acgccgcctt catccccggc ctgtctcctg 6180
agcccccgcg catcctagac cctttctcct ccaggagacg gatctctctc cgacctgcca 6240
cagatcccct attcaagacc acccagcttc tggtaccaga tcgcgcccat ctaggttatt 6300
tccgtgggat actgagacac ccccggtcca agcctcccct ccaccactgc gcccttctcc 6360
ctgaggacct cagctttccc tcgaggccct cctacctttt gccgggagac cccccagcccc 6420
tgcaggggcg gggcctcccc accacaccag ccctgttcgc gctctcggca gtgccggggg 6480
gcgccgcctc cccc 6494

<210> SEQ ID NO 28
<211> LENGTH: 9498
<212> TYPE: DNA
<213> ORGANISM: Artificial sequence
<220> FEATURE:
<223> OTHER INFORMATION: Clonetech, pLVX-tdTomato-C1 , empty vector

<400> SEQUENCE: 28
tggaagggct aattcactcc caaagaagac aagatatcct tgatctgtgg atctaccaca 60
cacaaggcta cttccctgat tagcagaact acacaccagg gccaggggtc agatatccac 120
tgacctttgg atggtgctac aagctagtac cagttgagcc agataaggta gaagaggcca 180
ataaaggaga gaacaccagc ttgttacacc ctgtgagcct gcatgggatg gatgacccgg 240
agagagaagt gttagagtgg aggtttgaca gccgcctagc atttcatcac gtggcccgag 300
agctgcatcc ggagtacttc aagaactgct gatatcgagc ttgctacaag ggactttccg 360
ctggggactt tccagggagg cgtggcctgg gcgggactgg ggagtggcga gccctcagat 420
cctgcatata agcagctgct ttttgcctgt actgggtctc tctggttaga ccagatctga 480
gcctgggagc tctctggcta actagggaac ccactgctta agcctcaata aagcttgcct 540
tgagtgcttc aagtagtgtg tgcccgtctg ttgtgtgact ctggtaacta gagatccctc 600
agaccctttt agtcagtgtg gaaaatctct agcagtggcg cccgaacagg gacttgaaag 660
cgaaagggaa accagaggag ctctctcgac gcaggactcg gcttgctgaa gcgcgcacgg 720
caagaggcga ggggcggcga ctggtgagta cgccaaaaat tttgactagc ggaggctaga 780
aggagagaga tgggtgcgag agcgtcagta ttaagcgggg gagaattaga tcgcgatggg 840
aaaaaattcg gttaaggcca gggggaaaga aaaaatataa attaaaacat atagtatggg 900
caagcaggga gctagaacga ttcgcagtta atcctggcct gttagaaaca tcagaaggct 960
gtagacaaat actgggacag ctacaaccat cccttcagac aggatcagaa gaacttagat 1020
cattatataa tacagtagca accctctatt gtgtgcatca aaggatagag ataaaagaca 1080
ccaaggaagc tttagacaag atagaggaag agcaaaacaa aagtaagacc accgcacagc 1140
aagcggccgg ccgctgatct tcagacctgg aggaggagat atgagggaca attggagaag 1200
tgaattatat aaatataaag tagtaaaaat tgaaccatta ggagtagcac ccaccaaggc 1260
aaagagaaga gtggtgcaga gagaaaaaag agcagtggga ataggagctt tgttccttgg 1320
gttcttggga gcagcaggaa gcactatggg cgcagcgtca atgacgctga cggtacaggc 1380
cagacaatta ttgtctggta tagtgcagca gcagaacaat ttgctgaggg ctattgaggc 1440
gcaacagcat ctgttgcaac tcacagtctg gggcatcaag cagctccagg caagaatcct 1500
ggctgtggaa agatacctaa aggatcaaca gctcctgggg atttggggtt gctctggaaa 1560
actcatttgc accactgctg tgccttggaa tgctagttgg agtaataaat ctctggaaca 1620
gatttggaat cacacgacct ggatggagtg ggacagagaa attaacaatt acacaagctt 1680
aatacactcc ttaattgaag aatcgcaaaa ccagcaagaa aagaatgaac aagaattatt 1740
ggaattagat aaatgggcaa gtttgtggaa ttggtttaac ataacaaatt ggctgtggta 1800
tataaaatta ttcataatga tagtaggagg cttggtaggt ttaagaatag tttttgctgt 1860
actttctata gtgaatagag ttaggcaggg atattcacca ttatcgtttc agacccacct 1920
cccaaccccg aggggacccg acaggcccga aggaatagaa gaagaaggtg gagagagaga 1980
cagagacaga tccattcgat tagtgaacgg atctcgacgg tatcgccttt aaaagaaaag 2040

```
gggggattgg ggggtacagt gcaggggaaa gaatagtaga cataatagca acagacatac   2100
aaactaaaga attacaaaaa caaattacaa aaattcaaaa ttttcgggtt tattacaggg   2160
acagcagaga tccagtttat cgataagctt gggagttccg cgttacataa cttacggtaa   2220
atggcccgcc tggctgaccg cccaacgacc cccgcccatt gacgtcaata atgacgtatg   2280
ttcccatagt aacgccaata gggactttcc attgacgtca atgggtggag tatttacggt   2340
aaactgccca cttggcagta catcaagtgt atcatatgcc aagtacgccc cctattgacg   2400
tcaatgacgg taaatggccc gcctggcatt atgcccagta catgacctta tgggactttc   2460
ctacttggca gtacatctac gtattagtca tcgctattac catggtgatg cggttttggc   2520
agtacatcaa tgggcgtgga tagcggtttg actcacgggg atttccaagt ctccacccca   2580
ttgacgtcaa tgggagtttg ttttggcacc aaaatcaacg ggactttcca aaatgtcgta   2640
acaactccgc cccattgacg caaatgggcg gtaggcgtgt acggtgggag gtctatataa   2700
gcagagctcg tttagtgaac cgtcagatcg cctggagacg ccatccacgc tgttttgacc   2760
tccatagaag acaccgactc tactagagga tctaccggtc gccaccatgg tgagcaaggg   2820
cgaggaggtc atcaaagagt tcatgcgctt caaggtgcgc atggagggct ccatgaacgg   2880
ccacgagttc gagatcgagg gcgagggcga gggccgcccc tacgagggca cccagaccgc   2940
caagctgaag gtgaccaagg gcggccccct gcccttcgcc tgggacatcc tgtcccccca   3000
gttcatgtac ggctccaagg cgtacgtgaa gcaccccgcc gacatccccg attacaagaa   3060
gctgtccttc cccgagggct tcaagtggga gcgcgtgatg aacttcgagg acggcggtct   3120
ggtgaccgtg acccaggact cctccctgca ggacggcacg ctgatctaca aggtgaagat   3180
gcgcggcacc aacttccccc ccgacggccc cgtaatgcag aagaagacca tgggctggga   3240
ggcctccacc gagcgcctgt accccccgcga cggcgtgctg aagggcgaga tccaccaggc   3300
cctgaagctg aaggacggcg gccactacct ggtggagttc aagaccatct acatggccaa   3360
gaagcccgtg caactgcccg gctactacta cgtggacacc aagctggaca tcacctccca   3420
caacgaggac tacaccatcg tggaacagta cgagcgctcc gagggccgcc accacctgtt   3480
cctggggcat ggcaccggca gcaccggcag cggcagctcc ggcaccgcct cctccgagga   3540
caacaacatg gccgtcatca aagagttcat gcgcttcaag gtgcgcatgg agggctccat   3600
gaacggccac gagttcgaga tcgagggcga gggcgagggc cgcccctacg agggcaccca   3660
gaccgccaag ctgaaggtga ccaagggcgg cccccctgccc ttcgcctggg acatcctgtc   3720
cccccagttc atgtacggct ccaaggcgta cgtgaagcac cccgccgaca tccccgatta   3780
caagaagctg tccttccccg agggcttcaa gtgggagcgc gtgatgaact tcgaggacgg   3840
cggtctggtg accgtgaccc aggactcctc cctgcaggac ggcacgctga tctacaaggt   3900
gaagatgcgc ggcaccaact tcccccccga cggccccgta atgcagaaga agaccatggg   3960
ctgggaggcc tccaccgagc gcctgtaccc ccgcgacggc gtgctgaagg gcgagatcca   4020
ccaggccctg aagctgaagg acggcggcca ctacctggtg gagttcaaga ccatctacat   4080
ggccaagaag cccgtgcaac tgcccggcta ctactacgtg gacaccaagc tggacatcac   4140
ctcccacaac gaggactaca ccatcgtgga acagtacgag cgctccgagg gccgccacca   4200
cctgttcctg tacggcatgg acgagctgta caagtccgga ctcagatctc gagctcaagc   4260
ttcgaattct gcagtcgacg gtaccgcggg cccgggatcc accggatcta gataactgat   4320
cataattcta ccgggtaggg gaggcgcttt tcccaaggca gtctggagca tgcgctttag   4380
```

-continued

```
cagccccgct gggcacttgg cgctacacaa gtggcctctg gcctcgcaca cattccacat   4440
ccaccggtag gcgccaaccg gctccgttct ttggtggccc cttcgcgcca ccttctactc   4500
ctcccctagt caggaagttc ccccccgccc cgcagctcgc gtcgtgcagg acgtgacaaa   4560
tggaagtagc acgtctcact agtctcgtgc agatggacag caccgctgag caatggaagc   4620
gggtaggcct ttggggcagc ggccaatagc agctttgctc cttcgctttc tgggctcaga   4680
ggctgggaag gggtgggtcc gggggcgggc tcaggggcgg gctcaggggc ggggcgggcg   4740
cccgaaggtc ctccggaggc ccggcattct gcacgcttca aaagcgcacg tctgccgcgc   4800
tgttctcctc ttcctcatct ccgggccttt cgacctgcag cccaagctta ccatgaccga   4860
gtacaagccc acggtgcgcc tcgccacccg cgacgacgtc cccagggccg tacgcaccct   4920
cgccgccgcg ttcgccgact accccgccac gcgccacacc gtcgatccgg accgccacat   4980
cgagcgggtc accgagctgc aagaactctt cctcacgcgc gtcgggctcg acatcggcaa   5040
ggtgtgggtc gcggacgacg gcgccgcggt ggcggtctgg accacgccgg agagcgtcga   5100
agcgggggcg gtgttcgccg agatcggccc gcgcatggcc gagttgagcg gttcccggct   5160
ggccgcgcag caacagatgg aaggcctcct ggcgccgcac cggcccaagg agcccgcgtg   5220
gttcctggcc accgtcggcg tctcgcccga ccaccagggc aagggtctgg gcagcgccgt   5280
cgtgctcccc ggagtggagg cggccgagcg cgccggggtg cccgccttcc tggagacctc   5340
cgcgccccgc aacctcccct tctacgagcg gctcggcttc accgtcaccg ccgacgtcga   5400
ggtgcccgaa ggaccgcgca cctggtgcat gacccgcaag cccggtgcct gaccgcgtct   5460
ggaacaatca acctctggat tacaaaattt gtgaaagatt gactggtatt cttaactatg   5520
ttgctccttt tacgctatgt ggatacgctg ctttaatgcc tttgtatcat gctattgctt   5580
cccgtatggc tttcattttc tcctccttgt ataaatcctg gttgctgtct ctttatgagg   5640
agttgtggcc cgttgtcagg caacgtggcg tggtgtgcac tgtgtttgct gacgcaaccc   5700
ccactggttg gggcattgcc accacctgtc agctcctttc cgggactttc gctttccccc   5760
tccctattgc cacggcggaa ctcatcgccg cctgccttgc ccgctgctgg acaggggctc   5820
ggctgttggg cactgacaat tccgtggtgt tgtcggggaa gctgacgtcc tttccatggc   5880
tgctcgcctg tgttgccacc tggattctgc gcgggacgtc cttctgctac gtcccttcgg   5940
ccctcaatcc agcggacctt ccttcccgcg gcctgctgcc ggctctgcgg cctcttccgc   6000
gtcttcgcct tcgccctcag acgagtcgga tctccctttg ggccgcctcc ccgcctggaa   6060
ttaattctgc agtcgagacc tagaaaaaca tggagcaatc acaagtagca atacagcagc   6120
taccaatgct gattgtgcct ggctagaagc acaagaggag gaggaggtgg gttttccagt   6180
cacacctcag gtacctttaa gaccaatgac ttacaaggca gctgtagatc ttagccactt   6240
tttaaaagaa aagaggggac tggaagggct aattcactcc caacgaagac aagatatcct   6300
tgatctgtgg atctaccaca cacaaggcta cttccctgat tagcagaact acacaccagg   6360
gccaggggtc agatatccac tgacctttgg atggtgctac aagctagtac cagttgagcc   6420
agataaggta gaagaggcca ataaaggaga gaacaccagc ttgttacacc ctgtgagcct   6480
gcatgggatg gatgacccgg agagagaagt gttagagtgg aggtttgaca gccgcctagc   6540
atttcatcac gtggcccgag agctgcatcc ggagtacttc aagaactgct gatatcgagc   6600
ttgctacaag ggactttccg ctggggactt tccagggagg cgtggcctgg gcgggactgg   6660
ggagtggcga gccctcagat cctgcatata agcagctgct ttttgcctgt actgggtctc   6720
tctggttaga ccagatctga gcctgggagc tctctggcta actagggaac ccactgctta   6780
```

```
agcctcaata aagcttgcct tgagtgcttc aagtagtgtg tgcccgtctg ttgtgtgact   6840
ctggtaacta gagatccctc agaccctttt agtcagtgtg gaaaatctct agcagtagta   6900
gttcatgtca tcttattatt cagtatttat aacttgcaaa gaaatgaata tcagagagtg   6960
agaggccttg acattgctag cgttttaccg tcgacctcta gctagagctt ggcgtaatca   7020
tggtcatagc tgtttcctgt gtgaaattgt tatccgctca caattccaca caacatacga   7080
gccggaagca taaagtgtaa agcctggggt gcctaatgag tgagctaact cacattaatt   7140
gcgttgcgct cactgcccgc tttccagtcg ggaaacctgt cgtgccagct gcattaatga   7200
atcggccaac gcgcggggag aggcggtttg cgtattgggc gctcttccgc ttcctcgctc   7260
actgactcgc tgcgctcggt cgttcggctg cggcgagcgg tatcagctca ctcaaaggcg   7320
gtaatacggt tatccacaga atcaggggat aacgcaggaa agaacatgtg agcaaaaggc   7380
cagcaaaagg ccaggaaccg taaaaaggcc gcgttgctgg cgtttttcca taggctccgc   7440
ccccctgacg agcatcacaa aaatcgacgc tcaagtcaga ggtggcgaaa cccgacagga   7500
ctataaagat accaggcgtt tccccctgga agctccctcg tgcgctctcc tgttccgacc   7560
ctgccgctta ccggatacct gtccgccttt ctcccttcgg gaagcgtggc gctttctcat   7620
agctcacgct gtaggtatct cagttcggtg taggtcgttc gctccaagct gggctgtgtg   7680
cacgaacccc ccgttcagcc cgaccgctgc gccttatccg gtaactatcg tcttgagtcc   7740
aacccggtaa gacacgactt atcgccactg gcagcagcca ctggtaacag gattagcaga   7800
gcgaggtatg taggcggtgc tacagagttc ttgaagtggt ggcctaacta cggctacact   7860
agaagaacag tatttggtat ctgcgctctg ctgaagccag ttaccttcgg aaaaagagtt   7920
ggtagctctt gatccggcaa acaaaccacc gctggtagcg gtggtttttt tgtttgcaag   7980
cagcagatta cgcgcagaaa aaaaggatct caagaagatc ctttgatctt ttctacgggg   8040
tctgacgctc agtggaacga aaactcacgt taagggattt tggtcatgag attatcaaaa   8100
aggatcttca cctagatcct tttaaattaa aaatgaagtt ttaaatcaat ctaaagtata   8160
tatgagtaaa cttggtctga cagttaccaa tgcttaatca gtgaggcacc tatctcagcg   8220
atctgtctat ttcgttcatc catagttgcc tgactccccg tcgtgtagat aactacgata   8280
cgggagggct taccatctgg ccccagtgct gcaatgatac cgcgagaccc acgctcaccg   8340
gctccagatt tatcagcaat aaaccagcca gccggaaggg ccgagcgcag aagtggtcct   8400
gcaactttat ccgcctccat ccagtctatt aattgttgcc gggaagctag agtaagtagt   8460
tcgccagtta atagtttgcg caacgttgtt gccattgcta caggcatcgt ggtgtcacgc   8520
tcgtcgtttg gtatggcttc attcagctcc ggttcccaac gatcaaggcg agttacatga   8580
tcccccatgt tgtgcaaaaa agcggttagc tccttcggtc ctccgatcgt tgtcagaagt   8640
aagttggccg cagtgttatc actcatggtt atggcagcac tgcataattc tcttactgtc   8700
atgccatccg taagatgctt ttctgtgact ggtgagtact caaccaagtc attctgagaa   8760
tagtgtatgc ggcgaccgag ttgctcttgc ccggcgtcaa tacgggataa taccgcgcca   8820
catagcagaa ctttaaaagt gctcatcatt ggaaaacgtt cttcggggcg aaaactctca   8880
aggatcttac cgctgttgag atccagttcg atgtaaccca ctcgtgcacc caactgatct   8940
tcagcatctt ttactttcac cagcgtttct gggtgagcaa aaacaggaag gcaaaatgcc   9000
gcaaaaaagg gaataagggc gacacggaaa tgttgaatac tcatactctt cctttttcaa   9060
tattattgaa gcatttatca gggttattgt ctcatgagcg gatacatatt tgaatgtatt   9120
```

```
tagaaaaata aacaaatagg ggttccgcgc acatttcccc gaaaagtgcc acctgacgtc   9180

gacggatcgg gagatcaact tgtttattgc agcttataat ggttacaaat aaagcaatag   9240

catcacaaat ttcacaaata aagcattttt ttcactgcat tctagttgtg gtttgtccaa   9300

actcatcaat gtatcttatc atgtctggat caactggata actcaagcta accaaaatca   9360

tcccaaactt cccaccccat accctattac cactgccaat tacctgtggt ttcatttact   9420

ctaaacctgt gattcctctg aattattttc attttaaaga aattgtattt gttaaatatg   9480

tactacaaac ttagtagt                                                 9498
```

```
<210> SEQ ID NO 29
<211> LENGTH: 12195
<212> TYPE: DNA
<213> ORGANISM: Artificial sequence
<220> FEATURE:
<223> OTHER INFORMATION: pLVX-tdTomato-C1-HA hNFAT3 WT

<400> SEQUENCE: 29

ggatccaccg gatctagata actgatcata attctaccgg gtaggggagg cgcttttccc     60

aaggcagtct ggagcatgcg ctttagcagc cccgctgggc acttggcgct acacaagtgg    120

cctctggcct cgcacacatt ccacatccac cggtaggcgc caaccggctc cgttctttgg    180

tggccccttc gcgccacctt ctactcctcc cctagtcagg aagttccccc ccgccccgca    240

gctcgcgtcg tgcaggacgt gacaaatgga agtagcacgt ctcactagtc tcgtgcagat    300

ggacagcacc gctgagcaat ggaagcgggt aggcctttgg ggcagcggcc aatagcagct    360

ttgctccttc gctttctggg ctcagaggct gggaaggggt gggtccgggg gcgggctcag    420

gggcgggctc aggggcgggg cgggcgcccg aaggtcctcc ggaggcccgg cattctgcac    480

gcttcaaaag cgcacgtctg ccgcgctgtt ctcctcttcc tcatctccgg gcctttcgac    540

ctgcagccca agcttaccat gaccgagtac aagcccacgg tgcgcctcgc cacccgcgac    600

gacgtcccca gggccgtacg caccctcgcc gccgcgttcg ccgactaccc cgccacgcgc    660

cacaccgtcg atccggaccg ccacatcgag cgggtcaccg agctgcaaga actcttcctc    720

acgcgcgtcg ggctcgacat cggcaaggtg tgggtcgcgg acgacggcgc cgcggtggcg    780

gtctggacca cgccggagag cgtcgaagcg ggggcggtgt tcgccgagat cggcccgcgc    840

atggccgagt tgagcggttc ccggctggcc gcgcagcaac agatggaagg cctcctggcg    900

ccgcaccggc ccaaggagcc cgcgtggttc ctggccaccg tcggcgtctc gcccgaccac    960

cagggcaagg gtctgggcag cgccgtcgtg ctccccggag tggaggcggc cgagcgcgcc   1020

ggggtgcccg ccttcctgga gacctccgcg ccccgcaacc tccccttcta cgagcggctc   1080

ggcttcaccg tcaccgccga cgtcgaggtg cccgaaggac cgcgcacctg gtgcatgacc   1140

cgcaagcccg gtgcctgacc gcgtctggaa caatcaacct ctggattaca aaatttgtga   1200

aagattgact ggtattctta actatgttgc tccttttacg ctatgtggat acgctgcttt   1260

aatgcctttg tatcatgcta ttgcttcccg tatggctttc attttctcct ccttgtataa   1320

atcctggttg ctgtctcttt atgaggagtt gtggcccgtt gtcaggcaac gtggcgtggt   1380

gtgcactgtg tttgctgacg caacccccac tggttggggc attgccacca cctgtcagct   1440

cctttccggg actttcgctt tccccctccc tattgccacg gcggaactca tcgccgcctg   1500

ccttgcccgc tgctggacag gggctcggct gttgggcact gacaattccg tggtgttgtc   1560

ggggaagctg acgtcctttc catggctgct cgcctgtgtt gccacctgga ttctgcgcgg   1620

gacgtccttc tgctacgtcc cttcggccct caatccagcg gaccttcctt cccgcggcct   1680
```

-continued

```
gctgccggct ctgcggcctc ttccgcgtct tcgccttcgc cctcagacga gtcggatctc   1740
cctttgggcc gcctccccgc ctggaattaa ttctgcagtc gagacctaga aaaacatgga   1800
gcaatcacaa gtagcaatac agcagctacc aatgctgatt gtgcctggct agaagcacaa   1860
gaggaggagg aggtgggttt tccagtcaca cctcaggtac ctttaagacc aatgacttac   1920
aaggcagctg tagatcttag ccactttta aaagaaaaga ggggactgga agggctaatt   1980
cactcccaac gaagacaaga tatccttgat ctgtggatct accacacaca aggctacttc   2040
cctgattagc agaactacac accagggcca ggggtcagat atccactgac ctttggatgg   2100
tgctacaagc tagtaccagt tgagccagat aaggtagaag aggccaataa aggagagaac   2160
accagcttgt tacaccctgt gagcctgcat gggatggatg acccggagag agaagtgtta   2220
gagtggaggt ttgacagccg cctagcattt catcacgtgg cccgagagct gcatccggag   2280
tacttcaaga actgctgata tcgagcttgc tacaagggac tttccgctgg ggactttcca   2340
gggaggcgtg gcctgggcgg gactggggag tggcgagccc tcagatcctg catataagca   2400
gctgcttttt gcctgtactg ggtctctctg gttagaccag atctgagcct gggagctctc   2460
tggctaacta gggaacccac tgcttaagcc tcaataaagc ttgccttgag tgcttcaagt   2520
agtgtgtgcc cgtctgttgt gtgactctgg taactagaga tccctcagac ccttttagtc   2580
agtgtggaaa atctctagca gtagtagttc atgtcatctt attattcagt atttataact   2640
tgcaaagaaa tgaatatcag agagtgagag gccttgacat tgctagcgtt ttaccgtcga   2700
cctctagcta gagcttggcg taatcatggt catagctgtt tcctgtgtga aattgttatc   2760
cgctcacaat tccacacaac atacgagccg gaagcataaa gtgtaaagcc tggggtgcct   2820
aatgagtgag ctaactcaca ttaattgcgt tgcgctcact gcccgctttc cagtcgggaa   2880
acctgtcgtg ccagctgcat taatgaatcg gccaacgcgc ggggagaggc ggtttgcgta   2940
ttgggcgctc ttccgcttcc tcgctcactg actcgctgcg ctcggtcgtt cggctgcggc   3000
gagcggtatc agctcactca aaggcggtaa tacggttatc cacagaatca ggggataacg   3060
caggaaagaa catgtgagca aaaggccagc aaaaggccag gaaccgtaaa aaggccgcgt   3120
tgctggcgtt tttccatagg ctccgccccc ctgacgagca tcacaaaaat cgacgctcaa   3180
gtcagaggtg gcgaaacccg acaggactat aaagatacca ggcgtttccc cctggaagct   3240
ccctcgtgcg ctctcctgtt ccgaccctgc cgcttaccgg atacctgtcc gcctttctcc   3300
cttcgggaag cgtggcgctt tctcatagct cacgctgtag gtatctcagt tcggtgtagg   3360
tcgttcgctc caagctgggc tgtgtgcacg aaccccccgt tcagcccgac cgctgcgcct   3420
tatccggtaa ctatcgtctt gagtccaacc cggtaagaca cgacttatcg ccactggcag   3480
cagccactgg taacaggatt agcagagcga ggtatgtagg cggtgctaca gagttcttga   3540
agtggtggcc taactacggc tacactagaa gaacagtatt tggtatctgc gctctgctga   3600
agccagttac cttcggaaaa agagttggta gctcttgatc cggcaaacaa accaccgctg   3660
gtagcggtgg tttttttgtt tgcaagcagc agattacgcg cagaaaaaaa ggatctcaag   3720
aagatccttt gatcttttct acggggtctg acgctcagtg gaacgaaaac tcacgttaag   3780
ggattttggt catgagatta tcaaaaagga tcttcaccta gatcctttta aattaaaaat   3840
gaagttttaa atcaatctaa agtatatatg agtaaacttg gtctgacagt taccaatgct   3900
taatcagtga ggcacctatc tcagcgatct gtctatttcg ttcatccata gttgcctgac   3960
tccccgtcgt gtagataact acgatacggg agggcttacc atctggcccc agtgctgcaa   4020
```

-continued tgataccgcg agacccacgc tcaccggctc cagatttatc agcaataaac cagccagccg 4080
gaagggccga gcgcagaagt ggtcctgcaa ctttatccgc ctccatccag tctattaatt 4140
gttgccggga agctagagta agtagttcgc cagttaatag tttgcgcaac gttgttgcca 4200
ttgctacagg catcgtggtg tcacgctcgt cgtttggtat ggcttcattc agctccggtt 4260
cccaacgatc aaggcgagtt acatgatccc ccatgttgtg caaaaaagcg gttagctcct 4320
tcggtcctcc gatcgttgtc agaagtaagt tggccgcagt gttatcactc atggttatgg 4380
cagcactgca taattctctt actgtcatgc catccgtaag atgcttttct gtgactggtg 4440
agtactcaac caagtcattc tgagaatagt gtatgcggcg accgagttgc tcttgcccgg 4500
cgtcaatacg ggataatacc gcgccacata gcagaacttt aaaagtgctc atcattggaa 4560
aacgttcttc ggggcgaaaa ctctcaagga tcttaccgct gttgagatcc agttcgatgt 4620
aacccactcg tgcacccaac tgatcttcag catcttttac tttcaccagc gtttctgggt 4680
gagcaaaaac aggaaggcaa aatgccgcaa aaaagggaat aagggcgaca cggaaatgtt 4740
gaatactcat actcttcctt tttcaatatt attgaagcat ttatcagggt tattgtctca 4800
tgagcggata catatttgaa tgtatttaga aaaataaaca aataggggtt ccgcgcacat 4860
ttccccgaaa agtgccacct gacgtcgacg gatcgggaga tcaacttgtt tattgcagct 4920
tataatggtt acaaataaag caatagcatc acaaatttca caaataaagc atttttttca 4980
ctgcattcta gttgtggttt gtccaaactc atcaatgtat cttatcatgt ctggatcaac 5040
tggataactc aagctaacca aaatcatccc aaacttccca ccccataccc tattaccact 5100
gccaattacc tgtggtttca tttactctaa acctgtgatt cctctgaatt attttcattt 5160
taaagaaatt gtatttgtta aatatgtact acaaacttag tagttggaag ggctaattca 5220
ctcccaaaga agacaagata tccttgatct gtggatctac cacacacaag gctacttccc 5280
tgattagcag aactacacac cagggccagg ggtcagatat ccactgacct ttggatggtg 5340
ctacaagcta gtaccagttg agccagataa ggtagaagag gccaataaag gagagaacac 5400
cagcttgtta caccctgtga gcctgcatgg gatggatgac ccggagagag aagtgttaga 5460
gtggaggttt gacagccgcc tagcatttca tcacgtggcc cgagagctgc atccggagta 5520
cttcaagaac tgctgatatc gagcttgcta caagggactt tccgctgggg actttccagg 5580
gaggcgtggc ctgggcggga ctggggagtg gcgagccctc agatcctgca tataagcagc 5640
tgctttttgc ctgtactggg tctctctggt tagaccagat ctgagcctgg gagctctctg 5700
gctaactagg gaacccactg cttaagcctc aataaagctt gccttgagtg cttcaagtag 5760
tgtgtgcccg tctgttgtgt gactctggta actagagatc cctcagaccc ttttagtcag 5820
tgtggaaaat ctctagcagt ggcgcccgaa cagggacttg aaagcgaaag ggaaaccaga 5880
ggagctctct cgacgcagga ctcggcttgc tgaagcgcgc acggcaagag gcgaggggcg 5940
gcgactggtg agtacgccaa aaattttgac tagcggaggc tagaaggaga gagatgggtg 6000
cgagagcgtc agtattaagc gggggagaat tagatcgcga tgggaaaaaa ttcggttaag 6060
gccaggggga aagaaaaaat ataaattaaa acatatagta tgggcaagca gggagctaga 6120
acgattcgca gttaatcctg gcctgttaga aacatcagaa ggctgtagac aaatactggg 6180
acagctacaa ccatcccttc agacaggatc agaagaactt agatcattat ataatacagt 6240
agcaaccctc tattgtgtgc atcaaaggat agagataaaa gacaccaagg aagctttaga 6300
caagatagag gaagagcaaa acaaaagtaa gaccaccgca cagcaagcgg ccggccgctg 6360
atcttcagac ctggaggagg agatatgagg gacaattgga gaagtgaatt atataaatat 6420

```
aaagtagtaa aaattgaacc attaggagta gcacccacca aggcaaagag aagagtggtg   6480
cagagagaaa aaagagcagt gggaatagga gctttgttcc ttgggttctt gggagcagca   6540
ggaagcacta tgggcgcagc gtcaatgacg ctgacggtac aggccagaca attattgtct   6600
ggtatagtgc agcagcagaa caatttgctg agggctattg aggcgcaaca gcatctgttg   6660
caactcacag tctggggcat caagcagctc caggcaagaa tcctggctgt ggaaagatac   6720
ctaaaggatc aacagctcct ggggatttgg ggttgctctg gaaaactcat ttgcaccact   6780
gctgtgcctt ggaatgctag ttggagtaat aaatctctgg aacagatttg gaatcacacg   6840
acctggatgg agtgggacag agaaattaac aattacacaa gcttaataca ctccttaatt   6900
gaagaatcgc aaaaccagca agaaaagaat gaacaagaat tattggaatt agataaatgg   6960
gcaagtttgt ggaattggtt taacataaca aattggctgt ggtatataaa attattcata   7020
atgatagtag gaggcttggt aggtttaaga atagtttttg ctgtactttc tatagtgaat   7080
agagttaggc agggatattc accattatcg tttcagaccc acctcccaac cccgagggga   7140
cccgacaggc ccgaaggaat agaagaagaa ggtggagaga gagacagaga cagatccatt   7200
cgattagtga acggatctcg acggtatcgc ctttaaaaga aaagggggga ttggggggta   7260
cagtgcaggg gaaagaatag tagacataat agcaacagac atacaaacta aagaattaca   7320
aaaacaaatt acaaaaattc aaaattttcg ggtttattac agggacagca gagatccagt   7380
ttatcgataa gcttgggagt tccgcgttac ataacttacg gtaaatggcc cgcctggctg   7440
accgcccaac gacccccgcc cattgacgtc aataatgacg tatgttccca tagtaacgcc   7500
aatagggact ttccattgac gtcaatgggt ggagtattta cggtaaactg cccacttggc   7560
agtacatcaa gtgtatcata tgccaagtac gccccctatt gacgtcaatg acggtaaatg   7620
gcccgcctgg cattatgccc agtacatgac cttatgggac tttcctactt ggcagtacat   7680
ctacgtatta gtcatcgcta ttaccatggt gatgcggttt tggcagtaca tcaatgggcg   7740
tggatagcgg tttgactcac ggggatttcc aagtctccac cccattgacg tcaatgggag   7800
tttgttttgg caccaaaatc aacgggactt tccaaaatgt cgtaacaact ccgccccatt   7860
gacgcaaatg ggcggtaggc gtgtacggtg ggaggtctat ataagcagag ctcgtttagt   7920
gaaccgtcag atcgcctgga gacgccatcc acgctgtttt gacctccata gaagacaccg   7980
actctactag aggatctacc ggtcgccacc atggtgagca agggcgagga ggtcatcaaa   8040
gagttcatgc gcttcaaggt gcgcatggag ggctccatga acggccacga gttcgagatc   8100
gagggcgagg gcgagggccg cccctacgag ggcacccaga ccgccaagct gaaggtgacc   8160
aagggcggcc ccctgccctt cgcctgggac atcctgtccc cccagttcat gtacggctcc   8220
aaggcgtacg tgaagcaccc cgccgacatc cccgattaca agaagctgtc cttccccgag   8280
ggcttcaagt gggagcgcgt gatgaacttc gaggacggcg gtctggtgac cgtgacccag   8340
gactcctccc tgcaggacgg cacgctgatc tacaaggtga agatgcgcgg caccaacttc   8400
ccccccgacg gccccgtaat gcagaagaag accatgggct gggaggcctc caccgagcgc   8460
ctgtaccccc gcgacggcgt gctgaagggc gagatccacc aggccctgaa gctgaaggac   8520
ggcggccact acctggtgga gttcaagacc atctacatgg ccaagaagcc cgtgcaactg   8580
cccggctact actacgtgga caccaagctg gacatcacct cccacaacga ggactacacc   8640
atcgtggaac agtacgagcg ctccgagggc cgccaccacc tgttcctggg gcatggcacc   8700
ggcagcaccg gcagcggcag ctccggcacc gcctcctccg aggacaacaa catggccgtc   8760
```

```
atcaaagagt tcatgcgctt caaggtgcgc atggagggct ccatgaacgg ccacgagttc   8820
gagatcgagg gcgagggcga gggccgcccc tacgagggca cccagaccgc caagctgaag   8880
gtgaccaagg gcggccccct gcccttcgcc tgggacatcc tgtcccccca gttcatgtac   8940
ggctccaagg cgtacgtgaa gcaccccgcc gacatccccg attacaagaa gctgtccttc   9000
cccgagggct tcaagtggga gcgcgtgatg aacttcgagg acggcggtct ggtgaccgtg   9060
acccaggact cctccctgca ggacggcacg ctgatctaca aggtgaagat gcgcggcacc   9120
aacttccccc ccgacggccc cgtaatgcag aagaagacca tgggctggga ggcctccacc   9180
gagcgcctgt accccgcga cggcgtgctg aagggcgaga tccaccaggc cctgaagctg   9240
aaggacggcg gccactacct ggtggagttc aagaccatct acatggccaa gaagcccgtg   9300
caactgcccg gctactacta cgtggacacc aagctggaca tcacctccca caacgaggac   9360
tacaccatcg tggaacagta cgagcgctcc gagggccgcc accacctgtt cctgtacggc   9420
atggacgagc tgtacaagtc cggactcaga tctcgagtgg cctatccata tgacgtacca   9480
gattatgcgg gggcggccag ctgcgaggat gaggagctgg aatttaagct ggtgttcggg   9540
gaggaaaagg aggccccccc gctgggcgcg gggggattgg gggaagaact ggactcagag   9600
gatgccccgc catgctgccg tctggccttg ggagagcccc ctccctatgg cgctgcacct   9660
atcggtattc cccgacctcc accccctcgg cctggcatgc attcgccacc gccgcgacca   9720
gccccctcac ctggcacctg ggagagccag cccgccaggt cggtgaggct gggaggacca   9780
ggagggggtg ctgggggtgc tgggggtggc cgtgttctcg agtgtcccag catccgcatc   9840
acctccatct ctcccacgcc ggagccgcca gcagcgctgg aggacaaccc tgatgcctgg   9900
ggggacggct ctcctagaga ttaccccca ccagaaggct ttgggggcta cagagaagca   9960
ggggcccagg gtgggggggc cttcttcagc ccaagccctg gcagcagcag cctgtcctcg  10020
tggagcttct tctccgatgc ctctgacgag gcagccctgt atgcagcctg cgacgaggtg  10080
gagtctgagc taaatgaggc ggcctcccgc tttggcctgg gctccccgct gccctcgccc  10140
cgggcctccc ctcggccatg gaccccgaa gatccctgga gcctgtatgg tccaagcccc  10200
ggaggccgag ggccagagga tagctggcta ctcctcagtg ctcctgggcc caccccagcc  10260
tccccgcggc ctgcctctcc atgtggcaag cggcgctatt ccagctcggg aaccccatct  10320
tcagcctccc cagctctgtc ccgccgtggc agcctggggg aagaggggtc tgagccacct  10380
ccaccacccc cattgcctct ggcccgggac ccgggctccc ctggtccctt tgactatgtg  10440
ggggccccac cagctgagag catccctcag aagacacggc ggacttccag cgagcaggca  10500
gtggctctgc ctcggtctga ggagcctgcc tcatgcaatg ggaagctgcc cttgggagca  10560
gaggagtctg tggctcctcc aggaggttcc cggaaggagg tggctggcat ggactacctg  10620
gcagtgccct ccccactcgc ttggtccaag gcccggattg gggacacag ccctatcttc  10680
aggacctctg ccctaccccc actggactgg cctctgccca gccaatatga gcagctggag  10740
ctgaggatcg aggtacagcc tagagcccac caccgggccc actatgagac agaaggcagc  10800
cgtggagctg tcaaagctgc ccctggcggt caccccgtag tcaagctcct aggctacagt  10860
gagaagccac tgaccctaca gatgttcatc ggcactgcag atgaaaggaa cctgcggcct  10920
catgccttct atcaggtgca ccgtatcaca ggcaagatgg tggccacggc cagctatgaa  10980
gccgtagtca gtggcaccaa ggtgttggag atgactctgc tgcctgagaa caacatggcg  11040
gccaacattg actgcgcggg aatcctgaag cttcggaatt cagacattga gcttcggaag  11100
ggtgagacgg acatcgggcg caaaaacaca cgtgtacggc tggtgttccg ggtacacgtg  11160
```

```
ccccagggcg gcgggaaggt cgtctcagta caggcagcat cggtgcccat cgagtgctcc  11220

cagcgctcag cccaggagct gccccaggtg gaggcctaca gccccagtgc ctgctctgtg  11280

agaggaggcg aggaactggt actgaccggc tccaacttcc tgccagactc caaggtggtg  11340

ttcattgaga ggggtcctga tgggaagctg caatgggagg aggaggccac agtgaaccga  11400

ctgcagagca acgaggtgac gctgaccctg actgtccccg agtacagcaa caagagggtt  11460

tcccggccag tccaggtcta cttttatgtc tccaatgggc ggaggaaacg cagtcctacc  11520

cagagtttca ggtttctgcc tgtgatctgc aaagaggagc ccctaccgga ctcatctctg  11580

cggggtttcc cttcagcatc ggcaaccccc tttggcactg acatggactt ctcaccaccc  11640

aggcccccct accctcccta tccccatgaa gaccctgctt gcgaaactcc ttacctatca  11700

gaaggcttcg gctatggcat gccccctctg tacccccaga cggggccccc accatcctac  11760

agaccgggcc tgcggatgtt ccctgagact aggggtacca caggttgtgc ccaaccacct  11820

gcagtttcct tccttccccg ccccttccct agtgacccgt atggagggcg gggctcctct  11880

ttcccccctgg ggctgccatt ctctccgcca gccccctttc ggccgcctcc tcttcctgca  11940

tccccaccgc ttgaaggccc cttcccttcc cagagtgatg tgcatcccct acctgctgag  12000

ggatacaata aggtagggcc aggctatggc cctggggagg gggctccgga gcaggagaaa  12060

tccaggggtg gctacagcag cggcttccga gacagtgtcc ctatccaggg tatcacgctg  12120

gaggaagtga gtgagatcat tggccgagac ctgagtggct tccctgcacc tcctggagaa  12180

gagcctcctg cctga                                                  12195
```

<210> SEQ ID NO 30
<211> LENGTH: 11940
<212> TYPE: DNA
<213> ORGANISM: Artificial sequence
<220> FEATURE:
<223> OTHER INFORMATION: pLVX-tdTomato-C1-HA hNFAT3-85C

<400> SEQUENCE: 30

```
ggatccaccg gatctagata actgatcata attctaccgg gtaggggagg cgcttttccc     60

aaggcagtct ggagcatgcg ctttagcagc cccgctgggc acttggcgct acacaagtgg    120

cctctggcct cgcacacatt ccacatccac cggtaggcgc caaccggctc cgttctttgg    180

tggccccttc gcgccacctt ctactcctcc cctagtcagg aagttccccc ccgccccgca    240

gctcgcgtcg tgcaggacgt gacaaatgga agtagcacgt ctcactagtc tcgtgcagat    300

ggacagcacc gctgagcaat ggaagcgggt aggcctttgg ggcagcggcc aatagcagct    360

ttgctccttc gctttctggg ctcagaggct gggaaggggt gggtccgggg gcgggctcag    420

gggcgggctc aggggcgggg cgggcgcccg aaggtcctcc ggaggcccgg cattctgcac    480

gcttcaaaag cgcacgtctg ccgcgctgtt ctcctcttcc tcatctccgg gcctttcgac    540

ctgcagccca agcttaccat gaccgagtac aagcccacgg tgcgcctcgc cacccgcgac    600

gacgtcccca gggccgtacg caccctcgcc gccgcgttcg ccgactaccc cgccacgcgc    660

cacaccgtcg atccggaccg ccacatcgag cgggtcaccg agctgcaaga actcttcctc    720

acgcgcgtcg ggctcgacat cggcaaggtg tgggtcgcgg acgacggcgc cgcggtggcg    780

gtctggacca cgccggagag cgtcgaagcg ggggcggtgt tcgccgagat cggcccgcgc    840

atggccgagt tgagcggttc ccggctggcc gcgcagcaac agatggaagg cctcctggcg    900

ccgcaccggc ccaaggagcc cgcgtggttc ctggccaccg tcggcgtctc gcccgaccac    960
```

-continued

```
cagggcaagg gtctgggcag cgccgtcgtg ctccccggag tggaggcggc cgagcgcgcc   1020
ggggtgcccg ccttcctgga gacctccgcg ccccgcaacc tccccttcta cgagcggctc   1080
ggcttcaccg tcaccgccga cgtcgaggtg cccgaaggac cgcgcacctg gtgcatgacc   1140
cgcaagcccg gtgcctgacc gcgtctggaa caatcaacct ctggattaca aaatttgtga   1200
aagattgact ggtattctta actatgttgc tccttttacg ctatgtggat acgctgcttt   1260
aatgcctttg tatcatgcta ttgcttcccg tatggctttc attttctcct ccttgtataa   1320
atcctggttg ctgtctcttt atgaggagtt gtggcccgtt gtcaggcaac gtggcgtggt   1380
gtgcactgtg tttgctgacg caacccccac tggttggggc attgccacca cctgtcagct   1440
cctttccggg actttcgctt tccccctccc tattgccacg gcggaactca tcgccgcctg   1500
ccttgcccgc tgctggacag gggctcggct gttgggcact gacaattccg tggtgttgtc   1560
ggggaagctg acgtcctttc catggctgct cgcctgtgtt gccacctgga ttctgcgcgg   1620
gacgtccttc tgctacgtcc cttcggccct caatccagcg gaccttcctt cccgcggcct   1680
gctgccggct ctgcggcctc ttccgcgtct tcgccttcgc cctcagacga gtcggatctc   1740
cctttgggcc gcctccccgc ctggaattaa ttctgcagtc gagacctaga aaaacatgga   1800
gcaatcacaa gtagcaatac agcagctacc aatgctgatt gtgcctggct agaagcacaa   1860
gaggaggagg aggtgggttt tccagtcaca cctcaggtac ctttaagacc aatgacttac   1920
aaggcagctg tagatcttag ccactttta aaagaaaaga ggggactgga agggctaatt    1980
cactcccaac gaagacaaga tatccttgat ctgtggatct accacacaca aggctacttc   2040
cctgattagc agaactacac accagggcca ggggtcagat atccactgac ctttggatgg   2100
tgctacaagc tagtaccagt tgagccagat aaggtagaag aggccaataa aggagagaac   2160
accagcttgt tacaccctgt gagcctgcat gggatggatg acccggagag agaagtgtta   2220
gagtggaggt ttgacagccg cctagcattt catcacgtgg cccgagagct gcatccggag   2280
tacttcaaga actgctgata tcgagcttgc tacaagggac tttccgctgg ggactttcca   2340
gggaggcgtg gcctgggcgg gactggggag tggcgagccc tcagatcctg catataagca   2400
gctgcttttt gcctgtactg ggtctctctg gttagaccag atctgagcct gggagctctc   2460
tggctaacta gggaacccac tgcttaagcc tcaataaagc ttgccttgag tgcttcaagt   2520
agtgtgtgcc cgtctgttgt gtgactctgg taactagaga tccctcagac ccttttagtc   2580
agtgtggaaa atctctagca gtagtagttc atgtcatctt attattcagt atttataact   2640
tgcaaagaaa tgaatatcag agagtgagag gccttgacat tgctagcgtt ttaccgtcga   2700
cctctagcta gagcttggcg taatcatggt catagctgtt tcctgtgtga aattgttatc   2760
cgctcacaat tccacacaac atacgagccg gaagcataaa gtgtaaagcc tggggtgcct   2820
aatgagtgag ctaactcaca ttaattgcgt tgcgctcact gcccgctttc cagtcgggaa   2880
acctgtcgtg ccagctgcat taatgaatcg gccaacgcgc ggggagaggc ggtttgcgta   2940
ttgggcgctc ttccgcttcc tcgctcactg actcgctgcg ctcggtcgtt cggctgcggc   3000
gagcggtatc agctcactca aaggcggtaa tacggttatc cacagaatca ggggataacg   3060
caggaaagaa catgtgagca aaaggccagc aaaaggccag gaaccgtaaa aaggccgcgt   3120
tgctggcgtt tttccatagg ctccgccccc ctgacgagca tcacaaaaat cgacgctcaa   3180
gtcagaggtg gcgaaacccg acaggactat aaagatacca ggcgtttccc cctggaagct   3240
ccctcgtgcg ctctcctgtt ccgaccctgc cgcttaccgg atacctgtcc gcctttctcc   3300
cttcgggaag cgtggcgctt tctcatagct cacgctgtag gtatctcagt tcggtgtagg   3360
```

-continued

```
tcgttcgctc caagctgggc tgtgtgcacg aaccccccgt tcagcccgac cgctgcgcct   3420
tatccggtaa ctatcgtctt gagtccaacc cggtaagaca cgacttatcg ccactggcag   3480
cagccactgg taacaggatt agcagagcga ggtatgtagg cggtgctaca gagttcttga   3540
agtggtggcc taactacggc tacactagaa gaacagtatt tggtatctgc gctctgctga   3600
agccagttac cttcggaaaa agagttggta gctcttgatc cggcaaacaa accaccgctg   3660
gtagcggtgg tttttttgtt tgcaagcagc agattacgcg cagaaaaaaa ggatctcaag   3720
aagatccttt gatcttttct acggggtctg acgctcagtg gaacgaaaac tcacgttaag   3780
ggattttggt catgagatta tcaaaaagga tcttcaccta gatcctttta aattaaaaat   3840
gaagttttaa atcaatctaa agtatatatg agtaaacttg gtctgacagt taccaatgct   3900
taatcagtga ggcacctatc tcagcgatct gtctatttcg ttcatccata gttgcctgac   3960
tccccgtcgt gtagataact acgatacggg agggcttacc atctggcccc agtgctgcaa   4020
tgataccgcg agacccacgc tcaccggctc cagatttatc agcaataaac cagccagccg   4080
gaagggccga gcgcagaagt ggtcctgcaa ctttatccgc ctccatccag tctattaatt   4140
gttgccggga agctagagta agtagttcgc cagttaatag tttgcgcaac gttgttgcca   4200
ttgctacagg catcgtggtg tcacgctcgt cgtttggtat ggcttcattc agctccggtt   4260
cccaacgatc aaggcgagtt acatgatccc ccatgttgtg caaaaaagcg gttagctcct   4320
tcggtcctcc gatcgttgtc agaagtaagt tggccgcagt gttatcactc atggttatgg   4380
cagcactgca taattctctt actgtcatgc catccgtaag atgcttttct gtgactggtg   4440
agtactcaac caagtcattc tgagaatagt gtatgcggcg accgagttgc tcttgcccgg   4500
cgtcaatacg ggataatacc gcgccacata gcagaacttt aaaagtgctc atcattggaa   4560
aacgttcttc ggggcgaaaa ctctcaagga tcttaccgct gttgagatcc agttcgatgt   4620
aacccactcg tgcacccaac tgatcttcag catcttttac tttcaccagc gtttctgggt   4680
gagcaaaaac aggaaggcaa aatgccgcaa aaaagggaat aagggcgaca cggaaatgtt   4740
gaatactcat actcttcctt tttcaatatt attgaagcat ttatcagggt tattgtctca   4800
tgagcggata catatttgaa tgtatttaga aaaataaaca aataggggtt ccgcgcacat   4860
ttccccgaaa agtgccacct gacgtcgacg gatcgggaga tcaacttgtt tattgcagct   4920
tataatggtt acaaataaag caatagcatc acaaatttca caaataaagc atttttttca   4980
ctgcattcta gttgtggttt gtccaaactc atcaatgtat cttatcatgt ctggatcaac   5040
tggataactc aagctaacca aaatcatccc aaacttccca ccccataccc tattaccact   5100
gccaattacc tgtggtttca tttactctaa acctgtgatt cctctgaatt attttcattt   5160
taaagaaatt gtatttgtta aatatgtact acaaacttag tagttggaag ggctaattca   5220
ctcccaaaga agacaagata tccttgatct gtggatctac cacacacaag gctacttccc   5280
tgattagcag aactacacac cagggccagg ggtcagatat ccactgacct ttggatggtg   5340
ctacaagcta gtaccagttg agccagataa ggtagaagag gccaataaag gagagaacac   5400
cagcttgtta caccctgtga gcctgcatgg gatggatgac ccggagagag aagtgttaga   5460
gtggaggttt gacagccgcc tagcatttca tcacgtggcc cgagagctgc atccggagta   5520
cttcaagaac tgctgatatc gagcttgcta caagggactt tccgctgggg actttccagg   5580
gaggcgtggc ctgggcggga ctggggagtg gcgagccctc agatcctgca tataagcagc   5640
tgctttttgc ctgtactggg tctctctggt tagaccagat ctgagcctgg gagctctctg   5700
```

```
gctaactagg gaacccactg cttaagcctc aataaagctt gccttgagtg cttcaagtag   5760
tgtgtgcccg tctgttgtgt gactctggta actagagatc cctcagaccc ttttagtcag   5820
tgtggaaaat ctctagcagt ggcgcccgaa cagggacttg aaagcgaaag ggaaaccaga   5880
ggagctctct cgacgcagga ctcggcttgc tgaagcgcgc acggcaagag gcgaggggcg   5940
gcgactggtg agtacgccaa aaattttgac tagcggaggc tagaaggaga gagatgggtg   6000
cgagagcgtc agtattaagc gggggagaat tagatcgcga tgggaaaaaa ttcggttaag   6060
gccaggggga aagaaaaaat ataaattaaa acatatagta tgggcaagca gggagctaga   6120
acgattcgca gttaatcctg gcctgttaga aacatcagaa ggctgtagac aaatactggg   6180
acagctacaa ccatcccttc agacaggatc agaagaactt agatcattat ataatacagt   6240
agcaaccctc tattgtgtgc atcaaaggat agagataaaa gacaccaagg aagctttaga   6300
caagatagag gaagagcaaa acaaaagtaa gaccaccgca cagcaagcgg ccggccgctg   6360
atcttcagac ctggaggagg agatatgagg gacaattgga gaagtgaatt atataaatat   6420
aaagtagtaa aaattgaacc attaggagta gcacccacca aggcaaagag aagagtggtg   6480
cagagagaaa aaagagcagt gggaatagga gctttgttcc ttgggttctt gggagcagca   6540
ggaagcacta tgggcgcagc gtcaatgacg ctgacggtac aggccagaca attattgtct   6600
ggtatagtgc agcagcagaa caatttgctg agggctattg aggcgcaaca gcatctgttg   6660
caactcacag tctggggcat caagcagctc caggcaagaa tcctggctgt ggaaagatac   6720
ctaaaggatc aacagctcct ggggatttgg ggttgctctg gaaaactcat ttgcaccact   6780
gctgtgcctt ggaatgctag ttggagtaat aaatctctgg aacagatttg gaatcacacg   6840
acctggatgg agtgggacag agaaattaac aattacacaa gcttaataca ctccttaatt   6900
gaagaatcgc aaaaccagca agaaaagaat gaacaagaat tattggaatt agataaatgg   6960
gcaagtttgt ggaattggtt taacataaca aattggctgt ggtatataaa attattcata   7020
atgatagtag gaggcttggt aggtttaaga atagtttttg ctgtactttc tatagtgaat   7080
agagttaggc agggatattc accattatcg tttcagaccc acctcccaac cccgagggga   7140
cccgacaggc ccgaaggaat agaagaagaa ggtggagaga gagacagaga cagatccatt   7200
cgattagtga acggatctcg acggtatcgc ctttaaaaga aaagggggga ttggggggta   7260
cagtgcaggg gaaagaatag tagacataat agcaacagac atacaaacta aagaattaca   7320
aaaacaaatt acaaaaattc aaaattttcg ggtttattac agggacagca gagatccagt   7380
ttatcgataa gcttgggagt tccgcgttac ataacttacg gtaaatggcc cgcctggctg   7440
accgcccaac gacccccgcc cattgacgtc aataatgacg tatgttccca tagtaacgcc   7500
aatagggact ttccattgac gtcaatgggt ggagtattta cggtaaactg cccacttggc   7560
agtacatcaa gtgtatcata tgccaagtac gccccctatt gacgtcaatg acggtaaatg   7620
gcccgcctgg cattatgccc agtacatgac cttatgggac tttcctactt ggcagtacat   7680
ctacgtatta gtcatcgcta ttaccatggt gatgcggttt tggcagtaca tcaatgggcg   7740
tggatagcgg tttgactcac ggggatttcc aagtctccac cccattgacg tcaatgggag   7800
tttgttttgg caccaaaatc aacgggactt tccaaaatgt cgtaacaact ccgccccatt   7860
gacgcaaatg ggcggtaggc gtgtacggtg ggaggtctat ataagcagag ctcgtttagt   7920
gaaccgtcag atcgcctgga gacgccatcc acgctgtttt gacctccata gaagacaccg   7980
actctactag aggatctacc ggtcgccacc atggtgagca agggcgagga ggtcatcaaa   8040
gagttcatgc gcttcaaggt gcgcatggag ggctccatga acggccacga gttcgagatc   8100
```

-continued

```
gagggcgagg gcgagggccg cccctacgag ggcacccaga ccgccaagct gaaggtgacc   8160
aagggcggcc ccctgccctt cgcctgggac atcctgtccc cccagttcat gtacggctcc   8220
aaggcgtacg tgaagcaccc cgccgacatc cccgattaca agaagctgtc cttccccgag   8280
ggcttcaagt gggagcgcgt gatgaacttc gaggacggcg gtctggtgac cgtgacccag   8340
gactcctccc tgcaggacgg cacgctgatc tacaaggtga agatgcgcgg caccaacttc   8400
ccccccgacg gccccgtaat gcagaagaag accatgggct gggaggcctc caccgagcgc   8460
ctgtaccccc gcgacggcgt gctgaagggc gagatccacc aggccctgaa gctgaaggac   8520
ggcggccact acctggtgga gttcaagacc atctacatgg ccaagaagcc cgtgcaactg   8580
cccggctact actacgtgga caccaagctg gacatcacct cccacaacga ggactacacc   8640
atcgtggaac agtacgagcg ctccgagggc cgccaccacc tgttcctggg gcatggcacc   8700
ggcagcaccg gcagcggcag ctccggcacc gcctcctccg aggacaacaa catggccgtc   8760
atcaaagagt tcatgcgctt caaggtgcgc atggagggct ccatgaacgg ccacgagttc   8820
gagatcgagg gcgagggcga gggccgcccc tacgagggca cccagaccgc caagctgaag   8880
gtgaccaagg gcggcccct gcccttcgcc tgggacatcc tgtcccccca gttcatgtac   8940
ggctccaagg cgtacgtgaa gcaccccgcc gacatccccg attacaagaa gctgtccttc   9000
cccgagggct tcaagtggga gcgcgtgatg aacttcgagg acggcggtct ggtgaccgtg   9060
acccaggact cctccctgca ggacggcacg ctgatctaca aggtgaagat gcgcggcacc   9120
aacttccccc ccgacggccc cgtaatgcag aagaagacca tgggctggga ggcctccacc   9180
gagcgcctgt acccccgcga cggcgtgctg aagggcgaga tccaccaggc cctgaagctg   9240
aaggacggcg gccactacct ggtggagttc aagaccatct acatggccaa gaagcccgtg   9300
caactgcccg gctactacta cgtggacacc aagctggaca tcacctccca caacgaggac   9360
tacaccatcg tggaacagta cgagcgctcc gagggccgcc accacctgtt cctgtacggc   9420
atggacgagc tgtacaagtc cggactcaga tctcgagtgg cctatccata tgacgtacca   9480
gattatgcgg gggcggccag ctgcgaggat gaggagctgg aatttaagct ggtgttcggg   9540
gaggaaaagg aggccccccc gctgggcgcg gggggattgg gggaagaact ggactcagag   9600
gatgccccgc catgctgccg tctggccttg ggagagcccc ctccctatgg cgctgcacct   9660
atcggtattc cccgacctcc accccctcgg cctggcatgc attcgccacc gccgcgacca   9720
gcccccctcac ctggcacctg ggagagccag cccgccaggt cggtgaggct gggaggacca   9780
ggagggggtg ctgggggtgc tgggggtggc cgtgttctcg agtgtcccag catccgcatc   9840
acctccatct ctcccacgcc ggagccgcca gcagcgctgg aggacaaccc tgatgcctgg   9900
ggggacggct ctcctagaga ttaccccccca ccagaaggct ttgggggcta cagagaagca   9960
ggggcccagg gtgggggggc cttcttcagc ccaagccctg gcagcagcag cctgtcctcg  10020
tggagcttct tctccgatgc ctctgatgag gcagccctgt atgcagcctg cgacgaggtg  10080
gagtctgagc taaatgaggc ggcctcccgc tttggcctgg gctccccgct gccctcgccc  10140
cgggcctccc ctcggccatg gacccccgaa gatccctgga gcctgtatgg tccaagcccc  10200
ggaggccgag ggccagagga tagctggcta ctcctcagtg ctcctgggcc caccccagcc  10260
tccccgcggc ctgcctctcc atgtggcaag cggcgctatt ccagctcggg aaccccatct  10320
tcagcctccc cagctctgtc ccgccgtggc agcctggggg aagaggggtc tgagccacct  10380
ccaccacccc cattgcctct ggcccgggac ccgggctccc ctggtccctt tgactatgtg  10440
```

```
ggggccccac cagctgagag catccctcag aagacacggc ggacttccag cgagcaggca  10500
gtggctctgc ctcggtctga ggagcctgcc tcatgcaatg ggaagctgcc cttgggagca  10560
gaggagtctg tggctcctcc aggaggttcc cggaaggagg tggctggcat ggactacctg  10620
gcagtgccct ccccactcgc ttggtccaag gcccggattg gggacacag ccctatcttc  10680
aggacctctg ccctacccc actggactgg cctctgccca gccaatatga gcagctggag  10740
ctgaggatcg aggtacagcc tagagcccac caccgggccc actatgagac agaaggcagc  10800
cgtggagctg tcaaagctgc ccctggcggt caccccgtag tcaagctcct aggctacagt  10860
gagaagccac tgaccctaca gatgttcatc ggcactgcag atgaaaggaa cctgcggcct  10920
catgccttct atcaggtgca ccgtatcaca ggcaagatgg tggccacggc cagctatgaa  10980
gccgtagtca gtggcaccaa ggtgttggag atgactctgc tgcctgagaa caacatggcg  11040
gccaacattg actgcgcggg aatcctgaag cttcggaatt cagacattga gcttcggaag  11100
ggtgagacgg acatcgggcg caaaaacaca cgtgtacggc tggtgttccg ggtacacgtg  11160
ccccagggcg gcgggaaggt cgtctcagta caggcagcat cggtgcccat cgagtgctcc  11220
cagcgctcag cccaggagct gccccaggtg gaggcctaca gccccagtgc ctgctctgtg  11280
agaggaggcg aggaactggt actgactggc tccaacttcc tgccagactc caaggtggtg  11340
ttcattgaga ggggtcctga tgggaagctg caatgggagg aggaggccac agtgaaccga  11400
ctgcagagca acgaggtgac gctgaccctg actgtccccg agtacagcaa caagagggtt  11460
tcccggccag tccaggtcta cttttatgtc tccaatgggc ggaggaaacg cagtcctacc  11520
cagagtttca ggtttctgcc tgtgatctgc aaagaggagc cctaccgga ctcatctctg  11580
cggggtttcc cttcagcatc ggcaaccccc tttggcactg acatggactt ctcaccaccc  11640
aggccccct accccctccta tccccatgaa gaccctgctt gcgaaactcc ttacctatca  11700
gaaggcttcg gctatggcat gcccccctctg tacccccaga cggggccccc accatcctac  11760
agaccgggcc tgcggatgtt ccctgagact aggggtacca caggttgtgc ccaaccacct  11820
gcagtttcct tccttccccg ccccttccct agtgacccgt atggagggcg gggctcctct  11880
ttcccctgg ggctgccatt ctctccgcca gccccctttc ggccgcctcc tcttccttga  11940
```

<210> SEQ ID NO 31
<211> LENGTH: 11121
<212> TYPE: DNA
<213> ORGANISM: Artificial sequence
<220> FEATURE:
<223> OTHER INFORMATION: pLVX-tdTomato-C1 hdNFAT3 WT

<400> SEQUENCE: 31

```
ggatccaccg gatctagata actgatcata attctaccgg gtaggggagg cgcttttccc     60
aaggcagtct ggagcatgcg ctttagcagc cccgctgggc acttggcgct acacaagtgg    120
cctctggcct cgcacacatt ccacatccac cggtaggcgc caaccggctc cgttctttgg    180
tggcccccttc gcgccacctt ctactcctcc cctagtcagg aagttccccc ccgccccgca   240
gctcgcgtcg tgcaggacgt gacaaatgga agtagcacgt ctcactagtc tcgtgcagat    300
ggacagcacc gctgagcaat ggaagcgggt aggcctttgg ggcagcggcc aatagcagct    360
ttgctccttc gctttctggg ctcagaggct gggaaggggt gggtccgggg gcgggctcag    420
gggcgggctc aggggcgggg cgggcgcccg aaggtcctcc ggaggcccgg cattctgcac    480
gcttcaaaag cgcacgtctg ccgcgctgtt ctcctcttcc tcatctccgg gcctttcgac    540
ctgcagccca agcttaccat gaccgagtac aagcccacgg tgcgcctcgc cacccgcgac    600
```

```
gacgtcccca gggccgtacg caccctcgcc gccgcgttcg ccgactaccc cgccacgcgc    660
cacaccgtcg atccggaccg ccacatcgag cgggtcaccg agctgcaaga actcttcctc    720
acgcgcgtcg ggctcgacat cggcaaggtg tgggtcgcgg acgacggcgc cgcggtggcg    780
gtctggacca cgccggagag cgtcgaagcg ggggcggtgt tcgccgagat cggcccgcgc    840
atggccgagt tgagcggttc ccggctggcc gcgcagcaac agatggaagg cctcctggcg    900
ccgcaccggc ccaaggagcc cgcgtggttc ctggccaccg tcggcgtctc gcccgaccac    960
cagggcaagg gtctgggcag cgccgtcgtg ctccccggag tggaggcggc cgagcgcgcc   1020
ggggtgcccg ccttcctgga gacctccgcg ccccgcaacc tccccttcta cgagcggctc   1080
ggcttcaccg tcaccgccga cgtcgaggtg cccgaaggac cgcgcacctg gtgcatgacc   1140
cgcaagcccg gtgcctgacc gcgtctggaa caatcaacct ctggattaca aaatttgtga   1200
aagattgact ggtattctta actatgttgc tccttttacg ctatgtggat acgctgcttt   1260
aatgcctttg tatcatgcta ttgcttcccg tatggctttc attttctcct ccttgtataa   1320
atcctggttg ctgtctcttt atgaggagtt gtggcccgtt gtcaggcaac gtggcgtggt   1380
gtgcactgtg tttgctgacg caacccccac tggttggggc attgccacca cctgtcagct   1440
cctttccggg actttcgctt tccccctccc tattgccacg gcggaactca tcgccgcctg   1500
ccttgcccgc tgctggacag gggctcggct gttgggcact gacaattccg tggtgttgtc   1560
ggggaagctg acgtcctttc catggctgct cgcctgtgtt gccacctgga ttctgcgcgg   1620
gacgtccttc tgctacgtcc cttcggccct caatccagcg gaccttcctt cccgcggcct   1680
gctgccggct ctgcggcctc ttccgcgtct tcgccttcgc cctcagacga gtcggatctc   1740
cctttgggcc gcctccccgc ctggaattaa ttctgcagtc gagacctaga aaaacatgga   1800
gcaatcacaa gtagcaatac agcagctacc aatgctgatt gtgcctggct agaagcacaa   1860
gaggaggagg aggtgggttt tccagtcaca cctcaggtac ctttaagacc aatgacttac   1920
aaggcagctg tagatcttag ccacttttta aaagaaaaga ggggactgga agggctaatt   1980
cactcccaac gaagacaaga tatccttgat ctgtggatct accacacaca aggctacttc   2040
cctgattagc agaactacac accagggcca ggggtcagat atccactgac ctttggatgg   2100
tgctacaagc tagtaccagt tgagccagat aaggtagaag aggccaataa aggagagaac   2160
accagcttgt tacaccctgt gagcctgcat gggatggatg acccggagag agaagtgtta   2220
gagtggaggt ttgacagccg cctagcattt catcacgtgg cccgagagct gcatccggag   2280
tacttcaaga actgctgata tcgagcttgc tacaagggac tttccgctgg ggactttcca   2340
gggaggcgtg gcctgggcgg gactggggag tggcgagccc tcagatcctg catataagca   2400
gctgcttttt gcctgtactg ggtctctctg gttagaccag atctgagcct gggagctctc   2460
tggctaacta gggaacccac tgcttaagcc tcaataaagc ttgccttgag tgcttcaagt   2520
agtgtgtgcc cgtctgttgt gtgactctgg taactagaga tccctcagac ccttttagtc   2580
agtgtggaaa atctctagca gtagtagttc atgtcatctt attattcagt atttataact   2640
tgcaaagaaa tgaatatcag agagtgagag gccttgacat tgctagcgtt ttaccgtcga   2700
cctctagcta gagcttggcg taatcatggt catagctgtt tcctgtgtga aattgttatc   2760
cgctcacaat tccacacaac atacgagccg gaagcataaa gtgtaaagcc tggggtgcct   2820
aatgagtgag ctaactcaca ttaattgcgt tgcgctcact gcccgctttc cagtcgggaa   2880
acctgtcgtg ccagctgcat taatgaatcg gccaacgcgc ggggagaggc ggtttgcgta   2940
```

-continued

```
ttgggcgctc ttccgcttcc tcgctcactg actcgctgcg ctcggtcgtt cggctgcggc   3000
gagcggtatc agctcactca aaggcggtaa tacggttatc cacagaatca ggggataacg   3060
caggaaagaa catgtgagca aaaggccagc aaaaggccag gaaccgtaaa aaggccgcgt   3120
tgctggcgtt tttccatagg ctccgccccc ctgacgagca tcacaaaaat cgacgctcaa   3180
gtcagaggtg gcgaaacccg acaggactat aaagatacca ggcgtttccc cctggaagct   3240
ccctcgtgcg ctctcctgtt ccgaccctgc cgcttaccgg atacctgtcc gcctttctcc   3300
cttcgggaag cgtggcgctt tctcatagct cacgctgtag gtatctcagt tcggtgtagg   3360
tcgttcgctc caagctgggc tgtgtgcacg aaccccccgt tcagcccgac cgctgcgcct   3420
tatccggtaa ctatcgtctt gagtccaacc cggtaagaca cgacttatcg ccactggcag   3480
cagccactgg taacaggatt agcagagcga ggtatgtagg cggtgctaca gagttcttga   3540
agtggtggcc taactacggc tacactagaa gaacagtatt tggtatctgc gctctgctga   3600
agccagttac cttcggaaaa agagttggta gctcttgatc cggcaaacaa accaccgctg   3660
gtagcggtgg tttttttgtt tgcaagcagc agattacgcg cagaaaaaaa ggatctcaag   3720
aagatccttt gatcttttct acggggtctg acgctcagtg gaacgaaaac tcacgttaag   3780
ggattttggt catgagatta tcaaaaagga tcttcaccta gatcctttta aattaaaaat   3840
gaagttttaa atcaatctaa agtatatatg agtaaacttg gtctgacagt taccaatgct   3900
taatcagtga ggcacctatc tcagcgatct gtctatttcg ttcatccata gttgcctgac   3960
tccccgtcgt gtagataact acgatacggg agggcttacc atctggcccc agtgctgcaa   4020
tgataccgcg agacccacgc tcaccggctc cagatttatc agcaataaac cagccagccg   4080
gaagggccga gcgcagaagt ggtcctgcaa ctttatccgc ctccatccag tctattaatt   4140
gttgccggga agctagagta agtagttcgc cagttaatag tttgcgcaac gttgttgcca   4200
ttgctacagg catcgtggtg tcacgctcgt cgtttggtat ggcttcattc agctccggtt   4260
cccaacgatc aaggcgagtt acatgatccc ccatgttgtg caaaaaagcg gttagctcct   4320
tcggtcctcc gatcgttgtc agaagtaagt tggccgcagt gttatcactc atggttatgg   4380
cagcactgca taattctctt actgtcatgc catccgtaag atgcttttct gtgactggtg   4440
agtactcaac caagtcattc tgagaatagt gtatgcggcg accgagttgc tcttgcccgg   4500
cgtcaatacg ggataatacc gcgccacata gcagaacttt aaaagtgctc atcattggaa   4560
aacgttcttc ggggcgaaaa ctctcaagga tcttaccgct gttgagatcc agttcgatgt   4620
aacccactcg tgcacccaac tgatcttcag catcttttac tttcaccagc gtttctgggt   4680
gagcaaaaac aggaaggcaa aatgccgcaa aaaagggaat aagggcgaca cggaaatgtt   4740
gaatactcat actcttcctt tttcaatatt attgaagcat ttatcagggt tattgtctca   4800
tgagcggata catatttgaa tgtatttaga aaaataaaca aataggggtt ccgcgcacat   4860
ttccccgaaa agtgccacct gacgtcgacg gatcgggaga tcaacttgtt tattgcagct   4920
tataatggtt acaaataaag caatagcatc acaaatttca caaataaagc atttttttca   4980
ctgcattcta gttgtggttt gtccaaactc atcaatgtat cttatcatgt ctggatcaac   5040
tggataactc aagctaacca aaatcatccc aaacttccca ccccataccc tattaccact   5100
gccaattacc tgtggtttca tttactctaa acctgtgatt cctctgaatt attttcattt   5160
taaagaaatt gtatttgtta aatatgtact acaaacttag tagttggaag ggctaattca   5220
ctcccaaaga agacaagata tccttgatct gtggatctac cacacacaag gctacttccc   5280
tgattagcag aactacacac cagggccagg ggtcagatat ccactgacct ttggatggtg   5340
```

```
ctacaagcta gtaccagttg agccagataa ggtagaagag gccaataaag gagagaacac   5400
cagcttgtta caccctgtga gcctgcatgg gatggatgac ccggagagag aagtgttaga   5460
gtggaggttt gacagccgcc tagcatttca tcacgtggcc cgagagctgc atccggagta   5520
cttcaagaac tgctgatatc gagcttgcta caagggactt tccgctgggg actttccagg   5580
gaggcgtggc ctgggcggga ctggggagtg gcgagccctc agatcctgca tataagcagc   5640
tgctttttgc ctgtactggg tctctctggt tagaccagat ctgagcctgg gagctctctg   5700
gctaactagg gaacccactg cttaagcctc aataaagctt gccttgagtg cttcaagtag   5760
tgtgtgcccg tctgttgtgt gactctggta actagagatc cctcagaccc ttttagtcag   5820
tgtggaaaat ctctagcagt ggcgcccgaa cagggacttg aaagcgaaag ggaaaccaga   5880
ggagctctct cgacgcagga ctcggcttgc tgaagcgcgc acggcaagag gcgaggggcg   5940
gcgactggtg agtacgccaa aaattttgac tagcggaggc tagaaggaga gagatgggtg   6000
cgagagcgtc agtattaagc gggggagaat tagatcgcga tgggaaaaaa ttcggttaag   6060
gccaggggga aagaaaaaat ataaattaaa acatatagta tgggcaagca gggagctaga   6120
acgattcgca gttaatcctg gcctgttaga aacatcagaa ggctgtagac aaatactggg   6180
acagctacaa ccatcccttc agacaggatc agaagaactt agatcattat ataatacagt   6240
agcaaccctc tattgtgtgc atcaaaggat agagataaaa gacaccaagg aagctttaga   6300
caagatagag gaagagcaaa acaaaagtaa gaccaccgca cagcaagcgg ccggccgctg   6360
atcttcagac ctggaggagg agatatgagg gacaattgga gaagtgaatt atataaatat   6420
aaagtagtaa aaattgaacc attaggagta gcacccacca aggcaaagag aagagtggtg   6480
cagagagaaa aaagagcagt gggaatagga gctttgttcc ttgggttctt gggagcagca   6540
ggaagcacta tgggcgcagc gtcaatgacg ctgacggtac aggccagaca attattgtct   6600
ggtatagtgc agcagcagaa caatttgctg agggctattg aggcgcaaca gcatctgttg   6660
caactcacag tctggggcat caagcagctc caggcaagaa tcctggctgt ggaaagatac   6720
ctaaaggatc aacagctcct ggggatttgg ggttgctctg gaaaactcat ttgcaccact   6780
gctgtgcctt ggaatgctag ttggagtaat aaatctctgg aacagatttg gaatcacacg   6840
acctggatgg agtgggacag agaaattaac aattacacaa gcttaataca ctccttaatt   6900
gaagaatcgc aaaaccagca agaaaagaat gaacaagaat tattggaatt agataaatgg   6960
gcaagtttgt ggaattggtt taacataaca aattggctgt ggtatataaa attattcata   7020
atgatagtag gaggcttggt aggtttaaga atagtttttg ctgtactttc tatagtgaat   7080
agagttaggc agggatattc accattatcg tttcagaccc acctcccaac cccgagggga   7140
cccgacaggc ccgaaggaat agaagaagaa ggtggagaga gagacagaga cagatccatt   7200
cgattagtga acggatctcg acggtatcgc ctttaaaaga aaagggggga ttggggggta   7260
cagtgcaggg gaaagaatag tagacataat agcaacagac atacaaacta aagaattaca   7320
aaaacaaatt acaaaaattc aaaattttcg ggtttattac agggacagca gagatccagt   7380
ttatcgataa gcttgggagt tccgcgttac ataacttacg gtaaatggcc cgcctggctg   7440
accgcccaac gacccccgcc cattgacgtc aataatgacg tatgttccca tagtaacgcc   7500
aatagggact ttccattgac gtcaatgggt ggagtattta cggtaaactg cccacttggc   7560
agtacatcaa gtgtatcata tgccaagtac gccccctatt gacgtcaatg acggtaaatg   7620
gcccgcctgg cattatgccc agtacatgac cttatgggac tttcctactt ggcagtacat   7680
```

-continued

```
ctacgtatta gtcatcgcta ttaccatggt gatgcggttt tggcagtaca tcaatgggcg   7740
tggatagcgg tttgactcac ggggatttcc aagtctccac cccattgacg tcaatgggag   7800
tttgttttgg caccaaaatc aacgggactt tccaaaatgt cgtaacaact ccgccccatt   7860
gacgcaaatg ggcggtaggc gtgtacggtg ggaggtctat ataagcagag ctcgtttagt   7920
gaaccgtcag atcgcctgga gacgccatcc acgctgtttt gacctccata gaagacaccg   7980
actctactag aggatctacc ggtcgccacc atggtgagca agggcgagga ggtcatcaaa   8040
gagttcatgc gcttcaaggt gcgcatggag ggctccatga acggccacga gttcgagatc   8100
gagggcgagg gcgagggccg cccctacgag ggcacccaga ccgccaagct gaaggtgacc   8160
aagggcggcc ccctgccctt cgcctgggac atcctgtccc cccagttcat gtacggctcc   8220
aaggcgtacg tgaagcaccc cgccgacatc cccgattaca agaagctgtc cttccccgag   8280
ggcttcaagt gggagcgcgt gatgaacttc gaggacggcg gtctggtgac cgtgacccag   8340
gactcctccc tgcaggacgg cacgctgatc tacaaggtga agatgcgcgg caccaacttc   8400
ccccccgacg gccccgtaat gcagaagaag accatgggct gggaggcctc caccgagcgc   8460
ctgtaccccc gcgacggcgt gctgaagggc gagatccacc aggccctgaa gctgaaggac   8520
ggcggccact acctggtgga gttcaagacc atctacatgg ccaagaagcc cgtgcaactg   8580
cccggctact actacgtgga caccaagctg gacatcacct cccacaacga ggactacacc   8640
atcgtggaac agtacgagcg ctccgagggc cgccaccacc tgttcctggg gcatggcacc   8700
ggcagcaccg gcagcggcag ctccggcacc gcctcctccg aggacaacaa catggccgtc   8760
atcaaagagt tcatgcgctt caaggtgcgc atggagggct ccatgaacgg ccacgagttc   8820
gagatcgagg gcgagggcga gggccgcccc tacgagggca cccagaccgc caagctgaag   8880
gtgaccaagg gcggccccct gcccttcgcc tgggacatcc tgtcccccca gttcatgtac   8940
ggctccaagg cgtacgtgaa gcaccccgcc gacatccccg attacaagaa gctgtccttc   9000
cccgagggct tcaagtggga gcgcgtgatg aacttcgagg acggcggtct ggtgaccgtg   9060
acccaggact cctccctgca ggacggcacg ctgatctaca aggtgaagat gcgcggcacc   9120
aacttccccc ccgacggccc cgtaatgcag aagaagacca tgggctggga ggcctccacc   9180
gagcgcctgt acccccgcga cggcgtgctg aagggcgaga tccaccaggc cctgaagctg   9240
aaggacggcg gccactacct ggtggagttc aagaccatct acatggccaa gaagcccgtg   9300
caactgcccg gctactacta cgtggacacc aagctggaca tcacctccca caacgaggac   9360
tacaccatcg tggaacagta cgagcgctcc gagggccgcc accacctgtt cctgtacggc   9420
atggacgagc tgtacaagtc cggactcaga tctcgagctc aagcttcgaa ttctgcagtc   9480
gacggtaccg cgggcccggg atccatggcc tatccatatg acgtaccaga ttatgcggac   9540
tacctggcag tgccctcccc actcgcttgg tccaaggccc ggattggggg acacagccct   9600
atcttcagga cctctgccct acccccactg gactggcctc tgcccagcca atatgagcag   9660
ctggagctga ggatcgaggt acagcctaga gcccaccacc gggcccacta tgagacagaa   9720
ggcagccgtg gagctgtcaa agctgcccct ggcggtcacc ccgtagtcaa gctcctaggc   9780
tacagtgaga agccactgac cctacagatg ttcatcggca ctgcagatga aaggaacctg   9840
cggcctcatg ccttctatca ggtgcaccgt atcacaggca agatggtggc cacggccagc   9900
tatgaagccg tagtcagtgg caccaaggtg ttggagatga ctctgctgcc tgagaacaac   9960
atggcggcca acattgactg cgcgggaatc ctgaagcttc ggaattcaga cattgagctt  10020
cggaagggtg agacggacat cgggcgcaaa aacacacgtg tacggctggt gttccgggta  10080
```

```
cacgtgcccc agggcggcgg gaaggtcgtc tcagtacagg cagcatcggt gcccatcgag  10140

tgctcccagc gctcagccca ggagctgccc caggtggagg cctacagccc cagtgcctgc  10200

tctgtgagag gaggcgagga actggtactg accggctcca acttcctgcc agactccaag  10260

gtggtgttca ttgagagggg tcctgatggg aagctgcaat gggaggagga ggccacagtg  10320

aaccgactgc agagcaacga ggtgacgctg accctgactg tccccgagta cagcaacaag  10380

agggtttccc ggccagtcca ggtctacttt tatgtctcca atgggcggag gaaacgcagt  10440

cctacccaga gtttcaggtt tctgcctgtg atctgcaaag aggagcccct accggactca  10500

tctctgcggg gtttcccttc agcatcggca acccccttg gcactgacat ggacttctca  10560

ccacccaggc ccccctaccc ctcctatccc catgaagacc ctgcttgcga aactccttac  10620

ctatcagaag gcttcggcta tggcatgccc cctctgtacc cccagacggg gcccccacca  10680

tcctacagac cgggcctgcg gatgttccct gagactaggg gtaccacagg ttgtgcccaa  10740

ccacctgcag tttccttcct tccccgcccc ttccctagtg acccgtatgg agggcggggc  10800

tcctctttcc ccctggggct gccattctct ccgccagccc cctttcggcc gcctcctctt  10860

cctgcatccc caccgcttga aggccccttc ccttcccaga gtgatgtgca tcccctacct  10920

gctgagggat acaataaggt agggccaggc tatggccctg gggagggggc tccggagcag  10980

gagaaatcca ggggtggcta cagcagcggc ttccgagaca gtgtccctat ccagggtatc  11040

acgctggagg aagtgagtga gatcattggc cgagacctga gtggcttccc tgcacctcct  11100

ggagaagagc ctcctgcctg a                                            11121
```

```
<210> SEQ ID NO 32
<211> LENGTH: 10886
<212> TYPE: DNA
<213> ORGANISM: Artificial sequence
<220> FEATURE:
<223> OTHER INFORMATION: pLVX-tdTomato-C1 hdNFAT3-85C

<400> SEQUENCE: 32

ggatccaccg gatctagata actgatcata attctaccgg gtaggggagg cgcttttccc     60

aaggcagtct ggagcatgcg ctttagcagc cccgctgggc acttggcgct acacaagtgg    120

cctctggcct cgcacacatt ccacatccac cggtaggcgc caaccggctc cgttctttgg    180

tggccccttc gcgccacctt ctactcctcc cctagtcagg aagttccccc ccgccccgca    240

gctcgcgtcg tgcaggacgt gacaaatgga agtagcacgt ctcactagtc tcgtgcagat    300

ggacagcacc gctgagcaat ggaagcgggt aggcctttgg ggcagcggcc aatagcagct    360

ttgctccttc gctttctggg ctcagaggct gggaaggggt gggtccgggg gcgggctcag    420

gggcgggctc aggggcgggg cgggcgcccg aaggtcctcc ggaggcccgg cattctgcac    480

gcttcaaaag cgcacgtctg ccgcgctgtt ctcctcttcc tcatctccgg gcctttcgac    540

ctgcagccca agcttaccat gaccgagtac aagcccacgg tgcgcctcgc cacccgcgac    600

gacgtcccca gggccgtacg caccctcgcc gccgcgttcg ccgactaccc cgccacgcgc    660

cacaccgtcg atccggaccg ccacatcgag cgggtcaccg agctgcaaga actcttcctc    720

acgcgcgtcg ggctcgacat cggcaaggtg tgggtcgcgg acgacggcgc cgcggtggcg    780

gtctggacca cgccggagag cgtcgaagcg ggggcggtgt tcgccgagat cggcccgcgc    840

atggccgagt tgagcggttc ccggctggcc gcgcagcaac agatggaagg cctcctggcg    900

ccgcaccggc ccaaggagcc cgcgtggttc ctggccaccg tcggcgtctc gcccgaccac    960
```

-continued

```
cagggcaagg gtctgggcag cgccgtcgtg ctccccggag tggaggcggc cgagcgcgcc   1020
ggggtgcccg ccttcctgga gacctccgcg ccccgcaacc tccccttcta cgagcggctc   1080
ggcttcaccg tcaccgccga cgtcgaggtg cccgaaggac cgcgcacctg gtgcatgacc   1140
cgcaagcccg gtgcctgacc gcgtctggaa caatcaacct ctggattaca aaatttgtga   1200
aagattgact ggtattctta actatgttgc tccttttacg ctatgtggat acgctgcttt   1260
aatgcctttg tatcatgcta ttgcttcccg tatggctttc attttctcct ccttgtataa   1320
atcctggttg ctgtctcttt atgaggagtt gtggcccgtt gtcaggcaac gtggcgtggt   1380
gtgcactgtg tttgctgacg caacccccac tggttggggc attgccacca cctgtcagct   1440
cctttccggg actttcgctt tccccctccc tattgccacg gcggaactca tcgccgcctg   1500
ccttgcccgc tgctggacag gggctcggct gttgggcact gacaattccg tggtgttgtc   1560
ggggaagctg acgtcctttc catggctgct cgcctgtgtt gccacctgga ttctgcgcgg   1620
gacgtccttc tgctacgtcc cttcggccct caatccagcg gaccttcctt cccgcggcct   1680
gctgccggct ctgcggcctc ttccgcgtct tcgccttcgc cctcagacga gtcggatctc   1740
cctttgggcc gcctccccgc ctggaattaa ttctgcagtc gagacctaga aaaacatgga   1800
gcaatcacaa gtagcaatac agcagctacc aatgctgatt gtgcctggct agaagcacaa   1860
gaggaggagg aggtgggttt tccagtcaca cctcaggtac ctttaagacc aatgacttac   1920
aaggcagctg tagatcttag ccacttttta aaagaaaaga ggggactgga agggctaatt   1980
cactcccaac gaagacaaga tatccttgat ctgtggatct accacacaca aggctacttc   2040
cctgattagc agaactacac accagggcca ggggtcagat atccactgac ctttggatgg   2100
tgctacaagc tagtaccagt tgagccagat aaggtagaag aggccaataa aggagagaac   2160
accagcttgt tacaccctgt gagcctgcat gggatggatg acccggagag agaagtgtta   2220
gagtggaggt ttgacagccg cctagcattt catcacgtgg cccgagagct gcatccggag   2280
tacttcaaga actgctgata tcgagcttgc tacaagggac tttccgctgg ggactttcca   2340
gggaggcgtg gcctgggcgg gactggggag tggcgagccc tcagatcctg catataagca   2400
gctgcttttt gcctgtactg ggtctctctg gttagaccag atctgagcct gggagctctc   2460
tggctaacta gggaacccac tgcttaagcc tcaataaagc ttgccttgag tgcttcaagt   2520
agtgtgtgcc cgtctgttgt gtgactctgg taactagaga tccctcagac ccttttagtc   2580
agtgtggaaa atctctagca gtagtagttc atgtcatctt attattcagt atttataact   2640
tgcaaagaaa tgaatatcag agagtgagag gccttgacat tgctagcgtt ttaccgtcga   2700
cctctagcta gagcttggcg taatcatggt catagctgtt tcctgtgtga aattgttatc   2760
cgctcacaat tccacacaac atacgagccg gaagcataaa gtgtaaagcc tggggtgcct   2820
aatgagtgag ctaactcaca ttaattgcgt tgcgctcact gcccgctttc cagtcgggaa   2880
acctgtcgtg ccagctgcat taatgaatcg gccaacgcgc ggggagaggc ggtttgcgta   2940
ttgggcgctc ttccgcttcc tcgctcactg actcgctgcg ctcggtcgtt cggctgcggc   3000
gagcggtatc agctcactca aaggcggtaa tacggttatc cacagaatca ggggataacg   3060
caggaaagaa catgtgagca aaaggccagc aaaaggccag gaaccgtaaa aaggccgcgt   3120
tgctggcgtt tttccatagg ctccgccccc ctgacgagca tcacaaaaat cgacgctcaa   3180
gtcagaggtg gcgaaacccg acaggactat aaagatacca ggcgtttccc cctggaagct   3240
ccctcgtgcg ctctcctgtt ccgaccctgc cgcttaccgg atacctgtcc gcctttctcc   3300
cttcgggaag cgtggcgctt tctcatagct cacgctgtag gtatctcagt tcggtgtagg   3360
```

```
tcgttcgctc caagctgggc tgtgtgcacg aaccccccgt tcagcccgac cgctgcgcct   3420
tatccggtaa ctatcgtctt gagtccaacc cggtaagaca cgacttatcg ccactggcag   3480
cagccactgg taacaggatt agcagagcga ggtatgtagg cggtgctaca gagttcttga   3540
agtggtggcc taactacggc tacactagaa gaacagtatt tggtatctgc gctctgctga   3600
agccagttac cttcggaaaa agagttggta gctcttgatc cggcaaacaa accaccgctg   3660
gtagcggtgg tttttttgtt tgcaagcagc agattacgcg cagaaaaaaa ggatctcaag   3720
aagatccttt gatcttttct acggggtctg acgctcagtg gaacgaaaac tcacgttaag   3780
ggattttggt catgagatta tcaaaaagga tcttcaccta gatcctttta aattaaaaat   3840
gaagttttaa atcaatctaa agtatatatg agtaaacttg gtctgacagt taccaatgct   3900
taatcagtga ggcacctatc tcagcgatct gtctatttcg ttcatccata gttgcctgac   3960
tccccgtcgt gtagataact acgatacggg agggcttacc atctggcccc agtgctgcaa   4020
tgataccgcg agacccacgc tcaccggctc cagatttatc agcaataaac cagccagccg   4080
gaagggccga gcgcagaagt ggtcctgcaa ctttatccgc ctccatccag tctattaatt   4140
gttgccggga agctagagta agtagttcgc cagttaatag tttgcgcaac gttgttgcca   4200
ttgctacagg catcgtggtg tcacgctcgt cgtttggtat ggcttcattc agctccggtt   4260
cccaacgatc aaggcgagtt acatgatccc ccatgttgtg caaaaaagcg gttagctcct   4320
tcggtcctcc gatcgttgtc agaagtaagt tggccgcagt gttatcactc atggttatgg   4380
cagcactgca taattctctt actgtcatgc catccgtaag atgcttttct gtgactggtg   4440
agtactcaac caagtcattc tgagaatagt gtatgcggcg accgagttgc tcttgcccgg   4500
cgtcaatacg ggataatacc gcgccacata gcagaacttt aaaagtgctc atcattggaa   4560
aacgttcttc ggggcgaaaa ctctcaagga tcttaccgct gttgagatcc agttcgatgt   4620
aacccactcg tgcacccaac tgatcttcag catcttttac tttcaccagc gtttctgggt   4680
gagcaaaaac aggaaggcaa aatgccgcaa aaaagggaat aagggcgaca cggaaatgtt   4740
gaatactcat actcttcctt tttcaatatt attgaagcat ttatcagggt tattgtctca   4800
tgagcggata catatttgaa tgtatttaga aaaataaaca aataggggtt ccgcgcacat   4860
ttccccgaaa agtgccacct gacgtcgacg gatcgggaga tcaacttgtt tattgcagct   4920
tataatggtt acaaataaag caatagcatc acaaatttca caaataaagc atttttttca   4980
ctgcattcta gttgtggttt gtccaaactc atcaatgtat cttatcatgt ctggatcaac   5040
tggataactc aagctaacca aaatcatccc aaacttccca ccccataccc tattaccact   5100
gccaattacc tgtggtttca tttactctaa acctgtgatt cctctgaatt attttcattt   5160
taaagaaatt gtatttgtta aatatgtact acaaacttag tagttggaag ggctaattca   5220
ctcccaaaga agacaagata tccttgatct gtggatctac cacacacaag gctacttccc   5280
tgattagcag aactacacac cagggccagg ggtcagatat ccactgacct ttggatggtg   5340
ctacaagcta gtaccagttg agccagataa ggtagaagag gccaataaag gagagaacac   5400
cagcttgtta caccctgtga gcctgcatgg gatggatgac ccggagagag aagtgttaga   5460
gtggaggttt gacagccgcc tagcatttca tcacgtggcc cgagagctgc atccggagta   5520
cttcaagaac tgctgatatc gagcttgcta caagggactt tccgctgggg actttccagg   5580
gaggcgtggc ctgggcggga ctggggagtg gcgagccctc agatcctgca tataagcagc   5640
tgctttttgc ctgtactggg tctctctggt tagaccagat ctgagcctgg gagctctctg   5700
```

gctaactagg gaacccactg cttaagcctc aataaagctt gccttgagtg cttcaagtag 5760
tgtgtgcccg tctgttgtgt gactctggta actagagatc cctcagaccc ttttagtcag 5820
tgtggaaaat ctctagcagt ggcgcccgaa cagggacttg aaagcgaaag ggaaaccaga 5880
ggagctctct cgacgcagga ctcggcttgc tgaagcgcgc acggcaagag gcgaggggcg 5940
gcgactggtg agtacgccaa aaattttgac tagcggaggc tagaaggaga gagatgggtg 6000
cgagagcgtc agtattaagc gggggagaat tagatcgcga tgggaaaaaa ttcggttaag 6060
gccaggggga aagaaaaaat ataaattaaa acatatagta tgggcaagca gggagctaga 6120
acgattcgca gttaatcctg gcctgttaga aacatcagaa ggctgtagac aaatactggg 6180
acagctacaa ccatcccttc agacaggatc agaagaactt agatcattat ataatacagt 6240
agcaaccctc tattgtgtgc atcaaaggat agagataaaa gacaccaagg aagctttaga 6300
caagatagag gaagagcaaa acaaaagtaa gaccaccgca cagcaagcgg ccggccgctg 6360
atcttcagac ctggaggagg agatatgagg gacaattgga gaagtgaatt atataaatat 6420
aaagtagtaa aaattgaacc attaggagta gcacccacca aggcaaagag aagagtggtg 6480
cagagagaaa aaagagcagt gggaatagga gctttgttcc ttgggttctt gggagcagca 6540
ggaagcacta tgggcgcagc gtcaatgacg ctgacggtac aggccagaca attattgtct 6600
ggtatagtgc agcagcagaa caatttgctg agggctattg aggcgcaaca gcatctgttg 6660
caactcacag tctggggcat caagcagctc caggcaagaa tcctggctgt ggaaagatac 6720
ctaaaggatc aacagctcct ggggatttgg ggttgctctg gaaaactcat ttgcaccact 6780
gctgtgcctt ggaatgctag ttggagtaat aaatctctgg aacagatttg gaatcacacg 6840
acctggatgg agtgggacag agaaattaac aattacacaa gcttaataca ctccttaatt 6900
gaagaatcgc aaaaccagca agaaaagaat gaacaagaat tattggaatt agataaatgg 6960
gcaagtttgt ggaattggtt taacataaca aattggctgt ggtatataaa attattcata 7020
atgatagtag gaggcttggt aggtttaaga atagtttttg ctgtactttc tatagtgaat 7080
agagttaggc agggatattc accattatcg tttcagaccc acctcccaac cccgagggga 7140
cccgacaggc ccgaaggaat agaagaagaa ggtggagaga gagacagaga cagatccatt 7200
cgattagtga acggatctcg acggtatcgc ctttaaaaga aaagggggga ttggggggta 7260
cagtgcaggg gaaagaatag tagacataat agcaacagac atacaaacta aagaattaca 7320
aaaacaaatt acaaaaattc aaaattttcg ggtttattac agggacagca gagatccagt 7380
ttatcgataa gcttgggagt tccgcgttac ataacttacg gtaaatggcc cgcctggctg 7440
accgcccaac gacccccgcc cattgacgtc aataatgacg tatgttccca tagtaacgcc 7500
aatagggact ttccattgac gtcaatgggt ggagtattta cggtaaactg cccacttggc 7560
agtacatcaa gtgtatcata tgccaagtac gccccctatt gacgtcaatg acggtaaatg 7620
gcccgcctgg cattatgccc agtacatgac cttatgggac tttcctactt ggcagtacat 7680
ctacgtatta gtcatcgcta ttaccatggt gatgcggttt tggcagtaca tcaatgggcg 7740
tggatagcgg tttgactcac ggggatttcc aagtctccac cccattgacg tcaatgggag 7800
tttgttttgg caccaaaatc aacgggactt tccaaaatgt cgtaacaact ccgccccatt 7860
gacgcaaatg ggcggtaggc gtgtacggtg ggaggtctat ataagcagag ctcgtttagt 7920
gaaccgtcag atcgcctgga gacgccatcc acgctgtttt gacctccata gaagacaccg 7980
actctactag aggatctacc ggtcgccacc atggtgagca agggcgagga ggtcatcaaa 8040
gagttcatgc gcttcaaggt gcgcatggag ggctccatga acggccacga gttcgagatc 8100

```
gagggcgagg gcgagggccg cccctacgag ggcacccaga ccgccaagct gaaggtgacc   8160
aagggcggcc ccctgccctt cgcctgggac atcctgtccc cccagttcat gtacggctcc   8220
aaggcgtacg tgaagcaccc cgccgacatc cccgattaca agaagctgtc cttccccgag   8280
ggcttcaagt gggagcgcgt gatgaacttc gaggacggcg gtctggtgac cgtgacccag   8340
gactcctccc tgcaggacgg cacgctgatc tacaaggtga agatgcgcgg caccaacttc   8400
ccccccgacg gccccgtaat gcagaagaag accatgggct gggaggcctc caccgagcgc   8460
ctgtaccccc gcgacggcgt gctgaagggc gagatccacc aggccctgaa gctgaaggac   8520
ggcggccact acctggtgga gttcaagacc atctacatgg ccaagaagcc cgtgcaactg   8580
cccggctact actacgtgga caccaagctg gacatcacct cccacaacga ggactacacc   8640
atcgtggaac agtacgagcg ctccgagggc cgccaccacc tgttcctggg gcatggcacc   8700
ggcagcaccg gcagcggcag ctccggcacc gcctcctccg aggacaacaa catggccgtc   8760
atcaaagagt tcatgcgctt caaggtgcgc atggagggct ccatgaacgg ccacgagttc   8820
gagatcgagg gcgagggcga gggccgcccc tacgagggca cccagaccgc caagctgaag   8880
gtgaccaagg gcggcccccct gcccttcgcc tgggacatcc tgtcccccca gttcatgtac   8940
ggctccaagg cgtacgtgaa gcaccccgcc gacatccccg attacaagaa gctgtccttc   9000
cccgagggct tcaagtggga gcgcgtgatg aacttcgagg acggcggtct ggtgaccgtg   9060
acccaggact cctccctgca ggacggcacg ctgatctaca aggtgaagat gcgcggcacc   9120
aacttccccc ccgacggccc cgtaatgcag aagaagacca tgggctggga ggcctccacc   9180
gagcgcctgt acccccgcga cggcgtgctg aagggcgaga tccaccaggc cctgaagctg   9240
aaggacggcg gccactacct ggtggagttc aagaccatct acatggccaa gaagcccgtg   9300
caactgcccg gctactacta cgtggacacc aagctggaca tcacctccca caacgaggac   9360
tacaccatcg tggaacagta cgagcgctcc gagggccgcc accacctgtt cctgtacggc   9420
atggacgagc tgtacaagtc cggactcaga tctcgagctc aagcttcgaa ttctgcagtc   9480
gacggtaccg cgggcccggg atccatggcc tatccatatg acgtaccaga ttatgcggac   9540
tacctggcag tgccctcccc actcgcttgg tccaaggccc ggattggggg acacagccct   9600
atcttcagga cctctgccct acccccactg gactggcctc tgcccagcca atatgagcag   9660
ctggagctga ggatcgaggt acagcctaga gcccaccacc gggcccacta tgagacagaa   9720
ggcagccgtg gagctgtcaa agctgcccct ggcggtcacc ccgtagtcaa gctcctaggc   9780
tacagtgaga agccactgac cctacagatg ttcatcggca ctgcagatga aaggaacctg   9840
cggcctcatg ccttctatca ggtgcaccgt atcacaggca agatggtggc cacggccagc   9900
tatgaagccg tagtcagtgg caccaaggtg ttggagatga ctctgctgcc tgagaacaac   9960
atggcggcca acattgactg cgcgggaatc ctgaagcttc ggaattcaga cattgagctt  10020
cggaagggtg agacggacat cgggcgcaaa aacacacgtg tacggctggt gttccgggta  10080
cacgtgcccc agggcggcgg gaaggtcgtc tcagtacagg cagcatcggt gcccatcgag  10140
tgctcccagc gctcagccca ggagctgccc caggtggagg cctacagccc cagtgcctgc  10200
tctgtgagag gaggcgagga actggtactg accggctcca acttcctgcc agactccaag  10260
gtggtgttca ttgagagggg tcctgatggg aagctgcaat gggaggagga ggccacagtg  10320
aaccgactgc agagcaacga ggtgacgctg accctgactg tccccgagta cagcaacaag  10380
agggtttccc ggccagtcca ggtctacttt tatgtctcca atgggcggag gaaacgcagt  10440
```

```
cctacccaga gtttcaggtt tctgcctgtg atctgcaaag aggagcccct accggactca  10500

tctctgcggg gtttcccttc agcatcggca acccccttg gcactgacat ggacttctca  10560

ccacccaggc ccccctaccc ctcctatccc catgaagacc ctgcttgcga aactccttac  10620

ctatcagaag gcttcggcta tggcatgccc cctctgtacc cccagacggg gcccccacca  10680

tcctacagac cgggcctgcg gatgttccct gagactaggg gtaccacagg ttgtgcccaa  10740

ccacctgcag tttccttcct tccccgcccc ttccctagtg acccgtatgg agggcggggc  10800

tcctctttcc ccctggggct gccattctct ccgccagccc cctttcggcc gcctcctctt  10860

cctctcgagt ctagagggcc cgttta                                      10886
```

<210> SEQ ID NO 33
<211> LENGTH: 11121
<212> TYPE: DNA
<213> ORGANISM: Artificial sequence
<220> FEATURE:
<223> OTHER INFORMATION: pLVX-tdTomato-C1-hCD63

<400> SEQUENCE: 33

```
ggatccaccg gatctagata actgatcata attctaccgg gtaggggagg cgcttttccc     60

aaggcagtct ggagcatgcg ctttagcagc cccgctgggc acttggcgct acacaagtgg    120

cctctggcct cgcacacatt ccacatccac cggtaggcgc caaccggctc cgttctttgg    180

tggccccttc gcgccacctt ctactcctcc cctagtcagg aagttccccc ccgccccgca    240

gctcgcgtcg tgcaggacgt gacaaatgga agtagcacgt ctcactagtc tcgtgcagat    300

ggacagcacc gctgagcaat ggaagcgggt aggcctttgg ggcagcggcc aatagcagct    360

ttgctccttc gctttctggg ctcagaggct gggaaggggt gggtccgggg gcgggctcag    420

gggcgggctc aggggcgggg cgggcgcccg aaggtcctcc ggaggcccgg cattctgcac    480

gcttcaaaag cgcacgtctg ccgcgctgtt ctcctcttcc tcatctccgg gcctttcgac    540

ctgcagccca agcttaccat gaccgagtac aagcccacgg tgcgcctcgc cacccgcgac    600

gacgtcccca gggccgtacg caccctcgcc gccgcgttcg ccgactaccc cgccacgcgc    660

cacaccgtcg atccggaccg ccacatcgag cgggtcaccg agctgcaaga actcttcctc    720

acgcgcgtcg ggctcgacat cggcaaggtg tgggtcgcgg acgacggcgc cgcggtggcg    780

gtctggacca cgccggagag cgtcgaagcg ggggcggtgt tcgccgagat cggcccgcgc    840

atggccgagt tgagcggttc ccggctggcc gcgcagcaac agatggaagg cctcctggcg    900

ccgcaccggc ccaaggagcc cgcgtggttc ctggccaccg tcggcgtctc gcccgaccac    960

cagggcaagg gtctgggcag cgccgtcgtg ctccccggag tggaggcggc cgagcgcgcc   1020

ggggtgcccg ccttcctgga gacctccgcg ccccgcaacc tccccttcta cgagcggctc   1080

ggcttcaccg tcaccgccga cgtcgaggtg cccgaaggac cgcgcacctg gtgcatgacc   1140

cgcaagcccg gtgcctgacc gcgtctggaa caatcaacct ctggattaca aaatttgtga   1200

aagattgact ggtattctta actatgttgc tccttttacg ctatgtggat acgctgcttt   1260

aatgcctttg tatcatgcta ttgcttcccg tatggctttc attttctcct ccttgtataa   1320

atcctggttg ctgtctcttt atgaggagtt gtggcccgtt gtcaggcaac gtggcgtggt   1380

gtgcactgtg tttgctgacg caacccccac tggttggggc attgccacca cctgtcagct   1440

cctttccggg actttcgctt tccccctccc tattgccacg gcggaactca tcgccgcctg   1500

ccttgcccgc tgctggacag gggctcggct gttgggcact gacaattccg tggtgttgtc   1560

ggggaagctg acgtcctttc catggctgct cgcctgtgtt gccacctgga ttctgcgcgg   1620
```

-continued

```
gacgtccttc tgctacgtcc cttcggccct caatccagcg gaccttcctt cccgcggcct   1680
gctgccggct ctgcggcctc ttccgcgtct tcgccttcgc cctcagacga gtcggatctc   1740
cctttgggcc gcctccccgc ctggaattaa ttctgcagtc gagacctaga aaaacatgga   1800
gcaatcacaa gtagcaatac agcagctacc aatgctgatt gtgcctggct agaagcacaa   1860
gaggaggagg aggtgggttt tccagtcaca cctcaggtac ctttaagacc aatgacttac   1920
aaggcagctg tagatcttag ccactttta aaagaaaaga ggggactgga agggctaatt   1980
cactcccaac gaagacaaga tatccttgat ctgtggatct accacacaca aggctacttc   2040
cctgattagc agaactacac accagggcca ggggtcagat atccactgac ctttggatgg   2100
tgctacaagc tagtaccagt tgagccagat aaggtagaag aggccaataa aggagagaac   2160
accagcttgt tacaccctgt gagcctgcat gggatggatg acccggagag agaagtgtta   2220
gagtggaggt ttgacagccg cctagcattt catcacgtgg cccgagagct gcatccggag   2280
tacttcaaga actgctgata tcgagcttgc tacaagggac tttccgctgg ggactttcca   2340
gggaggcgtg gcctgggcgg gactggggag tggcgagccc tcagatcctg catataagca   2400
gctgcttttt gcctgtactg ggtctctctg gttagaccag atctgagcct gggagctctc   2460
tggctaacta gggaacccac tgcttaagcc tcaataaagc ttgccttgag tgcttcaagt   2520
agtgtgtgcc cgtctgttgt gtgactctgg taactagaga tccctcagac ccttttagtc   2580
agtgtggaaa atctctagca gtagtagttc atgtcatctt attattcagt atttataact   2640
tgcaaagaaa tgaatatcag agagtgagag gccttgacat tgctagcgtt ttaccgtcga   2700
cctctagcta gagcttggcg taatcatggt catagctgtt tcctgtgtga aattgttatc   2760
cgctcacaat tccacacaac atacgagccg gaagcataaa gtgtaaagcc tggggtgcct   2820
aatgagtgag ctaactcaca ttaattgcgt tgcgctcact gcccgctttc cagtcgggaa   2880
acctgtcgtg ccagctgcat taatgaatcg gccaacgcgc ggggagaggc ggtttgcgta   2940
ttgggcgctc ttccgcttcc tcgctcactg actcgctgcg ctcggtcgtt cggctgcggc   3000
gagcggtatc agctcactca aaggcggtaa tacggttatc cacagaatca ggggataacg   3060
caggaaagaa catgtgagca aaaggccagc aaaaggccag gaaccgtaaa aaggccgcgt   3120
tgctggcgtt tttccatagg ctccgccccc ctgacgagca tcacaaaaat cgacgctcaa   3180
gtcagaggtg gcgaaacccg acaggactat aaagatacca ggcgtttccc cctggaagct   3240
ccctcgtgcg ctctcctgtt ccgaccctgc cgcttaccgg atacctgtcc gcctttctcc   3300
cttcgggaag cgtggcgctt tctcatagct cacgctgtag gtatctcagt tcggtgtagg   3360
tcgttcgctc caagctgggc tgtgtgcacg aaccccccgt tcagcccgac cgctgcgcct   3420
tatccggtaa ctatcgtctt gagtccaacc cggtaagaca cgacttatcg ccactggcag   3480
cagccactgg taacaggatt agcagagcga ggtatgtagg cggtgctaca gagttcttga   3540
agtggtggcc taactacggc tacactagaa gaacagtatt tggtatctgc gctctgctga   3600
agccagttac cttcggaaaa agagttggta gctcttgatc cggcaaacaa accaccgctg   3660
gtagcggtgg tttttttgtt tgcaagcagc agattacgcg cagaaaaaaa ggatctcaag   3720
aagatccttt gatcttttct acggggtctg acgctcagtg gaacgaaaac tcacgttaag   3780
ggattttggt catgagatta tcaaaaagga tcttcaccta gatcctttta aattaaaaat   3840
gaagttttaa atcaatctaa agtatatatg agtaaacttg gtctgacagt taccaatgct   3900
taatcagtga ggcacctatc tcagcgatct gtctatttcg ttcatccata gttgcctgac   3960
```

-continued

```
tccccgtcgt gtagataact acgatacggg agggcttacc atctggcccc agtgctgcaa   4020
tgataccgcg agacccacgc tcaccggctc cagatttatc agcaataaac cagccagccg   4080
gaagggccga gcgcagaagt ggtcctgcaa ctttatccgc ctccatccag tctattaatt   4140
gttgccggga agctagagta agtagttcgc cagttaatag tttgcgcaac gttgttgcca   4200
ttgctacagg catcgtggtg tcacgctcgt cgtttggtat ggcttcattc agctccggtt   4260
cccaacgatc aaggcgagtt acatgatccc ccatgttgtg caaaaaagcg gttagctcct   4320
tcggtcctcc gatcgttgtc agaagtaagt tggccgcagt gttatcactc atggttatgg   4380
cagcactgca taattctctt actgtcatgc catccgtaag atgcttttct gtgactggtg   4440
agtactcaac caagtcattc tgagaatagt gtatgcggcg accgagttgc tcttgcccgg   4500
cgtcaatacg ggataatacc gcgccacata gcagaacttt aaaagtgctc atcattggaa   4560
aacgttcttc ggggcgaaaa ctctcaagga tcttaccgct gttgagatcc agttcgatgt   4620
aacccactcg tgcacccaac tgatcttcag catcttttac tttcaccagc gtttctgggt   4680
gagcaaaaac aggaaggcaa aatgccgcaa aaaagggaat aagggcgaca cggaaatgtt   4740
gaatactcat actcttcctt tttcaatatt attgaagcat ttatcagggt tattgtctca   4800
tgagcggata catatttgaa tgtatttaga aaaataaaca aataggggtt ccgcgcacat   4860
ttccccgaaa agtgccacct gacgtcgacg gatcgggaga tcaacttgtt tattgcagct   4920
tataatggtt acaaataaag caatagcatc acaaatttca caaataaagc atttttttca   4980
ctgcattcta gttgtggttt gtccaaactc atcaatgtat cttatcatgt ctggatcaac   5040
tggataactc aagctaacca aaatcatccc aaacttccca ccccataccc tattaccact   5100
gccaattacc tgtggtttca tttactctaa acctgtgatt cctctgaatt attttcattt   5160
taaagaaatt gtatttgtta aatatgtact acaaacttag tagttggaag ggctaattca   5220
ctcccaaaga agacaagata tccttgatct gtggatctac cacacacaag gctacttccc   5280
tgattagcag aactacacac cagggccagg ggtcagatat ccactgacct ttggatggtg   5340
ctacaagcta gtaccagttg agccagataa ggtagaagag gccaataaag gagagaacac   5400
cagcttgtta caccctgtga gcctgcatgg gatggatgac ccggagagag aagtgttaga   5460
gtggaggttt gacagccgcc tagcatttca tcacgtggcc cgagagctgc atccggagta   5520
cttcaagaac tgctgatatc gagcttgcta caagggactt tccgctgggg actttccagg   5580
gaggcgtggc ctgggcggga ctggggagtg gcgagccctc agatcctgca tataagcagc   5640
tgctttttgc ctgtactggg tctctctggt tagaccagat ctgagcctgg gagctctctg   5700
gctaactagg gaacccactg cttaagcctc aataaagctt gccttgagtg cttcaagtag   5760
tgtgtgcccg tctgttgtgt gactctggta actagagatc cctcagaccc ttttagtcag   5820
tgtggaaaat ctctagcagt ggcgcccgaa cagggacttg aaagcgaaag ggaaaccaga   5880
ggagctctct cgacgcagga ctcggcttgc tgaagcgcgc acggcaagag gcgaggggcg   5940
gcgactggtg agtacgccaa aaattttgac tagcggaggc tagaaggaga gagatgggtg   6000
cgagagcgtc agtattaagc gggggagaat tagatcgcga tgggaaaaaa ttcggttaag   6060
gccaggggga aagaaaaaat ataaattaaa acatatagta tgggcaagca gggagctaga   6120
acgattcgca gttaatcctg gcctgttaga aacatcagaa ggctgtagac aaatactggg   6180
acagctacaa ccatcccttc agacaggatc agaagaactt agatcattat ataatacagt   6240
agcaaccctc tattgtgtgc atcaaaggat agagataaaa gacaccaagg aagctttaga   6300
caagatagag gaagagcaaa acaaaagtaa gaccaccgca cagcaagcgg ccggccgctg   6360
```

atcttcagac ctggaggagg agatatgagg gacaattgga gaagtgaatt atataaatat 6420
aaagtagtaa aaattgaacc attaggagta gcacccacca aggcaaagag aagagtggtg 6480
cagagagaaa aaagagcagt gggaatagga gctttgttcc ttgggttctt gggagcagca 6540
ggaagcacta tgggcgcagc gtcaatgacg ctgacggtac aggccagaca attattgtct 6600
ggtatagtgc agcagcagaa caatttgctg agggctattg aggcgcaaca gcatctgttg 6660
caactcacag tctggggcat caagcagctc caggcaagaa tcctggctgt ggaaagatac 6720
ctaaaggatc aacagctcct ggggatttgg ggttgctctg gaaaactcat ttgcaccact 6780
gctgtgcctt ggaatgctag ttggagtaat aaatctctgg aacagatttg gaatcacacg 6840
acctggatgg agtgggacag agaaattaac aattacacaa gcttaataca ctccttaatt 6900
gaagaatcgc aaaaccagca agaaaagaat gaacaagaat tattggaatt agataaatgg 6960
gcaagtttgt ggaattggtt taacataaca aattggctgt ggtatataaa attattcata 7020
atgatagtag gaggcttggt aggtttaaga atagtttttg ctgtactttc tatagtgaat 7080
agagttaggc agggatattc accattatcg tttcagaccc acctcccaac cccgagggga 7140
cccgacaggc ccgaaggaat agaagaagaa ggtggagaga gagacagaga cagatccatt 7200
cgattagtga acggatctcg acggtatcgc ctttaaaaga aaaggggggga ttgggggta 7260
cagtgcaggg gaaagaatag tagacataat agcaacagac atacaaacta aagaattaca 7320
aaaacaaatt acaaaaattc aaaattttcg ggtttattac agggacagca gagatccagt 7380
ttatcgataa gcttgggagt tccgcgttac ataacttacg gtaaatggcc cgcctggctg 7440
accgcccaac gacccccgcc cattgacgtc aataatgacg tatgttccca tagtaacgcc 7500
aatagggact ttccattgac gtcaatgggt ggagtattta cggtaaactg cccacttggc 7560
agtacatcaa gtgtatcata tgccaagtac gccccctatt gacgtcaatg acggtaaatg 7620
gcccgcctgg cattatgccc agtacatgac cttatgggac tttcctactt ggcagtacat 7680
ctacgtatta gtcatcgcta ttaccatggt gatgcggttt tggcagtaca tcaatgggcg 7740
tggatagcgg tttgactcac ggggatttcc aagtctccac cccattgacg tcaatgggag 7800
tttgttttgg caccaaaatc aacgggactt tccaaaatgt cgtaacaact ccgccccatt 7860
gacgcaaatg ggcggtaggc gtgtacggtg ggaggtctat ataagcagag ctcgtttagt 7920
gaaccgtcag atcgcctgga gacgccatcc acgctgtttt gacctccata gaagacaccg 7980
actctactag aggatctacc ggtcgccacc atggtgagca agggcgagga ggtcatcaaa 8040
gagttcatgc gcttcaaggt gcgcatggag ggctccatga acggccacga gttcgagatc 8100
gagggcgagg gcgagggccg cccctacgag ggcacccaga ccgccaagct gaaggtgacc 8160
aagggcggcc ccctgccctt cgcctgggac atcctgtccc cccagttcat gtacggctcc 8220
aaggcgtacg tgaagcaccc cgccgacatc cccgattaca agaagctgtc cttccccgag 8280
ggcttcaagt gggagcgcgt gatgaacttc gaggacggcg gtctggtgac cgtgacccag 8340
gactcctccc tgcaggacgg cacgctgatc tacaaggtga agatgcgcgg caccaacttc 8400
ccccccgacg gccccgtaat gcagaagaag accatgggct gggaggcctc caccgagcgc 8460
ctgtaccccc gcgacggcgt gctgaagggc gagatccacc aggccctgaa gctgaaggac 8520
ggcggccact acctggtgga gttcaagacc atctacatgg ccaagaagcc cgtgcaactg 8580
cccggctact actacgtgga caccaagctg gacatcacct cccacaacga ggactacacc 8640
atcgtggaac agtacgagcg ctccgagggc cgccaccacc tgttcctggg gcatggcacc 8700

```
ggcagcaccg gcagcggcag ctccggcacc gcctcctccg aggacaacaa catggccgtc   8760
atcaaagagt tcatgcgctt caaggtgcgc atggagggct ccatgaacgg ccacgagttc   8820
gagatcgagg gcgagggcga gggccgcccc tacgagggca cccagaccgc caagctgaag   8880
gtgaccaagg gcggccccct gcccttcgcc tgggacatcc tgtcccccca gttcatgtac   8940
ggctccaagg cgtacgtgaa gcaccccgcc gacatccccg attacaagaa gctgtccttc   9000
cccgagggct tcaagtggga gcgcgtgatg aacttcgagg acggcggtct ggtgaccgtg   9060
acccaggact cctccctgca ggacggcacg ctgatctaca aggtgaagat gcgcggcacc   9120
aacttccccc ccgacggccc cgtaatgcag aagaagacca tgggctggga ggcctccacc   9180
gagcgcctgt acccccgcga cggcgtgctg aagggcgaga tccaccaggc cctgaagctg   9240
aaggacggcg gccactacct ggtggagttc aagaccatct acatggccaa gaagcccgtg   9300
caactgcccg gctactacta cgtggacacc aagctggaca tcacctccca caacgaggac   9360
tacaccatcg tggaacagta cgagcgctcc gagggccgcc accacctgtt cctgtacggc   9420
atggacgagc tgtacaagtc cggactcaga tctcgagctc aagcttcgaa ttctgcagtc   9480
gacggtaccg cgggcccggg atccatggcc tatccatatg acgtaccaga ttatgcggac   9540
tacctggcag tgccctcccc actcgcttgg tccaaggccc ggattggggg acacagccct   9600
atcttcagga cctctgccct acccccactg gactggcctc tgcccagcca atatgagcag   9660
ctggagctga ggatcgaggt acagcctaga gcccaccacc gggcccacta tgagacagaa   9720
ggcagccgtg gagctgtcaa agctgcccct ggcggtcacc ccgtagtcaa gctcctaggc   9780
tacagtgaga agccactgac cctacagatg ttcatcggca ctgcagatga aaggaacctg   9840
cggcctcatg ccttctatca ggtgcaccgt atcacaggca agatggtggc cacggccagc   9900
tatgaagccg tagtcagtgg caccaaggtg ttggagatga ctctgctgcc tgagaacaac   9960
atggcggcca acattgactg cgcgggaatc ctgaagcttc ggaattcaga cattgagctt  10020
cggaagggtg agacggacat cgggcgcaaa aacacacgtg tacggctggt gttccgggta  10080
cacgtgcccc agggcggcgg gaaggtcgtc tcagtacagg cagcatcggt gcccatcgag  10140
tgctcccagc gctcagccca ggagctgccc caggtggagg cctacagccc cagtgcctgc  10200
tctgtgagag gaggcgagga actggtactg accggctcca acttcctgcc agactccaag  10260
gtggtgttca ttgagagggg tcctgatggg aagctgcaat gggaggagga ggccacagtg  10320
aaccgactgc agagcaacga ggtgacgctg accctgactg tccccgagta cagcaacaag  10380
agggtttccc ggccagtcca ggtctacttt tatgtctcca atgggcggag gaaacgcagt  10440
cctacccaga gtttcaggtt tctgcctgtg atctgcaaag aggagcccct accggactca  10500
tctctgcggg gtttcccttc agcatcggca accccctttg gcactgacat ggacttctca  10560
ccacccaggc cccctaccc ctcctatccc catgaagacc ctgcttgcga aactccttac  10620
ctatcagaag gcttcggcta tggcatgccc cctctgtacc cccagacggg gcccccacca  10680
tcctacagac cgggcctgcg gatgttccct gagactaggg gtaccacagg ttgtgcccaa  10740
ccacctgcag tttccttcct tccccgcccc ttccctagtg acccgtatgg agggcggggc  10800
tcctctttcc ccctggggct gccattctct ccgccagccc cctttcggcc gcctcctctt  10860
cctgcatccc caccgcttga aggcccctc ccttcccaga gtgatgtgca tcccctacct  10920
gctgagggat acaataaggt agggccaggc tatggccctg gggagggggc tccggagcag  10980
gagaaatcca ggggtggcta cagcagcggc ttccgagaca gtgtccctat ccagggtatc  11040
acgctggagg aagtgagtga gatcattggc cgagacctga gtggcttccc tgcacctcct  11100
```

ggagaagagc ctcctgcctg a 11121

<210> SEQ ID NO 34
<211> LENGTH: 476
<212> TYPE: PRT
<213> ORGANISM: Artificial sequence
<220> FEATURE:
<223> OTHER INFORMATION: Clonetech, pLVX-tdTomato-C1 , empty vector

<400> SEQUENCE: 34

Met Val Ser Lys Gly Glu Glu Val Ile Lys Glu Phe Met Arg Phe Lys
1 5 10 15

Val Arg Met Glu Gly Ser Met Asn Gly His Glu Phe Glu Ile Glu Gly
20 25 30

Glu Gly Glu Gly Arg Pro Tyr Glu Gly Thr Gln Thr Ala Lys Leu Lys
35 40 45

Val Thr Lys Gly Gly Pro Leu Pro Phe Ala Trp Asp Ile Leu Ser Pro
50 55 60

Gln Phe Met Tyr Gly Ser Lys Ala Tyr Val Lys His Pro Ala Asp Ile
65 70 75 80

Pro Asp Tyr Lys Lys Leu Ser Phe Pro Glu Gly Phe Lys Trp Glu Arg
85 90 95

Val Met Asn Phe Glu Asp Gly Gly Leu Val Thr Val Thr Gln Asp Ser
100 105 110

Ser Leu Gln Asp Gly Thr Leu Ile Tyr Lys Val Lys Met Arg Gly Thr
115 120 125

Asn Phe Pro Pro Asp Gly Pro Val Met Gln Lys Lys Thr Met Gly Trp
130 135 140

Glu Ala Ser Thr Glu Arg Leu Tyr Pro Arg Asp Gly Val Leu Lys Gly
145 150 155 160

Glu Ile His Gln Ala Leu Lys Leu Lys Asp Gly Gly His Tyr Leu Val
165 170 175

Glu Phe Lys Thr Ile Tyr Met Ala Lys Lys Pro Val Gln Leu Pro Gly
180 185 190

Tyr Tyr Tyr Val Asp Thr Lys Leu Asp Ile Thr Ser His Asn Glu Asp
195 200 205

Tyr Thr Ile Val Glu Gln Tyr Glu Arg Ser Glu Gly Arg His His Leu
210 215 220

Phe Leu Gly His Gly Thr Gly Ser Thr Gly Ser Gly Ser Ser Gly Thr
225 230 235 240

Ala Ser Ser Glu Asp Asn Asn Met Ala Val Ile Lys Glu Phe Met Arg
245 250 255

Phe Lys Val Arg Met Glu Gly Ser Met Asn Gly His Glu Phe Glu Ile
260 265 270

Glu Gly Glu Gly Glu Gly Arg Pro Tyr Glu Gly Thr Gln Thr Ala Lys
275 280 285

Leu Lys Val Thr Lys Gly Gly Pro Leu Pro Phe Ala Trp Asp Ile Leu
290 295 300

Ser Pro Gln Phe Met Tyr Gly Ser Lys Ala Tyr Val Lys His Pro Ala
305 310 315 320

Asp Ile Pro Asp Tyr Lys Lys Leu Ser Phe Pro Glu Gly Phe Lys Trp
325 330 335

Glu Arg Val Met Asn Phe Glu Asp Gly Gly Leu Val Thr Val Thr Gln
340 345 350

```
Asp Ser Ser Leu Gln Asp Gly Thr Leu Ile Tyr Lys Val Lys Met Arg
        355                 360                 365

Gly Thr Asn Phe Pro Pro Asp Gly Pro Val Met Gln Lys Lys Thr Met
    370                 375                 380

Gly Trp Glu Ala Ser Thr Glu Arg Leu Tyr Pro Arg Asp Gly Val Leu
385                 390                 395                 400

Lys Gly Glu Ile His Gln Ala Leu Lys Leu Lys Asp Gly Gly His Tyr
                405                 410                 415

Leu Val Glu Phe Lys Thr Ile Tyr Met Ala Lys Lys Pro Val Gln Leu
            420                 425                 430

Pro Gly Tyr Tyr Tyr Val Asp Thr Lys Leu Asp Ile Thr Ser His Asn
        435                 440                 445

Glu Asp Tyr Thr Ile Val Glu Gln Tyr Glu Arg Ser Glu Gly Arg His
    450                 455                 460

His Leu Phe Leu Tyr Gly Met Asp Glu Leu Tyr Lys
465                 470                 475


<210> SEQ ID NO 35
<211> LENGTH: 941
<212> TYPE: PRT
<213> ORGANISM: Artificial sequence
<220> FEATURE:
<223> OTHER INFORMATION: pLVX-tdTomato-C1-HA hNFAT3 WT

<400> SEQUENCE: 35

Val Glu Gln Tyr Glu Arg Ser Glu Gly Arg His His Leu Phe Leu Tyr
1               5                   10                  15

Gly Met Asp Glu Leu Tyr Lys Ser Gly Leu Arg Ser Arg Val Ala Tyr
            20                  25                  30

Pro Tyr Asp Val Pro Asp Tyr Ala Gly Ala Ala Ser Cys Glu Asp Glu
        35                  40                  45

Glu Leu Glu Phe Lys Leu Val Phe Gly Glu Glu Lys Glu Ala Pro Pro
    50                  55                  60

Leu Gly Ala Gly Gly Leu Gly Glu Glu Leu Asp Ser Glu Asp Ala Pro
65                  70                  75                  80

Pro Cys Cys Arg Leu Ala Leu Gly Glu Pro Pro Pro Tyr Gly Ala Ala
                85                  90                  95

Pro Ile Gly Ile Pro Arg Pro Pro Pro Pro Arg Pro Gly Met His Ser
            100                 105                 110

Pro Pro Pro Arg Pro Ala Pro Ser Pro Gly Thr Trp Glu Ser Gln Pro
        115                 120                 125

Ala Arg Ser Val Arg Leu Gly Gly Pro Gly Gly Gly Ala Gly Gly Ala
    130                 135                 140

Gly Gly Gly Arg Val Leu Glu Cys Pro Ser Ile Arg Ile Thr Ser Ile
145                 150                 155                 160

Ser Pro Thr Pro Glu Pro Pro Ala Ala Leu Glu Asp Asn Pro Asp Ala
                165                 170                 175

Trp Gly Asp Gly Ser Pro Arg Asp Tyr Pro Pro Pro Glu Gly Phe Gly
            180                 185                 190

Gly Tyr Arg Glu Ala Gly Ala Gln Gly Gly Gly Ala Phe Phe Ser Pro
        195                 200                 205

Ser Pro Gly Ser Ser Ser Leu Ser Ser Trp Ser Phe Phe Ser Asp Ala
    210                 215                 220

Ser Asp Glu Ala Ala Leu Tyr Ala Ala Cys Asp Glu Val Glu Ser Glu
225                 230                 235                 240
```

-continued

```
Leu Asn Glu Ala Ala Ser Arg Phe Gly Leu Gly Ser Pro Leu Pro Ser
                245                 250                 255

Pro Arg Ala Ser Pro Arg Pro Trp Thr Pro Glu Asp Pro Trp Ser Leu
            260                 265                 270

Tyr Gly Pro Ser Pro Gly Gly Arg Gly Pro Glu Asp Ser Trp Leu Leu
        275                 280                 285

Leu Ser Ala Pro Gly Pro Thr Pro Ala Ser Pro Arg Pro Ala Ser Pro
    290                 295                 300

Cys Gly Lys Arg Arg Tyr Ser Ser Ser Gly Thr Pro Ser Ser Ala Ser
305                 310                 315                 320

Pro Ala Leu Ser Arg Arg Gly Ser Leu Gly Glu Glu Gly Ser Glu Pro
                325                 330                 335

Pro Pro Pro Pro Pro Leu Pro Leu Ala Arg Asp Pro Gly Ser Pro Gly
            340                 345                 350

Pro Phe Asp Tyr Val Gly Ala Pro Pro Ala Glu Ser Ile Pro Gln Lys
        355                 360                 365

Thr Arg Arg Thr Ser Ser Glu Gln Ala Val Ala Leu Pro Arg Ser Glu
    370                 375                 380

Glu Pro Ala Ser Cys Asn Gly Lys Leu Pro Leu Gly Ala Glu Glu Ser
385                 390                 395                 400

Val Ala Pro Pro Gly Gly Ser Arg Lys Glu Val Ala Gly Met Asp Tyr
                405                 410                 415

Leu Ala Val Pro Ser Pro Leu Ala Trp Ser Lys Ala Arg Ile Gly Gly
            420                 425                 430

His Ser Pro Ile Phe Arg Thr Ser Ala Leu Pro Pro Leu Asp Trp Pro
        435                 440                 445

Leu Pro Ser Gln Tyr Glu Gln Leu Glu Leu Arg Ile Glu Val Gln Pro
    450                 455                 460

Arg Ala His His Arg Ala His Tyr Glu Thr Glu Gly Ser Arg Gly Ala
465                 470                 475                 480

Val Lys Ala Ala Pro Gly Gly His Pro Val Val Lys Leu Leu Gly Tyr
                485                 490                 495

Ser Glu Lys Pro Leu Thr Leu Gln Met Phe Ile Gly Thr Ala Asp Glu
            500                 505                 510

Arg Asn Leu Arg Pro His Ala Phe Tyr Gln Val His Arg Ile Thr Gly
        515                 520                 525

Lys Met Val Ala Thr Ala Ser Tyr Glu Ala Val Val Ser Gly Thr Lys
    530                 535                 540

Val Leu Glu Met Thr Leu Leu Pro Glu Asn Asn Met Ala Ala Asn Ile
545                 550                 555                 560

Asp Cys Ala Gly Ile Leu Lys Leu Arg Asn Ser Asp Ile Glu Leu Arg
                565                 570                 575

Lys Gly Glu Thr Asp Ile Gly Arg Lys Asn Thr Arg Val Arg Leu Val
            580                 585                 590

Phe Arg Val His Val Pro Gln Gly Gly Gly Lys Val Val Ser Val Gln
        595                 600                 605

Ala Ala Ser Val Pro Ile Glu Cys Ser Gln Arg Ser Ala Gln Glu Leu
    610                 615                 620

Pro Gln Val Glu Ala Tyr Ser Pro Ser Ala Cys Ser Val Arg Gly Gly
625                 630                 635                 640

Glu Glu Leu Val Leu Thr Gly Ser Asn Phe Leu Pro Asp Ser Lys Val
                645                 650                 655

Val Phe Ile Glu Arg Gly Pro Asp Gly Lys Leu Gln Trp Glu Glu Glu
```

```
            660                 665                 670

Ala Thr Val Asn Arg Leu Gln Ser Asn Glu Val Thr Leu Thr Leu Thr
        675                 680                 685

Val Pro Glu Tyr Ser Asn Lys Arg Val Ser Arg Pro Val Gln Val Tyr
    690                 695                 700

Phe Tyr Val Ser Asn Gly Arg Arg Lys Arg Ser Pro Thr Gln Ser Phe
705                 710                 715                 720

Arg Phe Leu Pro Val Ile Cys Lys Glu Glu Pro Leu Pro Asp Ser Ser
                725                 730                 735

Leu Arg Gly Phe Pro Ser Ala Ser Ala Thr Pro Phe Gly Thr Asp Met
            740                 745                 750

Asp Phe Ser Pro Pro Arg Pro Pro Tyr Pro Ser Tyr Pro His Glu Asp
        755                 760                 765

Pro Ala Cys Glu Thr Pro Tyr Leu Ser Glu Gly Phe Gly Tyr Gly Met
    770                 775                 780

Pro Pro Leu Tyr Pro Gln Thr Gly Pro Pro Pro Ser Tyr Arg Pro Gly
785                 790                 795                 800

Leu Arg Met Phe Pro Glu Thr Arg Gly Thr Thr Gly Cys Ala Gln Pro
                805                 810                 815

Pro Ala Val Ser Phe Leu Pro Arg Pro Phe Pro Ser Asp Pro Tyr Gly
            820                 825                 830

Gly Arg Gly Ser Ser Phe Pro Leu Gly Leu Pro Phe Ser Pro Pro Ala
        835                 840                 845

Pro Phe Arg Pro Pro Pro Leu Pro Ala Ser Pro Pro Leu Glu Gly Pro
    850                 855                 860

Phe Pro Ser Gln Ser Asp Val His Pro Leu Pro Ala Glu Gly Tyr Asn
865                 870                 875                 880

Lys Val Gly Pro Gly Tyr Gly Pro Gly Glu Gly Ala Pro Glu Gln Glu
                885                 890                 895

Lys Ser Arg Gly Gly Tyr Ser Ser Gly Phe Arg Asp Ser Val Pro Ile
            900                 905                 910

Gln Gly Ile Thr Leu Glu Glu Val Ser Glu Ile Ile Gly Arg Asp Leu
        915                 920                 925

Ser Gly Phe Pro Ala Pro Pro Gly Glu Glu Pro Pro Ala
    930                 935                 940
```

<210> SEQ ID NO 36
<211> LENGTH: 1309
<212> TYPE: PRT
<213> ORGANISM: Artificial sequence
<220> FEATURE:
<223> OTHER INFORMATION: pLVX-tdTomato-C1-HA hNFAT3-85C

<400> SEQUENCE: 36

```
Met Val Ser Lys Gly Glu Glu Val Ile Lys Glu Phe Met Arg Phe Lys
1               5                   10                  15

Val Arg Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Met Tyr Gly Ser Lys Ala Tyr Val Lys His Pro Ala Asp Ile
65                  70                  75                  80

Pro Asp Tyr Lys Lys Leu Ser Phe Pro Glu Gly Phe Lys Trp Glu Arg
```

```
                85                  90                  95

Val Met Asn Phe Glu Asp Gly Gly Leu Val Thr Val Thr Gln Asp Ser
            100                 105                 110

Ser Leu Gln Asp Gly Thr Leu Ile Tyr Lys Val Lys Met Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
        195                 200                 205

Tyr Thr Ile Val Glu Gln Tyr Glu Arg Ser Glu Gly Arg His His Leu
    210                 215                 220

Phe Leu Gly His Gly Thr Gly Ser Thr Gly Ser Gly Ser Ser Gly Thr
225                 230                 235                 240

Ala Ser Ser Glu Asp Asn Asn Met Ala Val Ile Lys Glu Phe Met Arg
                245                 250                 255

Phe Lys Val Arg Met Glu Gly Ser Met Asn Gly His Glu Phe Glu Ile
            260                 265                 270

Glu Gly Glu Gly Glu Gly Arg Pro Tyr Glu Gly Thr Gln Thr Ala Lys
        275                 280                 285

Leu Lys Val Thr Lys Gly Gly Pro Leu Pro Phe Ala Trp Asp Ile Leu
    290                 295                 300

Ser Pro Gln Phe Met Tyr Gly Ser Lys Ala Tyr Val Lys His Pro Ala
305                 310                 315                 320

Asp Ile Pro Asp Tyr Lys Lys Leu Ser Phe Pro Glu Gly Phe Lys Trp
                325                 330                 335

Glu Arg Val Met Asn Phe Glu Asp Gly Gly Leu Val Thr Val Thr Gln
            340                 345                 350

Asp Ser Ser Leu Gln Asp Gly Thr Leu Ile Tyr Lys Val Lys Met Arg
        355                 360                 365

Gly Thr Asn Phe Pro Pro Asp Gly Pro Val Met Gln Lys Lys Thr Met
    370                 375                 380

Gly Trp Glu Ala Ser Thr Glu Arg Leu Tyr Pro Arg Asp Gly Val Leu
385                 390                 395                 400

Lys Gly Glu Ile His Gln Ala Leu Lys Leu Lys Asp Gly Gly His Tyr
                405                 410                 415

Leu Val Glu Phe Lys Thr Ile Tyr Met Ala Lys Lys Pro Val Gln Leu
            420                 425                 430

Pro Gly Tyr Tyr Tyr Val Asp Thr Lys Leu Asp Ile Thr Ser His Asn
        435                 440                 445

Glu Asp Tyr Thr Ile Val Glu Gln Tyr Glu Arg Ser Glu Gly Arg His
    450                 455                 460

His Leu Phe Leu Tyr Gly Met Asp Glu Leu Tyr Lys Ser Gly Leu Arg
465                 470                 475                 480

Ser Arg Val Ala Tyr Pro Tyr Asp Val Pro Asp Tyr Ala Gly Ala Ala
                485                 490                 495

Ser Cys Glu Asp Glu Glu Leu Glu Phe Lys Leu Val Phe Gly Glu Glu
            500                 505                 510
```

```
Lys Glu Ala Pro Pro Leu Gly Ala Gly Gly Leu Gly Glu Glu Leu Asp
        515                 520                 525

Ser Glu Asp Ala Pro Pro Cys Cys Arg Leu Ala Leu Gly Glu Pro Pro
    530                 535                 540

Pro Tyr Gly Ala Ala Pro Ile Gly Ile Pro Arg Pro Pro Pro Pro Arg
545                 550                 555                 560

Pro Gly Met His Ser Pro Pro Pro Arg Pro Ala Pro Ser Pro Gly Thr
                565                 570                 575

Trp Glu Ser Gln Pro Ala Arg Ser Val Arg Leu Gly Gly Pro Gly Gly
            580                 585                 590

Gly Ala Gly Gly Ala Gly Gly Gly Arg Val Leu Glu Cys Pro Ser Ile
        595                 600                 605

Arg Ile Thr Ser Ile Ser Pro Thr Pro Glu Pro Pro Ala Ala Leu Glu
    610                 615                 620

Asp Asn Pro Asp Ala Trp Gly Asp Gly Ser Pro Arg Asp Tyr Pro Pro
625                 630                 635                 640

Pro Glu Gly Phe Gly Gly Tyr Arg Glu Ala Gly Ala Gln Gly Gly Gly
                645                 650                 655

Ala Phe Phe Ser Pro Ser Pro Gly Ser Ser Ser Leu Ser Ser Trp Ser
            660                 665                 670

Phe Phe Ser Asp Ala Ser Asp Glu Ala Ala Leu Tyr Ala Ala Cys Asp
        675                 680                 685

Glu Val Glu Ser Glu Leu Asn Glu Ala Ala Ser Arg Phe Gly Leu Gly
    690                 695                 700

Ser Pro Leu Pro Ser Pro Arg Ala Ser Pro Arg Pro Trp Thr Pro Glu
705                 710                 715                 720

Asp Pro Trp Ser Leu Tyr Gly Pro Ser Pro Gly Gly Arg Gly Pro Glu
                725                 730                 735

Asp Ser Trp Leu Leu Leu Ser Ala Pro Gly Pro Thr Pro Ala Ser Pro
            740                 745                 750

Arg Pro Ala Ser Pro Cys Gly Lys Arg Arg Tyr Ser Ser Ser Gly Thr
        755                 760                 765

Pro Ser Ser Ala Ser Pro Ala Leu Ser Arg Arg Gly Ser Leu Gly Glu
    770                 775                 780

Glu Gly Ser Glu Pro Pro Pro Pro Pro Pro Leu Pro Leu Ala Arg Asp
785                 790                 795                 800

Pro Gly Ser Pro Gly Pro Phe Asp Tyr Val Gly Ala Pro Pro Ala Glu
                805                 810                 815

Ser Ile Pro Gln Lys Thr Arg Arg Thr Ser Ser Glu Gln Ala Val Ala
            820                 825                 830

Leu Pro Arg Ser Glu Glu Pro Ala Ser Cys Asn Gly Lys Leu Pro Leu
        835                 840                 845

Gly Ala Glu Glu Ser Val Ala Pro Pro Gly Gly Ser Arg Lys Glu Val
    850                 855                 860

Ala Gly Met Asp Tyr Leu Ala Val Pro Ser Pro Leu Ala Trp Ser Lys
865                 870                 875                 880

Ala Arg Ile Gly Gly His Ser Pro Ile Phe Arg Thr Ser Ala Leu Pro
                885                 890                 895

Pro Leu Asp Trp Pro Leu Pro Ser Gln Tyr Glu Gln Leu Glu Leu Arg
            900                 905                 910

Ile Glu Val Gln Pro Arg Ala His His Arg Ala His Tyr Glu Thr Glu
        915                 920                 925
```

```
Gly Ser Arg Gly Ala Val Lys Ala Ala Pro Gly Gly His Pro Val Val
    930                 935                 940

Lys Leu Leu Gly Tyr Ser Glu Lys Pro Leu Thr Leu Gln Met Phe Ile
945                 950                 955                 960

Gly Thr Ala Asp Glu Arg Asn Leu Arg Pro His Ala Phe Tyr Gln Val
                965                 970                 975

His Arg Ile Thr Gly Lys Met Val Ala Thr Ala Ser Tyr Glu Ala Val
            980                 985                 990

Val Ser Gly Thr Lys Val Leu Glu  Met Thr Leu Leu Pro  Glu Asn Asn
        995                 1000                1005

Met Ala  Ala Asn Ile Asp Cys  Ala Gly Ile Leu Lys  Leu Arg Asn
    1010                 1015                 1020

Ser Asp  Ile Glu Leu Arg Lys  Gly Glu Thr Asp Ile  Gly Arg Lys
    1025                 1030                 1035

Asn Thr  Arg Val Arg Leu Val  Phe Arg Val His Val  Pro Gln Gly
    1040                 1045                 1050

Gly Gly  Lys Val Val Ser Val  Gln Ala Ala Ser Val  Pro Ile Glu
    1055                 1060                 1065

Cys Ser  Gln Arg Ser Ala Gln  Glu Leu Pro Gln Val  Glu Ala Tyr
    1070                 1075                 1080

Ser Pro  Ser Ala Cys Ser Val  Arg Gly Gly Glu Glu  Leu Val Leu
    1085                 1090                 1095

Thr Gly  Ser Asn Phe Leu Pro  Asp Ser Lys Val Val  Phe Ile Glu
    1100                 1105                 1110

Arg Gly  Pro Asp Gly Lys Leu  Gln Trp Glu Glu Glu  Ala Thr Val
    1115                 1120                 1125

Asn Arg  Leu Gln Ser Asn Glu  Val Thr Leu Thr Leu  Thr Val Pro
    1130                 1135                 1140

Glu Tyr  Ser Asn Lys Arg Val  Ser Arg Pro Val Gln  Val Tyr Phe
    1145                 1150                 1155

Tyr Val  Ser Asn Gly Arg Arg  Lys Arg Ser Pro Thr  Gln Ser Phe
    1160                 1165                 1170

Arg Phe  Leu Pro Val Ile Cys  Lys Glu Glu Pro Leu  Pro Asp Ser
    1175                 1180                 1185

Ser Leu  Arg Gly Phe Pro Ser  Ala Ser Ala Thr Pro  Phe Gly Thr
    1190                 1195                 1200

Asp Met  Asp Phe Ser Pro Pro  Arg Pro Pro Tyr Pro  Ser Tyr Pro
    1205                 1210                 1215

His Glu  Asp Pro Ala Cys Glu  Thr Pro Tyr Leu Ser  Glu Gly Phe
    1220                 1225                 1230

Gly Tyr  Gly Met Pro Pro Leu  Tyr Pro Gln Thr Gly  Pro Pro Pro
    1235                 1240                 1245

Ser Tyr  Arg Pro Gly Leu Arg  Met Phe Pro Glu Thr  Arg Gly Thr
    1250                 1255                 1260

Thr Gly  Cys Ala Gln Pro Pro  Ala Val Ser Phe Leu  Pro Arg Pro
    1265                 1270                 1275

Phe Pro  Ser Asp Pro Tyr Gly  Gly Arg Gly Ser Ser  Phe Pro Leu
    1280                 1285                 1290

Gly Leu  Pro Phe Ser Pro Pro  Ala Pro Phe Arg Pro  Pro Pro Leu
    1295                 1300                 1305

Pro
```

<210> SEQ ID NO 37

<211> LENGTH: 1036
<212> TYPE: PRT
<213> ORGANISM: Artificial sequence
<220> FEATURE:
<223> OTHER INFORMATION: pLVX-tdTomato-C1 h?NFAT3 WT

<400> SEQUENCE: 37

Met Val Ser Lys Gly Glu Glu Val Ile Lys Glu Phe Met Arg Phe Lys
1 5 10 15

Val Arg Met Glu Gly Ser Met Asn Gly His Glu Phe Glu Ile Glu Gly
20 25 30

Glu Gly Glu Gly Arg Pro Tyr Glu Gly Thr Gln Thr Ala Lys Leu Lys
35 40 45

Val Thr Lys Gly Gly Pro Leu Pro Phe Ala Trp Asp Ile Leu Ser Pro
50 55 60

Gln Phe Met Tyr Gly Ser Lys Ala Tyr Val Lys His Pro Ala Asp Ile
65 70 75 80

Pro Asp Tyr Lys Lys Leu Ser Phe Pro Glu Gly Phe Lys Trp Glu Arg
85 90 95

Val Met Asn Phe Glu Asp Gly Gly Leu Val Thr Val Thr Gln Asp Ser
100 105 110

Ser Leu Gln Asp Gly Thr Leu Ile Tyr Lys Val Lys Met Arg Gly Thr
115 120 125

Asn Phe Pro Pro Asp Gly Pro Val Met Gln Lys Lys Thr Met Gly Trp
130 135 140

Glu Ala Ser Thr Glu Arg Leu Tyr Pro Arg Asp Gly Val Leu Lys Gly
145 150 155 160

Glu Ile His Gln Ala Leu Lys Leu Lys Asp Gly Gly His Tyr Leu Val
165 170 175

Glu Phe Lys Thr Ile Tyr Met Ala Lys Lys Pro Val Gln Leu Pro Gly
180 185 190

Tyr Tyr Tyr Val Asp Thr Lys Leu Asp Ile Thr Ser His Asn Glu Asp
195 200 205

Tyr Thr Ile Val Glu Gln Tyr Glu Arg Ser Glu Gly Arg His His Leu
210 215 220

Phe Leu Gly His Gly Thr Gly Ser Thr Gly Ser Gly Ser Ser Gly Thr
225 230 235 240

Ala Ser Ser Glu Asp Asn Asn Met Ala Val Ile Lys Glu Phe Met Arg
245 250 255

Phe Lys Val Arg Met Glu Gly Ser Met Asn Gly His Glu Phe Glu Ile
260 265 270

Glu Gly Glu Gly Glu Gly Arg Pro Tyr Glu Gly Thr Gln Thr Ala Lys
275 280 285

Leu Lys Val Thr Lys Gly Gly Pro Leu Pro Phe Ala Trp Asp Ile Leu
290 295 300

Ser Pro Gln Phe Met Tyr Gly Ser Lys Ala Tyr Val Lys His Pro Ala
305 310 315 320

Asp Ile Pro Asp Tyr Lys Lys Leu Ser Phe Pro Glu Gly Phe Lys Trp
325 330 335

Glu Arg Val Met Asn Phe Glu Asp Gly Gly Leu Val Thr Val Thr Gln
340 345 350

Asp Ser Ser Leu Gln Asp Gly Thr Leu Ile Tyr Lys Val Lys Met Arg
355 360 365

Gly Thr Asn Phe Pro Pro Asp Gly Pro Val Met Gln Lys Lys Thr Met
370 375 380

```
Gly Trp Glu Ala Ser Thr Glu Arg Leu Tyr Pro Arg Asp Gly Val Leu
385                 390                 395                 400

Lys Gly Glu Ile His Gln Ala Leu Lys Leu Lys Asp Gly Gly His Tyr
                405                 410                 415

Leu Val Glu Phe Lys Thr Ile Tyr Met Ala Lys Lys Pro Val Gln Leu
            420                 425                 430

Pro Gly Tyr Tyr Tyr Val Asp Thr Lys Leu Asp Ile Thr Ser His Asn
        435                 440                 445

Glu Asp Tyr Thr Ile Val Glu Gln Tyr Glu Arg Ser Glu Gly Arg His
    450                 455                 460

His Leu Phe Leu Tyr Gly Met Asp Glu Leu Tyr Lys Ser Gly Leu Arg
465                 470                 475                 480

Ser Arg Ala Gln Ala Ser Asn Ser Ala Val Asp Gly Thr Ala Gly Pro
                485                 490                 495

Gly Ser Met Ala Tyr Pro Tyr Asp Val Pro Asp Tyr Ala Asp Tyr Leu
            500                 505                 510

Ala Val Pro Ser Pro Leu Ala Trp Ser Lys Ala Arg Ile Gly Gly His
        515                 520                 525

Ser Pro Ile Phe Arg Thr Ser Ala Leu Pro Pro Leu Asp Trp Pro Leu
    530                 535                 540

Pro Ser Gln Tyr Glu Gln Leu Glu Leu Arg Ile Glu Val Gln Pro Arg
545                 550                 555                 560

Ala His His Arg Ala His Tyr Glu Thr Glu Gly Ser Arg Gly Ala Val
                565                 570                 575

Lys Ala Ala Pro Gly Gly His Pro Val Val Lys Leu Leu Gly Tyr Ser
            580                 585                 590

Glu Lys Pro Leu Thr Leu Gln Met Phe Ile Gly Thr Ala Asp Glu Arg
        595                 600                 605

Asn Leu Arg Pro His Ala Phe Tyr Gln Val His Arg Ile Thr Gly Lys
    610                 615                 620

Met Val Ala Thr Ala Ser Tyr Glu Ala Val Val Ser Gly Thr Lys Val
625                 630                 635                 640

Leu Glu Met Thr Leu Leu Pro Glu Asn Asn Met Ala Ala Asn Ile Asp
                645                 650                 655

Cys Ala Gly Ile Leu Lys Leu Arg Asn Ser Asp Ile Glu Leu Arg Lys
            660                 665                 670

Gly Glu Thr Asp Ile Gly Arg Lys Asn Thr Arg Val Arg Leu Val Phe
        675                 680                 685

Arg Val His Val Pro Gln Gly Gly Gly Lys Val Val Ser Val Gln Ala
    690                 695                 700

Ala Ser Val Pro Ile Glu Cys Ser Gln Arg Ser Ala Gln Glu Leu Pro
705                 710                 715                 720

Gln Val Glu Ala Tyr Ser Pro Ser Ala Cys Ser Val Arg Gly Gly Glu
                725                 730                 735

Glu Leu Val Leu Thr Gly Ser Asn Phe Leu Pro Asp Ser Lys Val Val
            740                 745                 750

Phe Ile Glu Arg Gly Pro Asp Gly Lys Leu Gln Trp Glu Glu Glu Ala
        755                 760                 765

Thr Val Asn Arg Leu Gln Ser Asn Glu Val Thr Leu Thr Leu Thr Val
    770                 775                 780

Pro Glu Tyr Ser Asn Lys Arg Val Ser Arg Pro Val Gln Val Tyr Phe
785                 790                 795                 800
```

-continued

```
Tyr Val Ser Asn Gly Arg Arg Lys Arg Ser Pro Thr Gln Ser Phe Arg
                805                 810                 815

Phe Leu Pro Val Ile Cys Lys Glu Glu Pro Leu Pro Asp Ser Ser Leu
            820                 825                 830

Arg Gly Phe Pro Ser Ala Ser Ala Thr Pro Phe Gly Thr Asp Met Asp
        835                 840                 845

Phe Ser Pro Pro Arg Pro Pro Tyr Pro Ser Tyr Pro His Glu Asp Pro
    850                 855                 860

Ala Cys Glu Thr Pro Tyr Leu Ser Glu Gly Phe Gly Tyr Gly Met Pro
865                 870                 875                 880

Pro Leu Tyr Pro Gln Thr Gly Pro Pro Pro Ser Tyr Arg Pro Gly Leu
                885                 890                 895

Arg Met Phe Pro Glu Thr Arg Gly Thr Thr Gly Cys Ala Gln Pro Pro
            900                 905                 910

Ala Val Ser Phe Leu Pro Arg Pro Phe Pro Ser Asp Pro Tyr Gly Gly
        915                 920                 925

Arg Gly Ser Ser Phe Pro Leu Gly Leu Pro Phe Ser Pro Pro Ala Pro
    930                 935                 940

Phe Arg Pro Pro Pro Leu Pro Ala Ser Pro Pro Leu Glu Gly Pro Phe
945                 950                 955                 960

Pro Ser Gln Ser Asp Val His Pro Leu Pro Ala Glu Gly Tyr Asn Lys
                965                 970                 975

Val Gly Pro Gly Tyr Gly Pro Gly Glu Gly Ala Pro Glu Gln Glu Lys
            980                 985                 990

Ser Arg Gly Gly Tyr Ser Ser Gly  Phe Arg Asp Ser Val  Pro Ile Gln
        995                 1000                1005

Gly Ile  Thr Leu Glu Glu Val  Ser Glu Ile Ile Gly  Arg Asp Leu
    1010                 1015                 1020

Ser Gly  Phe Pro Ala Pro Pro  Gly Glu Glu Pro Pro  Ala
    1025                 1030                 1035
```